US012421524B2

(12) United States Patent
Du et al.

(10) Patent No.: US 12,421,524 B2
(45) Date of Patent: Sep. 23, 2025

(54) EXPRESSION VECTORS FOR EUKARYOTIC EXPRESSION SYSTEMS

(71) Applicant: Merck Sharp & Dohme LLC, Rahway, NJ (US)

(72) Inventors: Zhimei Du, Basking Ridge, NJ (US); Bo Jiang, Westfield, NJ (US); Xiaoyan Tang, Wayne, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 1103 days.

(21) Appl. No.: 17/277,663

(22) PCT Filed: Sep. 23, 2019

(86) PCT No.: PCT/US2019/052373

§ 371 (c)(1),
(2) Date: Mar. 18, 2021

(87) PCT Pub. No.: WO2020/068631

PCT Pub. Date: Apr. 2, 2020

(65) Prior Publication Data

US 2022/0033845 A1 Feb. 3, 2022

Related U.S. Application Data

(60) Provisional application No. 62/735,417, filed on Sep. 24, 2018.

(51) Int. Cl.
*C12N 15/85* (2006.01)
*C07K 16/06* (2006.01)

(52) U.S. Cl.
CPC .............. *C12N 15/85* (2013.01); *C07K 16/06* (2013.01); *C07K 2317/14* (2013.01);
(Continued)

(58) Field of Classification Search
CPC ............... C12N 15/85; C12N 2510/02; C12N 2800/90; C12N 2820/55; C12N 2830/40;
(Continued)

(56) References Cited

U.S. PATENT DOCUMENTS

| | | |
|---|---|---|
| 4,816,567 A | 3/1989 | Cabilly et al. |
| 8,663,989 B2 | 3/2014 | Stitz |

(Continued)

FOREIGN PATENT DOCUMENTS

| | | |
|---|---|---|
| CN | 100494370 C | 6/2009 |
| CN | 108330135 A | 7/2018 |

(Continued)

OTHER PUBLICATIONS

PiggyBac Product Insert, SBI, System Biosciences (Year: 2014).*
(Continued)

*Primary Examiner* — Ram R Shukla
*Assistant Examiner* — Shabana S Meyering
(74) *Attorney, Agent, or Firm* — Su Kyung Suh; Andrew W. Custer

(57) ABSTRACT

The invention provides expression vectors for expressing recombinant proteins (e.g., biologics) in mammalian cells. Also provided are host cells comprising the expression vectors, methods of producing the recombinant proteins, and methods of propagating the expression vectors.

12 Claims, 8 Drawing Sheets

Specification includes a Sequence Listing.

(52) U.S. Cl.
CPC ...... *C12N 2510/02* (2013.01); *C12N 2800/90* (2013.01); *C12N 2820/55* (2013.01); *C12N 2830/40* (2013.01); *C12N 2840/203* (2013.01)

(58) Field of Classification Search
CPC .. C12N 2840/203; C12N 15/70; C12N 15/63; C07K 16/06; C07K 2317/14
See application file for complete search history.

(56) References Cited

U.S. PATENT DOCUMENTS

| | | | | |
|---|---|---|---|---|
| 9,752,159 | B2 | 9/2017 | Krishnan et al. | |
| 2003/0082735 | A1* | 5/2003 | McGrew | C12N 15/1055 530/391.1 |
| 2006/0141577 | A1 | 6/2006 | Otte et al. | |
| 2006/0212949 | A1* | 9/2006 | Alphey | C12N 15/85 800/13 |
| 2009/0042297 | A1 | 2/2009 | George, Jr. et al. | |
| 2011/0014624 | A1 | 1/2011 | McCarthy et al. | |
| 2012/0301919 | A1 | 11/2012 | Yang et al. | |
| 2014/0134719 | A1* | 5/2014 | Deshpande | C07K 16/22 435/327 |
| 2014/0227786 | A1 | 8/2014 | Stitz | |
| 2018/0163230 | A1 | 6/2018 | Bublot et al. | |
| 2019/0055580 | A1* | 2/2019 | McGrew | C12Y 302/01023 |

FOREIGN PATENT DOCUMENTS

| | | | | |
|---|---|---|---|---|
| EP | 2733202 | A1 | 5/2014 | |
| EP | 3101134 | A1 | 12/2016 | |
| KR | 20030086429 | A | 11/2003 | |
| WO | 1997025420 | A1 | 7/1997 | |
| WO | 2013092743 | A2 | 6/2013 | |
| WO | 2015016786 | A1 | 2/2015 | |
| WO | 2015021077 | A1 | 2/2015 | |
| WO | 2016003368 | A1 | 1/2016 | |
| WO | 2016074016 | A1 | 5/2016 | |
| WO | WO-2017081082 | A2 * | 5/2017 | A61K 39/12 |
| WO | 2017106795 | A1 | 6/2017 | |
| WO | 2018006880 | A1 | 1/2018 | |
| WO | 2018161017 | A1 | 9/2018 | |

OTHER PUBLICATIONS

PGEM vector map, Author: Promega, 1999. (Year: 1999).*
X65308.2, pGEM vector sequence deposited in Genbank, Author: Promega, 1999. (Year: 1999).*
Moritz (Sci Rep 5, 16952, 2015) (Year: 2015).*
Lonza (Retrieved from the internet Sep. 19, 2024 <https://dam.lonza.com/dmm3bwsv3/assetstream.aspx?assetid=12674&mediaformatid=10061&destinationid=10016>). (Year: 1992).*
Aldrich, Teri L. et al., Improved bicistronic mammalian expression vectors using expression augmenting sequence element (EASE), Cytotechnology, 1998, 9-17, 28.
Berger, Shelley L. et al., An operational definition of epigenetics, Genes & Development, 2009, 781-783, 23.
Birch, John R. et al., Antibody production, Advanced Drug Delivery Reviews, 2006, 671-685, 58.
Bire, Solenne et al., Optimization of the piggyBac Transposon Using mRNA and Insulators: Toward a More Reliable Gene Delivery System, PLoS One, 2013, 1-10, 8(12): e82559.
Bochkov, Yury A. et al., Translational efficiency of EMCV IRES in bicistronic vectors is dependent upon IRES sequence and gene location, BioTechniques, 2006, 283-292, 41.
Carswell, Susan et al., Efficiency of Utilization of the Simian Virus 40 Late Polyadenylation Site: Effects of Upstream Sequences, Molecular and Cellular Biology, 1989, 4248-4258, 9(10).
Cary, Lynne Csiszar, et al., Transposon Mutagenesis of Baculoviruses: Analysis of Trichoplusia ni Transposon IFP2 Insertions within the FP-Locus of Nuclear Polyhedrosis Viruses, Virology, 1989, 156-169, 172.
Chung, Jay H. et al., A 5' Element of the Chicken Beta-Globin Domain Serves as an Insulator in Human Erythroid Cells and Protects against Position Effect in *Drosophila*, Cell, 1993, 505-514, 74(3).
Chung, Jay H. et al., Characterization of the chicken beta-globin insulator, PNAS USA, 1997, 575-580, 94.
Clackson et al., Making Antibody Fragments Using Phage Display Libraries, Nature, 1991, pp. 624-628, vol. 352.
Clontech Laboratories Inc. pIRESneo3 Vector Information. May 20, 2008. Protocol No. PT2645-5. Version No. PR852532. Accessed Dec. 31, 2019. https://www.takarabio.com/assets/documents/Vector Documents/PT3645-5.pdf. first page, first-second paragraphs; first page, figure; second page, first paragraph; second page, location of features; second page, propagation in *E. coli*.
Dillon, Niall et al., Transcriptional regulation of multigene loci: multilevel control, Trends Genet., 1993, 134-137, 9.
Duke, Gregory M. et al., Sequence and Structural Elements That Contribute to Efficient Encephalomyocarditis Virus RNA Translation, Journal of Virology, 1992, 1602-1609, 66(3).
Fiers, W. et al., Complete nucleotide sequence of SV40 DNA, Nature, 1978, 113-120, 273.
Gasser, S.M. et al., A glimpse at chromosomal order, Trends Genet., 1987, 16-22, 3.
GenBank EF467048.1, (3 pages).
GenBank LC417349.1, (2 pages.
GenBank X17403.1 (89 pages).
GenBank: AF193761.1 (4 pages).
GenBank: AH001475 (2 pages).
GenBank: J02400.1 (17 pages).
GenBank: J04364.2 (2 pages).
GenBank: M81861.1, (3 pages).
GenBank: U78775.2 (2 pages).
Grosveld, Frank et al., Position-Independent, High-Level Expression of the Human Beta-Globin Gene in Transgenic Mice, Cell, 1987, 975-985, 51.
Hartzell, Stephen W. et al., Mapping of the late promoter of simian virus 40, PNAS USA, 1984, 23-27, 81.
Jang, Sung K. et al., Cap-independent translation of encephalomyocarditis virus RNA: structural elements of the internal ribosomal entry site and involvement of a cellular 57-kD RNA-binding protein, Genes & Development, 1990, 1560-1572, 4(9).
Kaufman, Randal J. et al., Improved vectors for stable expression of foreign genes in mammalian cells by use of the untranslated leader sequence from EMC virus, Nucleic Acids Research, 1991, 4485-4490, 19.
Kaufman, Randal J., Identification of the components necessary for adenovirus translational control and their utilization in cDNA expression vectors, PNAS USA, 1985, 689-693, 82.
Kellum, Rebecca et al., A Position-Effect Assay for Boundaries of Higher Order Chromosomal Domains, Cell, 1991, 941-950, 64.
Kohler et al., Continuous Cultures of Fused Cells Secreting Antibody of Predefined Specificity, Nature, 1975, pp. 495-497, vol. 256.
Ludwig, Dale L., Mammalian Expression Cassette Engineering for High-Level Protein Production, BioProcess International, 2006, S14-S23, 4.
Marks et al., By passing Immunization, J. Mol. Biol., 1991, pp. 581-597, 222.
McBratney, Susan et al., Internal initiation of translation, Current Opinion in Cell Biology, 1993, 961-965, 5.
Phi-Van, Loc et al., The Chicken Lysozyme 5' Matrix Attachment Region Increases Transcription from a Heterologous Promoter in Heterologous Cells and Dampens Position Effects on the Expression of Transfected Genes, Molecular and Cellular Biology, 1980, 2302-2307, 10.
Presta, Leonard G. et al., Selection, design, and engineering of therapeutic antibodies, J. Allergy Clin. Immunol., 2005, 731-736, 116(4).
Schuler, A., Development of a novel expression system for the production of recombinant proteins in Chinese hamster ovary cells based on the selection with a metabolic enzyme, Technischen Universitat Carolo-Wilhelmina, 2013, 1-98, Dissertation.

(56) References Cited

OTHER PUBLICATIONS

Thein, S.L. et al., Molecular basis for dominantly inherited inclusion body beta-thalassemia, PNAS USA, 1990, 3924-3928, 87.
Wurm, Flurian M. et al., Production of recombinant protein therapeutics in cultivated mammalian cells, Nature Biotechnology, 2004, 1393-1398, 22.
Fakhro, Samah, Analysis of S/MAR vectors for gene therapy in muscle, University of London, 2011, 1-336, N/A.
Li, Qin et al., Effect of β-globin MAR characteristic elements on transgene expression, Molecular Medicine Reports, 2013, 1871-1874, 7.
Sharma, Nynne et al., The Impact of cHS4 Insulators on DNA Transposon Vector Mobilization and Silencing in Retinal Pigment Epithelium Cells, PLoS One, 2012, 1-12, 10:e48421.
Author names: Nynne Sharma, Anne Kruse Hollensen, Rasmus O. Bak, Nicklas Heine Staunstrup, Lisbeth Dahl Schrøder, and Jacob Giehm Mikkelsen, Title: The Impact of cHS4 Insulators on DNA Transposon Vector Mobilization and Silencing in Retinal Pigment Epithelium Cells, pages being submitted: 1-12, publication date: Oct. 26, 2012, publisher detalls: PLoS One, vol. 7, Issue No. 10, and place of publication: Retrieved from internet: https://journals.plos.org/plosone/article?id=10.1371/journal.pone.0048421 on Mar. 25, 2022.
Author name: Samah Fakhro, Title: Analysis of S/MAR vectors for gene therapy in muscle, pages being submitted: 1-336, publication date: Apr. 2011, publisher details: Diss. Royal Holloway, University of London, PhD Thesis, and place and evidence of publication: Retrieved from internet: https://ethos.bl.uk/OrderDetails.do?uin=uk.bl.ethos.549574 and https://core.ac.uk/download/pdf/78863834.pdf on Mar. 25, 2022.
Author names: Qin LI, Welhua Dong, Tianyun Wang, Zhonghe Liu, Fang Wang, Xiaoyin Wang, Chunpeng Zhao, Junhe Zhang, and Li Wang, Title: Effect of globin MAR characteristic elements on transgene expression, pages being submitted: 1871-1874, publication date: Apr. 10, 2013, publisher details: Molecular Medicine Reports, vol. 7, Issue No. 6, and place of publication: Retrieved from internet: https://www.spandidospublications.com/10.3892/mmr.2013.1424?text=fulltext# on Mar. 25, 2022.

* cited by examiner

```
                    SEQUENCE LISTING

<160> NUMBER OF SEQ ID NOS: 29

<210> SEQ ID NO 1
<211> LENGTH: 569
<212> TYPE: DNA
<213> ORGANISM: Artificial Sequence
<220> FEATURE:
<223> OTHER INFORMATION: IRES-1

<400> SEQUENCE: 1

cccctaacgt tactggccga agccgcttgg aataaggccg gtgtgcgttt gtctatatgt     60

tattttccac catattgccg tcttttggca atgtgagggc ccggaaacct ggccctgtct    120

tcttgacgag cattcctagg ggtctttccc ctctcgccaa aggaatgcaa ggtctgttga    180

atgtcgtgaa ggaagcagtt cctctggaag cttcttgaag acaaacaacg tctgtagcga    240

ccctttgcag gcagcggaac cccccacctg gcgacaggtg cctctgcggc caaaagccac    300

gtgtataaga tacacctgca aaggcggcac aaccccagtg ccacgttgtg agttggatag    360

ttgtggaaag agtcaaatgg ctctcctcaa gcgtattcaa caaggggctg aaggatgccc    420

agaaggtacc ccattgtatg ggatctgatc tggggcctcg gtgcacatgc tttacatgtg    480

tttagtcgag gttaaaaaac gtctaggccc cccgaaccac ggggacgtgg ttttcctttg    540

aaaaacacga tgataatatg gccacaacc                                      569


<210> SEQ ID NO 2
<211> LENGTH: 556
<212> TYPE: DNA
<213> ORGANISM: Artificial Sequence
<220> FEATURE:
<223> OTHER INFORMATION: IRES-2

<400> SEQUENCE: 2

cccctaacgt tactggccga agccgcttgg aataaggccg gtgtgcgttt gtctatatgt     60

tattttccac catattgccg tcttttggca atgtgagggc ccggaaacct ggccctgtct    120

tcttgacgag cattcctagg ggtctttccc ctctcgccaa aggaatgcaa ggtctgttga    180

atgtcgtgaa ggaagcagtt cctctggaag cttcttgaag acaaacaacg tctgtagcga    240

ccctttgcag gcagcggaac cccccacctg gcgacaggtg cctctgcggc caaaagccac    300

gtgtataaga tacacctgca aaggcggcac aaccccagtg ccacgttgtg agttggatag    360

ttgtggaaag agtcaaatgg ctctcctcaa gcgtattcaa caaggggctg aaggatgccc    420

agaaggtacc ccattgtatg ggatctgatc tggggcctcg gtgcacatgc tttacatgtg    480
```

```
tttagtcgag gttaaaaaac gtctaggccc cccgaaccac ggggacgtgg ttttcctttg    540

aaaaacacga tgataa                                                    556


<210> SEQ ID NO 3
<211> LENGTH: 549
<212> TYPE: DNA
<213> ORGANISM: Artificial Sequence
<220> FEATURE:
<223> OTHER INFORMATION: IRES-3

<400> SEQUENCE: 3

cccctaacgt tactggccga agccgcttgg aataaggccg gtgtgcgttt gtctatatgt     60

tattttccac catattgccg tcttttggca atgtgagggc ccggaaacct ggccctgtct    120

tcttgacgag cattcctagg ggtctttccc ctctcgccaa aggaatgcaa ggtctgttga    180

atgtcgtgaa ggaagcagtt cctctggaag cttcttgaag acaaacaacg tctgtagcga    240

ccctttgcag gcagcggaac cccccacctg gcgacaggtg cctctgcggc caaaagccac    300

gtgtataaga tacacctgca aaggcggcac aaccccagtg ccacgttgtg agttggatag    360

ttgtggaaag agtcaaatgg ctctcctcaa gcgtattcaa caaggggctg aaggatgccc    420

agaaggtacc ccattgtatg ggatctgatc tggggcctcg gtgcacatgc tttacatgtg    480

tttagtcgag gttaaaaaac gtctaggccc cccgaaccac ggggacgtgg ttttcctttg    540

aaaaacacg                                                            549


<210> SEQ ID NO 4
<211> LENGTH: 6215
<212> TYPE: DNA
<213> ORGANISM: Artificial Sequence
<220> FEATURE:
<223> OTHER INFORMATION: pCLD116

<400> SEQUENCE: 4

ccaatgatct taagttaacc ctagaaagat aatcatattg tgacgtacgt taaagataat     60

catgcgtaaa attgacgcat gtgttttatc ggtctgtata tcgaggttta tttattaatt    120

tgaatagata ttaagtttta ttatatttac acttacatac taataataaa ttcaacaaac    180

aatttattta tgtttattta tttattaaaa aaaaacaaaa actcaaaatt tcttctataa    240

agtaacaaaa cttttatcga atttgcagcc cgggactagc tagagggaca gccccccccc    300

aaagccccca gggatgtaat tacgtccctc ccccgctagg gggcagcagc gagccgcccg    360

gggctccgct ccggtccggc gctccccccg catccccgag ccggcagcgt gcggggacag    420

cccgggcacg gggaaggtgg cacgggatcg ctttcctctg aacgcttctc gctgctcttt    480

gagcctgcag acacctgggg ggatacgggg aaaacttaag atccgaccgg tgctgtggaa    540

tgtgtgtcag ttagggtgtg gaaagtcccc aggctcccca gcaggcagaa gtatgcaaag    600

catgcatctc aattagtcag caaccaggtg tggaaagtcc ccaggctccc cagcaggcag    660

aagtatgcaa agcatgcatc tcaattagtc agcaaccata gtcccgcccc taactccgcc    720

catcccgccc ctaactccgc ccagttccgc ccattctccg ctccatcgtt cagattttac    780

cacatttgta gaggttttac ttgctttaaa aaacctccca cacctccccc tgaacctgaa    840

acataaaatg aatgcaattg ttgttgttaa cttgtttatt gcagcttata atggttacaa    900

ataaagcaat agcatcacaa atttcacaaa taaagcattt ttttcactgc attctagttg    960

tggtttgtcc aaactcatca atgtatctta tcatgtctgc tcgaagcggc cggccgcccc   1020
```

-continued gactctagat tagtttttgt attggaaggg ctcgtcgcca gtctcattga gaaggcatgt 1080
gcggacgatg gcttctgtca ctgcaaaggg gtcacaattg gcagaggggc ggcggtcttc 1140
aaagtaacct ttcttctcct ggccgacagt ccggggaatg cggatgctgg cactgcgatt 1200
ggcgacacca gcagaaaagt cgttgatgtt ggacgtttcg tggaacccag tcagacgacg 1260
ggcattgtcc aggcccccct tgggatcgta ggctcgaatg tggtaccggt gccgcttgct 1320
tagtttctcg atggcctcct cgatgtgctt cagaccattc tcctcccgca tggccttggt 1380
gctaaagttg gtatggcagc ctgcaccatt ccagttccca ggaatgggct tggggtcaaa 1440
ggttgctatt accccaaagt cttcacatac tcgatgcaag atgaaacggg ccacccagag 1500
atgatctccc atgcggattc cttcacaggg tcctatttgg aactcccact gggcaggcat 1560
gacctcagca tttgttcctg taatcttgac cccagcatac aagcaggcgc ggtagtgagc 1620
ctccacgata tccctgccat aggctttgtc tgcgcccaca ccacagtaat acggaccttg 1680
gggcccagga aagccattgg aaggccaacc aaaagggtgc ccatctgttc ccatcagagt 1740
atactcctgt tccattccaa accaggggtg ctggttgctc accatgtcca ttatccgttt 1800
acacgagtgc cttaaattgg tctctgcagg cttccggttg tacttgaaaa cttcacagaa 1860
caccagcttg ttgggatctc tgcggaaggg gtcccgaaac atggcaacag ggctgagata 1920
catgtcactg ttggagccct cagactgaaa ggtactagag ccatcaaaat tccactcagg 1980
taactcttct acacacttgg gctcacagtc cagggtgcgg gttttgcagc gcagtccttc 2040
tccagtacca tcaacccaga tatacatggc ttggactttc tcaccctggg gcaggcacaa 2100
gtacatttgc ttgatgtttt tgttcaagtg ggaacttgct gaggtggcca tggtggcggc 2160
tttgcaaaag cctaggcctc caaaaaagcc tcctcactac ttctggaata gctcagaggc 2220
cgaggcggcc tcggcctctg cataaataaa aaaaattagt cagcgatggg gcggagaatg 2280
ggcggaactg ggcggagtta ggggcgggat gggcggagtt aggggcggga ctatggttgc 2340
tgactaattg agatgcaatc actgacacac attccacagc tgcctcgcgc gtttcggtga 2400
tgacggtgaa aacctctgac acatgcagct cccggagacg gtcacagctt gtctgtaagc 2460
ggatgccggg agcagacaag cccgtcaggg cgcgtcagcg ggtgttggcg ggtgtcgggg 2520
cgcagccatg acccagtcac gtagcgatag cggagtgtat actggcttaa ctatgcggca 2580
tcagagcaga ttgtactgag cctcgagcga tgtacgggcc agatatacgc gttgacattg 2640
attattgact agttattaat agtaatcaat tacggggtca ttagttcata gcccatatat 2700
ggagttccgc gttacataac ttacggtaaa tggcccgcct ggctgaccgc ccaacgaccc 2760
ccgcccattg acgtcaataa tgacgtatgt tcccatagta acgccaatag ggactttcca 2820
ttgacgtcaa tgggtggact atttacggta aactgcccac ttggcagtac atcaagtgta 2880
tcatatgcca agtacgcccc ctattgacgt caatgacggt aaatggcccg cctggcatta 2940
tgcccagtac atgaccttat gggactttcc tacttggcag tacatctacg tattagtcat 3000
cgctattacc atggtgatgc ggttttggca gtacatcaat gggcgtggat agcggtttga 3060
ctcacgggga tttccaagtc tccaccccat tgacgtcaat gggagtttgt tttggcacca 3120
aaatcaacgg gactttccaa aatgtcgtaa caactccgcc ccattgacgc aaatgggcgg 3180
taggcgtgta cggtgggagg tctatataag cagagctctc tggctaacta gagaacccac 3240
tgcttactgg cttatcgaaa ttaatacgac tcactatagc aattgcacgt gtggccacag 3300
gtaagtttaa agctcaggtc gagaccgggc ctttgtccgg cgctcccttg gagcctacct 3360
agactcagcc ggctctccac gctttgcctg accctgcttg ctcaactcta cgtctttgtt 3420
tcgttttctg ttcctttctc tccacaggcg gatccgaatt ctgaagatct agatccccct 3480
cgctttcttg ctgtccaatt tctattaaag gttcctttgt tccctaagtc caactactaa 3540
actgggggat attatgaagg gccttgagca tctggattct gcctaataaa aaacatttat 3600
tttcattgca atgatgtatt taaattattt ctgaatattt tactaaaaag ggaatgtggg 3660
aggtcagtgc atttaaaaca taaagaaatg aagaggggga tcttcgcgaa tccatcgatg 3720
agggacagcc ccccccaaa gcccccaggg atgtaattac gtccctcccc cgctaggggg 3780
cagcagcgag ccgcccgggg ctccgctccg gtccggcgct ccccccgcat ccccgagccg 3840
gcagcgtgcg gggacagccc gggcacgggg aaggtggcac gggatcgctt tcctctgaac 3900
gcttctcgct gctctttgag cctgcagaca cctgggggga tacggggaaa atagacaccg 3960
cggtggagct ccagcttttg ttccctttag tgagggttaa ttagttctta atacgactca 4020
ctatagggcg aattggctac cgggccgccc atcgagggta tcataagctt atatctataa 4080
caagaaaata tatatataat aagttatcac gtaagtagaa catgaaataa caatataatt 4140
atcgtatgag ttaaatctta aaagtcacgt aaaagataat catgcgtcat tttgactcac 4200
gcggtcgtta tagttcaaaa tcagtgacac ttaccgcatt gacaagcacg cctcacggga 4260
gctccaagcg gcgactgaga tgtcctaaat gcacagcgac ggattcgcgc tatttagaaa 4320
gagagagcaa tatttcaaga atgcatgcgt caattttacg cagactatct ttctagggtt 4380
aaatcgatat cggaaagaac atgtgagcaa aaggccagca aaaggccagg aaccgtaaaa 4440
aggccgcgtt gctggcgttt ttccataggc tccgcccccc tgacgagcat cacaaaaatc 4500
gacgctcaag tcagaggtgg cgaaacccga caggactata aagataccag gcgtttcccc 4560
ctggaagctc cctcgtgcgc tctcctgttc cgaccctgcc gcttaccgga tacctgtccg 4620
cctttctccc ttcgggaagc gtggcgcttt ctcatagctc acgctgtagg tatctcagtt 4680
cggtgtaggt cgttcgctcc aagctgggct gtgtgcacga accccccgtt cagcccgacc 4740
gctgcgcctt atccggtaac tatcgtcttg agtccaaccc ggtaagacac gacttatcgc 4800
cactggcagc agccactggt aacaggatta gcagagcgag gtatgtaggc ggtgctacag 4860
agttcttgaa gtggtggcct aactacggct acactagaag aacagtattt ggtatctgcg 4920
ctctgctgaa gccagttacc ttcggaaaaa gagttggtag ctcttgatcc ggcaaacaaa 4980
ccaccgctgg tagcggtggt ttttttgttt gcaagcagca gattacgcgc agaaaaaaag 5040
gatctcaaga agatcctttg atcttttcta cggggtctga cgctcagtgg aacgaaaact 5100
cacgttaagg gattttggtc atgagattat caaaaaggat cttcacctag atccttttaa 5160
attaaaaatg aagttttaaa tcaatctaaa gtatatatga gtaaacttgg tctgacagtt 5220
accaatgctt aatcagtgag gcacctatct cagcgatctg tctatttcgt tcatccatag 5280
ttgcctgact ccccgtcgtg tagataacta cgatacggga gggcttacca tctggcccca 5340
gtgctgcaat gataccgcga gacccacgct caccggctcc agatttatca gcaataaacc 5400
agccagccgg aagggccgag cgcagaagtg gtcctgcaac tttatccgcc tccatccagt 5460
ctattaattg ttgccgggaa gctagagtaa gtagttcgcc agttaatagt ttgcgcaacg 5520
ttgttgccat tgctacaggc atcgtggtgt cacgctcgtc gtttggtatg gcttcattca 5580
gctccggttc ccaacgatca aggcgagtta catgatcccc catgttgtgc aaaaaagcgg 5640
ttagctcctt cggtcctccg atcgttgtca gaagtaagtt ggccgcagtg ttatcactca 5700
tggttatggc agcactgcat aattctctta ctgtcatgcc atccgtaaga tgcttttctg 5760

-continued

```
tgactggtga gtactcaacc aagtcattct gagaatagtg tatgcggcga ccgagttgct   5820

cttgcccggc gtcaatacgg gataataccg cgccacatag cagaacttta aaagtgctca   5880

tcattggaaa acgttcttcg gggcgaaaac tctcaaggat cttaccgctg ttgagatcca   5940

gttcgatgta acccactcgt gcacccaact gatcttcagc atcttttact ttcaccagcg   6000

tttctgggtg agcaaaaaca ggaaggcaaa atgccgcaaa aaagggaata agggcgacac   6060

ggaaatgttg aatactcata ctcttccttt ttcaatatta ttgaagcatt tatcagggtt   6120

attgtctcat gagcggatac atatttgaat gtatttagaa aaataaacaa ataggggttc   6180

cgcgcacatt tccccgaaaa gtgccacctg acgtc                              6215
```

<210> SEQ ID NO 5
<211> LENGTH: 9542
<212> TYPE: DNA
<213> ORGANISM: Artificial Sequence
<220> FEATURE:
<223> OTHER INFORMATION: pCLD21

<400> SEQUENCE: 5

```
ccttcccttc taccacaccc taattgtaat ccattttaat ttcctggtca cagtcctgtc     60

tctccttcca ttgtaccttg ccctttttcta aagagcgact gcaaagtatg tttgcgtagg    120

tgaggatcta aaactttatg aggtacgaac atcacagaat tactttgtaa tttcagttta    180

ttgtaggctt ggctttttgg ggagggttta cgtcttagac ctcttagtgc ttctttgttt    240

catggtgttc taacttcgaa gcatctctgt agctttaatg gattcctttt ctgaaagctt    300

tgctctcttt cttcccctc ggctttctct taggcaagag ggctaactgt aaagtaaggc    360

ttactgcctt gtgtttccaa atgtgtccga agaggaagtg tcttctgtga atcctgttat    420

gcatgaataa caggaaatag aaagaaattc actttcatta ttataaaagt aatatgttcg    480

tttaaaaaat tctaatgaag agctggagat gcaacccagg ggtagagcac acactcagca    540

tgcaggaggc cctgggtcca atcttggaat ctcctctcag ttaacctgat ctctagctga    600

ttagtagtga gtgcaagccc actttcctct tctgcctcat tgctcagtga taacagctgt    660

taaactttgt cttattctaa aactacctct gtgcaaatgc tagcacaata atatatatca    720

tatgcacatg atttttttt tatcttgaaa agtaagtcag tatagctaca aagttcactt    780

ggcattgtca acatttcaca ggcgtaatat tcctcctcta gtactgtcct cttcattctt    840

tgtgaccaag tttggagaga gtgcacaaat gccagggagg tttgtgggaa ggtttctcat    900

gttctggtaa ggcgagtaag aaaatagtct catgcaggtg aaatgagtgc tatgcagtat    960

atattatacc agagaacagc aaatgaccaa attcacactg aactagttca gtaaaattgg   1020

ctttgtcaaa gctttccttg cttaaaatgt aattccctgt catcctagtt ctggtctgga   1080

ttcttttcct ggagtcttga cttccagatt ccctgtggac ttttgtttga gtttcaagct   1140

tttgaaatat agaaacctat ctaacttaac aaacttggga gagaaaagac tccagaacaa   1200

ctgaaaacag accaggctaa atgaatagac tttattcctc tcttcttacc tgcagttttc   1260

agatatgcag agttggagcg gatcttagag gttgattcat tcatgcctga agaaaacaca   1320

ttttatagac cctgtgccca agttcgtggt ggacatcacc ctttatttac taattgcact   1380

acataacagg cattttagaa gactgctcca gtcagagacc ccgccttaga ggaatctgta   1440

aaccctgaac tcctatcact catgagcact agttatgttt ggaatgccgt attaaaacaa   1500

aagttacatt tctaaactta aaattttcta gcacagagac agtgggagta gctaactttg   1560

atagacattt ttctactaaa agtctttcta agtacataat cttctgtaag ttggaaaaca   1620
```

-continued

```
gcaaaataga acgtctccta cgtagttaat ctttttgcat aatttgcaca tgtaggagtt   1680
attagtatac gggtaagttt tcactttttc ccccaactgg agtgtcttgt ggctgggttt   1740
gaaaaaggga acgggaggcc gctggagggg attggtaaat gagataaaac accactcatt   1800
caactcagtg actcagcatt taaattttcc ataaaaggat taaaggaaaa ttaaacaaat   1860
tcttaaagcc aagactctgg agaaacttgt tggtgtgctt tagttttcac tgttatgact   1920
catgaattta tgcataaatt agtacattta taaaaacata gcctttttag agttttctgt   1980
ttggctaaag tgccattgtt agcatttgga attacctttt tatgtcttat atttttttcca   2040
aataaaaata aatgtttctg ctgtcttact actgaaacta cgttgtgagc actttaaatt   2100
tctcaaagca gtttcgcctg ttatacttgg cgcttagtca tcgtcgtaca caacaggacc   2160
tgattaagaa ggctgtgctg cctctaagcc gggctagatt gtagccacta gcaaccaggc   2220
tgcaataatt tccctttgat gacatcatcc actgtggaag aacccagttg cttcagccag   2280
tcgaactata cagttccaac ctcatcaaat atggcatctc ccttgcctgc tatagcaggg   2340
ggaggaaaaa atgccaccat ctttttaatc tagcaagctt ctcttttctt catctttttt   2400
tttttctttt aaaaaaattc tgatcatgga tgcttcttcc gatccctatt tgccttatga   2460
cgggggagga gacaatatcc ccttgaggga attacataaa agaggtaaga gcatcccctt   2520
gctctgaatc ctctgttggt tgttgtgcat gcggctgggc ggttctgggg acaggctgtc   2580
tgttgtcctc ttgctgcaat gtgctgctta gttgccctgc cttgttgctg tgggagaatg   2640
cgaccttccc agcagggctg gccctccctg attgtttgct ctgtgcagat tagccctgct   2700
tcagatcaca tagggctgca gactccatct tctgtgtgaa aatgctttcg gtttgattgc   2760
agaaataagc tgcctttaca gccagctaaa gtcctggtgg ttggttggca cctgcaaagt   2820
agtatttttg tacctctgga aacttatatt ttctttacac agcaatatca agtgccggta   2880
tgccattctg ttttggctgc tgccaattac catgtagact ttgcaccaca gagtaatagt   2940
aaaagctcct agctgcattt tataacattt aaaaatagca ggaaagaaga attatttttg   3000
atttaacatg tttttgtcat ttaacgtctt aactgattga catactatat tgtctgtctc   3060
gtgggtatct tgtacaactt gataggataa agcaatttag tttttttttt ttttttttaaa   3120
tacatccaga atgtaagtcg tcagtagttt tcgaacagat aagtaatggt gttaatcttt   3180
tggcaggctt tgccttggtc tccttaaagc taattaggtg ttacttaatt aaactgctct   3240
tttgctcatt ttcttaaatt attttttttaa aagatagttg gcatttgctg ttctagaaat   3300
aaacttcaag aaacattctt tagccagatg acttcatgta tgagccatgt tagtttgaat   3360
tatttgcttg gtgttataaa ctttatggtt taataccaac ttttattatg tttacaaggt   3420
aaataaggaa aatttcaagt acattttgta tcctgagaac aaatttaagt tccatagaat   3480
ttaggaatta caatgtattc aacagatact tacttgtcat actgtgcctg caaaacaata   3540
attagactct gaacaggtgc aacaattttc tgtagaatta gacaagtctt cttttggcag   3600
gtgttactaa gtaggccatt tcccaaggaa cagggaattt gccaggcttt tgtggtggag   3660
agaatagaat gaataaatgc tgtggggagt aaagagcttg tcagaagatg attagttctg   3720
tggcaccaaa accaagagat cagttttcct gtgagaagta aaggaagcat tgtagaaaaa   3780
tagatgtgtt gaagtctacc ggtggagttc cgcgttacat aacttacggt aaatggcccg   3840
cctggctgac cgcccaacga cccccgccca ttgacgtcaa taatgacgta tgttcccata   3900
gtaacgccaa tagggacttt ccattgacgt caatgggtgg agtatttacg gtaaactgcc   3960
```

```
cacttggcag tacatcaagt gtatcatatg ccaagtacgc cccctattga cgtcaatgac   4020
ggtaaatggc ccgcctggca ttatgcccag tacatgacct tatgggactt tcctacttgg   4080
cagtacatct acgtattagt catcgctatt accattgtga tgcggttttg gcagtacatc   4140
aatgggcgtg gatagcggtt tgactcacgg ggatttccaa gtctccaccc cattgacgtc   4200
aatgggagtt tgttttggca ccaaaatcaa cgggactttc caaaatgtcg taacaactcc   4260
gccccattga cgcaaatggg cggtaggcgt gtacggtggg aggtctatat aagcagagct   4320
cgtttagtga accgtcagat ctacctcttc cgcatcgctg tctgcgaggg ccagctgttg   4380
gggtgagtac tccctctcaa aagcgggcat gacttctgcg ctaagattgt cagtttccaa   4440
aaacgaggag gatttgatat tcacctggcc cgcggtgatg cctttgaggg tggccgcgtc   4500
catctggtca gaaaagacaa tctttttgtt gtcaagcttc cttgatgatg tcatacttat   4560
cctgtccctt tttttccac agctcgcggt tgaggacaaa ctcttcgcgg tctttccagt   4620
actcttggat cggaaacccg tcggcctccg aacggtactc cgccaccgag ggacctgagc   4680
gagtccgcat cgaccggatc ggaaaacctc ggatccgaat tcatagataa ctgatccagt   4740
gcccctaacg ttactggccg aagccgcttg gaataaggcc ggtgtgcgtt tgtctatatg   4800
ttattttcca ccatattgcc gtcttttggc aatgtgaggg cccggaaacc tggccctgtc   4860
ttcttgacga gcattcctag gggtctttcc cctctcgcca aaggaatgca aggtctgttg   4920
aatgtcgtga aggaagcagt tcctctggaa gcttcttgaa gacaaacaac gtctgtagcg   4980
accctttgca ggcagcggaa ccccccacct ggcgacaggt gcctctgcgg ccaaaagcca   5040
cgtgtataag atacacctgc aaaggcggca caaccccagt gccacgttgt gagttggata   5100
gttgtggaaa gagtcaaatg gctctcctca agcgtattca acaaggggct gaaggatgcc   5160
cagaaggtac cccattgtat gggatctgat ctggggcctc ggtgcacatg ctttacatgt   5220
gtttagtcga ggttaaaaaa cgtctaggcc ccccgaacca cggggacgtg gttttccttt   5280
gaaaaacacg atgataatat ggccacaacc atggccacct cagcaagttc ccacttgaac   5340
aaaaacatca agcaaatgta cttgtgcctg ccccagggtg agaaagtcca agccatgtat   5400
atctgggttg atggtactgg agaaggactg cgctgcaaaa cccgcaccct ggactgtgag   5460
cccaagtgtg tagaagagtt acctgagtgg aattttgatg gctctagtac ctttcagtct   5520
gagggctcca acagtgacat gtatctcagc cctgttgcca tgtttcggga ccccttccgc   5580
agagatccca acaagctggt gttctgtgaa gttttcaagt acaaccggaa gcctgcagag   5640
accaatttaa ggcactcgtg taaacggata atggacatgg tgagcaacca gcacccctgg   5700
tttggaatgg aacaggagta tactctgatg ggaacagatg ggcacccttt tggttggcct   5760
tccaatggct ttcctgggcc ccaaggtccg tattactgtg gtgtgggcgc agacaaagcc   5820
tatggcaggg atatcgtgga ggctcactac cgcgcctgct tgtatgctgg ggtcaagatt   5880
acaggaacaa atgctgaggt catgcctgcc cagtgggagt tccaaatagg accctgtgaa   5940
ggaatccgca tgggagatca tctctgggtg gcccgtttca tcttgcatcg agtatgtgaa   6000
gactttgggg taatagcaac ctttgacccc aagcccattc ctgggaactg gaatggtgca   6060
ggctgccata ccaactttag caccaaggcc atgcgggagg agaatggtct gaagcacatc   6120
gaggaggcca tcgagaaact aagcaagcgg caccggtacc acattcgagc ctacgatccc   6180
aaggggggcc tggacaatgc ccgtcgtctg actgggttcc acgaaacgtc caacatcaac   6240
gacttttctg ctggtgtcgc caatcgcagt gccagcatcc gcattccccg gactgtcggc   6300
caggagaaga aaggttactt tgaagaccgc cgcccctctg ccaattgtga cccctttgca   6360
```

-continued

```
gtgacagaag ccatcgtccg cacatgcctt ctcaatgaga ctggcgacga gcccttccaa   6420
tacaaaaact aatctagatc cccctcgctt tcttgctgtc caatttctat taaaggttcc   6480
tttgttccct aagtccaact actaaactgg gggatattat gaagggcctt gagcatctgg   6540
attctgccta ataaaaaaca tttattttca ttgcaatgat gtatttaaat tatttctgaa   6600
tattttacta aaaagggaat gtgggaggtc agtgcattta aaacataaag aaatgaagag   6660
ggggatcttc gcgacctgca ggtctcccta tagtgagtcg tattaatttc gataagccag   6720
ctgcattaat gaatcggcca acgcgcgggg agaggcggtt tgcgtattgg gcgctcttcc   6780
gcttcctcgc tcactgactc gctgcgctcg gtcgttcggc tgcggcgagc ggtatcagct   6840
cactcaaagg cggtaatacg gttatccaca gaatcagggg ataacgcagg aaagaacatg   6900
tgagcaaaag gccagcaaaa ggccaggaac cgtaaaaagg ccgcgttgct ggcgtttttc   6960
cataggctcc gcccccctga cgagcatcac aaaaatcgac gctcaagtca gaggtggcga   7020
aacccgacag gactataaag ataccaggcg tttccccctg gaagctccct cgtgcgctct   7080
cctgttccga ccctgccgct taccggatac ctgtccgcct ttctcccttc gggaagcgtg   7140
gcgctttctc atagctcacg ctgtaggtat ctcagttcgg tgtaggtcgt tcgctccaag   7200
ctgggctgtg tgcacgaacc ccccgttcag cccgaccgct gcgccttatc cggtaactat   7260
cgtcttgagt ccaacccggt aagacacgac ttatcgccac tggcagcagc cactggtaac   7320
aggattagca gagcgaggta tgtaggcggt gctacagagt tcttgaagtg gtggcctaac   7380
tacggctaca ctagaaggac agtatttggt atctgcgctc tgctgaagcc agttaccttc   7440
ggaaaaagag ttggtagctc ttgatccggc aaacaaacca ccgctggtag cggtggtttt   7500
tttgtttgca agcagcagat tacgcgcaga aaaaaaggat ctcaagaaga tcctttgatc   7560
ttttctacgg ggtctgacgc tcagtggaac gaaaactcac gttaagggat tttggtcatg   7620
agattatcaa aaaggatctt cacctagatc cttttaaatt aaaaatgaag ttttaaatca   7680
atctaaagta tatatgagta aacttggtct gacagttacc aatgcttaat cagtgaggca   7740
cctatctcag cgatctgtct atttcgttca tccatagttg cctgactccc cgtcgtgtag   7800
ataactacga tacgggaggg cttaccatct ggccccagtg ctgcaatgat accgcgagac   7860
ccacgctcac cggctccaga tttatcagca ataaaccagc cagccggaag ggccgagcgc   7920
agaagtggtc ctgcaacttt atccgcctcc atccagtcta ttaattgttg ccgggaagct   7980
agagtaagta gttcgccagt taatagtttg cgcaacgttg ttgccattgc tacaggcatc   8040
gtggtgtcac gctcgtcgtt tggtatggct tcattcagct ccggttccca acgatcaagg   8100
cgagttacat gatcccccat gttgtgcaaa aaagcggtta gctccttcgg tcctccgatc   8160
gttgtcagaa gtaagttggc cgcagtgtta tcactcatgg ttatggcagc actgcataat   8220
tctcttactg tcatgccatc cgtaagatgc ttttctgtga ctggtgagta ctcaaccaag   8280
tcattctgag aatagtgtat gcggcgaccg agttgctctt gcccggcgtc aatacgggat   8340
aataccgcgc cacatagcag aactttaaaa gtgctcatca ttggaaaacg ttcttcgggg   8400
cgaaaactct caaggatctt accgctgttg agatccagtt cgatgtaacc cactcgtgca   8460
cccaactgat cttcagcatc ttttactttc accagcgttt ctgggtgagc aaaaacagga   8520
aggcaaaatg ccgcaaaaaa gggaataagg gcgacacgga aatgttgaat actcatactc   8580
ttcctttttc aatattattg aagcatttat cagggttatt gtctcatgag cggatacata   8640
tttgaatgta tttagaaaaa taaacaaata ggggttccgc gcacatttcc ccgaaaagtg   8700
```

ccacctgacg tctaagaaac cattattatc atgacattaa cctataaaaa taggcgtatc 8760
acgaggccct ttcgtctcgc gcgtttcggt gatgacggtg aaaacctctg acacatgcag 8820
ctcccggaga cggtcacagc ttgtctgtaa gcggatgccg ggagcagaca agcccgtcag 8880
ggcgcgtcag cgggtgttgg cgggtgtcgg ggctggctta actatgcggc atcagagcag 8940
attgtactga gagtgcacca tatcgacgct ctcccttatg cgactcctgc attaggaagc 9000
agcccagtag taggttgagg ccgttgagca ccgccgccgc aaggaatggt gcatgcaagg 9060
agatggcgcc caacagtccc ccggccacgg ggcctgccac catacccacg ccgaaacaag 9120
cgctcatgag cccgaagtgg cgagcccgat cttccccatc ggtgatgtcg gcgatatagg 9180
cgccagcaac cgcacctgtg gcgccggtga tgccggccac gatgcgtccg gcgtagagga 9240
tctggctagc gatgaccctg ctgattggtt cgctgaccat ttccggggtg cggaacggcg 9300
ttaccagaaa ctcagaaggt tcgtccaacc aaaccgactc tgacggcagt ttacgagaga 9360
gatgataggg tctgcttcag taagccagat gctacacaat taggcttgta catattgtcg 9420
ttagaacgcg gctacaatta atacataacc ttatgtatca tacacatacg atttaggtga 9480
cactatagaa tacacctgca ggacgcgtac tgagagcgct attctgaact tttcttttgt 9540
tc 9542

<210> SEQ ID NO 6
<211> LENGTH: 9522
<212> TYPE: DNA
<213> ORGANISM: Artificial Sequence
<220> FEATURE:
<223> OTHER INFORMATION: pCLD22

<400> SEQUENCE: 6
ccttcccttc taccacaccc taattgtaat ccattttaat ttcctggtca cagtcctgtc 60
tctccttcca ttgtaccttg cccttttcta aagagcgact gcaaagtatg tttgcgtagg 120
tgaggatcta aaactttatg aggtacgaac atcacagaat tactttgtaa tttcagttta 180
ttgtaggctt ggctttttgg ggagggttta cgtcttagac ctcttagtgc ttctttgttt 240
catggtgttc taacttcgaa gcatctctgt agctttaatg gattcctttt ctgaaagctt 300
tgctctcttt cttccccctc ggctttctct taggcaagag ggctaactgt aaagtaaggc 360
ttactgcctt gtgtttccaa atgtgtccga agaggaagtg tcttctgtga atcctgttat 420
gcatgaataa caggaaatag aaagaaattc actttcatta ttataaaagt aatatgttcg 480
tttaaaaaat tctaatgaag agctggagat gcaacccagg ggtagagcac acactcagca 540
tgcaggaggc cctgggtcca atcttggaat ctcctctcag ttaacctgat ctctagctga 600
ttagtagtga gtgcaagccc actttcctct tctgcctcat tgctcagtga taacagctgt 660
taaactttgt cttattctaa aactacctct gtgcaaatgc tagcacaata atatatatca 720
tatgcacatg attttttttt tatcttgaaa agtaagtcag tatagctaca aagttcactt 780
ggcattgtca acatttcaca ggcgtaatat tcctcctcta gtactgtcct cttcattctt 840
tgtgaccaag tttggagaga gtgcacaaat gccagggagg tttgtgggaa ggtttctcat 900
gttctggtaa ggcgagtaag aaaatagtct catgcaggtg aaatgagtgc tatgcagtat 960
atattatacc agagaacagc aaatgaccaa attcacactg aactagttca gtaaaattgg 1020
ctttgtcaaa gctttccttg cttaaaatgt aattccctgt catcctagtt ctggtctgga 1080
ttcttttcct ggagtcttga cttccagatt ccctgtggac ttttgtttga gtttcaagct 1140
tttgaaatat agaaacctat ctaacttaac aaacttggga gagaaaagac tccagaacaa 1200

-continued

```
ctgaaaacag accaggctaa atgaatagac tttattcctc tcttcttacc tgcagttttc   1260
agatatgcag agttggagcg gatcttagag gttgattcat tcatgcctga agaaaacaca   1320
ttttatagac cctgtgccca agttcgtggt ggacatcacc ctttatttac taattgcact   1380
acataacagg cattttagaa gactgctcca gtcagagacc ccgccttaga ggaatctgta   1440
aaccctgaac tcctatcact catgagcact agttatgttt ggaatgccgt attaaaacaa   1500
aagttacatt tctaaactta aaattttcta gcacagagac agtgggagta gctaactttg   1560
atagacattt ttctactaaa agtctttcta agtacataat cttctgtaag ttggaaaaca   1620
gcaaaataga acgtctccta cgtagttaat ctttttgcat aatttgcaca tgtaggagtt   1680
attagtatac gggtaagttt tcactttttc ccccaactgg agtgtcttgt ggctgggttt   1740
gaaaaaggga acgggaggcc gctggagggg attggtaaat gagataaaac accactcatt   1800
caactcagtg actcagcatt taaattttcc ataaaaggat taaaggaaaa ttaaacaaat   1860
tcttaaagcc aagactctgg agaaacttgt tggtgtgctt tagttttcac tgttatgact   1920
catgaattta tgcataaatt agtacattta taaaaacata gccttttttag agttttctgt   1980
ttggctaaag tgccattgtt agcatttgga attacctttt tatgtcttat atttttttcca   2040
aataaaaata aatgtttctg ctgtcttact actgaaacta cgttgtgagc actttaaatt   2100
tctcaaagca gtttcgcctg ttatacttgg cgcttagtca tcgtcgtaca caacaggacc   2160
tgattaagaa ggctgtgctg cctctaagcc gggctagatt gtagccacta gcaaccaggc   2220
tgcaataatt tccctttgat gacatcatcc actgtggaag aacccagttg cttcagccag   2280
tcgaactata cagttccaac ctcatcaaat atggcatctc ccttgcctgc tatagcaggg   2340
ggaggaaaaa atgccaccat ctttttaatc tagcaagctt ctcttttctt catctttttt   2400
tttttctttt aaaaaaattc tgatcatgga tgcttcttcc gatccctatt tgccttatga   2460
cgggggagga gacaatatcc ccttgaggga attacataaa agaggtaaga gcatcccctt   2520
gctctgaatc ctctgttggt tgttgtgcat gcggctgggc ggttctgggg acaggctgtc   2580
tgttgtcctc ttgctgcaat gtgctgctta gttgccctgc cttgttgctg tgggagaatg   2640
cgaccttccc agcagggctg gccctccctg attgtttgct ctgtgcagat tagccctgct   2700
tcagatcaca tagggctgca gactccatct tctgtgtgaa aatgctttcg gtttgattgc   2760
agaaataagc tgcctttaca gccagctaaa gtcctggtgg ttggttggca cctgcaaagt   2820
agtatttttg tacctctgga aacttatatt ttctttacac agcaatatca agtgccggta   2880
tgccattctg ttttggctgc tgccaattac catgtagact ttgcaccaca gagtaatagt   2940
aaaagctcct agctgcattt tataacattt aaaaatagca ggaaagaaga attatttttg   3000
atttaacatg tttttgtcat ttaacgtctt aactgattga catactatat tgtctgtctc   3060
gtgggtatct tgtacaactt gataggataa agcaatttag tttttttttt tttttttaaa   3120
tacatccaga atgtaagtcg tcagtagttt tcgaacagat aagtaatggt gttaatcttt   3180
tggcaggctt tgccttggtc tccttaaagc taattaggtg ttacttaatt aaactgctct   3240
tttgctcatt ttcttaaatt attttttttaa aagatagttg gcatttgctg ttctagaaat   3300
aaacttcaag aaacattctt tagccagatg acttcatgta tgagccatgt tagtttgaat   3360
tatttgcttg gtgttataaa ctttatggtt taataccaac ttttattatg tttacaaggt   3420
aaataaggaa aatttcaagt acattttgta tcctgagaac aaatttaagt tccatagaat   3480
ttaggaatta caatgtattc aacagatact tacttgtcat actgtgcctg caaaacaata   3540
```

-continued

```
attagactct gaacaggtgc aacaattttc tgtagaatta gacaagtctt cttttggcag   3600
gtgttactaa gtaggccatt tcccaaggaa cagggaattt gccaggcttt tgtggtggag   3660
agaatagaat gaataaatgc tgtggggagt aaagagcttg tcagaagatg attagttctg   3720
tggcaccaaa accaagagat cagttttcct gtgagaagta aaggaagcat tgtagaaaaa   3780
tagatgtgtt gaagtctacc ggtggagttc cgcgttacat aacttacggt aaatggcccg   3840
cctggctgac cgcccaacga cccccgccca ttgacgtcaa taatgacgta tgttcccata   3900
gtaacgccaa tagggacttt ccattgacgt caatgggtgg agtatttacg gtaaactgcc   3960
cacttggcag tacatcaagt gtatcatatg ccaagtacgc cccctattga cgtcaatgac   4020
ggtaaatggc ccgcctggca ttatgcccag tacatgacct tatgggactt tcctacttgg   4080
cagtacatct acgtattagt catcgctatt accattgtga tgcggttttg gcagtacatc   4140
aatgggcgtg gatagcggtt tgactcacgg ggatttccaa gtctccaccc cattgacgtc   4200
aatgggagtt tgttttggca ccaaaatcaa cgggactttc caaaatgtcg taacaactcc   4260
gccccattga cgcaaatggg cggtaggcgt gtacggtggg aggtctatat aagcagagct   4320
cgtttagtga accgtcagat ctacctcttc cgcatcgctg tctgcgaggg ccagctgttg   4380
gggtgagtac tccctctcaa aagcgggcat gacttctgcg ctaagattgt cagtttccaa   4440
aaacgaggag gatttgatat tcacctggcc cgcggtgatg cctttgaggg tggccgcgtc   4500
catctggtca gaaaagacaa tctttttgtt gtcaagcttc cttgatgatg tcatacttat   4560
cctgtccctt tttttccac agctcgcggt tgaggacaaa ctcttcgcgg tctttccagt   4620
actcttggat cggaaacccg tcggcctccg aacggtactc cgccaccgag ggacctgagc   4680
gagtccgcat cgaccggatc ggaaaacctc ggatccgaat tcatagataa ctgatccagt   4740
gcccctaacg ttactggccg aagccgcttg gaataaggcc ggtgtgcgtt tgtctatatg   4800
ttattttcca ccatattgcc gtcttttggc aatgtgaggg cccggaaacc tggccctgtc   4860
ttcttgacga gcattcctag gggtctttcc cctctcgcca aaggaatgca aggtctgttg   4920
aatgtcgtga aggaagcagt tcctctggaa gcttcttgaa gacaaacaac gtctgtagcg   4980
accctttgca ggcagcggaa ccccccacct ggcgacaggt gcctctgcgg ccaaaagcca   5040
cgtgtataag atacacctgc aaaggcggca caaccccagt gccacgttgt gagttggata   5100
gttgtggaaa gagtcaaatg gctctcctca agcgtattca acaaggggct gaaggatgcc   5160
cagaaggtac cccattgtat gggatctgat ctggggcctc ggtgcacatg ctttacatgt   5220
gtttagtcga ggttaaaaaa cgtctaggcc ccccgaacca cggggacgtg gttttccttt   5280
gaaaaacacg atggccacct cagcaagttc ccacttgaac aaaaacatca agcaaatgta   5340
cttgtgcctg ccccagggtg agaaagtcca agccatgtat atctgggttg atggtactgg   5400
agaaggactg cgctgcaaaa cccgcaccct ggactgtgag cccaagtgtg tagaagagtt   5460
acctgagtgg aattttgatg gctctagtac ctttcagtct gagggctcca acagtgacat   5520
gtatctcagc cctgttgcca tgtttcggga ccccttccgc agagatccca acaagctggt   5580
gttctgtgaa gttttcaagt acaaccggaa gcctgcagag accaatttaa ggcactcgtg   5640
taaacggata atggacatgg tgagcaacca gcacccctgg tttggaatgg aacaggagta   5700
tactctgatg ggaacagatg ggcacccttt tggttggcct tccaatggct ttcctgggcc   5760
ccaaggtccg tattactgtg gtgtgggcgc agacaaagcc tatggcaggg atatcgtgga   5820
ggctcactac cgcgcctgct tgtatgctgg ggtcaagatt acaggaacaa atgctgaggt   5880
catgcctgcc cagtgggagt tccaaatagg accctgtgaa ggaatccgca tgggagatca   5940
```

```
tctctgggtg gcccgtttca tcttgcatcg agtatgtgaa gactttgggg taatagcaac   6000
ctttgacccc aagcccattc ctgggaactg gaatggtgca ggctgccata ccaactttag   6060
caccaaggcc atgcgggagg agaatggtct gaagcacatc gaggaggcca tcgagaaact   6120
aagcaagcgg caccggtacc acattcgagc ctacgatccc aaggggggcc tggacaatgc   6180
ccgtcgtctg actgggttcc acgaaacgtc caacatcaac gacttttctg ctggtgtcgc   6240
caatcgcagt gccagcatcc gcattccccg gactgtcggc caggagaaga aaggttactt   6300
tgaagaccgc cgcccctctg ccaattgtga cccctttgca gtgacagaag ccatcgtccg   6360
cacatgcctt ctcaatgaga ctggcgacga gcccttccaa tacaaaaact aatctagatc   6420
cccctcgctt tcttgctgtc caatttctat taaaggttcc tttgttccct aagtccaact   6480
actaaactgg gggatattat gaagggcctt gagcatctgg attctgccta ataaaaaaca   6540
tttattttca ttgcaatgat gtatttaaat tatttctgaa tattttacta aaaagggaat   6600
gtgggaggtc agtgcattta aaacataaag aaatgaagag gggggatcttc gcgacctgca   6660
ggtctcccta tagtgagtcg tattaatttc gataagccag ctgcattaat gaatcggcca   6720
acgcgcgggg agaggcggtt tgcgtattgg gcgctcttcc gcttcctcgc tcactgactc   6780
gctgcgctcg gtcgttcggc tgcggcgagc ggtatcagct cactcaaagg cggtaatacg   6840
gttatccaca gaatcagggg ataacgcagg aaagaacatg tgagcaaaag gccagcaaaa   6900
ggccaggaac cgtaaaaagg ccgcgttgct ggcgtttttc cataggctcc gcccccctga   6960
cgagcatcac aaaaatcgac gctcaagtca gaggtggcga aacccgacag gactataaag   7020
ataccaggcg tttccccctg gaagctccct cgtgcgctct cctgttccga ccctgccgct   7080
taccggatac ctgtccgcct ttctcccttc gggaagcgtg gcgctttctc atagctcacg   7140
ctgtaggtat ctcagttcgg tgtaggtcgt tcgctccaag ctgggctgtg tgcacgaacc   7200
ccccgttcag cccgaccgct gcgccttatc cggtaactat cgtcttgagt ccaacccggt   7260
aagacacgac ttatcgccac tggcagcagc cactggtaac aggattagca gagcgaggta   7320
tgtaggcggt gctacagagt tcttgaagtg gtggcctaac tacggctaca ctagaaggac   7380
agtatttggt atctgcgctc tgctgaagcc agttaccttc ggaaaaagag ttggtagctc   7440
ttgatccggc aaacaaacca ccgctggtag cggtggtttt tttgtttgca agcagcagat   7500
tacgcgcaga aaaaaaggat ctcaagaaga tcctttgatc ttttctacgg ggtctgacgc   7560
tcagtggaac gaaaactcac gttaagggat tttggtcatg agattatcaa aaaggatctt   7620
cacctagatc cttttaaatt aaaaatgaag ttttaaatca atctaaagta tatatgagta   7680
aacttggtct gacagttacc aatgcttaat cagtgaggca cctatctcag cgatctgtct   7740
atttcgttca tccatagttg cctgactccc cgtcgtgtag ataactacga tacgggaggg   7800
cttaccatct ggccccagtg ctgcaatgat accgcgagac ccacgctcac cggctccaga   7860
tttatcagca ataaaccagc cagccggaag ggccgagcgc agaagtggtc ctgcaacttt   7920
atccgcctcc atccagtcta ttaattgttg ccgggaagct agagtaagta gttcgccagt   7980
taatagtttg cgcaacgttg ttgccattgc tacaggcatc gtggtgtcac gctcgtcgtt   8040
tggtatggct tcattcagct ccggttccca acgatcaagg cgagttacat gatcccccat   8100
gttgtgcaaa aaagcggtta gctccttcgg tcctccgatc gttgtcagaa gtaagttggc   8160
cgcagtgtta tcactcatgg ttatggcagc actgcataat tctcttactg tcatgccatc   8220
cgtaagatgc ttttctgtga ctggtgagta ctcaaccaag tcattctgag aatagtgtat   8280
```

-continued gcggcgaccg agttgctctt gcccggcgtc aatacgggat aataccgcgc cacatagcag 8340
aactttaaaa gtgctcatca ttggaaaacg ttcttcgggg cgaaaactct caaggatctt 8400
accgctgttg agatccagtt cgatgtaacc cactcgtgca cccaactgat cttcagcatc 8460
ttttactttc accagcgttt ctgggtgagc aaaaacagga aggcaaaatg ccgcaaaaaa 8520
gggaataagg gcgacacgga aatgttgaat actcatactc ttcctttttc aatattattg 8580
aagcatttat cagggttatt gtctcatgag cggatacata tttgaatgta tttagaaaaa 8640
taaacaaata ggggttccgc gcacatttcc ccgaaaagtg ccacctgacg tctaagaaac 8700
cattattatc atgacattaa cctataaaaa taggcgtatc acgaggccct ttcgtctcgc 8760
gcgtttcggt gatgacggtg aaaacctctg acacatgcag ctcccggaga cggtcacagc 8820
ttgtctgtaa gcggatgccg ggagcagaca agcccgtcag ggcgcgtcag cgggtgttgg 8880
cgggtgtcgg ggctggctta actatgcggc atcagagcag attgtactga gagtgcacca 8940
tatcgacgct ctcccttatg cgactcctgc attaggaagc agcccagtag taggttgagg 9000
ccgttgagca ccgccgccgc aaggaatggt gcatgcaagg agatggcgcc caacagtccc 9060
ccggccacgg ggcctgccac catacccacg ccgaaacaag cgctcatgag cccgaagtgg 9120
cgagcccgat cttccccatc ggtgatgtcg gcgatatagg cgccagcaac cgcacctgtg 9180
gcgccggtga tgccggccac gatgcgtccg gcgtagagga tctggctagc gatgaccctg 9240
ctgattggtt cgctgaccat ttccggggtg cggaacggcg ttaccagaaa ctcagaaggt 9300
tcgtccaacc aaaccgactc tgacggcagt ttacgagaga gatgataggg tctgcttcag 9360
taagccagat gctacacaat taggcttgta catattgtcg ttagaacgcg gctacaatta 9420
atacataacc ttatgtatca tacacatacg atttaggtga cactatagaa tacacctgca 9480
ggacgcgtac tgagagcgct attctgaact tttcttttgt tc 9522

<210> SEQ ID NO 7
<211> LENGTH: 10767
<212> TYPE: DNA
<213> ORGANISM: Artificial Sequence
<220> FEATURE:
<223> OTHER INFORMATION: pCLD12

<400> SEQUENCE: 7
ccctagaaag ataatcatat tgtgacgtac gttaaagata atcatgcgta aaattgacgc 60
atgtgtttta tcggtctgta tatcgaggtt tatttattaa tttgaataga tattaagttt 120
tattatattt acacttacat actaataata aattcaacaa acaatttatt tatgtttatt 180
tatttattaa aaaaaaacaa aaactcaaaa tttcttctat aaagtaacaa aacttttatc 240
gaatttgcag cccgggacta gctagaggga cagccccccc ccaaagcccc cagggatgta 300
attacgtccc tcccccgcta gggggcagca gcgagccgcc cggggctccg ctccggtccg 360
gcgctccccc cgcatccccg agccggcagc gtgcggggac agcccgggca cggggaaggt 420
ggcacgggat cgctttcctc tgaacgcttc tcgctgctct ttgagcctgc agacacctgg 480
ggggatacgg ggaaaactta agatccgacc ggacgcgtac tgagagcgct attctgaact 540
tttcttttgt tcccttccct tctaccacac cctaattgta atccatttta atttcctggt 600
cacagtcctg tctctccttc cattgtacct tgccctttc taaagagcga ctgcaaagta 660
tgtttgcgta ggtgaggatc taaaacttta tgaggtacga acatcacaga attactttgt 720
aatttcagtt tattgtaggc ttggcttttt ggggagggtt tacgtcttag acctcttagt 780
gcttctttgt ttcatggtgt tctaacttcg aagcatctct gtagctttaa tggattcctt 840

```
ttctgaaagc tttgctctct ttcttccccc tcggctttct cttaggcaag agggctaact    900
gtaaagtaag gcttactgcc ttgtgtttcc aaatgtgtcc gaagaggaag tgtcttctgt    960
gaatcctgtt atgcatgaat aacaggaaat agaaagaaat tcactttcat tattataaaa   1020
gtaatatgtt cgtttaaaaa attctaatga agagctggag atgcaaccca ggggtagagc   1080
acacactcag catgcaggag gccctgggtc caatcttgga atctcctctc agttaacctg   1140
atctctagct gattagtagt gagtgcaagc ccactttcct cttctgcctc attgctcagt   1200
gataacagct gttaaacttt gtcttattct aaaactacct ctgtgcaaat gctagcacaa   1260
taatatatat catatgcaca tgattttttt tttatcttga aaagtaagtc agtatagcta   1320
caaagttcac ttggcattgt caacatttca caggcgtaat attcctcctc tagtactgtc   1380
ctcttcattc tttgtgacca agtttggaga gagtgcacaa atgccaggga ggtttgtggg   1440
aaggtttctc atgttctggt aaggcgagta agaaaatagt ctcatgcagg tgaaatgagt   1500
gctatgcagt atatattata ccagagaaca gcaaatgacc aaattcacac tgaactagtt   1560
cagtaaaatt ggctttgtca aagctttcct tgcttaaaat gtaattccct gtcatcctag   1620
ttctggtctg gattcttttc ctggagtctt gacttccaga ttccctgtgg acttttgttt   1680
gagtttcaag cttttgaaat atagaaacct atctaactta acaaacttgg gagagaaaag   1740
actccagaac aactgaaaac agaccaggct aaatgaatag actttattcc tctcttctta   1800
cctgcagttt tcagatatgc agagttggag cggatcttag aggttgattc attcatgcct   1860
gaagaaaaca cattttatag accctgtgcc caagttcgtg gtggacatca ccctttattt   1920
actaattgca ctacataaca ggcattttag aagactgctc cagtcagaga ccccgcctta   1980
gaggaatctg taaaccctga actcctatca ctcatgagca ctagttatgt ttggaatgcc   2040
gtattaaaac aaaagttaca tttctaaact taaaatttc tagcacagag acagtgggag   2100
tagctaactt tgatagacat ttttctacta aaagtctttc taagtacata atcttctgta   2160
agttggaaaa cagcaaaata gaacgtctcc tacgtagtta atctttttgc ataatttgca   2220
catgtaggag ttattagtat acgggtaagt tttcactttt tcccccaact ggagtgtctt   2280
gtggctgggt ttgaaaaagg gaacgggagg ccgctggagg ggattggtaa atgagataaa   2340
acaccactca ttcaactcag tgactcagca tttaaatttt ccataaaagg attaaaggaa   2400
aattaaacaa attcttaaag ccaagactct ggagaaactt gttggtgtgc tttagttttc   2460
actgttatga ctcatgaatt tatgcataaa ttagtacatt tataaaaaca tagccttttt   2520
agagttttct gtttggctaa agtgccattg ttagcattgg gaattacctt tttatgtctt   2580
atattttttc caaataaaaa taaatgtttc tgctgtctta ctactgaaac tacgttgtga   2640
gcactttaaa tttctcaaag cagtttcgcc tgttatactt ggcgcttagt catcgtcgta   2700
cacaacagga cctgattaag aaggctgtgc tgcctctaag ccgggctaga ttgtagccac   2760
tagcaaccag gctgcaataa tttccctttg atgacatcat ccactgtgga agaacccagt   2820
tgcttcagcc agtcgaacta tacagttcca acctcatcaa atatggcatc tcccttgcct   2880
gctatagcag gggaggaaa aaatgccacc atctttttaa tctagcaagc ttctcttttc   2940
ttcatctttt tttttttctt ttaaaaaaat tctgatcatg gatgcttctt ccgatcccta   3000
tttgccttat gacgggggag gagacaatat ccccttgagg gaattacata aaagaggtaa   3060
gagcatcccc ttgctctgaa tcctctgttg gttgttgtgc atgcggctgg gcggttctgg   3120
ggacaggctg tctgttgtcc tcttgctgca atgtgctgct tagttgccct gccttgttgc   3180
```

-continued

```
tgtgggagaa tgcgaccttc ccagcagggc tggccctccc tgattgtttg ctctgtgcag   3240
attagccctg cttcagatca catagggctg cagactccat cttctgtgtg aaaatgcttt   3300
cggtttgatt gcagaaataa gctgccttta cagccagcta aagtcctggt ggttggttgg   3360
cacctgcaaa gtagtatttt tgtacctctg gaaacttata ttttctttac acagcaatat   3420
caagtgccgg tatgccattc tgttttggct gctgccaatt accatgtaga ctttgcacca   3480
cagagtaata gtaaaagctc ctagctgcat tttataacat ttaaaaatag caggaaagaa   3540
gaattatttt tgatttaaca tgtttttgtc atttaacgtc ttaactgatt gacatactat   3600
attgtctgtc tcgtgggtat cttgtacaac ttgataggat aaagcaattt agtttttttt   3660
ttttttttta aatacatcca gaatgtaagt cgtcagtagt tttcgaacag ataagtaatg   3720
gtgttaatct tttggcaggc tttgccttgg tctccttaaa gctaattagg tgttacttaa   3780
ttaaactgct cttttgctca ttttcttaaa ttattttttt aaaagatagt tggcatttgc   3840
tgttctagaa ataaacttca agaaacattc tttagccaga tgacttcatg tatgagccat   3900
gttagtttga attatttgct tggtgttata aactttatgg tttaatacca acttttatta   3960
tgtttacaag gtaaataagg aaaatttcaa gtacattttg tatcctgaga acaaatttaa   4020
gttccataga atttaggaat tacaatgtat tcaacagata cttacttgtc atactgtgcc   4080
tgcaaaacaa taattagact ctgaacaggt gcaacaattt tctgtagaat tagacaagtc   4140
ttcttttggc aggtgttact aagtaggcca tttcccaagg aacagggaat ttgccaggct   4200
tttgtggtgg agagaataga atgaataaat gctgtgggga gtaaagagct tgtcagaaga   4260
tgattagttc tgtggcacca aaaccaagag atcagttttc ctgtgagaag taaaggaagc   4320
attgtagaaa aatagatgtg ttgaagtcta ccggtggagt tccgcgttac ataacttacg   4380
gtaaatggcc cgcctggctg accgcccaac gacccccgcc cattgacgtc aataatgacg   4440
tatgttccca tagtaacgcc aatagggact ttccattgac gtcaatgggt ggagtattta   4500
cggtaaactg cccacttggc agtacatcaa gtgtatcata tgccaagtac gccccctatt   4560
gacgtcaatg acggtaaatg gcccgcctgg cattatgccc agtacatgac cttatgggac   4620
tttcctactt ggcagtacat ctacgtatta gtcatcgcta ttaccattgt gatgcggttt   4680
tggcagtaca tcaatgggcg tggatagcgg tttgactcac ggggatttcc aagtctccac   4740
cccattgacg tcaatgggag tttgttttgg caccaaaatc aacgggactt tccaaaatgt   4800
cgtaacaact ccgccccatt gacgcaaatg ggcggtaggc gtgtacggtg ggaggtctat   4860
ataagcagag ctcgtttagt gaaccgtcag atctacctct tccgcatcgc tgtctgcgag   4920
ggccagctgt tggggtgagt actccctctc aaaagcgggc atgacttctg cgctaagatt   4980
gtcagtttcc aaaaacgagg aggatttgat attcacctgg cccgcggtga tgcctttgag   5040
ggtggccgcg tccatctggt cagaaaagac aatctttttg ttgtcaagct tccttgatga   5100
tgtcatactt atcctgtccc ttttttttcc acagctcgcg gttgaggaca aactcttcgc   5160
ggtctttcca gtactcttgg atcggaaacc cgtcggcctc cgaacggtac tccgccaccg   5220
agggacctga gcgagtccgc atcgaccgga tcggaaaacc tcggatccga attcatagat   5280
aactgatcca gtgcccctaa cgttactggc cgaagccgct tggaataagg ccggtgtgcg   5340
tttgtctata tgttattttc caccatattg ccgtcttttg gcaatgtgag ggcccggaaa   5400
cctggccctg tcttcttgac gagcattcct aggggtcttt cccctctcgc caaaggaatg   5460
caaggtctgt tgaatgtcgt gaaggaagca gttcctctgg aagcttcttg aagacaaaca   5520
acgtctgtag cgaccctttg caggcagcgg aaccccccac ctggcgacag gtgcctctgc   5580
```

ggccaaaagc cacgtgtata agatacacct gcaaaggcgg cacaacccca gtgccacgtt 5640
gtgagttgga tagttgtgga aagagtcaaa tggctctcct caagcgtatt caacaagggg 5700
ctgaaggatg cccagaaggt accccattgt atgggatctg atctggggcc tcggtgcaca 5760
tgctttacat gtgtttagtc gaggttaaaa aacgtctagg ccccccgaac cacggggacg 5820
tggttttcct ttgaaaaaca cgatgataat atggccacaa ccatggccac ctcagcaagt 5880
tcccacttga acaaaaacat caagcaaatg tacttgtgcc tgccccaggg tgagaaagtc 5940
caagccatgt atatctgggt tgatggtact ggagaaggac tgcgctgcaa aacccgcacc 6000
ctggactgtg agcccaagtg tgtagaagag ttacctgagt ggaattttga tggctctagt 6060
acctttcagt ctgagggctc caacagtgac atgtatctca gccctgttgc catgtttcgg 6120
gaccccttcc gcagagatcc caacaagctg gtgttctgtg aagttttcaa gtacaaccgg 6180
aagcctgcag agaccaattt aaggcactcg tgtaaacgga taatggacat ggtgagcaac 6240
cagcacccct ggtttggaat ggaacaggag tatactctga tgggaacaga tgggcaccct 6300
tttggttggc cttccaatgg ctttcctggg ccccaaggtc cgtattactg tggtgtgggc 6360
gcagacaaag cctatggcag ggatatcgtg gaggctcact accgcgcctg cttgtatgct 6420
ggggtcaaga ttacaggaac aaatgctgag gtcatgcctg cccagtggga gttccaaata 6480
ggaccctgtg aaggaatccg catgggagat catctctggg tggcccgttt catcttgcat 6540
cgagtatgtg aagactttgg ggtaatagca acctttgacc ccaagcccat tcctgggaac 6600
tggaatggtg caggctgcca taccaacttt agcaccaagg ccatgcggga ggagaatggt 6660
ctgaagcaca tcgaggaggc catcgagaaa ctaagcaagc ggcaccggta ccacattcga 6720
gcctacgatc ccaagggggg cctggacaat gcccgtcgtc tgactgggtt ccacgaaacg 6780
tccaacatca acgacttttc tgctggtgtc gccaatcgca gtgccagcat ccgcattccc 6840
cggactgtcg gccaggagaa gaaaggttac tttgaagacc gccgcccctc tgccaattgt 6900
gacccctttg cagtgacaga agccatcgtc cgcacatgcc ttctcaatga gactggcgac 6960
gagcccttcc aatacaaaaa ctaatctaga tccccctcgc tttcttgctg tccaatttct 7020
attaaaggtt cctttgttcc ctaagtccaa ctactaaact gggggatatt atgaagggcc 7080
ttgagcatct ggattctgcc taataaaaaa catttatttt cattgcaatg atgtatttaa 7140
attatttctg aatattttac taaaaaggga atgtgggagg tcagtgcatt taaaacataa 7200
agaaatgaag agggggatct tcgcgatact gcatcgatga gggacagccc ccccccaaag 7260
cccccaggga tgtaattacg tccctccccc gctagggggc agcagcgagc cgcccggggc 7320
tccgctccgg tccggcgctc cccccgcatc cccgagccgg cagcgtgcgg ggacagcccg 7380
ggcacgggga aggtggcacg ggatcgcttt cctctgaacg cttctcgctg ctctttgagc 7440
ctgcagacac ctggggggat acggggaaaa tagacaccgc ggtggagctc cagcttttgt 7500
tccctttagt gagggttaat tagttcttaa tacgactcac tatagggcga attggctacc 7560
gggccgccca tcgagggtat cataagctta tatctataac aagaaaatat atatataata 7620
agttatcacg taagtagaac atgaaataac aatataatta tcgtatgagt taaatcttaa 7680
aagtcacgta aaagataatc atgcgtcatt ttgactcacg cggtcgttat agttcaaaat 7740
cagtgacact taccgcattg acaagcacgc ctcacgggag ctccaagcgg cgactgagat 7800
gtcctaaatg cacagcgacg gattcgcgct atttagaaag agagagcaat atttcaagaa 7860
tgcatgcgtc aattttacgc agactatctt tctagggtta aatcgataga tgcgatcctg 7920

-continued

```
caggtctccc tatagtgagt cgtattaatt tcgataagcc agctgcatta atgaatcggc   7980
caacgcgcgg ggagaggcgg tttgcgtatt gggcgctctt ccgcttcctc gctcactgac   8040
tcgctgcgct cggtcgttcg gctgcggcga gcggtatcag ctcactcaaa ggcggtaata   8100
cggttatcca cagaatcagg ggataacgca ggaaagaaca tgtgagcaaa aggccagcaa   8160
aaggccagga accgtaaaaa ggccgcgttg ctggcgtttt tccataggct ccgcccccct   8220
gacgagcatc acaaaaatcg acgctcaagt cagaggtggc gaaacccgac aggactataa   8280
agataccagg cgtttccccc tggaagctcc ctcgtgcgct ctcctgttcc gaccctgccg   8340
cttaccggat acctgtccgc ctttctccct tcgggaagcg tggcgctttc tcatagctca   8400
cgctgtaggt atctcagttc ggtgtaggtc gttcgctcca agctgggctg tgtgcacgaa   8460
ccccccgttc agcccgaccg ctgcgcctta tccggtaact atcgtcttga gtccaacccg   8520
gtaagacacg acttatcgcc actggcagca gccactggta acaggattag cagagcgagg   8580
tatgtaggcg gtgctacaga gttcttgaag tggtggccta actacggcta cactagaagg   8640
acagtatttg gtatctgcgc tctgctgaag ccagttacct tcggaaaaag agttggtagc   8700
tcttgatccg gcaaacaaac caccgctggt agcggtggtt tttttgtttg caagcagcag   8760
attacgcgca gaaaaaaagg atctcaagaa gatcctttga tcttttctac ggggtctgac   8820
gctcagtgga acgaaaactc acgttaaggg attttggtca tgagattatc aaaaaggatc   8880
ttcacctaga tccttttaaa ttaaaaatga agttttaaat caatctaaag tatatatgag   8940
taaacttggt ctgacagtta ccaatgctta atcagtgagg cacctatctc agcgatctgt   9000
ctatttcgtt catccatagt tgcctgactc cccgtcgtgt agataactac gatacgggag   9060
ggcttaccat ctggccccag tgctgcaatg ataccgcgag acccacgctc accggctcca   9120
gatttatcag caataaacca gccagccgga agggccgagc gcagaagtgg tcctgcaact   9180
ttatccgcct ccatccagtc tattaattgt tgccgggaag ctagagtaag tagttcgcca   9240
gttaatagtt tgcgcaacgt tgttgccatt gctacaggca tcgtggtgtc acgctcgtcg   9300
tttggtatgg cttcattcag ctccggttcc caacgatcaa ggcgagttac atgatccccc   9360
atgttgtgca aaaaagcggt tagctccttc ggtcctccga tcgttgtcag aagtaagttg   9420
gccgcagtgt tatcactcat ggttatggca gcactgcata attctcttac tgtcatgcca   9480
tccgtaagat gcttttctgt gactggtgag tactcaacca agtcattctg agaatagtgt   9540
atgcggcgac cgagttgctc ttgcccggcg tcaatacggg ataataccgc gccacatagc   9600
agaactttaa aagtgctcat cattggaaaa cgttcttcgg ggcgaaaact ctcaaggatc   9660
ttaccgctgt tgagatccag ttcgatgtaa cccactcgtg cacccaactg atcttcagca   9720
tcttttactt tcaccagcgt ttctgggtga gcaaaaacag gaaggcaaaa tgccgcaaaa   9780
aagggaataa gggcgacacg gaaatgttga atactcatac tcttcctttt tcaatattat   9840
tgaagcattt atcagggtta ttgtctcatg agcggataca tatttgaatg tatttagaaa   9900
aataaacaaa taggggttcc gcgcacattt ccccgaaaag tgccacctga cgtctaagaa   9960
accattatta tcatgacatt aacctataaa aataggcgta tcacgaggcc ctttcgtctc  10020
gcgcgtttcg gtgatgacgg tgaaaacctc tgacacatgc agctcccgga gacggtcaca  10080
gcttgtctgt aagcggatgc cgggagcaga caagcccgtc agggcgcgtc agcgggtgtt  10140
ggcgggtgtc ggggctggct taactatgcg gcatcagagc agattgtact gagagtgcac  10200
catatcgacg ctctccctta tgcgactcct gcattaggaa gcagcccagt agtaggttga  10260
ggccgttgag caccgccgcc gcaaggaatg gtgcatgcaa ggagatggcg cccaacagtc  10320
```

```
ccccggccac ggggcctgcc accataccca cgccgaaaca agcgctcatg agcccgaagt  10380

ggcgagcccg atcttcccca tcggtgatgt cggcgatata ggcgccagca accgcacctg  10440

tggcgccggt gatgccggcc acgatgcgtc cggcgtagag gatctggcta gcgatgaccc  10500

tgctgattgg ttcgctgacc atttccgggg tgcggaacgg cgttaccaga aactcagaag  10560

gttcgtccaa ccaaaccgac tctgacggca gtttacgaga gagatgatag ggtctgcttc  10620

agtaagccag atgctacaca attaggcttg tacatattgt cgttagaacg cggctacaat  10680

taatacataa ccttatgtat catacacata cgatttaggt gacactatag aatacacctg  10740

caggacgtcc caatgatctt aagttaa                                      10767
```

```
<210> SEQ ID NO 8
<211> LENGTH: 10747
<212> TYPE: DNA
<213> ORGANISM: Artificial Sequence
<220> FEATURE:
<223> OTHER INFORMATION: pCLD14

<400> SEQUENCE: 8
```

```
ccctagaaag ataatcatat tgtgacgtac gttaaagata atcatgcgta aaattgacgc     60

atgtgtttta tcggtctgta tatcgaggtt tatttattaa tttgaataga tattaagttt    120

tattatattt acacttacat actaataata aattcaacaa acaatttatt tatgtttatt    180

tatttattaa aaaaaaacaa aaactcaaaa tttcttctat aaagtaacaa aacttttatc    240

gaatttgcag cccgggacta gctagaggga cagccccccc ccaaagcccc cagggatgta    300

attacgtccc tcccccgcta gggggcagca gcgagccgcc cggggctccg ctccggtccg    360

gcgctccccc cgcatccccg agccggcagc gtgcggggac agcccgggca cggggaaggt    420

ggcacgggat cgctttcctc tgaacgcttc tcgctgctct ttgagcctgc agacacctgg    480

ggggatacgg ggaaaactta agatccgacc ggacgcgtac tgagagcgct attctgaact    540

tttcttttgt tcccttccct tctaccacac cctaattgta atccatttta atttcctggt    600

cacagtcctg tctctccttc cattgtacct tgcccttttc taaagagcga ctgcaaagta    660

tgtttgcgta ggtgaggatc taaaacttta tgaggtacga acatcacaga attactttgt    720

aatttcagtt tattgtaggc ttggcttttt ggggagggtt tacgtcttag acctcttagt    780

gcttctttgt ttcatggtgt tctaacttcg aagcatctct gtagctttaa tggattcctt    840

ttctgaaagc tttgctctct ttcttccccc tcggctttct cttaggcaag agggctaact    900

gtaaagtaag gcttactgcc ttgtgtttcc aaatgtgtcc gaagaggaag tgtcttctgt    960

gaatcctgtt atgcatgaat aacaggaaat agaaagaaat tcactttcat tattataaaa   1020

gtaatatgtt cgtttaaaaa attctaatga agagctggag atgcaaccca ggggtagagc   1080

acacactcag catgcaggag gccctgggtc caatcttgga atctcctctc agttaacctg   1140

atctctagct gattagtagt gagtgcaagc ccactttcct cttctgcctc attgctcagt   1200

gataacagct gttaaacttt gtcttattct aaaactacct ctgtgcaaat gctagcacaa   1260

taatatatat catatgcaca tgattttttt tttatcttga aaagtaagtc agtatagcta   1320

caaagttcac ttggcattgt caacatttca caggcgtaat attcctcctc tagtactgtc   1380

ctcttcattc tttgtgacca agtttggaga gagtgcacaa atgccaggga ggtttgtggg   1440

aaggtttctc atgttctggt aaggcgagta agaaaatagt ctcatgcagg tgaaatgagt   1500

gctatgcagt atatattata ccagagaaca gcaaatgacc aaattcacac tgaactagtt   1560
```

```
cagtaaaatt ggctttgtca aagctttcct tgcttaaaat gtaattccct gtcatcctag   1620
ttctggtctg gattcttttc ctggagtctt gacttccaga ttccctgtgg acttttgttt   1680
gagtttcaag cttttgaaat atagaaacct atctaactta acaaacttgg gagagaaaag   1740
actccagaac aactgaaaac agaccaggct aaatgaatag actttattcc tctcttctta   1800
cctgcagttt tcagatatgc agagttggag cggatcttag aggttgattc attcatgcct   1860
gaagaaaaca cattttatag accctgtgcc caagttcgtg gtggacatca ccctttattt   1920
actaattgca ctacataaca ggcattttag aagactgctc cagtcagaga ccccgcctta   1980
gaggaatctg taaaccctga actcctatca ctcatgagca ctagttatgt ttggaatgcc   2040
gtattaaaac aaaagttaca tttctaaact taaaatttc tagcacagag acagtgggag    2100
tagctaactt tgatagacat ttttctacta aaagtctttc taagtacata atcttctgta   2160
agttggaaaa cagcaaaata gaacgtctcc tacgtagtta atctttttgc ataatttgca   2220
catgtaggag ttattagtat acgggtaagt tttcactttt tcccccaact ggagtgtctt   2280
gtggctgggt ttgaaaaagg gaacgggagg ccgctggagg ggattggtaa atgagataaa   2340
acaccactca ttcaactcag tgactcagca tttaaatttt ccataaaagg attaaaggaa   2400
aattaaacaa attcttaaag ccaagactct ggagaaactt gttggtgtgc tttagttttc   2460
actgttatga ctcatgaatt tatgcataaa ttagtacatt tataaaaaca tagccttttt   2520
agagttttct gtttggctaa agtgccattg ttagcatttg gaattacctt tttatgtctt   2580
atatttttc caaataaaaa taaatgtttc tgctgtctta ctactgaaac tacgttgtga    2640
gcactttaaa tttctcaaag cagtttcgcc tgttatactt ggcgcttagt catcgtcgta   2700
cacaacagga cctgattaag aaggctgtgc tgcctctaag ccgggctaga ttgtagccac   2760
tagcaaccag gctgcaataa tttccctttg atgacatcat ccactgtgga agaacccagt   2820
tgcttcagcc agtcgaacta tacagttcca acctcatcaa atatggcatc tcccttgcct   2880
gctatagcag gggaggaaa aaatgccacc atctttttaa tctagcaagc ttctcttttc    2940
ttcatctttt tttttttctt ttaaaaaaat tctgatcatg gatgcttctt ccgatcccta   3000
tttgccttat gacgggggag gagacaatat ccccttgagg gaattacata aaagaggtaa   3060
gagcatcccc ttgctctgaa tcctctgttg gttgttgtgc atgcggctgg gcggttctgg   3120
ggacaggctg tctgttgtcc tcttgctgca atgtgctgct tagttgccct gccttgttgc   3180
tgtgggagaa tgcgaccttc ccagcagggc tggccctccc tgattgtttg ctctgtgcag   3240
attagccctg cttcagatca catagggctg cagactccat cttctgtgtg aaaatgcttt   3300
cggtttgatt gcagaaataa gctgccttta cagccagcta aagtcctggt ggttggttgg   3360
cacctgcaaa gtagtatttt tgtacctctg gaaacttata ttttctttac acagcaatat   3420
caagtgccgg tatgccattc tgttttggct gctgccaatt accatgtaga ctttgcacca   3480
cagagtaata gtaaaagctc ctagctgcat tttataacat ttaaaaatag caggaaagaa   3540
gaattatttt tgatttaaca tgtttttgtc atttaacgtc ttaactgatt gacatactat   3600
attgtctgtc tcgtgggtat cttgtacaac ttgataggat aaagcaattt agtttttttt   3660
ttttttttta aatacatcca gaatgtaagt cgtcagtagt tttcgaacag ataagtaatg   3720
gtgttaatct tttggcaggc tttgccttgg tctccttaaa gctaattagg tgttacttaa   3780
ttaaactgct cttttgctca ttttcttaaa ttattttttt aaaagatagt tggcatttgc   3840
tgttctagaa ataaacttca agaaacattc tttagccaga tgacttcatg tatgagccat   3900
gttagtttga attatttgct tggtgttata aactttatgg tttaatacca acttttatta   3960
```

-continued tgtttacaag gtaaataagg aaaatttcaa gtacattttg tatcctgaga acaaatttaa 4020
gttccataga atttaggaat tacaatgtat tcaacagata cttacttgtc atactgtgcc 4080
tgcaaaacaa taattagact ctgaacaggt gcaacaattt tctgtagaat tagacaagtc 4140
ttcttttggc aggtgttact aagtaggcca tttcccaagg aacagggaat ttgccaggct 4200
tttgtggtgg agagaataga atgaataaat gctgtgggga gtaaagagct tgtcagaaga 4260
tgattagttc tgtggcacca aaaccaagag atcagttttc ctgtgagaag taaaggaagc 4320
attgtagaaa aatagatgtg ttgaagtcta ccggtggagt tccgcgttac ataacttacg 4380
gtaaatggcc cgcctggctg accgcccaac gacccccgcc cattgacgtc aataatgacg 4440
tatgttccca tagtaacgcc aatagggact ttccattgac gtcaatgggt ggagtattta 4500
cggtaaactg cccacttggc agtacatcaa gtgtatcata tgccaagtac gccccctatt 4560
gacgtcaatg acggtaaatg gcccgcctgg cattatgccc agtacatgac cttatgggac 4620
tttcctactt ggcagtacat ctacgtatta gtcatcgcta ttaccattgt gatgcggttt 4680
tggcagtaca tcaatgggcg tggatagcgg tttgactcac ggggatttcc aagtctccac 4740
cccattgacg tcaatgggag tttgttttgg caccaaaatc aacgggactt tccaaaatgt 4800
cgtaacaact ccgccccatt gacgcaaatg ggcggtaggc gtgtacggtg ggaggtctat 4860
ataagcagag ctcgtttagt gaaccgtcag atctacctct tccgcatcgc tgtctgcgag 4920
ggccagctgt tggggtgagt actccctctc aaaagcgggc atgacttctg cgctaagatt 4980
gtcagtttcc aaaaacgagg aggatttgat attcacctgg cccgcggtga tgcctttgag 5040
ggtggccgcg tccatctggt cagaaaagac aatctttttg ttgtcaagct tccttgatga 5100
tgtcatactt atcctgtccc ttttttttcc acagctcgcg gttgaggaca aactcttcgc 5160
ggtctttcca gtactcttgg atcggaaacc cgtcggcctc cgaacggtac tccgccaccg 5220
agggacctga gcgagtccgc atcgaccgga tcggaaaacc tcggatccga attcatagat 5280
aactgatcca gtgcccctaa cgttactggc cgaagccgct tggaataagg ccggtgtgcg 5340
tttgtctata tgttattttc caccatattg ccgtcttttg gcaatgtgag ggcccggaaa 5400
cctggccctg tcttcttgac gagcattcct aggggtcttt cccctctcgc caaaggaatg 5460
caaggtctgt tgaatgtcgt gaaggaagca gttcctctgg aagcttcttg aagacaaaca 5520
acgtctgtag cgaccctttg caggcagcgg aaccccccac ctggcgacag gtgcctctgc 5580
ggccaaaagc cacgtgtata agatacacct gcaaaggcgg cacaacccca gtgccacgtt 5640
gtgagttgga tagttgtgga aagagtcaaa tggctctcct caagcgtatt caacaagggg 5700
ctgaaggatg cccagaaggt accccattgt atgggatctg atctggggcc tcggtgcaca 5760
tgctttacat gtgtttagtc gaggttaaaa aacgtctagg ccccccgaac cacggggacg 5820
tggttttcct ttgaaaaaca cgatggccac ctcagcaagt tcccacttga acaaaaacat 5880
caagcaaatg tacttgtgcc tgccccaggg tgagaaagtc caagccatgt atatctgggt 5940
tgatggtact ggagaaggac tgcgctgcaa aacccgcacc ctggactgtg agcccaagtg 6000
tgtagaagag ttacctgagt ggaattttga tggctctagt acctttcagt ctgagggctc 6060
caacagtgac atgtatctca gccctgttgc catgtttcgg gaccccttcc gcagagatcc 6120
caacaagctg gtgttctgtg aagttttcaa gtacaaccgg aagcctgcag agaccaattt 6180
aaggcactcg tgtaaacgga taatggacat ggtgagcaac cagcacccct ggtttggaat 6240
ggaacaggag tatactctga tgggaacaga tgggcaccct tttggttggc cttccaatgg 6300

-continued

```
ctttcctggg ccccaaggtc cgtattactg tggtgtgggc gcagacaaag cctatggcag   6360
ggatatcgtg gaggctcact accgcgcctg cttgtatgct ggggtcaaga ttacaggaac   6420
aaatgctgag gtcatgcctg cccagtggga gttccaaata ggaccctgtg aaggaatccg   6480
catgggagat catctctggg tggcccgttt catcttgcat cgagtatgtg aagactttgg   6540
ggtaatagca acctttgacc ccaagcccat tcctgggaac tggaatggtg caggctgcca   6600
taccaacttt agcaccaagg ccatgcggga ggagaatggt ctgaagcaca tcgaggaggc   6660
catcgagaaa ctaagcaagc ggcaccggta ccacattcga gcctacgatc ccaagggggg   6720
cctggacaat gcccgtcgtc tgactgggtt ccacgaaacg tccaacatca acgacttttc   6780
tgctggtgtc gccaatcgca gtgccagcat ccgcattccc cggactgtcg gccaggagaa   6840
gaaaggttac tttgaagacc gccgcccctc tgccaattgt gacccctttg cagtgacaga   6900
agccatcgtc cgcacatgcc ttctcaatga gactggcgac gagcccttcc aatacaaaaa   6960
ctaatctaga tccccctcgc tttcttgctg tccaatttct attaaaggtt cctttgttcc   7020
ctaagtccaa ctactaaact gggggatatt atgaagggcc ttgagcatct ggattctgcc   7080
taataaaaaa catttatttt cattgcaatg atgtatttaa attatttctg aatattttac   7140
taaaaaggga atgtgggagg tcagtgcatt taaaacataa agaaatgaag agggggatct   7200
tcgcgatact gcatcgatga gggacagccc ccccccaaag cccccaggga tgtaattacg   7260
tccctccccc gctagggggc agcagcgagc cgcccggggc tccgctccgg tccggcgctc   7320
cccccgcatc cccgagccgg cagcgtgcgg ggacagcccg ggcacgggga aggtggcacg   7380
ggatcgcttt cctctgaacg cttctcgctg ctctttgagc ctgcagacac ctgggggat    7440
acggggaaaa tagacaccgc ggtggagctc cagcttttgt tccctttagt gagggttaat   7500
tagttcttaa tacgactcac tatagggcga attggctacc gggccgccca tcgagggtat   7560
cataagctta tatctataac aagaaaatat atatataata agttatcacg taagtagaac   7620
atgaaataac aatataatta tcgtatgagt taaatcttaa aagtcacgta aaagataatc   7680
atgcgtcatt ttgactcacg cggtcgttat agttcaaaat cagtgacact taccgcattg   7740
acaagcacgc ctcacgggag ctccaagcgg cgactgagat gtcctaaatg cacagcgacg   7800
gattcgcgct atttagaaag agagagcaat atttcaagaa tgcatgcgtc aattttacgc   7860
agactatctt tctagggtta aatcgataga tgcgatcctg caggtctccc tatagtgagt   7920
cgtattaatt tcgataagcc agctgcatta atgaatcggc caacgcgcgg ggagaggcgg   7980
tttgcgtatt gggcgctctt ccgcttcctc gctcactgac tcgctgcgct cggtcgttcg   8040
gctgcggcga gcggtatcag ctcactcaaa ggcggtaata cggttatcca cagaatcagg   8100
ggataacgca ggaaagaaca tgtgagcaaa aggccagcaa aaggccagga accgtaaaaa   8160
ggccgcgttg ctggcgtttt tccataggct ccgcccccct gacgagcatc acaaaaatcg   8220
acgctcaagt cagaggtggc gaaacccgac aggactataa agataccagg cgtttccccc   8280
tggaagctcc ctcgtgcgct ctcctgttcc gaccctgccg cttaccggat acctgtccgc   8340
ctttctccct tcgggaagcg tggcgctttc tcatagctca cgctgtaggt atctcagttc   8400
ggtgtaggtc gttcgctcca agctgggctg tgtgcacgaa ccccccgttc agcccgaccg   8460
ctgcgcctta tccggtaact atcgtcttga gtccaacccg gtaagacacg acttatcgcc   8520
actggcagca gccactggta acaggattag cagagcgagg tatgtaggcg gtgctacaga   8580
gttcttgaag tggtggccta actacggcta cactagaagg acagtatttg gtatctgcgc   8640
tctgctgaag ccagttacct tcggaaaaag agttggtagc tcttgatccg gcaaacaaac   8700
```

caccgctggt agcggtggtt tttttgtttg caagcagcag attacgcgca gaaaaaaagg 8760
atctcaagaa gatcctttga tcttttctac ggggtctgac gctcagtgga acgaaaactc 8820
acgttaaggg attttggtca tgagattatc aaaaaggatc ttcacctaga tccttttaaa 8880
ttaaaaatga agttttaaat caatctaaag tatatatgag taaacttggt ctgacagtta 8940
ccaatgctta atcagtgagg cacctatctc agcgatctgt ctatttcgtt catccatagt 9000
tgcctgactc cccgtcgtgt agataactac gatacgggag ggcttaccat ctggccccag 9060
tgctgcaatg ataccgcgag acccacgctc accggctcca gatttatcag caataaacca 9120
gccagccgga agggccgagc gcagaagtgg tcctgcaact ttatccgcct ccatccagtc 9180
tattaattgt tgccgggaag ctagagtaag tagttcgcca gttaatagtt tgcgcaacgt 9240
tgttgccatt gctacaggca tcgtggtgtc acgctcgtcg tttggtatgg cttcattcag 9300
ctccggttcc caacgatcaa ggcgagttac atgatccccc atgttgtgca aaaaagcggt 9360
tagctccttc ggtcctccga tcgttgtcag aagtaagttg gccgcagtgt tatcactcat 9420
ggttatggca gcactgcata attctcttac tgtcatgcca tccgtaagat gcttttctgt 9480
gactggtgag tactcaacca agtcattctg agaatagtgt atgcggcgac cgagttgctc 9540
ttgcccggcg tcaatacggg ataataccgc gccacatagc agaactttaa aagtgctcat 9600
cattggaaaa cgttcttcgg ggcgaaaact ctcaaggatc ttaccgctgt tgagatccag 9660
ttcgatgtaa cccactcgtg cacccaactg atcttcagca tcttttactt tcaccagcgt 9720
ttctgggtga gcaaaaacag gaaggcaaaa tgccgcaaaa aagggaataa gggcgacacg 9780
gaaatgttga atactcatac tcttcctttt tcaatattat tgaagcattt atcagggtta 9840
ttgtctcatg agcggataca tatttgaatg tatttagaaa aataaacaaa taggggttcc 9900
gcgcacattt ccccgaaaag tgccacctga cgtctaagaa accattatta tcatgacatt 9960
aacctataaa aataggcgta tcacgaggcc ctttcgtctc gcgcgtttcg gtgatgacgg 10020
tgaaaacctc tgacacatgc agctcccgga gacggtcaca gcttgtctgt aagcggatgc 10080
cgggagcaga caagcccgtc agggcgcgtc agcgggtgtt ggcgggtgtc ggggctggct 10140
taactatgcg gcatcagagc agattgtact gagagtgcac catatcgacg ctctccctta 10200
tgcgactcct gcattaggaa gcagcccagt agtaggttga ggccgttgag caccgccgcc 10260
gcaaggaatg gtgcatgcaa ggagatggcg cccaacagtc ccccggccac ggggcctgcc 10320
accataccca cgccgaaaca agcgctcatg agcccgaagt ggcgagcccg atcttcccca 10380
tcggtgatgt cggcgatata ggcgccagca accgcacctg tggcgccggt gatgccggcc 10440
acgatgcgtc cggcgtagag gatctggcta gcgatgaccc tgctgattgg ttcgctgacc 10500
atttccgggg tgcggaacgg cgttaccaga aactcagaag gttcgtccaa ccaaaccgac 10560
tctgacggca gtttacgaga gagatgatag ggtctgcttc agtaagccag atgctacaca 10620
attaggcttg tacatattgt cgttagaacg cggctacaat taatacataa ccttatgtat 10680
catacacata cgatttaggt gacactatag aatacacctg caggacgtcc caatgatctt 10740
aagttaa 10747

<210> SEQ ID NO 9
<211> LENGTH: 63
<212> TYPE: DNA
<213> ORGANISM: Artificial Sequence
<220> FEATURE:
<223> OTHER INFORMATION: 5'ITR

<400> SEQUENCE: 9
ccctagaaag ataatcatat tgtgacgtac gttaaagata atcatgcgta aaattgacgc 60
atg 63

<210> SEQ ID NO 10
<211> LENGTH: 35
<212> TYPE: DNA
<213> ORGANISM: Artificial Sequence
<220> FEATURE:
<223> OTHER INFORMATION: 3'ITR

<400> SEQUENCE: 10
catgcgtcaa ttttacgcag actatctttc taggg 35

<210> SEQ ID NO 11
<211> LENGTH: 1211
<212> TYPE: DNA
<213> ORGANISM: Artificial Sequence
<220> FEATURE:
<223> OTHER INFORMATION: HS4 Insulator

<400> SEQUENCE: 11
gagctcacgg ggacagcccc cccccaaagc ccccagggat gtaattacgt ccctcccccg 60
ctagggggca gcagcgagcc gcccggggct ccgctccggt ccggcgctcc ccccgcatcc 120
ccgagccggc agcgtgcggg gacagcccgg gcacggggaa ggtggcacgg gatcgctttc 180
ctctgaacgc ttctcgctgc tctttgagcc tgcagacacc tgggggggata cggggaaaaa 240 gctttaggct gaaagagaga tttagaatga cagaatcata gaacggcctg ggttgcaaag 300
gagcacagtg ctcatccaga tccaaccccc tgctatgtgc agggtcatca accagcagcc 360
caggctgccc agagccacat ccagcctggc cttgaatgcc tgcagggatg gggcatccac 420
agcctccttg ggcaacctgt tcagtgcgtc accaccctct gggggaaaaa ctgcctcctc 480
atatccaacc caaacctccc ctgtctcagt gtaaagccat tccccccttgt cctatcaagg 540 gggagtttgc tgtgacattg ttggtctggg gtgacacatg tttgccaatt cagtgcatca 600
cggagaggca gatcttgggg ataaggaagt gcaggacagc atggacgtgg gacatgcagg 660
tgttgagggc tctgggacac tctccaagtc acagcgttca gaacagcctt aaggataaga 720
agataggata gaaggacaaa gagcaagtta aaacccagca tggagaggag cacaaaaagg 780
ccacagacac tgctggtccc tgtgtctgag cctgcatgtt tgatggtgtc tggatgcaag 840
cagaaggggt ggaagagctt gcctggagag atacagctgg gtcagtagga ctgggacagg 900
cagctggaga attgccatgt agatgttcat acaatcgtca aatcatgaag gctggaaaag 960
ccctccaaga tccccaagac caaccccaac ccacccaccg tgcccactgg ccatgtccct 1020
cagtgccaca tccccacagt tcttcatcac ctccagggac ggtgaccccc ccacctccgt 1080
gggcagctgt gccactgcag caccgctctt tggagaaggt aaatcttgct aaatccagcc 1140
cgaccctccc ctggcacaac gtaaggccat tatctctcat ccaactccag gacggagtca 1200
gtgagaatat t 1211

<210> SEQ ID NO 12
<211> LENGTH: 5837
<212> TYPE: DNA
<213> ORGANISM: Artificial Sequence
<220> FEATURE:
<223> OTHER INFORMATION: EASE

<400> SEQUENCE: 12

```
gaattctgaa cttttctttt gttcccttcc cttctaccac accctaattg taatccattt     60
taatttcctg gtcacagtcc tgtctctcct tccattgtac cttgcccttt tctaaagagc    120
gactgcaaag tatgtttgcg taggtgagga tctaaaactt tatgaggtac gaacatcaca    180
gaattacttt gtaatttcag tttattgtag gcttggcttt ttggggaggg tttacgtctt    240
agacctctta gtgcttcttt gtttcatggt gttctaactt cgaagcatct ctgtagcttt    300
aatggattcc ttttctgaaa gctttgctct ctttcttccc cctcggcttt ctcttaggca    360
agagggctaa ctgtaaagta aggcttactg ccttgtgttt ccaaatgtgt ccgaagagga    420
agtgtcttct gtgaatcctg ttatgcatga ataacaggaa atagaaagaa attcactttc    480
attattataa aagtaatatg ttcgtttaaa aaattctaat gaagagctgg agatgcaacc    540
caggggtaga gcacacactc agcatgcagg aggccctggg tccaatcttg gaatctcctc    600
tcagttaacc tgatctctag ctgattagta gtgagtgcaa gcccactttc ctcttctgcc    660
tcattgctca gtgataacag ctgttaaact ttgtcttatt ctaaaactac ctctgtgcaa    720
atgctagcac aataatatat atcatatgca catgattttt tttttatctt gaaaagtaag    780
tcagtatagc tacaaagttc acttggcatt gtcaacattt cacaggcgta atattcctcc    840
tctagtactg tcctcttcat tctttgtgac caagtttgga gagagtgcac aaatgccagg    900
gaggtttgtg ggaaggtttc tcatgttctg gtaaggcgag taagaaaata gtctcatgca    960
ggtgaaatga gtgctatgca gtatatatta taccagagaa cagcaaatga ccaaattcac   1020
actgaactag ttcagtaaaa ttggctttgt caaagctttc cttgcttaaa atgtaattcc   1080
ctgtcatcct agttctggtc tggattcttt tcctggagtc ttgacttcca gattccctgt   1140
ggacttttgt ttgagtttca agcttttgaa atatagaaac ctatctaact taacaaactt   1200
gggagagaaa agactccaga acaactgaaa acagaccagg ctaaatgaat agactttatt   1260
cctctcttct tacctgcagt tttcagatat gcagagttgg agcggatctt agaggttgat   1320
tcattcatgc ctgaagaaaa cacattttat agaccctgtg cccaagttcg tggtggacat   1380
cacccttat ttactaattg cactacataa caggcatttt agaagactgc tccagtcaga   1440
gaccccgcct tagaggaatc tgtaaaccct gaactcctat cactcatgag cactagttat   1500
gtttggaatg ccgtattaaa acaaaagtta catttctaaa cttaaaattt tctagcacag   1560
agacagtggg agtagctaac tttgatagac atttttctac taaaagtctt tctaagtaca   1620
taatcttctg taagttggaa aacagcaaaa tagaacgtct cctacgtagt taatcttttt   1680
gcataatttg cacatgtagg agttattagt atacgggtaa gttttcactt tttcccccaa   1740
ctggagtgtc ttgtggctgg gtttgaaaaa gggaacggga ggccgctgga ggggattggt   1800
aaatgagata aaacaccact cattcaactc agtgactcag catttaaatt ttccataaaa   1860
ggattaaagg aaaattaaac aaattcttaa agccaagact ctggagaaac ttgttggtgt   1920
gctttagttt tcactgttat gactcatgaa tttatgcata aattagtaca tttataaaaa   1980
catagccttt ttagagtttt ctgtttggct aaagtgccat tgttagcatt tggaattacc   2040
tttttatgtc ttatattttt tccaaataaa aataaatgtt tctgctgtct tactactgaa   2100
actacgttgt gagcacttta aatttctcaa agcagtttcg cctgttatac ttggcgctta   2160
gtcatcgtcg tacacaacag gacctgatta agaaggctgt gctgcctcta agccgggcta   2220
gattgtagcc actagcaacc aggctgcaat aatttccctt tgatgacatc atccactgtg   2280
gaagaaccca gttgcttcag ccagtcgaac tatacagttc caacctcatc aaatatggca   2340
```

```
tctcccttgc ctgctatagc agggggagga aaaaatgcca ccatcttttt aatctagcaa   2400
gcttctcttt tcttcatctt ttttttttc ttttaaaaaa attctgatca tggatgcttc    2460
ttccgatccc tatttgcctt atgacggggg aggagacaat atccccttga gggaattaca   2520
taaaagaggt aagagcatcc ccttgctctg aatcctctgt tggttgttgt gcatgcggct   2580
gggcggttct ggggacaggc tgtctgttgt cctcttgctg caatgtgctg cttagttgcc   2640
ctgccttgtt gctgtgggag aatgcgacct tcccagcagg gctggccctc cctgattgtt   2700
tgctctgtgc agattagccc tgcttcagat cacatagggc tgcagactcc atcttctgtg   2760
tgaaaatgct ttcggtttga ttgcagaaat aagctgcctt tacagccagc taaagtcctg   2820
gtggttggtt ggcacctgca aagtagtatt tttgtacctc tggaaactta tattttcttt   2880
acacagcaat atcaagtgcc ggtatgccat tctgttttgg ctgctgccaa ttaccatgta   2940
gactttgcac cacagagtaa tagtaaaagc tcctagctgc attttataac atttaaaaat   3000
agcaggaaag aagaattatt tttgatttaa catgtttttg tcatttaacg tcttaactga   3060
ttgacatact atattgtctg tctcgtgggt atcttgtaca acttgatagg ataaagcaat   3120
ttagtttttt tttttttttt taaatacatc cagaatgtaa gtcgtcagta gttttcgaac   3180
agataagtaa tggtgttaat cttttggcag gctttgcctt ggtctcctta aagctaatta   3240
ggtgttactt aattaaactg ctcttttgct cattttctta aattattttt ttaaaagata   3300
gttggcattt gctgttctag aaataaactt caagaaacat tctttagcca gatgacttca   3360
tgtatgagcc atgttagttt gaattatttg cttggtgtta taaactttat ggtttaatac   3420
caacttttat tatgtttaca aggtaaataa ggaaaatttc aagtacattt tgtatcctga   3480
gaacaaattt aagttccata gaatttagga attacaatgt attcaacaga tacttacttg   3540
tcatactgtg cctgcaaaac aataattaga ctctgaacag gtgcaacaat tttctgtaga   3600
attctgtgct tagtaaaagg ttgcttttta tattttgaga gaaatctatt taaagatcat   3660
ggcccatatt ttgtgcatat ttttttctgt ataccatttc catatatgtg tgtgtgtgta   3720
catatatgta tatatataaa atgttagaac atttgaggaa atagctaaaa gtacaaaagt   3780
aatgttttct aatttttttac tccccgaggt tatttctttt ttccttgttt tcctttctct  3840
ttgttcctat catcagtttc tagtaatact cttattgaac agtgattatt caaatgtcac   3900
attatttatt aatcagcatt taaatggtaa aaccagacag accatacttt ctctgagtga   3960
tgacaacatc catttttagt aatgataaac tagaagggtc aggcttgata gtctttgtca   4020
ggactaattt atagactgta aaggccaaaa gaaataagaa atgtcaaaac tcttgtgaaa   4080
ctagacatac agatattacc aagagagaaa ctagaaaaaa aaattctgtg acatggcctt   4140
aatttgccag gcaccatcgt gaaggcctaa acccctctta gaagctcact cagatgccat   4200
cctgcttctc tgatgagact tcctgtcaat acaaacatgg tttaggaaga atgagtgttt   4260
gcagtataaa ccagttattt actagcctta ctttaagaat atactgtagt gtccttgaga   4320
gagaaggtgt ttgttttctg taatttatga cccttttgaa accatagatc agcacaaagg   4380
aactggggat atggaaatgg gaacataact taaatccaga aaagtgaatc agattccctg   4440
tgaggacaaa atgcaatatt tagaaatagg atctttaggc tgggagggag aaaagaggaa   4500
aaaaatgaaa gtataacatt tttcataagt ataagatttc ataaaaaaat gaaatctata   4560
acatagaggg tgttgataaa gtaagcatgg atatgtttag taaagccgac agagctaaga   4620
attagctttg tgagtaattg gacttaatca aacttttcaa ggtgggatac aaatgaataa   4680
ttgtagaata aatggataaa agaatatgaa taaaatgaat agtgagtaaa aattaaaaat   4740
```

```
gaagcttttt acttaagtgc atattgtagt ggctagaaca aatagattca aaatagaaat   4800

catttatata ttcttgatta gaagataaaa tgttatttta gaaatagcca tctttggaag   4860

taaatttgct atgttgaaca accaggtttt cataatttgt ctcttatttt ttttcaggaa   4920

gaaaaaaaaa cttgacttat ttgtactgct aagttttatt caatgtgctt gcttgcttaa   4980

atttttaatg aagttttagt catttggtgg tcaaattcct tttatctact aatcgctttt   5040

cgtggctttg gcttttaaaa ttgtatttac tgcatttatt tgtgtgtatt aggagtcagg   5100

tggccatatg tgccatggca tgtgtatgga agcacttgtg gacatgaatc ttctctttcc   5160

acatgtgtgg gccactggaa tcaaactagt gtcaggcttg gcagcaattt ttaatgcact   5220

gagccttctc accacccct ggacttttgt ggggcagaag ggacaagtt taatatttta   5280

tttactccat gtagaaagcc tttaaaaaat gtagaaagcc tttaaactac ctattgtttt   5340

atttgaatta tgaagctctt gtgtttatat aaattacagt taggtactgt ggagactaat   5400

ggtagctaca atagtaatat taatagctaa aacttagtag aatctgattg agttaatttg   5460

gccctttcca tcataaggta ctcttcccaa gcatcacatg acctgtgctt aagtctggtg   5520

ggggcttatg gctttgatat tgaaaacaaa tcgtcaagga tgttaatttc ttgttactgc   5580

tattacactg aattttctat ggctctttag gagaggaaga gacaagtctt cttttggcag   5640

gtgttactaa gtaggccatt tcccaaggaa cagggaattt gccaggcttt tgtggtggag   5700

agaatagaat gaataaatgc tgtggggagt aaagagcttg tcagaagatg attagttctg   5760

tggcaccaaa accaagagat cagttttcct gtgagaagta aaggaagcat tgtagaaaaa   5820

tagatgtgtt gaagtct                                                  5837
```

```
<210> SEQ ID NO 13
<211> LENGTH: 280
<212> TYPE: DNA
<213> ORGANISM: Artificial Sequence
<220> FEATURE:
<223> OTHER INFORMATION: Beta-globin polyA

<400> SEQUENCE: 13

tgccctggcc cacaagtatc actaagctcg ctttcttgct gtccaatttc tattaaaggt     60

tcctttgttc cctaagtcca actactaaac tgggggatat tatgaagggc cttgagcatc    120

tggattctgc ctaataaaaa acatttattt tcattgcaat gatgtattta aattatttct    180

gaatatttta ctaaaaaggg aatgtgggag gtcagtgcat ttaaaacata aagaaatgaa    240

gagctagttc aaaccttggg aaaatacact atatcttaaa                          280
```

```
<210> SEQ ID NO 14
<211> LENGTH: 222
<212> TYPE: DNA
<213> ORGANISM: Artificial Sequence
<220> FEATURE:
<223> OTHER INFORMATION: SV40 late polyA

<400> SEQUENCE: 14

cagacatgat aagatacatt gatgagtttg gacaaaccac aactagaatg cagtgaaaaa     60

aatgctttat ttgtgaaatt tgtgatgcta ttgctttatt tgtaaccatt ataagctgca    120

ataaacaagt taacaacaac aattgcattc attttatgtt tcaggttcag ggggaggtgt    180

gggaggtttt ttaaagcaag taaaacctct acaaatgtgg ta                       222
```

```
<210> SEQ ID NO 15
```

```
<211> LENGTH: 197
<212> TYPE: DNA
<213> ORGANISM: Artificial Sequence
<220> FEATURE:
<223> OTHER INFORMATION: SV40 promoter

<400> SEQUENCE: 15

tgcatctcaa ttagtcagca accatagtcc cgcccctaac tccgcccatc cgcccctaa      60

ctccgcccag ttccgcccat tctccgcccc atcgctgact aatttttttt atttatgcag    120

aggccgaggc cgcctcggcc tctgagctat tccagaagta gtgaggaggc ttttttggag    180

gcctaggctt ttgcaaa                                                    197

<210> SEQ ID NO 16
<211> LENGTH: 538
<212> TYPE: DNA
<213> ORGANISM: Artificial Sequence
<220> FEATURE:
<223> OTHER INFORMATION: human CMV immediate-early enhancer/promoter

<400> SEQUENCE: 16

ggagttccgc gttacataac ttacggtaaa tggcccgcct ggctgaccgc ccaacgaccc     60

ccgcccattg acgtcaataa tgacgtatgt tcccatagta acgccaatag ggactttcca   120

ttgacgtcaa tgggtggagt atttacggta aactgcccac ttggcagtac atcaagtgta   180

tcatatgcca agtacgcccc ctattgacgt caatgacggt aaatggcccg cctggcatta   240

tgcccagtac atgaccttat gggactttcc tacttggcag tacatctacg tattagtcat   300

cgctattacc atggtgatgc ggttttggca gtacatcaat gggcgtggat agcggtttga   360

ctcacgggga tttccaagtc tccaccccat tgacgtcaat gggagtttgt tttggcacca   420

aaatcaacgg gactttccaa aatgtcgtaa caactccgcc ccattgacgc aaatgggcgg   480

taggcgtgta cggtgggagg tctatataag cagagctcgt ttagtgaacc gtcagatc     538

<210> SEQ ID NO 17
<211> LENGTH: 366
<212> TYPE: DNA
<213> ORGANISM: Artificial Sequence
<220> FEATURE:
<223> OTHER INFORMATION: TPL

<400> SEQUENCE: 17

ctcttccgca tcgctgtctg cgagggccag ctgttggggt gagtactccc tctcaaaagc     60

gggcatgact tctgcgctaa gattgtcagt ttccaaaaac gaggaggatt tgatattcac   120

ctggcccgcg gtgatgcctt tgagggtggc cgcgtccatc tggtcagaaa agacaatctt   180

tttgttgtca agcttccttg atgatgtcat acttatcctg tccctttttt ttccacagct   240

cgcggttgag gacaaactct tcgcggtctt tccagtactc ttggatcgga aacccgtcgg   300

cctccgaacg gtactccgcc accgagggac ctgagcgagt ccgcatcgac cggatcggaa   360

aacctc                                                               366

<210> SEQ ID NO 18
<211> LENGTH: 528
<212> TYPE: DNA
<213> ORGANISM: Artificial Sequence
<220> FEATURE:
<223> OTHER INFORMATION: Human CMV promoter, derived from GenBank
      X17403.1

<400> SEQUENCE: 18
```

```
gttacataac ttacggtaaa tggcccgcct ggctgaccgc ccaacgaccc ccgcccattg     60

acgtcaataa tgacgtatgt tcccatagta acgccaatag ggactttcca ttgacgtcaa    120

tgggtggagt atttacggta aactgcccac ttggcagtac atcaagtgta tcatatgcca    180

agtacgcccc ctattgacgt caatgacggt aaatggcccg cctggcatta tgcccagtac    240

atgaccttat gggactttcc tacttggcag tacatctacg tattagtcat cgctattacc    300

atggtgatgc ggttttggca gtacatcaat gggcgtggat agcggtttga ctcacgggga    360

tttccaagtc tccaccccat tgacgtcaat gggagtttgt tttggcacca aaatcaacgg    420

gactttccaa aatgtcgtaa caactccgcc ccattgacgc aaatgggcgg taggcgtgta    480

cggtgggagg tctatataag cagagctcgt ttagtgaacc gtcagatc                528
```

```
<210> SEQ ID NO 19
<211> LENGTH: 589
<212> TYPE: DNA
<213> ORGANISM: Artificial Sequence
<220> FEATURE:
<223> OTHER INFORMATION: Bacterial replication origin

<400> SEQUENCE: 19

tttccatagg ctccgccccc ctgacgagca tcacaaaaat cgacgctcaa gtcagaggtg     60

gcgaaacccg acaggactat aaagatacca ggcgtttccc cctggaagct ccctcgtgcg    120

ctctcctgtt ccgaccctgc cgcttaccgg atacctgtcc gcctttctcc cttcgggaag    180

cgtggcgctt tctcatagct cacgctgtag gtatctcagt tcggtgtagg tcgttcgctc    240

caagctgggc tgtgtgcacg aaccccccgt tcagcccgac cgctgcgcct tatccggtaa    300

ctatcgtctt gagtccaacc cggtaagaca cgacttatcg ccactggcag cagccactgg    360

taacaggatt agcagagcga ggtatgtagg cggtgctaca gagttcttga agtggtggcc    420

taactacggc tacactagaa ggacagtatt tggtatctgc gctctgctga agccagttac    480

cttcggaaaa agagttggta gctcttgatc cggcaaacaa accaccgctg gtagcggtgg    540

tttttttgtt tgcaagcagc agattacgcg cagaaaaaaa ggatctcaa               589
```

```
<210> SEQ ID NO 20
<211> LENGTH: 861
<212> TYPE: DNA
<213> ORGANISM: Artificial Sequence
<220> FEATURE:
<223> OTHER INFORMATION: Ampicillin resistance gene

<400> SEQUENCE: 20

ttaccaatgc ttaatcagtg aggcacctat ctcagcgatc tgtctatttc gttcatccat     60

agttgcctga ctccccgtcg tgtagataac tacgatacgg gagggcttac catctggccc    120

cagtgctgca atgataccgc gagacccacg ctcaccggct ccagatttat cagcaataaa    180

ccagccagcc ggaagggccg agcgcagaag tggtcctgca actttatccg cctccatcca    240

gtctattaat tgttgccggg aagctagagt aagtagttcg ccagttaata gtttgcgcaa    300

cgttgttgcc attgctacag gcatcgtggt gtcacgctcg tcgtttggta tggcttcatt    360

cagctccggt tcccaacgat caaggcgagt tacatgatcc cccatgttgt gcaaaaaagc    420

ggttagctcc ttcggtcctc cgatcgttgt cagaagtaag ttggccgcag tgttatcact    480

catggttatg gcagcactgc ataattctct tactgtcatg ccatccgtaa gatgcttttc    540

tgtgactggt gagtactcaa ccaagtcatt ctgagaatag tgtatgcggc gaccgagttg    600

ctcttgcccg gcgtcaatac gggataatac cgcgccacat agcagaactt taaaagtgct    660
```

```
catcattgga aaacgttctt cggggcgaaa actctcaagg atcttaccgc tgttgagatc    720

cagttcgatg taacccactc gtgcacccaa ctgatcttca gcatctttta ctttcaccag    780

cgtttctggg tgagcaaaaa caggaaggca aaatgccgca aaaaagggaa taagggcgac    840

acggaaatgt tgaatactca t                                              861


<210> SEQ ID NO 21
<211> LENGTH: 1122
<212> TYPE: DNA
<213> ORGANISM: Artificial Sequence
<220> FEATURE:
<223> OTHER INFORMATION: GS gene

<400> SEQUENCE: 21

atggccacct cagcaagttc ccacttgaac aaaaacatca agcaaatgta cttgtgcctg     60

ccccagggtg agaaagtcca agccatgtat atctgggttg atggtactgg agaaggactg    120

cgctgcaaaa cccgcaccct ggactgtgag cccaagtgtg tagaagagtt acctgagtgg    180

aattttgatg gctctagtac ctttcagtct gagggctcca acagtgacat gtatctcagc    240

cctgttgcca tgtttcggga ccccttccgc agagatccca acaagctggt gttctgtgaa    300

gttttcaagt acaaccggaa gcctgcagag accaatttaa ggcactcgtg taaacggata    360

atggacatgg tgagcaacca gcacccctgg tttggaatgg aacaggagta tactctgatg    420

ggaacagatg ggcacccttt tggttggcct tccaatggct ttcctgggcc ccaaggtccg    480

tattactgtg gtgtgggcgc agacaaagcc tatggcaggg atatcgtgga ggctcactac    540

cgcgcctgct tgtatgctgg ggtcaagatt acaggaacaa atgctgaggt catgcctgcc    600

cagtgggagt tccaaatagg accctgtgaa ggaatccgca tgggagatca tctctgggtg    660

gcccgtttca tcttgcatcg agtatgtgaa gactttgggg taatagcaac ctttgacccc    720

aagcccattc ctgggaactg gaatggtgca ggctgccata ccaactttag caccaaggcc    780

atgcgggagg agaatggtct gaagcacatc gaggaggcca tcgagaaact aagcaagcgg    840

caccggtacc acattcgagc ctacgatccc aagggggggcc tggacaatgc ccgtcgtctg    900

actgggttcc acgaaacgtc caacatcaac gacttttctg ctggtgtcgc caatcgcagt    960

gccagcatcc gcattccccg gactgtcggc caggagaaga aaggttactt tgaagaccgc   1020

cgcccctctg ccaattgtga ccccttttgca gtgacagaag ccatcgtccg cacatgcctt   1080

ctcaatgaga ctggcgacga gcccttccaa tacaaaaact aa                      1122


<210> SEQ ID NO 22
<211> LENGTH: 237
<212> TYPE: DNA
<213> ORGANISM: Artificial Sequence
<220> FEATURE:
<223> OTHER INFORMATION: SV40 enhancer

<400> SEQUENCE: 22

gctgtggaat gtgtgtcagt tagggtgtgg aaagtcccca ggctccccag caggcagaag     60

tatgcaaagc atgcatctca attagtcagc aaccaggtgt ggaaagtccc caggctcccc    120

agcaggcaga agtatgcaaa gcatgcatct caattagtca gcaaccatag tcccgcccct    180

aactccgccc atcccgcccc taactccgcc cagttccgcc cattctccgc tccatcg      237


<210> SEQ ID NO 23
<211> LENGTH: 570
<212> TYPE: DNA
```

<213> ORGANISM: Artificial Sequence
<220> FEATURE:
<223> OTHER INFORMATION: IRES-4

<400> SEQUENCE: 23
cccctaacgt tactggccga agccgcttgg aataaggccg gtgtgcgttt gtctatatgt 60
tattttccac catattgccg tcttttggca atgtgagggc ccggaaacct ggccctgtct 120
tcttgacgag cattcctagg ggtctttccc ctctcgccaa aggaatgcaa ggtctgttga 180
atgtcgtgaa ggaagcagtt cctctggaag cttcttgaag acaaacaacg tctgtagcga 240
ccctttgcag gcagcggaac cccccacctg gcgacaggtg cctctgcggc caaaagccac 300
gtgtataaga tacacctgca aaggcggcac aaccccagtg ccacgttgtg agttggatag 360
ttgtggaaag agtcaaatgg ctctcctcaa gcgtattcaa caaggggctg aaggatgccc 420
agaaggtacc ccattgtatg ggatctgatc tggggcctcg gtgcacatgc tttacatgtg 480
tttagtcgag gttaaaaaaa cgtctaggcc ccccgaacca cggggacgtg gttttccttt 540
gaaaaacacg atgataatat ggccacaacc 570

<210> SEQ ID NO 24
<211> LENGTH: 557
<212> TYPE: DNA
<213> ORGANISM: Artificial Sequence
<220> FEATURE:
<223> OTHER INFORMATION: IRES-5

<400> SEQUENCE: 24
cccctaacgt tactggccga agccgcttgg aataaggccg gtgtgcgttt gtctatatgt 60
tattttccac catattgccg tcttttggca atgtgagggc ccggaaacct ggccctgtct 120
tcttgacgag cattcctagg ggtctttccc ctctcgccaa aggaatgcaa ggtctgttga 180
atgtcgtgaa ggaagcagtt cctctggaag cttcttgaag acaaacaacg tctgtagcga 240
ccctttgcag gcagcggaac cccccacctg gcgacaggtg cctctgcggc caaaagccac 300
gtgtataaga tacacctgca aaggcggcac aaccccagtg ccacgttgtg agttggatag 360
ttgtggaaag agtcaaatgg ctctcctcaa gcgtattcaa caaggggctg aaggatgccc 420
agaaggtacc ccattgtatg ggatctgatc tggggcctcg gtgcacatgc tttacatgtg 480
tttagtcgag gttaaaaaaa cgtctaggcc ccccgaacca cggggacgtg gttttccttt 540
gaaaaacacg atgataa 557

<210> SEQ ID NO 25
<211> LENGTH: 550
<212> TYPE: DNA
<213> ORGANISM: Artificial Sequence
<220> FEATURE:
<223> OTHER INFORMATION: IRES-6

<400> SEQUENCE: 25
cccctaacgt tactggccga agccgcttgg aataaggccg gtgtgcgttt gtctatatgt 60
tattttccac catattgccg tcttttggca atgtgagggc ccggaaacct ggccctgtct 120
tcttgacgag cattcctagg ggtctttccc ctctcgccaa aggaatgcaa ggtctgttga 180
atgtcgtgaa ggaagcagtt cctctggaag cttcttgaag acaaacaacg tctgtagcga 240
ccctttgcag gcagcggaac cccccacctg gcgacaggtg cctctgcggc caaaagccac 300
gtgtataaga tacacctgca aaggcggcac aaccccagtg ccacgttgtg agttggatag 360
ttgtggaaag agtcaaatgg ctctcctcaa gcgtattcaa caaggggctg aaggatgccc 420
agaaggtacc ccattgtatg ggatctgatc tggggcctcg gtgcacatgc tttacatgtg 480
tttagtcgag gttaaaaaaa cgtctaggcc ccccgaacca cggggacgtg gttttccttt 540
gaaaaacacg 550

<210> SEQ ID NO 26
<211> LENGTH: 10754
<212> TYPE: DNA
<213> ORGANISM: Artificial Sequence
<220> FEATURE:
<223> OTHER INFORMATION: pCLD13

<400> SEQUENCE: 26
ccctagaaag ataatcatat tgtgacgtac gttaaagata atcatgcgta aaattgacgc 60
atgtgtttta tcggtctgta tatcgaggtt tatttattaa tttgaataga tattaagttt 120
tattatattt acacttacat actaataata aattcaacaa acaatttatt tatgtttatt 180
tatttattaa aaaaaaacaa aaactcaaaa tttcttctat aaagtaacaa aacttttatc 240
gaatttgcag cccgggacta gctagaggga cagcccccc ccaaagcccc cagggatgta 300
attacgtccc tcccccgcta gggggcagca gcgagccgcc cggggctccg ctccggtccg 360
gcgctccccc cgcatccccg agccggcagc gtgcggggac agcccgggca cggggaaggt 420
ggcacgggat cgctttcctc tgaacgcttc tcgctgctct ttgagcctgc agacacctgg 480
ggggatacgg ggaaaactta agatccgacc ggacgcgtac tgagagcgct attctgaact 540
tttcttttgt tcccttccct tctaccacac cctaattgta atccatttta atttcctggt 600
cacagtcctg tctctccttc cattgtacct tgccctttc taaagagcga ctgcaaagta 660
tgtttgcgta ggtgaggatc taaaacttta tgaggtacga acatcacaga attactttgt 720
aatttcagtt tattgtaggc ttggcttttt ggggagggtt tacgtcttag acctcttagt 780
gcttctttgt ttcatggtgt tctaacttcg aagcatctct gtagctttaa tggattcctt 840
ttctgaaagc tttgctctct ttcttccccc tcggctttct cttaggcaag agggctaact 900
gtaaagtaag gcttactgcc ttgtgtttcc aaatgtgtcc gaagaggaag tgtcttctgt 960
gaatcctgtt atgcatgaat aacaggaaat agaaagaaat tcactttcat tattataaaa 1020
gtaatatgtt cgtttaaaaa attctaatga agagctggag atgcaaccca ggggtagagc 1080
acacactcag catgcaggag gccctgggtc caatcttgga atctcctctc agttaacctg 1140
atctctagct gattagtagt gagtgcaagc ccactttcct cttctgcctc attgctcagt 1200
gataacagct gttaaacttt gtcttattct aaaactacct ctgtgcaaat gctagcacaa 1260
taatatatat catatgcaca tgattttttt tttatcttga aaagtaagtc agtatagcta 1320
caaagttcac ttggcattgt caacatttca caggcgtaat attcctcctc tagtactgtc 1380
ctcttcattc tttgtgacca agtttggaga gagtgcacaa atgccaggga ggtttgtggg 1440
aaggtttctc atgttctggt aaggcgagta agaaaatagt ctcatgcagg tgaaatgagt 1500
gctatgcagt atatattata ccagagaaca gcaaatgacc aaattcacac tgaactagtt 1560
cagtaaaatt ggctttgtca aagctttcct tgcttaaaat gtaattccct gtcatcctag 1620
ttctggtctg gattcttttc ctggagtctt gacttccaga ttccctgtgg acttttgttt 1680
gagtttcaag cttttgaaat atagaaacct atctaactta acaaacttgg gagagaaaag 1740
actccagaac aactgaaaac agaccaggct aaatgaatag actttattcc tctcttctta 1800
cctgcagttt tcagatatgc agagttggag cggatcttag aggttgattc attcatgcct 1860
gaagaaaaca cattttatag accctgtgcc caagttcgtg gtggacatca ccctttattt 1920
actaattgca ctacataaca ggcattttag aagactgctc cagtcagaga ccccgcctta 1980
gaggaatctg taaaccctga actcctatca ctcatgagca ctagttatgt ttggaatgcc 2040
gtattaaaac aaaagttaca tttctaaact taaaattttc tagcacagag acagtgggag 2100
tagctaactt tgatagacat ttttctacta aaagtctttc taagtacata atcttctgta 2160
agttggaaaa cagcaaaata gaacgtctcc tacgtagtta atctttttgc ataatttgca 2220
catgtaggag ttattagtat acgggtaagt tttcactttt tcccccaact ggagtgtctt 2280
gtggctgggt ttgaaaaagg gaacgggagg ccgctggagg ggattggtaa atgagataaa 2340
acaccactca ttcaactcag tgactcagca tttaaatttt ccataaaagg attaaaggaa 2400
aattaaacaa attcttaaag ccaagactct ggagaaactt gttggtgtgc tttagttttc 2460
actgttatga ctcatgaatt tatgcataaa ttagtacatt tataaaaaca tagccttttt 2520
agagttttct gtttggctaa agtgccattg ttagcatttg gaattacctt tttatgtctt 2580
atatttttc caaataaaaa taaatgtttc tgctgtctta ctactgaaac tacgttgtga 2640
gcactttaaa tttctcaaag cagtttcgcc tgttatactt ggcgcttagt catcgtcgta 2700
cacaacagga cctgattaag aaggctgtgc tgcctctaag ccgggctaga ttgtagccac 2760
tagcaaccag gctgcaataa tttccctttg atgacatcat ccactgtgga agaacccagt 2820
tgcttcagcc agtcgaacta tacagttcca acctcatcaa atatggcatc tcccttgcct 2880
gctatagcag gggaggaaa aaatgccacc atctttttaa tctagcaagc ttctcttttc 2940
ttcatctttt ttttttctt ttaaaaaaat tctgatcatg gatgcttctt ccgatcccta 3000
tttgccttat gacgggggag gagacaatat ccccttgagg gaattacata aaagaggtaa 3060
gagcatcccc ttgctctgaa tcctctgttg gttgttgtgc atgcggctgg gcggttctgg 3120
ggacaggctg tctgttgtcc tcttgctgca atgtgctgct tagttgccct gccttgttgc 3180
tgtgggagaa tgcgaccttc ccagcagggc tggccctccc tgattgtttg ctctgtgcag 3240
attagccctg cttcagatca catagggctg cagactccat cttctgtgtg aaaatgcttt 3300
cggtttgatt gcagaaataa gctgccttta cagccagcta aagtcctggt ggttggttgg 3360
cacctgcaaa gtagtatttt tgtacctctg gaaacttata ttttctttac acagcaatat 3420
caagtgccgg tatgccattc tgttttggct gctgccaatt accatgtaga ctttgcacca 3480
cagagtaata gtaaaagctc ctagctgcat tttataacat ttaaaaatag caggaaagaa 3540
gaattatttt tgatttaaca tgtttttgtc atttaacgtc ttaactgatt gacatactat 3600
attgtctgtc tcgtgggtat cttgtacaac ttgataggat aaagcaattt agttttttt 3660
ttttttttta aatacatcca gaatgtaagt cgtcagtagt tttcgaacag ataagtaatg 3720
gtgttaatct tttggcaggc tttgccttgg tctccttaaa gctaattagg tgttacttaa 3780
ttaaactgct cttttgctca ttttcttaaa ttattttttt aaaagatagt tggcatttgc 3840
tgttctagaa ataaacttca agaaacattc tttagccaga tgacttcatg tatgagccat 3900
gttagtttga attatttgct tggtgttata aactttatgg tttaatacca acttttatta 3960
tgtttacaag gtaaataagg aaaatttcaa gtacattttg tatcctgaga acaaatttaa 4020
gttccataga atttaggaat tacaatgtat tcaacagata cttacttgtc atactgtgcc 4080
tgcaaaacaa taattagact ctgaacaggt gcaacaattt tctgtagaat tagacaagtc 4140
ttcttttggc aggtgttact aagtaggcca tttcccaagg aacagggaat ttgccaggct 4200
tttgtggtgg agagaataga atgaataaat gctgtgggga gtaaagagct tgtcagaaga 4260
tgattagttc tgtggcacca aaaccaagag atcagttttc ctgtgagaag taaaggaagc 4320
attgtagaaa aatagatgtg ttgaagtcta ccggtggagt tccgcgttac ataacttacg 4380
gtaaatggcc cgcctggctg accgcccaac gacccccgcc cattgacgtc aataatgacg 4440
tatgttccca tagtaacgcc aatagggact ttccattgac gtcaatgggt ggagtattta 4500
cggtaaactg cccacttggc agtacatcaa gtgtatcata tgccaagtac gccccctatt 4560
gacgtcaatg acggtaaatg gcccgcctgg cattatgccc agtacatgac cttatgggac 4620
tttcctactt ggcagtacat ctacgtatta gtcatcgcta ttaccattgt gatgcggttt 4680
tggcagtaca tcaatgggcg tggatagcgg tttgactcac ggggatttcc aagtctccac 4740
cccattgacg tcaatgggag tttgttttgg caccaaaatc aacgggactt tccaaaatgt 4800
cgtaacaact ccgccccatt gacgcaaatg ggcggtaggc gtgtacggtg ggaggtctat 4860
ataagcagag ctcgtttagt gaaccgtcag atctacctct tccgcatcgc tgtctgcgag 4920
ggccagctgt tggggtgagt actccctctc aaaagcgggc atgacttctg cgctaagatt 4980
gtcagtttcc aaaaacgagg aggatttgat attcacctgg cccgcggtga tgcctttgag 5040
ggtggccgcg tccatctggt cagaaaagac aatctttttg ttgtcaagct tccttgatga 5100
tgtcatactt atcctgtccc tttttttcc acagctcgcg gttgaggaca aactcttcgc 5160
ggtctttcca gtactcttgg atcggaaacc cgtcggcctc cgaacggtac tccgccaccg 5220
agggacctga gcgagtccgc atcgaccgga tcggaaaacc tcggatccga attcatagat 5280
aactgatcca gtgcccctaa cgttactggc cgaagccgct tggaataagg ccggtgtgcg 5340
tttgtctata tgttattttc caccatattg ccgtcttttg gcaatgtgag ggcccggaaa 5400
cctggccctg tcttcttgac gagcattcct aggggtcttt cccctctcgc caaaggaatg 5460
caaggtctgt tgaatgtcgt gaaggaagca gttcctctgg aagcttcttg aagacaaaca 5520
acgtctgtag cgaccctttg caggcagcgg aaccccccac ctggcgacag gtgcctctgc 5580
ggccaaaagc cacgtgtata agatacacct gcaaaggcgg cacaacccca gtgccacgtt 5640
gtgagttgga tagttgtgga aagagtcaaa tggctctcct caagcgtatt caacaagggg 5700
ctgaaggatg cccagaaggt accccattgt atgggatctg atctggggcc tcggtgcaca 5760
tgctttacat gtgtttagtc gaggttaaaa aacgtctagg ccccccgaac cacggggacg 5820
tggttttcct ttgaaaaaca cgatgataaa tggccacctc agcaagttcc cacttgaaca 5880
aaaacatcaa gcaaatgtac ttgtgcctgc cccagggtga gaaagtccaa gccatgtata 5940
tctgggttga tggtactgga gaaggactgc gctgcaaaac ccgcaccctg gactgtgagc 6000
ccaagtgtgt agaagagtta cctgagtgga attttgatgg ctctagtacc tttcagtctg 6060
agggctccaa cagtgacatg tatctcagcc ctgttgccat gtttcgggac cccttccgca 6120
gagatcccaa caagctggtg ttctgtgaag ttttcaagta caaccggaag cctgcagaga 6180
ccaatttaag gcactcgtgt aaacggataa tggacatggt gagcaaccag cacccctggt 6240
ttggaatgga acaggagtat actctgatgg gaacagatgg gcaccctttt ggttggcctt 6300
ccaatggctt tcctgggccc caaggtccgt attactgtgg tgtgggcgca gacaaagcct 6360
atggcaggga tatcgtggag gctcactacc gcgcctgctt gtatgctggg gtcaagatta 6420
caggaacaaa tgctgaggtc atgcctgccc agtgggagtt ccaaatagga ccctgtgaag 6480
gaatccgcat gggagatcat ctctgggtgg cccgtttcat cttgcatcga gtatgtgaag 6540
actttggggt aatagcaacc tttgacccca agcccattcc tgggaactgg aatggtgcag 6600

-continued gctgccatac caactttagc accaaggcca tgcgggagga gaatggtctg aagcacatcg 6660
aggaggccat cgagaaacta agcaagcggc accggtacca cattcgagcc tacgatccca 6720
aggggggcct ggacaatgcc cgtcgtctga ctgggttcca cgaaacgtcc aacatcaacg 6780
acttttctgc tggtgtcgcc aatcgcagtg ccagcatccg cattccccgg actgtcggcc 6840
aggagaagaa aggttacttt gaagaccgcc gcccctctgc caattgtgac ccctttgcag 6900
tgacagaagc catcgtccgc acatgccttc tcaatgagac tggcgacgag cccttccaat 6960
acaaaaacta atctagatcc ccctcgcttt cttgctgtcc aatttctatt aaaggttcct 7020
ttgttcccta agtccaacta ctaaactggg ggatattatg aagggccttg agcatctgga 7080
ttctgcctaa taaaaaacat ttattttcat tgcaatgatg tatttaaatt atttctgaat 7140
attttactaa aaagggaatg tgggaggtca gtgcatttaa aacataaaga aatgaagagg 7200
gggatcttcg cgatactgca tcgatgaggg acagcccccc cccaaagccc ccagggatgt 7260
aattacgtcc ctcccccgct agggggcagc agcgagccgc ccggggctcc gctccggtcc 7320
ggcgctcccc ccgcatcccc gagccggcag cgtgcgggga cagcccgggc acggggaagg 7380
tggcacggga tcgctttcct ctgaacgctt ctcgctgctc tttgagcctg cagacacctg 7440
gggggatacg gggaaaatag acaccgcggt ggagctccag cttttgttcc ctttagtgag 7500
ggttaattag ttcttaatac gactcactat agggcgaatt ggctaccggg ccgcccatcg 7560
agggtatcat aagcttatat ctataacaag aaaatatata tataataagt tatcacgtaa 7620
gtagaacatg aaataacaat ataattatcg tatgagttaa atcttaaaag tcacgtaaaa 7680
gataatcatg cgtcattttg actcacgcgg tcgttatagt tcaaaatcag tgacacttac 7740
cgcattgaca agcacgcctc acgggagctc caagcggcga ctgagatgtc ctaaatgcac 7800
agcgacggat tcgcgctatt tagaaagaga gagcaatatt tcaagaatgc atgcgtcaat 7860
tttacgcaga ctatctttct agggttaaat cgatagatgc gatcctgcag gtctccctat 7920
agtgagtcgt attaatttcg ataagccagc tgcattaatg aatcggccaa cgcgcgggga 7980
gaggcggttt gcgtattggg cgctcttccg cttcctcgct cactgactcg ctgcgctcgg 8040
tcgttcggct gcggcgagcg gtatcagctc actcaaaggc ggtaatacgg ttatccacag 8100
aatcagggga taacgcagga aagaacatgt gagcaaaagg ccagcaaaag gccaggaacc 8160
gtaaaaaggc cgcgttgctg gcgtttttcc ataggctccg cccccctgac gagcatcaca 8220
aaaatcgacg ctcaagtcag aggtggcgaa acccgacagg actataaaga taccaggcgt 8280
ttccccctgg aagctccctc gtgcgctctc ctgttccgac cctgccgctt accggatacc 8340
tgtccgcctt tctcccttcg ggaagcgtgg cgctttctca tagctcacgc tgtaggtatc 8400
tcagttcggt gtaggtcgtt cgctccaagc tgggctgtgt gcacgaaccc cccgttcagc 8460
ccgaccgctg cgccttatcc ggtaactatc gtcttgagtc caacccggta agacacgact 8520
tatcgccact ggcagcagcc actggtaaca ggattagcag agcgaggtat gtaggcggtg 8580
ctacagagtt cttgaagtgg tggcctaact acggctacac tagaaggaca gtatttggta 8640
tctgcgctct gctgaagcca gttaccttcg gaaaaagagt tggtagctct tgatccggca 8700
aacaaaccac cgctggtagc ggtggttttt ttgtttgcaa gcagcagatt acgcgcagaa 8760
aaaaaggatc tcaagaagat cctttgatct tttctacggg gtctgacgct cagtggaacg 8820
aaaactcacg ttaagggatt ttggtcatga gattatcaaa aaggatcttc acctagatcc 8880
ttttaaatta aaaatgaagt tttaaatcaa tctaaagtat atatgagtaa acttggtctg 8940
acagttacca atgcttaatc agtgaggcac ctatctcagc gatctgtcta tttcgttcat 9000

```
ccatagttgc ctgactcccc gtcgtgtaga taactacgat acgggagggc ttaccatctg   9060

gccccagtgc tgcaatgata ccgcgagacc cacgctcacc ggctccagat ttatcagcaa   9120

taaaccagcc agccggaagg gccgagcgca gaagtggtcc tgcaacttta tccgcctcca   9180

tccagtctat taattgttgc cgggaagcta gagtaagtag ttcgccagtt aatagtttgc   9240

gcaacgttgt tgccattgct acaggcatcg tggtgtcacg ctcgtcgttt ggtatggctt   9300

cattcagctc cggttcccaa cgatcaaggc gagttacatg atcccccatg ttgtgcaaaa   9360

aagcggttag ctccttcggt cctccgatcg ttgtcagaag taagttggcc gcagtgttat   9420

cactcatggt tatggcagca ctgcataatt ctcttactgt catgccatcc gtaagatgct   9480

tttctgtgac tggtgagtac tcaaccaagt cattctgaga atagtgtatg cggcgaccga   9540

gttgctcttg cccggcgtca atacgggata ataccgcgcc acatagcaga actttaaaag   9600

tgctcatcat tggaaaacgt tcttcggggc gaaaactctc aaggatctta ccgctgttga   9660

gatccagttc gatgtaaccc actcgtgcac ccaactgatc ttcagcatct tttactttca   9720

ccagcgtttc tgggtgagca aaaacaggaa ggcaaaatgc cgcaaaaaag ggaataaggg   9780

cgacacggaa atgttgaata ctcatactct tcctttttca atattattga agcatttatc   9840

agggttattg tctcatgagc ggatacatat ttgaatgtat ttagaaaaat aaacaaatag   9900

gggttccgcg cacatttccc cgaaaagtgc cacctgacgt ctaagaaacc attattatca   9960

tgacattaac ctataaaaat aggcgtatca cgaggccctt tcgtctcgcg cgtttcggtg  10020

atgacggtga aaacctctga cacatgcagc tcccggagac ggtcacagct tgtctgtaag  10080

cggatgccgg gagcagacaa gcccgtcagg gcgcgtcagc gggtgttggc gggtgtcggg  10140

gctggcttaa ctatgcggca tcagagcaga ttgtactgag agtgcaccat atcgacgctc  10200

tcccttatgc gactcctgca ttaggaagca gcccagtagt aggttgaggc cgttgagcac  10260

cgccgccgca aggaatggtg catgcaagga gatggcgccc aacagtcccc cggccacggg  10320

gcctgccacc atacccacgc cgaaacaagc gctcatgagc ccgaagtggc gagcccgatc  10380

ttccccatcg gtgatgtcgg cgatataggc gccagcaacc gcacctgtgg cgccggtgat  10440

gccggccacg atgcgtccgg cgtagaggat ctggctagcg atgaccctgc tgattggttc  10500

gctgaccatt tccggggtgc ggaacggcgt taccagaaac tcagaaggtt cgtccaacca  10560

aaccgactct gacggcagtt tacgagagag atgatagggt ctgcttcagt aagccagatg  10620

ctacacaatt aggcttgtac atattgtcgt tagaacgcgg ctacaattaa tacataacct  10680

tatgtatcat acacatacga tttaggtgac actatagaat acacctgcag gacgtcccaa  10740

tgatcttaag ttaa                                                    10754
```

<210> SEQ ID NO 27
<211> LENGTH: 10768
<212> TYPE: DNA
<213> ORGANISM: Artificial Sequence
<220> FEATURE:
<223> OTHER INFORMATION: pCLD15

<400> SEQUENCE: 27

```
ccctagaaag ataatcatat tgtgacgtac gttaaagata atcatgcgta aaattgacgc     60

atgtgtttta tcggtctgta tatcgaggtt tatttattaa tttgaataga tattaagttt    120

tattatattt acacttacat actaataata aattcaacaa acaatttatt tatgtttatt    180

tatttattaa aaaaaaacaa aaactcaaaa tttcttctat aaagtaacaa aactttatc    240
```

-continued

```
gaatttgcag cccgggacta gctagaggga cagccccccc ccaaagcccc cagggatgta    300
attacgtccc tcccccgcta gggggcagca gcgagccgcc cggggctccg ctccggtccg    360
gcgctccccc cgcatccccg agccggcagc gtgcggggac agcccgggca cggggaaggt    420
ggcacgggat cgctttcctc tgaacgcttc tcgctgctct ttgagcctgc agacacctgg    480
ggggatacgg ggaaaactta agatccgacc ggacgcgtac tgagagcgct attctgaact    540
tttcttttgt tcccttccct tctaccacac cctaattgta atccatttta atttcctggt    600
cacagtcctg tctctccttc cattgtacct tgccctttc taaagagcga ctgcaaagta    660
tgtttgcgta ggtgaggatc taaaacttta tgaggtacga acatcacaga attactttgt    720
aatttcagtt tattgtaggc ttggcttttt ggggagggtt tacgtcttag acctcttagt    780
gcttctttgt ttcatggtgt tctaacttcg aagcatctct gtagctttaa tggattcctt    840
ttctgaaagc tttgctctct ttcttccccc tcggctttct cttaggcaag agggctaact    900
gtaaagtaag gcttactgcc ttgtgtttcc aaatgtgtcc gaagaggaag tgtcttctgt    960
gaatcctgtt atgcatgaat aacaggaaat agaaagaaat tcactttcat tattataaaa   1020
gtaatatgtt cgtttaaaaa attctaatga agagctggag atgcaaccca ggggtagagc   1080
acacactcag catgcaggag gccctgggtc caatcttgga atctcctctc agttaacctg   1140
atctctagct gattagtagt gagtgcaagc ccactttcct cttctgcctc attgctcagt   1200
gataacagct gttaaacttt gtcttattct aaaactacct ctgtgcaaat gctagcacaa   1260
taatatatat catatgcaca tgattttttt tttatcttga aaagtaagtc agtatagcta   1320
caaagttcac ttggcattgt caacatttca caggcgtaat attcctcctc tagtactgtc   1380
ctcttcattc tttgtgacca agtttggaga gagtgcacaa atgccaggga ggtttgtggg   1440
aaggtttctc atgttctggt aaggcgagta agaaaatagt ctcatgcagg tgaaatgagt   1500
gctatgcagt atatattata ccagagaaca gcaaatgacc aaattcacac tgaactagtt   1560
cagtaaaatt ggctttgtca aagctttcct tgcttaaaat gtaattccct gtcatcctag   1620
ttctggtctg gattcttttc ctggagtctt gacttccaga ttccctgtgg acttttgttt   1680
gagtttcaag cttttgaaat atagaaacct atctaactta acaaacttgg gagagaaaag   1740
actccagaac aactgaaaac agaccaggct aaatgaatag actttattcc tctcttctta   1800
cctgcagttt tcagatatgc agagttggag cggatcttag aggttgattc attcatgcct   1860
gaagaaaaca cattttatag accctgtgcc caagttcgtg gtggacatca ccctttattt   1920
actaattgca ctacataaca ggcattttag aagactgctc cagtcagaga ccccgcctta   1980
gaggaatctg taaaccctga actcctatca ctcatgagca ctagttatgt ttggaatgcc   2040
gtattaaaac aaaagttaca tttctaaact taaaatttc tagcacagag acagtgggag    2100
tagctaactt tgatagacat ttttctacta aaagtctttc taagtacata atcttctgta   2160
agttggaaaa cagcaaaata gaacgtctcc tacgtagtta atctttttgc ataatttgca   2220
catgtaggag ttattagtat acgggtaagt tttcactttt tcccccaact ggagtgtctt   2280
gtggctgggt ttgaaaaagg gaacgggagg ccgctggagg ggattggtaa atgagataaa   2340
acaccactca ttcaactcag tgactcagca tttaaatttt ccataaaagg attaaaggaa   2400
aattaaacaa attcttaaag ccaagactct ggagaaactt gttggtgtgc tttagttttc   2460
actgttatga ctcatgaatt tatgcataaa ttagtacatt tataaaaaca tagccttttt   2520
agagttttct gtttggctaa agtgccattg ttagcatttg gaattacctt tttatgtctt   2580
atattttttc caaataaaaa taaatgtttc tgctgtctta ctactgaaac tacgttgtga   2640
```

-continued gcactttaaa tttctcaaag cagtttcgcc tgttatactt ggcgcttagt catcgtcgta 2700
cacaacagga cctgattaag aaggctgtgc tgcctctaag ccgggctaga ttgtagccac 2760
tagcaaccag gctgcaataa tttccctttg atgacatcat ccactgtgga agaacccagt 2820
tgcttcagcc agtcgaacta tacagttcca acctcatcaa atatggcatc tcccttgcct 2880
gctatagcag gggaggaaa aaatgccacc atctttttaa tctagcaagc ttctcttttc 2940
ttcatctttt tttttttctt ttaaaaaaat tctgatcatg gatgcttctt ccgatcccta 3000
tttgccttat gacgggggag gagacaatat ccccttgagg gaattacata aaagaggtaa 3060
gagcatcccc ttgctctgaa tcctctgttg gttgttgtgc atgcggctgg gcggttctgg 3120
ggacaggctg tctgttgtcc tcttgctgca atgtgctgct tagttgccct gccttgttgc 3180
tgtgggagaa tgcgaccttc ccagcagggc tggccctccc tgattgtttg ctctgtgcag 3240
attagccctg cttcagatca catagggctg cagactccat cttctgtgtg aaaatgcttt 3300
cggtttgatt gcagaaataa gctgccttta cagccagcta aagtcctggt ggttggttgg 3360
cacctgcaaa gtagtatttt tgtacctctg gaaacttata ttttctttac acagcaatat 3420
caagtgccgg tatgccattc tgttttggct gctgccaatt accatgtaga ctttgcacca 3480
cagagtaata gtaaaagctc ctagctgcat tttataacat ttaaaaatag caggaaagaa 3540
gaattatttt tgatttaaca tgtttttgtc atttaacgtc ttaactgatt gacatactat 3600
attgtctgtc tcgtgggtat cttgtacaac ttgataggat aaagcaattt agttttttttt 3660 ttttttttta aatacatcca gaatgtaagt cgtcagtagt tttcgaacag ataagtaatg 3720
gtgttaatct tttggcaggc tttgccttgg tctccttaaa gctaattagg tgttacttaa 3780
ttaaactgct cttttgctca ttttcttaaa ttattttttt aaaagatagt tggcatttgc 3840
tgttctagaa ataaacttca agaaacattc tttagccaga tgacttcatg tatgagccat 3900
gttagtttga attatttgct tggtgttata aactttatgg tttaatacca acttttatta 3960
tgtttacaag gtaaataagg aaaatttcaa gtacattttg tatcctgaga acaaatttaa 4020
gttccataga atttaggaat tacaatgtat tcaacagata cttacttgtc atactgtgcc 4080
tgcaaaacaa taattagact ctgaacaggt gcaacaattt tctgtagaat tagacaagtc 4140
ttcttttggc aggtgttact aagtaggcca tttcccaagg aacagggaat ttgccaggct 4200
tttgtggtgg agagaataga atgaataaat gctgtgggga gtaaagagct tgtcagaaga 4260
tgattagttc tgtggcacca aaaccaagag atcagttttc ctgtgagaag taaaggaagc 4320
attgtagaaa aatagatgtg ttgaagtcta ccggtggagt tccgcgttac ataacttacg 4380
gtaaatggcc cgcctggctg accgcccaac gacccccgcc cattgacgtc aataatgacg 4440
tatgttccca tagtaacgcc aatagggact ttccattgac gtcaatgggt ggagtattta 4500
cggtaaactg cccacttggc agtacatcaa gtgtatcata tgccaagtac gccccctatt 4560
gacgtcaatg acggtaaatg gcccgcctgg cattatgccc agtacatgac cttatgggac 4620
tttcctactt ggcagtacat ctacgtatta gtcatcgcta ttaccattgt gatgcggttt 4680
tggcagtaca tcaatgggcg tggatagcgg tttgactcac ggggatttcc aagtctccac 4740
cccattgacg tcaatgggag tttgttttgg caccaaaatc aacgggactt tccaaaatgt 4800
cgtaacaact ccgccccatt gacgcaaatg ggcggtaggc gtgtacggtg ggaggtctat 4860
ataagcagag ctcgtttagt gaaccgtcag atctacctct tccgcatcgc tgtctgcgag 4920
ggccagctgt tggggtgagt actccctctc aaaagcgggc atgacttctg cgctaagatt 4980

-continued

```
gtcagtttcc aaaaacgagg aggatttgat attcacctgg cccgcggtga tgcctttgag   5040
ggtggccgcg tccatctggt cagaaaagac aatctttttg ttgtcaagct tccttgatga   5100
tgtcatactt atcctgtccc ttttttttcc acagctcgcg gttgaggaca aactcttcgc   5160
ggtctttcca gtactcttgg atcggaaacc cgtcggcctc cgaacggtac tccgccaccg   5220
agggacctga gcgagtccgc atcgaccgga tcggaaaacc tcggatccga attcatagat   5280
aactgatcca gtgcccctaa cgttactggc cgaagccgct tggaataagg ccggtgtgcg   5340
tttgtctata tgttattttc caccatattg ccgtcttttg gcaatgtgag ggcccggaaa   5400
cctggccctg tcttcttgac gagcattcct aggggtcttt cccctctcgc caaaggaatg   5460
caaggtctgt tgaatgtcgt gaaggaagca gttcctctgg aagcttcttg aagacaaaca   5520
acgtctgtag cgaccctttg caggcagcgg aaccccccac ctggcgacag gtgcctctgc   5580
ggccaaaagc cacgtgtata agatacacct gcaaaggcgg cacaacccca gtgccacgtt   5640
gtgagttgga tagttgtgga aagagtcaaa tggctctcct caagcgtatt caacaagggg   5700
ctgaaggatg cccagaaggt accccattgt atgggatctg atctggggcc tcggtgcaca   5760
tgctttacat gtgtttagtc gaggttaaaa aaacgtctag gccccccgaa ccacggggac   5820
gtggttttcc tttgaaaaac acgatgataa tatggccaca accatggcca cctcagcaag   5880
ttcccacttg aacaaaaaca tcaagcaaat gtacttgtgc ctgccccagg gtgagaaagt   5940
ccaagccatg tatatctggg ttgatggtac tggagaagga ctgcgctgca aaacccgcac   6000
cctggactgt gagcccaagt gtgtagaaga gttacctgag tggaattttg atggctctag   6060
tacctttcag tctgagggct ccaacagtga catgtatctc agccctgttg ccatgtttcg   6120
ggaccccttc cgcagagatc ccaacaagct ggtgttctgt gaagttttca agtacaaccg   6180
gaagcctgca gagaccaatt taaggcactc gtgtaaacgg ataatggaca tggtgagcaa   6240
ccagcacccc tggtttggaa tggaacagga gtatactctg atgggaacag atgggcaccc   6300
ttttggttgg ccttccaatg gctttcctgg gccccaaggt ccgtattact gtggtgtggg   6360
cgcagacaaa gcctatggca gggatatcgt ggaggctcac taccgcgcct gcttgtatgc   6420
tggggtcaag attacaggaa caaatgctga ggtcatgcct gcccagtggg agttccaaat   6480
aggaccctgt gaaggaatcc gcatgggaga tcatctctgg gtggcccgtt tcatcttgca   6540
tcgagtatgt gaagactttg gggtaatagc aacctttgac cccaagccca ttcctgggaa   6600
ctggaatggt gcaggctgcc ataccaactt tagcaccaag gccatgcggg aggagaatgg   6660
tctgaagcac atcgaggagg ccatcgagaa actaagcaag cggcaccggt accacattcg   6720
agcctacgat cccaaggggg gcctggacaa tgcccgtcgt ctgactgggt tccacgaaac   6780
gtccaacatc aacgactttt ctgctggtgt cgccaatcgc agtgccagca tccgcattcc   6840
ccggactgtc ggccaggaga agaaaggtta ctttgaagac cgccgcccct ctgccaattg   6900
tgaccccttt gcagtgacag aagccatcgt ccgcacatgc cttctcaatg agactggcga   6960
cgagcccttc caatacaaaa actaatctag atccccctcg ctttcttgct gtccaatttc   7020
tattaaaggt tcctttgttc cctaagtcca actactaaac tgggggatat tatgaagggc   7080
cttgagcatc tggattctgc ctaataaaaa acatttattt tcattgcaat gatgtattta   7140
aattatttct gaatatttta ctaaaaaggg aatgtgggag gtcagtgcat ttaaaacata   7200
aagaaatgaa gagggggatc ttcgcgatac tgcatcgatg agggacagcc cccccccaaa   7260
gcccccaggg atgtaattac gtccctcccc cgctaggggg cagcagcgag ccgcccgggg   7320
ctccgctccg gtccggcgct ccccccgcat ccccgagccg gcagcgtgcg gggacagccc   7380
```

gggcacgggg aaggtggcac gggatcgctt tcctctgaac gcttctcgct gctctttgag 7440
cctgcagaca cctgggggga tacggggaaa atagacaccg cggtggagct ccagcttttg 7500
ttccctttag tgagggttaa ttagttctta atacgactca ctatagggcg aattggctac 7560
cgggccgccc atcgagggta tcataagctt atatctataa caagaaaata tatatataat 7620
aagttatcac gtaagtagaa catgaaataa caatataatt atcgtatgag ttaaatctta 7680
aaagtcacgt aaaagataat catgcgtcat tttgactcac gcggtcgtta tagttcaaaa 7740
tcagtgacac ttaccgcatt gacaagcacg cctcacggga gctccaagcg gcgactgaga 7800
tgtcctaaat gcacagcgac ggattcgcgc tatttagaaa gagagagcaa tatttcaaga 7860
atgcatgcgt caattttacg cagactatct ttctagggtt aaatcgatag atgcgatcct 7920
gcaggtctcc ctatagtgag tcgtattaat ttcgataagc cagctgcatt aatgaatcgg 7980
ccaacgcgcg gggagaggcg gtttgcgtat tgggcgctct tccgcttcct cgctcactga 8040
ctcgctgcgc tcggtcgttc ggctgcggcg agcggtatca gctcactcaa aggcggtaat 8100
acggttatcc acagaatcag gggataacgc aggaaagaac atgtgagcaa aaggccagca 8160
aaaggccagg aaccgtaaaa aggccgcgtt gctggcgttt ttccataggc tccgcccccc 8220
tgacgagcat cacaaaaatc gacgctcaag tcagaggtgg cgaaacccga caggactata 8280
aagataccag gcgtttcccc ctggaagctc cctcgtgcgc tctcctgttc cgaccctgcc 8340
gcttaccgga tacctgtccg cctttctccc ttcgggaagc gtggcgcttt ctcatagctc 8400
acgctgtagg tatctcagtt cggtgtaggt cgttcgctcc aagctgggct gtgtgcacga 8460
accccccgtt cagcccgacc gctgcgcctt atccggtaac tatcgtcttg agtccaaccc 8520
ggtaagacac gacttatcgc cactggcagc agccactggt aacaggatta gcagagcgag 8580
gtatgtaggc ggtgctacag agttcttgaa gtggtggcct aactacggct acactagaag 8640
gacagtattt ggtatctgcg ctctgctgaa gccagttacc ttcggaaaaa gagttggtag 8700
ctcttgatcc ggcaaacaaa ccaccgctgg tagcggtggt ttttttgttt gcaagcagca 8760
gattacgcgc agaaaaaaag gatctcaaga agatcctttg atcttttcta cggggtctga 8820
cgctcagtgg aacgaaaact cacgttaagg gattttggtc atgagattat caaaaaggat 8880
cttcacctag atccttttaa attaaaaatg aagttttaaa tcaatctaaa gtatatatga 8940
gtaaacttgg tctgacagtt accaatgctt aatcagtgag gcacctatct cagcgatctg 9000
tctatttcgt tcatccatag ttgcctgact ccccgtcgtg tagataacta cgatacggga 9060
gggcttacca tctggcccca gtgctgcaat gataccgcga gacccacgct caccggctcc 9120
agatttatca gcaataaacc agccagccgg aagggccgag cgcagaagtg gtcctgcaac 9180
tttatccgcc tccatccagt ctattaattg ttgccgggaa gctagagtaa gtagttcgcc 9240
agttaatagt ttgcgcaacg ttgttgccat tgctacaggc atcgtggtgt cacgctcgtc 9300
gtttggtatg gcttcattca gctccggttc ccaacgatca aggcgagtta catgatcccc 9360
catgttgtgc aaaaaagcgg ttagctcctt cggtcctccg atcgttgtca gaagtaagtt 9420
ggccgcagtg ttatcactca tggttatggc agcactgcat aattctctta ctgtcatgcc 9480
atccgtaaga tgcttttctg tgactggtga gtactcaacc aagtcattct gagaatagtg 9540
tatgcggcga ccgagttgct cttgcccggc gtcaatacgg gataataccg cgccacatag 9600
cagaacttta aaagtgctca tcattggaaa acgttcttcg gggcgaaaac tctcaaggat 9660
cttaccgctg ttgagatcca gttcgatgta acccactcgt gcacccaact gatcttcagc 9720
atcttttact ttcaccagcg tttctgggtg agcaaaaaca ggaaggcaaa atgccgcaaa 9780
aaagggaata agggcgacac ggaaatgttg aatactcata ctcttccttt ttcaatatta 9840
ttgaagcatt tatcagggtt attgtctcat gagcggatac atatttgaat gtatttagaa 9900
aaataaacaa ataggggttc cgcgcacatt tccccgaaaa gtgccacctg acgtctaaga 9960
aaccattatt atcatgacat taacctataa aaataggcgt atcacgaggc cctttcgtct 10020
cgcgcgtttc ggtgatgacg gtgaaaacct ctgacacatg cagctcccgg agacggtcac 10080
agcttgtctg taagcggatg ccgggagcag acaagcccgt cagggcgcgt cagcgggtgt 10140
tggcgggtgt cggggctggc ttaactatgc ggcatcagag cagattgtac tgagagtgca 10200
ccatatcgac gctctccctt atgcgactcc tgcattagga agcagcccag tagtaggttg 10260
aggccgttga gcaccgccgc cgcaaggaat ggtgcatgca aggagatggc gcccaacagt 10320
cccccggcca cggggcctgc caccataccc acgccgaaac aagcgctcat gagcccgaag 10380
tggcgagccc gatcttcccc atcggtgatg tcggcgatat aggcgccagc aaccgcacct 10440
gtggcgccgg tgatgccggc cacgatgcgt ccggcgtaga ggatctggct agcgatgacc 10500
ctgctgattg gttcgctgac catttccggg gtgcggaacg gcgttaccag aaactcagaa 10560
ggttcgtcca accaaaccga ctctgacggc agtttacgag agagatgata gggtctgctt 10620
cagtaagcca gatgctacac aattaggctt gtacatattg tcgttagaac gcggctacaa 10680
ttaatacata accttatgta tcatacacat acgatttagg tgacactata gaatacacct 10740
gcaggacgtc ccaatgatct taagttaa 10768

<210> SEQ ID NO 28
<211> LENGTH: 10755
<212> TYPE: DNA
<213> ORGANISM: Artificial Sequence
<220> FEATURE:
<223> OTHER INFORMATION: pCLD16

<400> SEQUENCE: 28
ccctagaaag ataatcatat tgtgacgtac gttaaagata atcatgcgta aaattgacgc 60
atgtgtttta tcggtctgta tatcgaggtt tatttattaa tttgaataga tattaagttt 120
tattatattt acacttacat actaataata aattcaacaa acaatttatt tatgtttatt 180
tatttattaa aaaaaaacaa aaactcaaaa tttcttctat aaagtaacaa aacttttatc 240
gaatttgcag cccgggacta gctagaggga cagccccccc ccaaagcccc cagggatgta 300
attacgtccc tcccccgcta gggggcagca gcgagccgcc cggggctccg ctccggtccg 360
gcgctccccc cgcatccccg agccggcagc gtgcggggac agcccgggca cggggaaggt 420
ggcacgggat cgctttcctc tgaacgcttc tcgctgctct ttgagcctgc agacacctgg 480
ggggatacgg ggaaaactta agatccgacc ggacgcgtac tgagagcgct attctgaact 540
tttcttttgt tcccttccct tctaccacac cctaattgta atccatttta atttcctggt 600
cacagtcctg tctctccttc cattgtacct tgccctttc taaagagcga ctgcaaagta 660
tgtttgcgta ggtgaggatc taaaacttta tgaggtacga acatcacaga attactttgt 720
aatttcagtt tattgtaggc ttggcttttt ggggagggtt tacgtcttag acctcttagt 780
gcttctttgt ttcatggtgt tctaacttcg aagcatctct gtagctttaa tggattcctt 840
ttctgaaagc tttgctctct ttcttccccc tcggctttct cttaggcaag agggctaact 900
gtaaagtaag gcttactgcc ttgtgtttcc aaatgtgtcc gaagaggaag tgtcttctgt 960
gaatcctgtt atgcatgaat aacaggaaat agaaagaaat tcactttcat tattataaaa 1020
gtaatatgtt cgtttaaaaa attctaatga agagctggag atgcaaccca ggggtagagc 1080
acacactcag catgcaggag gccctgggtc caatcttgga atctcctctc agttaacctg 1140
atctctagct gattagtagt gagtgcaagc ccactttcct cttctgcctc attgctcagt 1200
gataacagct gttaaacttt gtcttattct aaaactacct ctgtgcaaat gctagcacaa 1260
taatatatat catatgcaca tgattttttt tttatcttga aaagtaagtc agtatagcta 1320
caaagttcac ttggcattgt caacatttca caggcgtaat attcctcctc tagtactgtc 1380
ctcttcattc tttgtgacca agtttggaga gagtgcacaa atgccaggga ggtttgtggg 1440
aaggtttctc atgttctggt aaggcgagta agaaaatagt ctcatgcagg tgaaatgagt 1500
gctatgcagt atatattata ccagagaaca gcaaatgacc aaattcacac tgaactagtt 1560
cagtaaaatt ggctttgtca aagctttcct tgcttaaaat gtaattccct gtcatcctag 1620
ttctggtctg gattcttttc ctggagtctt gacttccaga ttccctgtgg acttttgttt 1680
gagtttcaag cttttgaaat atagaaacct atctaactta acaaacttgg gagagaaaag 1740
actccagaac aactgaaaac agaccaggct aaatgaatag actttattcc tctcttctta 1800
cctgcagttt tcagatatgc agagttggag cggatcttag aggttgattc attcatgcct 1860
gaagaaaaca cattttatag accctgtgcc caagttcgtg gtggacatca ccctttattt 1920
actaattgca ctacataaca ggcattttag aagactgctc cagtcagaga ccccgcctta 1980
gaggaatctg taaaccctga actcctatca ctcatgagca ctagttatgt ttggaatgcc 2040
gtattaaaac aaaagttaca tttctaaact taaaattttc tagcacagag acagtgggag 2100
tagctaactt tgatagacat ttttctacta aaagtctttc taagtacata atcttctgta 2160
agttggaaaa cagcaaaata gaacgtctcc tacgtagtta atctttttgc ataatttgca 2220
catgtaggag ttattagtat acgggtaagt tttcactttt tcccccaact ggagtgtctt 2280
gtggctgggt ttgaaaaagg gaacgggagg ccgctggagg ggattggtaa atgagataaa 2340
acaccactca ttcaactcag tgactcagca tttaaatttt ccataaaagg attaaaggaa 2400
aattaaacaa attcttaaag ccaagactct ggagaaactt gttggtgtgc tttagttttc 2460
actgttatga ctcatgaatt tatgcataaa ttagtacatt tataaaaaca tagccttttt 2520
agagttttct gtttggctaa agtgccattg ttagcatttg gaattacctt tttatgtctt 2580
atatttttc caaataaaaa taaatgtttc tgctgtctta ctactgaaac tacgttgtga 2640
gcactttaaa tttctcaaag cagtttcgcc tgttatactt ggcgcttagt catcgtcgta 2700
cacaacagga cctgattaag aaggctgtgc tgcctctaag ccgggctaga ttgtagccac 2760
tagcaaccag gctgcaataa tttccctttg atgacatcat ccactgtgga agaacccagt 2820
tgcttcagcc agtcgaacta tacagttcca acctcatcaa atatggcatc tcccttgcct 2880
gctatagcag gggaggaaa aaatgccacc atctttttaa tctagcaagc ttctcttttc 2940
ttcatctttt tttttttctt ttaaaaaaat tctgatcatg gatgcttctt ccgatcccta 3000
tttgccttat gacgggggag gagacaatat ccccttgagg gaattacata aaagaggtaa 3060
gagcatcccc ttgctctgaa tcctctgttg gttgttgtgc atgcggctgg gcggttctgg 3120
ggacaggctg tctgttgtcc tcttgctgca atgtgctgct tagttgccct gccttgttgc 3180
tgtgggagaa tgcgaccttc ccagcagggc tggccctccc tgattgtttg ctctgtgcag 3240
attagccctg cttcagatca catagggctg cagactccat cttctgtgtg aaaatgcttt 3300
cggtttgatt gcagaaataa gctgccttta cagccagcta aagtcctggt ggttggttgg 3360

```
cacctgcaaa gtagtatttt tgtacctctg gaaacttata ttttctttac acagcaatat   3420
caagtgccgg tatgccattc tgttttggct gctgccaatt accatgtaga ctttgcacca   3480
cagagtaata gtaaaagctc ctagctgcat tttataacat ttaaaaatag caggaaagaa   3540
gaattatttt tgatttaaca tgtttttgtc atttaacgtc ttaactgatt gacatactat   3600
attgtctgtc tcgtgggtat cttgtacaac ttgataggat aaagcaattt agtttttttt   3660
ttttttttta aatacatcca gaatgtaagt cgtcagtagt tttcgaacag ataagtaatg   3720
gtgttaatct tttggcaggc tttgccttgg tctccttaaa gctaattagg tgttacttaa   3780
ttaaactgct cttttgctca ttttcttaaa ttattttttt aaaagatagt tggcatttgc   3840
tgttctagaa ataaacttca agaaacattc tttagccaga tgacttcatg tatgagccat   3900
gttagtttga attatttgct tggtgttata aactttatgg tttaatacca acttttatta   3960
tgtttacaag gtaaataagg aaaatttcaa gtacattttg tatcctgaga acaaatttaa   4020
gttccataga atttaggaat tacaatgtat tcaacagata cttacttgtc atactgtgcc   4080
tgcaaaacaa taattagact ctgaacaggt gcaacaattt tctgtagaat tagacaagtc   4140
ttcttttggc aggtgttact aagtaggcca tttcccaagg aacagggaat ttgccaggct   4200
tttgtggtgg agagaataga atgaataaat gctgtgggga gtaaagagct tgtcagaaga   4260
tgattagttc tgtggcacca aaaccaagag atcagttttc ctgtgagaag taaaggaagc   4320
attgtagaaa aatagatgtg ttgaagtcta ccggtggagt tccgcgttac ataacttacg   4380
gtaaatggcc cgcctggctg accgcccaac gacccccgcc cattgacgtc aataatgacg   4440
tatgttccca tagtaacgcc aatagggact ttccattgac gtcaatgggt ggagtattta   4500
cggtaaactg cccacttggc agtacatcaa gtgtatcata tgccaagtac gccccctatt   4560
gacgtcaatg acggtaaatg gcccgcctgg cattatgccc agtacatgac cttatgggac   4620
tttcctactt ggcagtacat ctacgtatta gtcatcgcta ttaccattgt gatgcggttt   4680
tggcagtaca tcaatgggcg tggatagcgg tttgactcac ggggatttcc aagtctccac   4740
cccattgacg tcaatgggag tttgttttgg caccaaaatc aacgggactt tccaaaatgt   4800
cgtaacaact ccgccccatt gacgcaaatg ggcggtaggc gtgtacggtg ggaggtctat   4860
ataagcagag ctcgtttagt gaaccgtcag atctacctct tccgcatcgc tgtctgcgag   4920
ggccagctgt tggggtgagt actccctctc aaaagcgggc atgacttctg cgctaagatt   4980
gtcagtttcc aaaaacgagg aggatttgat attcacctgg cccgcggtga tgcctttgag   5040
ggtggccgcg tccatctggt cagaaaagac aatctttttg ttgtcaagct tccttgatga   5100
tgtcatactt atcctgtccc ttttttttcc acagctcgcg gttgaggaca aactcttcgc   5160
ggtctttcca gtactcttgg atcggaaacc cgtcggcctc cgaacggtac tccgccaccg   5220
agggacctga gcgagtccgc atcgaccgga tcggaaaacc tcggatccga attcatagat   5280
aactgatcca gtgcccctaa cgttactggc cgaagccgct tggaataagg ccggtgtgcg   5340
tttgtctata tgttattttc caccatattg ccgtcttttg gcaatgtgag ggcccggaaa   5400
cctggccctg tcttcttgac gagcattcct aggggtcttt cccctctcgc caaaggaatg   5460
caaggtctgt tgaatgtcgt gaaggaagca gttcctctgg aagcttcttg aagacaaaca   5520
acgtctgtag cgaccctttg caggcagcgg aaccccccac ctggcgacag gtgcctctgc   5580
ggccaaaagc cacgtgtata agatacacct gcaaaggcgg cacaacccca gtgccacgtt   5640
gtgagttgga tagttgtgga aagagtcaaa tggctctcct caagcgtatt caacaagggg   5700
ctgaaggatg cccagaaggt accccattgt atgggatctg atctggggcc tcggtgcaca   5760
```

-continued

```
tgctttacat gtgtttagtc gaggttaaaa aaacgtctag gccccccgaa ccacggggac   5820
gtggttttcc tttgaaaaac acgatgataa atggccacct cagcaagttc ccacttgaac   5880
aaaaacatca agcaaatgta cttgtgcctg ccccagggtg agaaagtcca agccatgtat   5940
atctgggttg atggtactgg agaaggactg cgctgcaaaa cccgcaccct ggactgtgag   6000
cccaagtgtg tagaagagtt acctgagtgg aattttgatg gctctagtac ctttcagtct   6060
gagggctcca acagtgacat gtatctcagc cctgttgcca tgtttcggga ccccttccgc   6120
agagatccca acaagctggt gttctgtgaa gttttcaagt acaaccggaa gcctgcagag   6180
accaatttaa ggcactcgtg taaacggata atggacatgg tgagcaacca gcacccctgg   6240
tttggaatgg aacaggagta tactctgatg ggaacagatg ggcacccttt tggttggcct   6300
tccaatggct ttcctgggcc ccaaggtccg tattactgtg gtgtgggcgc agacaaagcc   6360
tatggcaggg atatcgtgga ggctcactac cgcgcctgct tgtatgctgg ggtcaagatt   6420
acaggaacaa atgctgaggt catgcctgcc cagtgggagt tccaaatagg accctgtgaa   6480
ggaatccgca tgggagatca tctctgggtg gcccgtttca tcttgcatcg agtatgtgaa   6540
gactttgggg taatagcaac ctttgacccc aagcccattc ctgggaactg gaatggtgca   6600
ggctgccata ccaactttag caccaaggcc atgcgggagg agaatggtct gaagcacatc   6660
gaggaggcca tcgagaaact aagcaagcgg caccggtacc acattcgagc ctacgatccc   6720
aaggggggcc tggacaatgc ccgtcgtctg actgggttcc acgaaacgtc caacatcaac   6780
gacttttctg ctggtgtcgc caatcgcagt gccagcatcc gcattccccg gactgtcggc   6840
caggagaaga aaggttactt tgaagaccgc cgcccctctg ccaattgtga cccctttgca   6900
gtgacagaag ccatcgtccg cacatgcctt ctcaatgaga ctggcgacga gcccttccaa   6960
tacaaaaact aatctagatc cccctcgctt tcttgctgtc caatttctat taaaggttcc   7020
tttgttccct aagtccaact actaaactgg gggatattat gaagggcctt gagcatctgg   7080
attctgccta ataaaaaaca tttattttca ttgcaatgat gtatttaaat tatttctgaa   7140
tattttacta aaaagggaat gtgggaggtc agtgcattta aaacataaag aaatgaagag   7200
ggggatcttc gcgatactgc atcgatgagg gacagccccc ccccaaagcc cccagggatg   7260
taattacgtc cctcccccgc tagggggcag cagcgagccg cccggggctc cgctccggtc   7320
cggcgctccc cccgcatccc cgagccggca gcgtgcgggg acagcccggg cacggggaag   7380
gtggcacggg atcgctttcc tctgaacgct tctcgctgct ctttgagcct gcagacacct   7440
ggggggatac ggggaaaata gacaccgcgg tggagctcca gcttttgttc cctttagtga   7500
gggttaatta gttcttaata cgactcacta tagggcgaat tggctaccgg gccgcccatc   7560
gagggtatca taagcttata tctataacaa gaaaatatat atataataag ttatcacgta   7620
agtagaacat gaaataacaa tataattatc gtatgagtta aatcttaaaa gtcacgtaaa   7680
agataatcat gcgtcatttt gactcacgcg gtcgttatag ttcaaaatca gtgacactta   7740
ccgcattgac aagcacgcct cacgggagct ccaagcggcg actgagatgt cctaaatgca   7800
cagcgacgga ttcgcgctat ttagaaagag agagcaatat ttcaagaatg catgcgtcaa   7860
ttttacgcag actatctttc tagggttaaa tcgatagatg cgatcctgca ggtctcccta   7920
tagtgagtcg tattaatttc gataagccag ctgcattaat gaatcggcca acgcgcgggg   7980
agaggcggtt tgcgtattgg gcgctcttcc gcttcctcgc tcactgactc gctgcgctcg   8040
gtcgttcggc tgcggcgagc ggtatcagct cactcaaagg cggtaatacg gttatccaca   8100
```

gaatcagggg ataacgcagg aaagaacatg tgagcaaaag gccagcaaaa ggccaggaac 8160
cgtaaaaagg ccgcgttgct ggcgtttttc cataggctcc gcccccctga cgagcatcac 8220
aaaaatcgac gctcaagtca gaggtggcga aacccgacag gactataaag ataccaggcg 8280
tttccccctg gaagctccct cgtgcgctct cctgttccga ccctgccgct taccggatac 8340
ctgtccgcct ttctcccttc gggaagcgtg gcgctttctc atagctcacg ctgtaggtat 8400
ctcagttcgg tgtaggtcgt tcgctccaag ctgggctgtg tgcacgaacc ccccgttcag 8460
cccgaccgct gcgccttatc cggtaactat cgtcttgagt ccaacccggt aagacacgac 8520
ttatcgccac tggcagcagc cactggtaac aggattagca gagcgaggta tgtaggcggt 8580
gctacagagt tcttgaagtg gtggcctaac tacggctaca ctagaaggac agtatttggt 8640
atctgcgctc tgctgaagcc agttaccttc ggaaaaagag ttggtagctc ttgatccggc 8700
aaacaaacca ccgctggtag cggtggtttt tttgtttgca agcagcagat tacgcgcaga 8760
aaaaaaggat ctcaagaaga tcctttgatc ttttctacgg ggtctgacgc tcagtggaac 8820
gaaaactcac gttaagggat tttggtcatg agattatcaa aaaggatctt cacctagatc 8880
cttttaaatt aaaaatgaag ttttaaatca atctaaagta tatatgagta aacttggtct 8940
gacagttacc aatgcttaat cagtgaggca cctatctcag cgatctgtct atttcgttca 9000
tccatagttg cctgactccc cgtcgtgtag ataactacga tacgggaggg cttaccatct 9060
ggccccagtg ctgcaatgat accgcgagac ccacgctcac cggctccaga tttatcagca 9120
ataaaccagc cagccggaag ggccgagcgc agaagtggtc ctgcaacttt atccgcctcc 9180
atccagtcta ttaattgttg ccgggaagct agagtaagta gttcgccagt taatagtttg 9240
cgcaacgttg ttgccattgc tacaggcatc gtggtgtcac gctcgtcgtt tggtatggct 9300
tcattcagct ccggttccca acgatcaagg cgagttacat gatcccccat gttgtgcaaa 9360
aaagcggtta gctccttcgg tcctccgatc gttgtcagaa gtaagttggc cgcagtgtta 9420
tcactcatgg ttatggcagc actgcataat tctcttactg tcatgccatc cgtaagatgc 9480
ttttctgtga ctggtgagta ctcaaccaag tcattctgag aatagtgtat gcggcgaccg 9540
agttgctctt gcccggcgtc aatacgggat aataccgcgc cacatagcag aactttaaaa 9600
gtgctcatca ttggaaaacg ttcttcgggg cgaaaactct caaggatctt accgctgttg 9660
agatccagtt cgatgtaacc cactcgtgca cccaactgat cttcagcatc ttttactttc 9720
accagcgttt ctgggtgagc aaaaacagga aggcaaaatg ccgcaaaaaa gggaataagg 9780
gcgacacgga aatgttgaat actcatactc ttcctttttc aatattattg aagcatttat 9840
cagggttatt gtctcatgag cggatacata tttgaatgta tttagaaaaa taaacaaata 9900
ggggttccgc gcacatttcc ccgaaaagtg ccacctgacg tctaagaaac cattattatc 9960
atgacattaa cctataaaaa taggcgtatc acgaggccct ttcgtctcgc gcgtttcggt 10020
gatgacggtg aaaacctctg acacatgcag ctcccggaga cggtcacagc ttgtctgtaa 10080
gcggatgccg ggagcagaca agcccgtcag ggcgcgtcag cgggtgttgg cgggtgtcgg 10140
ggctggctta actatgcggc atcagagcag attgtactga gagtgcacca tatcgacgct 10200
ctcccttatg cgactcctgc attaggaagc agcccagtag taggttgagg ccgttgagca 10260
ccgccgccgc aaggaatggt gcatgcaagg agatggcgcc caacagtccc ccggccacgg 10320
ggcctgccac catacccacg ccgaaacaag cgctcatgag cccgaagtgg cgagcccgat 10380
cttccccatc ggtgatgtcg gcgatatagg cgccagcaac cgcacctgtg gcgccggtga 10440
tgccggccac gatgcgtccg gcgtagagga tctggctagc gatgaccctg ctgattggtt 10500
cgctgaccat ttccggggtg cggaacggcg ttaccagaaa ctcagaaggt tcgtccaacc 10560
aaaccgactc tgacggcagt ttacgagaga gatgataggg tctgcttcag taagccagat 10620
gctacacaat taggcttgta catattgtcg ttagaacgcg gctacaatta atacataacc 10680
ttatgtatca tacacatacg atttaggtga cactatagaa tacacctgca ggacgtccca 10740
atgatcttaa gttaa 10755

<210> SEQ ID NO 29
<211> LENGTH: 10748
<212> TYPE: DNA
<213> ORGANISM: Artificial Sequence
<220> FEATURE:
<223> OTHER INFORMATION: pCLD17

<400> SEQUENCE: 29
ccctagaaag ataatcatat tgtgacgtac gttaaagata atcatgcgta aaattgacgc 60
atgtgtttta tcggtctgta tatcgaggtt tatttattaa tttgaataga tattaagttt 120
tattatattt acacttacat actaataata aattcaacaa acaatttatt tatgtttatt 180
tatttattaa aaaaaaacaa aaactcaaaa tttcttctat aaagtaacaa aacttttatc 240
gaatttgcag cccgggacta gctagaggga cagccccccc ccaaagcccc cagggatgta 300
attacgtccc tcccccgcta gggggcagca gcgagccgcc cggggctccg ctccggtccg 360
gcgctccccc cgcatccccg agccggcagc gtgcggggac agcccgggca cggggaaggt 420
ggcacgggat cgctttcctc tgaacgcttc tcgctgctct ttgagcctgc agacacctgg 480
ggggatacgg ggaaaactta agatccgacc ggacgcgtac tgagagcgct attctgaact 540
tttcttttgt tcccttccct tctaccacac cctaattgta atccatttta atttcctggt 600
cacagtcctg tctctccttc cattgtacct tgccctttc taaagagcga ctgcaaagta 660
tgtttgcgta ggtgaggatc taaaacttta tgaggtacga acatcacaga attactttgt 720
aatttcagtt tattgtaggc ttggcttttt ggggagggtt tacgtcttag acctcttagt 780
gcttctttgt ttcatggtgt tctaacttcg aagcatctct gtagctttaa tggattcctt 840
ttctgaaagc tttgctctct ttcttccccc tcggctttct cttaggcaag agggctaact 900
gtaaagtaag gcttactgcc ttgtgtttcc aaatgtgtcc gaagaggaag tgtcttctgt 960
gaatcctgtt atgcatgaat aacaggaaat agaaagaaat tcactttcat tattataaaa 1020
gtaatatgtt cgtttaaaaa attctaatga agagctggag atgcaaccca ggggtagagc 1080
acacactcag catgcaggag gccctgggtc caatcttgga atctcctctc agttaacctg 1140
atctctagct gattagtagt gagtgcaagc ccactttcct cttctgcctc attgctcagt 1200
gataacagct gttaaacttt gtcttattct aaaactacct ctgtgcaaat gctagcacaa 1260
taatatatat catatgcaca tgattttttt tttatcttga aaagtaagtc agtatagcta 1320
caaagttcac ttggcattgt caacatttca caggcgtaat attcctcctc tagtactgtc 1380
ctcttcattc tttgtgacca agtttggaga gagtgcacaa atgccaggga ggtttgtggg 1440
aaggtttctc atgttctggt aaggcgagta agaaaatagt ctcatgcagg tgaaatgagt 1500
gctatgcagt atatattata ccagagaaca gcaaatgacc aaattcacac tgaactagtt 1560
cagtaaaatt ggctttgtca aagctttcct tgcttaaaat gtaattccct gtcatcctag 1620
ttctggtctg gattcttttc ctggagtctt gacttccaga ttccctgtgg acttttgttt 1680
gagtttcaag cttttgaaat atagaaacct atctaactta acaaacttgg gagagaaaag 1740

-continued

```
actccagaac aactgaaaac agaccaggct aaatgaatag actttattcc tctcttctta   1800
cctgcagttt tcagatatgc agagttggag cggatcttag aggttgattc attcatgcct   1860
gaagaaaaca cattttatag accctgtgcc caagttcgtg gtggacatca ccctttattt   1920
actaattgca ctacataaca ggcattttag aagactgctc cagtcagaga ccccgcctta   1980
gaggaatctg taaaccctga actcctatca ctcatgagca ctagttatgt ttggaatgcc   2040
gtattaaaac aaaagttaca tttctaaact taaaattttc tagcacagag acagtgggag   2100
tagctaactt tgatagacat ttttctacta aaagtctttc taagtacata atcttctgta   2160
agttggaaaa cagcaaaata gaacgtctcc tacgtagtta atctttttgc ataatttgca   2220
catgtaggag ttattagtat acgggtaagt tttcactttt tcccccaact ggagtgtctt   2280
gtggctgggt ttgaaaaagg gaacgggagg ccgctggagg ggattggtaa atgagataaa   2340
acaccactca ttcaactcag tgactcagca tttaaatttt ccataaaagg attaaaggaa   2400
aattaaacaa attcttaaag ccaagactct ggagaaactt gttggtgtgc tttagttttc   2460
actgttatga ctcatgaatt tatgcataaa ttagtacatt tataaaaaca tagccttttt   2520
agagttttct gtttggctaa agtgccattg ttagcatttg gaattacctt tttatgtctt   2580
atatttttc caaataaaaa taaatgtttc tgctgtctta ctactgaaac tacgttgtga   2640
gcactttaaa tttctcaaag cagtttcgcc tgttatactt ggcgcttagt catcgtcgta   2700
cacaacagga cctgattaag aaggctgtgc tgcctctaag ccgggctaga ttgtagccac   2760
tagcaaccag gctgcaataa tttccctttg atgacatcat ccactgtgga agaacccagt   2820
tgcttcagcc agtcgaacta tacagttcca acctcatcaa atatggcatc tcccttgcct   2880
gctatagcag gggaggaaa aaatgccacc atctttttaa tctagcaagc ttctcttttc   2940
ttcatctttt tttttttctt ttaaaaaaat tctgatcatg gatgcttctt ccgatcccta   3000
tttgccttat gacgggggag gagacaatat ccccttgagg gaattacata aaagaggtaa   3060
gagcatcccc ttgctctgaa tcctctgttg gttgttgtgc atgcggctgg gcggttctgg   3120
ggacaggctg tctgttgtcc tcttgctgca atgtgctgct tagttgccct gccttgttgc   3180
tgtgggagaa tgcgaccttc ccagcagggc tggccctccc tgattgtttg ctctgtgcag   3240
attagccctg cttcagatca catagggctg cagactccat cttctgtgtg aaaatgcttt   3300
cggtttgatt gcagaaataa gctgccttta cagccagcta aagtcctggt ggttggttgg   3360
cacctgcaaa gtagtatttt tgtacctctg gaaacttata ttttctttac acagcaatat   3420
caagtgccgg tatgccattc tgttttggct gctgccaatt accatgtaga ctttgcacca   3480
cagagtaata gtaaaagctc ctagctgcat tttataacat ttaaaaatag caggaaagaa   3540
gaattatttt tgatttaaca tgtttttgtc atttaacgtc ttaactgatt gacatactat   3600
attgtctgtc tcgtgggtat cttgtacaac ttgataggat aaagcaattt agttttttt   3660
ttttttttta aatacatcca gaatgtaagt cgtcagtagt tttcgaacag ataagtaatg   3720
gtgttaatct tttggcaggc tttgccttgg tctccttaaa gctaattagg tgttacttaa   3780
ttaaactgct cttttgctca ttttcttaaa ttattttttt aaaagatagt tggcatttgc   3840
tgttctagaa ataaacttca agaaacattc tttagccaga tgacttcatg tatgagccat   3900
gttagtttga attatttgct tggtgttata aactttatgg tttaatacca acttttatta   3960
tgtttacaag gtaaataagg aaaatttcaa gtacattttg tatcctgaga acaaatttaa   4020
gttccataga atttaggaat tacaatgtat tcaacagata cttacttgtc atactgtgcc   4080
tgcaaaacaa taattagact ctgaacaggt gcaacaattt tctgtagaat tagacaagtc   4140
```

-continued

```
ttcttttggc aggtgttact aagtaggcca tttcccaagg aacagggaat ttgccaggct   4200
tttgtggtgg agagaataga atgaataaat gctgtgggga gtaaagagct tgtcagaaga   4260
tgattagttc tgtggcacca aaaccaagag atcagttttc ctgtgagaag taaaggaagc   4320
attgtagaaa aatagatgtg ttgaagtcta ccggtggagt tccgcgttac ataacttacg   4380
gtaaatggcc cgcctggctg accgcccaac gacccccgcc cattgacgtc aataatgacg   4440
tatgttccca tagtaacgcc aatagggact ttccattgac gtcaatgggt ggagtattta   4500
cggtaaactg cccacttggc agtacatcaa gtgtatcata tgccaagtac gccccctatt   4560
gacgtcaatg acggtaaatg gcccgcctgg cattatgccc agtacatgac cttatgggac   4620
tttcctactt ggcagtacat ctacgtatta gtcatcgcta ttaccattgt gatgcggttt   4680
tggcagtaca tcaatgggcg tggatagcgg tttgactcac ggggatttcc aagtctccac   4740
cccattgacg tcaatgggag tttgttttgg caccaaaatc aacgggactt tccaaaatgt   4800
cgtaacaact ccgccccatt gacgcaaatg ggcggtaggc gtgtacggtg ggaggtctat   4860
ataagcagag ctcgtttagt gaaccgtcag atctacctct tccgcatcgc tgtctgcgag   4920
ggccagctgt tggggtgagt actccctctc aaaagcgggc atgacttctg cgctaagatt   4980
gtcagtttcc aaaaacgagg aggatttgat attcacctgg cccgcggtga tgcctttgag   5040
ggtggccgcg tccatctggt cagaaaagac aatctttttg ttgtcaagct tccttgatga   5100
tgtcatactt atcctgtccc ttttttttcc acagctcgcg gttgaggaca aactcttcgc   5160
ggtctttcca gtactcttgg atcggaaacc cgtcggcctc cgaacggtac tccgccaccg   5220
agggacctga gcgagtccgc atcgaccgga tcggaaaacc tcggatccga attcatagat   5280
aactgatcca gtgcccctaa cgttactggc cgaagccgct tggaataagg ccggtgtgcg   5340
tttgtctata tgttattttc caccatattg ccgtcttttg gcaatgtgag ggcccggaaa   5400
cctggccctg tcttcttgac gagcattcct aggggtcttt cccctctcgc caaaggaatg   5460
caaggtctgt tgaatgtcgt gaaggaagca gttcctctgg aagcttcttg aagacaaaca   5520
acgtctgtag cgaccctttg caggcagcgg aaccccccac ctggcgacag gtgcctctgc   5580
ggccaaaagc cacgtgtata agatacacct gcaaaggcgg cacaacccca gtgccacgtt   5640
gtgagttgga tagttgtgga aagagtcaaa tggctctcct caagcgtatt caacaagggg   5700
ctgaaggatg cccagaaggt accccattgt atgggatctg atctggggcc tcggtgcaca   5760
tgctttacat gtgtttagtc gaggttaaaa aaacgtctag gccccccgaa ccacggggac   5820
gtggttttcc tttgaaaaac acgatggcca cctcagcaag ttcccacttg aacaaaaaca   5880
tcaagcaaat gtacttgtgc ctgccccagg gtgagaaagt ccaagccatg tatatctggg   5940
ttgatggtac tggagaagga ctgcgctgca aaacccgcac cctggactgt gagcccaagt   6000
gtgtagaaga gttacctgag tggaattttg atggctctag tacctttcag tctgagggct   6060
ccaacagtga catgtatctc agccctgttg ccatgtttcg ggaccccttc cgcagagatc   6120
ccaacaagct ggtgttctgt gaagttttca agtacaaccg gaagcctgca gagaccaatt   6180
taaggcactc gtgtaaacgg ataatggaca tggtgagcaa ccagcacccc tggtttggaa   6240
tggaacagga gtatactctg atgggaacag atgggcaccc ttttggttgg ccttccaatg   6300
gctttcctgg gccccaaggt ccgtattact gtggtgtggg cgcagacaaa gcctatggca   6360
gggatatcgt ggaggctcac taccgcgcct gcttgtatgc tggggtcaag attacaggaa   6420
caaatgctga ggtcatgcct gcccagtggg agttccaaat aggaccctgt gaaggaatcc   6480
```

```
gcatgggaga tcatctctgg gtggcccgtt tcatcttgca tcgagtatgt gaagactttg   6540
gggtaatagc aacctttgac cccaagccca ttcctgggaa ctggaatggt gcaggctgcc   6600
ataccaactt tagcaccaag gccatgcggg aggagaatgg tctgaagcac atcgaggagg   6660
ccatcgagaa actaagcaag cggcaccggt accacattcg agcctacgat cccaaggggg   6720
gcctggacaa tgcccgtcgt ctgactgggt tccacgaaac gtccaacatc aacgactttt   6780
ctgctggtgt cgccaatcgc agtgccagca tccgcattcc ccggactgtc ggccaggaga   6840
agaaaggtta ctttgaagac cgccgcccct ctgccaattg tgaccccttt gcagtgacag   6900
aagccatcgt ccgcacatgc cttctcaatg agactggcga cgagcccttc caatacaaaa   6960
actaatctag atccccctcg ctttcttgct gtccaatttc tattaaaggt tcctttgttc   7020
cctaagtcca actactaaac tgggggatat tatgaagggc cttgagcatc tggattctgc   7080
ctaataaaaa acatttattt tcattgcaat gatgtattta aattatttct gaatatttta   7140
ctaaaaaggg aatgtgggag gtcagtgcat ttaaaacata aagaaatgaa gagggggatc   7200
ttcgcgatac tgcatcgatg agggacagcc cccccccaaa gcccccaggg atgtaattac   7260
gtccctcccc cgctaggggg cagcagcgag ccgcccgggg ctccgctccg gtccggcgct   7320
ccccccgcat ccccgagccg gcagcgtgcg gggacagccc gggcacgggg aaggtggcac   7380
gggatcgctt tcctctgaac gcttctcgct gctctttgag cctgcagaca cctgggggga   7440
tacggggaaa atagacaccg cggtggagct ccagcttttg ttccctttag tgagggttaa   7500
ttagttctta atacgactca ctatagggcg aattggctac cgggccgccc atcgagggta   7560
tcataagctt atatctataa caagaaaata tatatataat aagttatcac gtaagtagaa   7620
catgaaataa caatataatt atcgtatgag ttaaatctta aaagtcacgt aaaagataat   7680
catgcgtcat tttgactcac gcggtcgtta tagttcaaaa tcagtgacac ttaccgcatt   7740
gacaagcacg cctcacggga gctccaagcg gcgactgaga tgtcctaaat gcacagcgac   7800
ggattcgcgc tatttagaaa gagagagcaa tatttcaaga atgcatgcgt caattttacg   7860
cagactatct ttctagggtt aaatcgatag atgcgatcct gcaggtctcc ctatagtgag   7920
tcgtattaat ttcgataagc cagctgcatt aatgaatcgg ccaacgcgcg gggagaggcg   7980
gtttgcgtat tgggcgctct tccgcttcct cgctcactga ctcgctgcgc tcggtcgttc   8040
ggctgcggcg agcggtatca gctcactcaa aggcggtaat acggttatcc acagaatcag   8100
gggataacgc aggaaagaac atgtgagcaa aaggccagca aaaggccagg aaccgtaaaa   8160
aggccgcgtt gctggcgttt ttccataggc tccgcccccc tgacgagcat cacaaaaatc   8220
gacgctcaag tcagaggtgg cgaaacccga caggactata aagataccag gcgtttcccc   8280
ctggaagctc cctcgtgcgc tctcctgttc cgaccctgcc gcttaccgga tacctgtccg   8340
cctttctccc ttcgggaagc gtggcgcttt ctcatagctc acgctgtagg tatctcagtt   8400
cggtgtaggt cgttcgctcc aagctgggct gtgtgcacga accccccgtt cagcccgacc   8460
gctgcgcctt atccggtaac tatcgtcttg agtccaaccc ggtaagacac gacttatcgc   8520
cactggcagc agccactggt aacaggatta gcagagcgag gtatgtaggc ggtgctacag   8580
agttcttgaa gtggtggcct aactacggct acactagaag gacagtattt ggtatctgcg   8640
ctctgctgaa gccagttacc ttcggaaaaa gagttggtag ctcttgatcc ggcaaacaaa   8700
ccaccgctgg tagcggtggt ttttttgttt gcaagcagca gattacgcgc agaaaaaaag   8760
gatctcaaga agatcctttg atcttttcta cggggtctga cgctcagtgg aacgaaaact   8820
cacgttaagg gattttggtc atgagattat caaaaaggat cttcacctag atccttttaa   8880
```

-continued

```
attaaaaatg aagttttaaa tcaatctaaa gtatatatga gtaaacttgg tctgacagtt   8940
accaatgctt aatcagtgag gcacctatct cagcgatctg tctatttcgt tcatccatag   9000
ttgcctgact ccccgtcgtg tagataacta cgatacggga gggcttacca tctggcccca   9060
gtgctgcaat gataccgcga gacccacgct caccggctcc agatttatca gcaataaacc   9120
agccagccgg aagggccgag cgcagaagtg gtcctgcaac tttatccgcc tccatccagt   9180
ctattaattg ttgccgggaa gctagagtaa gtagttcgcc agttaatagt ttgcgcaacg   9240
ttgttgccat tgctacaggc atcgtggtgt cacgctcgtc gtttggtatg gcttcattca   9300
gctccggttc ccaacgatca aggcgagtta catgatcccc catgttgtgc aaaaaagcgg   9360
ttagctcctt cggtcctccg atcgttgtca gaagtaagtt ggccgcagtg ttatcactca   9420
tggttatggc agcactgcat aattctctta ctgtcatgcc atccgtaaga tgcttttctg   9480
tgactggtga gtactcaacc aagtcattct gagaatagtg tatgcggcga ccgagttgct   9540
cttgcccggc gtcaatacgg gataataccg cgccacatag cagaacttta aaagtgctca   9600
tcattggaaa acgttcttcg gggcgaaaac tctcaaggat cttaccgctg ttgagatcca   9660
gttcgatgta acccactcgt gcacccaact gatcttcagc atcttttact ttcaccagcg   9720
tttctgggtg agcaaaaaca ggaaggcaaa atgccgcaaa aaagggaata agggcgacac   9780
ggaaatgttg aatactcata ctcttccttt ttcaatatta ttgaagcatt tatcagggtt   9840
attgtctcat gagcggatac atatttgaat gtatttagaa aaataaacaa ataggggttc   9900
cgcgcacatt tccccgaaaa gtgccacctg acgtctaaga aaccattatt atcatgacat   9960
taacctataa aaataggcgt atcacgaggc cctttcgtct cgcgcgtttc ggtgatgacg  10020
gtgaaaacct ctgacacatg cagctcccgg agacggtcac agcttgtctg taagcggatg  10080
ccgggagcag acaagcccgt cagggcgcgt cagcgggtgt tggcgggtgt cggggctggc  10140
ttaactatgc ggcatcagag cagattgtac tgagagtgca ccatatcgac gctctccctt  10200
atgcgactcc tgcattagga agcagcccag tagtaggttg aggccgttga gcaccgccgc  10260
cgcaaggaat ggtgcatgca aggagatggc gcccaacagt cccccggcca cggggcctgc  10320
caccataccc acgccgaaac aagcgctcat gagcccgaag tggcgagccc gatcttcccc  10380
atcggtgatg tcggcgatat aggcgccagc aaccgcacct gtggcgccgg tgatgccggc  10440
cacgatgcgt ccggcgtaga ggatctggct agcgatgacc ctgctgattg gttcgctgac  10500
catttccggg gtgcggaacg gcgttaccag aaactcagaa ggttcgtcca accaaaccga  10560
ctctgacggc agtttacgag agagatgata gggtctgctt cagtaagcca gatgctacac  10620
aattaggctt gtacatattg tcgttagaac gcggctacaa ttaatacata accttatgta  10680
tcatacacat acgatttagg tgacactata gaatacacct gcaggacgtc ccaatgatct  10740
taagttaa                                                           10748
```

EXPRESSION VECTORS FOR EUKARYOTIC EXPRESSION SYSTEMS

CROSS REFERENCE TO RELATED APPLICATIONS

This application is a U.S. National Phase application under 35 U.S.C. § 371 of PCT Application No. PCT/US2019/52373 filed on Sep. 23, 2019, which claims the benefit of priority to U.S. Provisional Application No. 62/735,417, filed on Sep. 24, 2018, the disclosure of which is incorporated herein by its entirety.

FIELD OF THE INVENTION

The present invention relates to expression vectors for expressing recombinant proteins (e.g., biologics or vaccines) in eukaryotic cells.

BACKGROUND OF THE INVENTION

Most biopharmaceuticals are produced in mammalian cells transfected with an expression vector that drives constitutive and high-level expression of the recombinant protein (See. e.g., Wurm, F. M., *Nature Biotech.* 22:1393-1398 (2004)). Chinese hamster ovary (CHO) cell line is one of the most commonly used cell lines in the commercial production of recombinant protein therapeutics, including monoclonal antibodies. Increased demand for protein therapeutics has bolstered efforts to augment cell line productivity through improvements in expression technology and optimization of process conditions. (See. e.g., Wurm, supra: Birch, J. R. & Racher, A. J., *Adv. Drug Delivery Rev.* 58:671-685 (2006)).

A well-designed expression vector is the first step toward achieving high production of recombinant proteins. (See. e.g., Ludwig, D. L., *BioProcess International* 4: S14-S23 (2006)). Expression vectors generally include a number of components, for example, one or more polypeptide expression cassettes, one or more selectable markers, and elements that allow replication of the vector in prokaryotic cells. In general, selection of the different components to be included in an expression vector will impact target polypeptide expression in mammalian host cells, and it is typically unpredictable if any new combination of components will support high levels of polypeptide expression.

SUMMARY OF THE INVENTION

The present disclosure provides expression vectors for eukaryotic expression systems that can 1) efficiently integrate into eukaryotic transcriptionally active hot spots: 2) block epigenetic gene silencing to ensure long term stable expression: 3) link the gene of interest (GOI) and the eukaryotic selectable marker to ensure consistent expression of GOI in the surviving eukaryotic cells: 4) remain stable to support various processes, including continuous perfusion; and 5) support faster timelines from construction to final clone selection.

In one aspect, provided herein is an expression vector comprising:

(a) a first expression cassette comprising the following elements in the order of upstream to downstream: a promoter operably linked to an insertion site for a GOI, an internal ribosome entry site (IRES), a polynucleotide encoding a eukaryotic selectable marker, and a polyadenylation (poly A) signal;

(b) a second expression cassette comprising a polynucleotide encoding a bacterial selectable marker; and (c) a bacterial plasmid origin of replication.

In certain embodiments of the various expression vectors provided herein, the first expression cassette further comprises one or more regulatory elements. In some embodiments, the regulatory element is an enhancer, an insulator, a locus control region (LCR), a matrix attachment region (MAR), a scaffold attachment region (SAR), an expression augmenting sequence element (EASE), an adenovirus tripartite leader (TPL), or a ubiquitous chromatin opening element (UCOE). In one embodiment, the regulatory element is an enhancer. In another embodiment, the regulatory element is an insulator. In yet another embodiment, the regulatory element is a LCR. In still another embodiment, the regulatory element is a MAR. In one embodiment, the regulatory element is a SAR. In another embodiment, the regulatory element is an EASE. In yet another embodiment, the regulatory element is a TPL. In still another embodiment, the regulatory element is a UCOE. In some embodiments, the first expression cassette further comprises one regulatory element. In other embodiments, the first expression cassette further comprises two regulatory elements. In yet other embodiments, the first expression cassette further comprises three regulatory elements. In still other embodiments, the first expression cassette further comprises four regulatory elements. In some embodiments, the first expression cassette further comprises five regulatory elements. In other embodiments, the first expression cassette further comprises six regulatory elements. In yet other embodiments, the first expression cassette further comprises seven regulatory elements. In still other embodiments, the first expression cassette further comprises eight or more regulatory elements.

In some embodiments, the expression vector further comprises two inverted terminal repeat (ITR) sequences flanking the first expression cassette. In other embodiments, the expression vector further comprises two inverted terminal repeat (ITR) sequences flanking the first expression cassette, and the first expression cassette further comprises one or more regulatory elements. In vet other embodiments, the expression vector further comprises two inverted terminal repeat (ITR) sequences flanking the first expression cassette, and the first expression cassette further comprises one or more regulatory elements selected from the group consisting of an enhancer, an insulator, a locus control region (LCR), a matrix attachment region (MAR), a scaffold attachment region (SAR), an expression augmenting sequence element (EASE), an adenovirus tripartite leader (TPL), and a ubiquitous chromatin opening element (UCOE). In certain embodiments, the expression vector further comprises two inverted terminal repeat (ITR) sequences flanking the first expression cassette, and the first expression cassette further comprises one regulatory element selected from the group consisting of an enhancer, an insulator, a locus control region (LCR), a matrix attachment region (MAR), a scaffold attachment region (SAR), an expression augmenting sequence element (EASE), an adenovirus tripartite leader (TPL), and a ubiquitous chromatin opening element (UCOE). In some embodiments, the expression vector further comprises two inverted terminal repeat (ITR) sequences flanking the first expression cassette, and the first expression cassette further comprises two regulatory elements selected from the group consisting of an enhancer, an insulator, a locus control region (LCR), a matrix attachment region (MAR), a scaffold attachment region (SAR), an expression augmenting sequence element (EASE), an adenovirus tripartite leader (TPL), and a ubiquitous chromatin opening element (UCOE). In other embodiments, the expression vector further comprises two inverted terminal repeat (ITR) sequences flanking the first expression cassette, and the first expression cassette further comprises three regulatory elements selected from the group consisting of an enhancer, an insulator, a locus control region (LCR), a matrix attachment region (MAR), a scaffold attachment region (SAR), an expression augmenting sequence element (EASE), an adenovirus tripartite leader (TPL), and a ubiquitous chromatin opening element (UCOE). In yet other embodiments, the expression vector further comprises two inverted terminal repeat (ITR) sequences flanking the first expression cassette, and the first expression cassette further comprises four regulatory elements selected from the group consisting of an enhancer, an insulator, a locus control region (LCR), a matrix attachment region (MAR), a scaffold attachment region (SAR), an expression augmenting sequence element (EASE), an adenovirus tripartite leader (TPL), and a ubiquitous chromatin opening element (UCOE). In still other embodiments, the expression vector further comprises two inverted terminal repeat (ITR) sequences flanking the first expression cassette, and the first expression cassette further comprises five regulatory elements selected from the group consisting of an enhancer, an insulator, a locus control region (LCR), a matrix attachment region (MAR), a scaffold attachment region (SAR), an expression augmenting sequence element (EASE), an adenovirus tripartite leader (TPL), and a ubiquitous chromatin opening element (UCOE). In some embodiments, the expression vector further comprises two inverted terminal repeat (ITR) sequences flanking the first expression cassette, and the first expression cassette further comprises six regulatory elements selected from the group consisting of an enhancer, an insulator, a locus control region (LCR), a matrix attachment region (MAR), a scaffold attachment region (SAR), an expression augmenting sequence element (EASE), an adenovirus tripartite leader (TPL), and a ubiquitous chromatin opening element (UCOE). In other embodiments, the expression vector further comprises two inverted terminal repeat (ITR) sequences flanking the first expression cassette, and the first expression cassette further comprises seven regulatory elements selected from the group consisting of an enhancer, an insulator, a locus control region (LCR), a matrix attachment region (MAR), a scaffold attachment region (SAR), an expression augmenting sequence element (EASE), an adenovirus tripartite leader (TPL), and a ubiquitous chromatin opening element (UCOE). In yet other embodiments, the expression vector further comprises two inverted terminal repeat (ITR) sequences flanking the first expression cassette, and the first expression cassette further comprises eight regulatory elements selected from the group consisting of an enhancer, an insulator, a locus control region (LCR), a matrix attachment region (MAR), a scaffold attachment region (SAR), an expression augmenting sequence element (EASE), an adenovirus tripartite leader (TPL), and a ubiquitous chromatin opening element (UCOE).

In other embodiments of the various expression vectors provided herein, the IRES comprises a polynucleotide sequence of SEQ ID NO: 1, 2, 3, 23, 24, or 25. In one embodiment, the IRES comprises a polynucleotide sequence of SEQ ID NO:1. In another embodiment, the IRES comprises a polynucleotide sequence of SEQ ID NO:2. In yet another embodiment, the IRES comprises a polynucleotide sequence of SEQ ID NO:3. In one embodiment, the IRES comprises a polynucleotide sequence of SEQ ID NO:23. In another embodiment, the IRES comprises a polynucleotide sequence of SEQ ID NO:24. In yet another embodiment, the IRES comprises a polynucleotide sequence of SEQ ID NO:25.

In some embodiments of the various expression vectors provided herein, the eukaryotic selectable marker is a neomycin phosphotransferase, a histidinol dehydrogenase, a hygromycin B phosphotransferase, a xanthine-guanine phosphoribosyltransferase, a dihydrofolate reductase, a tryptophan synthetase, a puromycin N-acetyl-transferase, a thymidine kinase, an adenine phosphoribosyl transferase, a glutamine synthetase, an adenosine deaminase, or metallothionein-1. In one embodiment, the eukaryotic selectable marker is a neomycin phosphotransferase. In another embodiment, the eukaryotic selectable marker is a histidinol dehydrogenase. In yet another embodiment, the eukaryotic selectable marker is a hygromycin B phosphotransferase. In still another embodiment, the eukaryotic selectable marker is a xanthine-guanine phosphoribosyltransferase. In one embodiment, the eukaryotic selectable marker is a dihydrofolate reductase. In another embodiment, the eukaryotic selectable marker is a tryptophan synthetase. In yet another embodiment, the eukaryotic selectable marker is a puromycin N-acetyl-transferase. In still another embodiment, the eukaryotic selectable marker is a thymidine kinase. In one embodiment, the eukaryotic selectable marker is an adenine phosphoribosyl transferase. In another embodiment, the eukaryotic selectable marker is a glutamine synthetase. In yet another embodiment, the eukaryotic selectable marker is an adenosine deaminase. In still another embodiment, the eukaryotic selectable marker is metallothionein-1.

In certain embodiments of the various expression vectors provided herein, the promoter is a human cytomegalovirus (CMV) immediate-early promoter, a human elongation factor 1 alpha (EF1a) promoter, a SV40 promoter, a phosphoglycerate kinase 1 (PGK1) promoter, a human ubiquitin C (Ubc) promoter, a human β-actin promoter, a CAG promoter, a yeast transcription elongation factor 1 (TEF1) promoter, a yeast glyceraldehyde 3-phosphate dehydrogenase (GAPDH) promoter, or a yeast alcohol dehydrogenase 1 (ADHI) promoter. In one embodiment, the promoter is a human CMV immediate-early promoter. In another embodiment, the promoter is a human EF1a promoter. In yet another embodiment, the promoter is a SV40 promoter. In still another embodiment, the promoter is a PGK1 promoter. In one embodiment, the promoter is a human Ubc promoter. In another embodiment, the promoter is a human β-actin promoter. In yet another embodiment, the promoter is a CAG promoter. In still another embodiment, the promoter is a yeast TEF1 promoter. In one embodiment, the promoter is a yeast GAPDH promoter. In another embodiment, the promoter is a yeast ADHI promoter.

In some embodiments of the various expression vectors provided herein, the enhancer is a human CMV immediate-early enhancer, a SV40 enhancer, a BK polyomarvirus (BKPyV) enhancer, an Epstein-Bar virus (EBV) enhancer, a c-Myc enhancer, an immunoglobulin heavy chain (IgH) enhancer, a Sp1-binding enhancer, an AP1-binding enhancer, or a CREB-binding enhancer. In one embodiment, the enhancer is a human CMV immediate-early enhancer. In another embodiment, the enhancer is a SV40 enhancer. In yet another embodiment, the enhancer is a BKPyV enhancer. In still another embodiment, the enhancer is an EBV enhancer. In one embodiment, the enhancer is a c-Myc enhancer. In another embodiment, the enhancer is an IgH enhancer. In yet another embodiment, the enhancer is a Sp1-binding enhancer. In still another embodiment, the enhancer is an API-binding enhancer. In one embodiment, the enhancer is a CREB-binding enhancer.

In certain embodiments, the enhancer is immediately adjacent to the promoter. In some embodiments, the enhancer is distant from the promoter with other DNA fragments between the enhancer and the promoter. In other embodiments, the enhancer is upstream of the promoter. In yet other embodiments, the enhancer is downstream of the promoter. In still other embodiments, the enhancer and the promoter are combined together as a combo enhancer/promoter. In one specific embodiment, the combo enhancer/promoter is a human CMV immediate-early enhancer/promoter. In another specific embodiment, the combo enhancer/promoter is a synthetic CAG promoter that comprises a CMV immediate-early enhancer and a chicken β-actin promoter.

In other embodiments of the various expression vectors provided herein, the insulator is HMR $tRNA^{Thr}$, Chal UAS, $UAS_{rpg}$, STAR, scs, scs', gypsy, Fab-7, Fab-8, $fas^{wb}$, sns, UR1, RO, Lys 5' A, HS4, 3'HS, BEAD-1, HS2-6, DMD/ICR, 5'HS5, apoB (−57 kb), apoB (+43 kb), or DM1. In one embodiment, the insulator is HMR $tRNA^{Thr}$. In another embodiment, the insulator is Chal UAS. In yet another embodiment, the insulator is $UAS_{rpg}$. In still another embodiment, the insulator is STAR. In one embodiment, the insulator is scs. In another embodiment, the insulator is scs'. In yet another embodiment, the insulator is gypsy. In still another embodiment, the insulator is Fab-7. In one embodiment, the insulator is Fab-8. In another embodiment, the insulator is $fas^{wb}$. In yet another embodiment, the insulator is sns. In still another embodiment, the insulator is URI. In one embodiment, the insulator is RO. In another embodiment, the insulator is Lys 5' A. In yet another embodiment, the insulator is HS4. In still another embodiment, the insulator is 3'HS. In one embodiment, the insulator is BEAD-1. In another embodiment, the insulator is HS2-6. In yet another embodiment, the insulator is DMD/ICR. In still another embodiment, the insulator is 5'HS5. In one embodiment, the insulator is apoB (−57 kb). In another embodiment, the insulator is apoB (+43 kb). In yet another embodiment, the insulator is DM1.

In certain embodiments of various expression vectors provided herein, the first expression cassette further comprises a first insulator and a second insulator. In some embodiments, the first insulator and the second insulators are the same insulator. In some embodiments, the first insulator and the second insulator are different insulators. In other embodiments, the first insulator and the second insulator are in the same direction. In yet other embodiments, the first insulator and the second insulator are in the opposite directions. In still other embodiments, the first insulator and the second insulator are HS4. In yet still other embodiments, the first insulator and the second insulator are HS4 in the opposite directions.

In yet other embodiments of the various expression vectors provided herein, the ITR is Tc1 ITR, Tc3 ITR, Minos ITR, Mos1 ITR, Famar1 ITR, Osmar5 ITR, Fot1 ITR, Impala ITR, ISY100 ITR, Mboumar-9 ITR, Sleeping Beauty ITR, Himar1 ITR, Frog Prince ITR, Hsmar1 ITR, SB100X ITR, piggyBac® ITR, or Tol2 ITR. In one embodiment, the ITR is Tc1 ITR. In another embodiment, the ITR is Tc3 ITR. In yet another embodiment, the ITR is Minos ITR. In still another embodiment, the ITR is Mos1 ITR. In one embodiment, the ITR is Famar1 ITR. In another embodiment, the ITR is Osmar5 ITR. In yet another embodiment, the ITR is Fot1 ITR. In still another embodiment, the ITR is Impala ITR. In one embodiment, the ITR is ISY100 ITR. In another embodiment, the ITR is Mboumar-9 ITR. In yet another embodiment, the ITR is Sleeping Beauty ITR. In still another embodiment, the ITR is Himar1 ITR. In one embodiment, the ITR is Frog Prince ITR. In another embodiment, the ITR is Hsmar1 ITR. In yet another embodiment, the ITR is SB100X ITR. In still another embodiment, the ITR is piggyBac® ITR. In one embodiment, the ITR is Tol2 ITR.

In certain embodiments of the various expression vectors provided herein, the bacterial selectable marker is an ampicillin resistance gene, a tetracycline resistance gene, a hygromycin resistance gene, a kanamycin resistance gene, a blasticidin resistance gene, or the like. In one embodiment, the bacterial selectable marker is an ampicillin resistance gene. In another embodiment, the bacterial selectable marker is a tetracycline resistance gene. In yet another embodiment, the bacterial selectable marker is a hygromycin resistance gene. In still another embodiment, the bacterial selectable marker is a kanamycin resistance gene. In yet still another embodiment, the bacterial selectable marker is a blasticidin resistance gene.

In another aspect, provided herein is an expression vector comprising:

(a) a first expression cassette comprising the following elements in the order of upstream to downstream: a first insulator, an EASE, a promoter, a TPL, an insertion site for a GOI, an IRES, a polynucleotide encoding a eukaryotic selectable marker, a polyA signal, and a second insulator;

(b) two ITR sequences flanking the first expression cassette;

(c) a second expression cassette comprising a polynucleotide encoding a bacterial selectable marker; and (d) a bacterial plasmid origin of replication.

In some embodiments of various expression vectors provided herein, the first expression cassette further comprises an enhancer. In certain embodiments, the enhancer is located between the EASE and the promoter.

In certain embodiments of the various expression vectors provided herein, the promoter is a human cytomegalovirus (CMV) immediate-early promoter, a human elongation factor 1 alpha (EF1a) promoter, a SV40 promoter, a phosphoglycerate kinase 1 (PGK1) promoter, a human ubiquitin C (Ubc) promoter, a human β-actin promoter, a CAG promoter, a yeast transcription elongation factor 1 (TEF1) promoter, a yeast glyceraldehyde 3-phosphate dehydrogenase (GAPDH) promoter, or a yeast alcohol dehydrogenase 1 (ADHI) promoter. In one embodiment, the promoter is a human CMV immediate-early promoter. In another embodiment, the promoter is a human EF1a promoter. In yet another embodiment, the promoter is a SV40 promoter. In still another embodiment, the promoter is a PGK1 promoter. In one embodiment, the promoter is a human Ubc promoter. In another embodiment, the promoter is a human β-actin promoter. In yet another embodiment, the promoter is a CAG promoter. In still another embodiment, the promoter is a yeast TEF1 promoter. In one embodiment, the promoter is a yeast GAPDH promoter. In another embodiment, the promoter is a yeast ADHI promoter.

In some embodiments of the various expression vectors provided herein, the enhancer is a human CMV immediate-early enhancer, a SV40 enhancer, a BK polyomarvirus (BKPyV) enhancer, an Epstein-Bar virus (EBV) enhancer, a c-Myc enhancer, an immunoglobulin heavy chain (IgH) enhancer, a Sp1-binding enhancer, an AP1-binding enhancer, or a CREB-binding enhancer. In one embodiment, the enhancer is a human CMV immediate-early enhancer. In another embodiment, the enhancer is a SV40 enhancer. In yet another embodiment, the enhancer is a BKPyV enhancer. In still another embodiment, the enhancer is an EBV enhancer. In one embodiment, the enhancer is a c-Myc enhancer. In another embodiment, the enhancer is an IgH enhancer. In yet another embodiment, the enhancer is a Sp1-binding enhancer. In still another embodiment, the enhancer is an API-binding enhancer. In one embodiment, the enhancer is a CREB-binding enhancer.

In certain embodiments, the enhancer is immediately adjacent to the promoter. In some embodiments, the enhancer is distant from the promoter with other DNA fragments between the enhancer and the promoter. In other embodiments, the enhancer is upstream of the promoter. In yet other embodiments, the enhancer is downstream of the promoter. In still other embodiments, the enhancer and the promoter are combined together as a combo enhancer/promoter. In one specific embodiment, the combo enhancer/promoter is a human CMV immediate-early enhancer/promoter. In another specific embodiment, the combo enhancer/promoter is a synthetic CAG promoter that comprises a CMV immediate-early enhancer and a chicken β-actin promoter.

In other embodiments of the various expression vectors provided herein, the insulator is HMR $tRNA^{Thr}$, Chal UAS, $UAS_{rpg}$, STAR, scs, scs', gypsy, Fab-7, Fab-8, $fas^{wb}$, sns, UR1, RO, Lys 5' A, HS4, 3'HS, BEAD-1, HS2-6, DMD/ICR, 5'HS5, apoB (−57 kb), apoB (+43 kb), or DM1. In one embodiment, the insulator is HMR $tRNA^{Thr}$. In another embodiment, the insulator is Chal UAS. In yet another embodiment, the insulator is $UAS_{rpg}$. In still another embodiment, the insulator is STAR. In one embodiment, the insulator is scs. In another embodiment, the insulator is scs'. In yet another embodiment, the insulator is gypsy. In still another embodiment, the insulator is Fab-7. In one embodiment, the insulator is Fab-8. In another embodiment, the insulator is $fas^{wb}$. In yet another embodiment, the insulator is sns. In still another embodiment, the insulator is URI. In one embodiment, the insulator is RO. In another embodiment, the insulator is Lys 5' A. In yet another embodiment, the insulator is HS4. In still another embodiment, the insulator is 3 HS. In one embodiment, the insulator is BEAD-1. In another embodiment, the insulator is HS2-6. In yet another embodiment, the insulator is DMD/ICR. In still another embodiment, the insulator is 5'HS5. In one embodiment, the insulator is apoB (−57 kb). In another embodiment, the insulator is apoB (+43 kb). In yet another embodiment, the insulator is DM1.

In some embodiments, the first insulator and the second insulators are the same insulator. In some embodiments, the first insulator and the second insulator are different insulators. In other embodiments, the first insulator and the second insulator are in the same direction. In yet other embodiments, the first insulator and the second insulator are in the opposite directions. In still other embodiments, the first insulator and the second insulator are HS4. In yet still other embodiments, the first insulator and the second insulator are HS4 in the opposite directions.

In yet other embodiments of the various expression vectors provided herein, the ITR is Tc1 ITR, Tc3 ITR, Minos ITR, Mos1 ITR, Famar1 ITR, Osmar5 ITR, Fot1 ITR, Impala ITR, ISY100 ITR, Mboumar-9 ITR, Sleeping Beauty ITR, Himar1 ITR, Frog Prince ITR, Hsmar1 ITR, SB100X ITR, piggyBac® ITR, or Tol2 ITR. In one embodiment, the ITR is Tc1 ITR. In another embodiment, the ITR is Tc3 ITR. In yet another embodiment, the ITR is Minos ITR. In still another embodiment, the ITR is Mos1 ITR. In one embodiment, the ITR is Famar1 ITR. In another embodiment, the ITR is Osmar5 ITR. In yet another embodiment, the ITR is Fot1 ITR. In still another embodiment, the ITR is Impala ITR. In one embodiment, the ITR is ISY100 ITR. In another embodiment, the ITR is Mboumar-9 ITR. In yet another embodiment, the ITR is Sleeping Beauty ITR. In still another embodiment, the ITR is Himar1 ITR. In one embodiment, the ITR is Frog Prince ITR. In another embodiment, the ITR is Hsmar1 ITR. In yet another embodiment, the ITR is SB100X ITR. In still another embodiment, the ITR is piggyBac® ITR. In one embodiment, the ITR is Tol2 ITR.

In other embodiments of the various expression vectors provided herein, the IRES comprises a polynucleotide sequence of SEQ ID NO: 1, 2, 3, 23, 24, or 25. In one embodiment, the IRES comprises a polynucleotide sequence of SEQ ID NO:1. In another embodiment, the IRES comprises a polynucleotide sequence of SEQ ID NO:2. In yet another embodiment, the IRES comprises a polynucleotide sequence of SEQ ID NO:3. In one embodiment, the IRES comprises a polynucleotide sequence of SEQ ID NO:23. In another embodiment, the IRES comprises a polynucleotide sequence of SEQ ID NO:24. In yet another embodiment, the IRES comprises a polynucleotide sequence of SEQ ID NO:25.

In some embodiments of the various expression vectors provided herein, the eukaryotic selectable marker is a neomycin phosphotransferase, a histidinol dehydrogenase, a hygromycin B phosphotransferase, a xanthine-guanine phosphoribosyltransferase, a dihydrofolate reductase, a tryptophan synthetase, a puromycin N-acetyl-transferase, a thymidine kinase, an adenine phosphoribosyl transferase, a glutamine synthetase, an adenosine deaminase, or metallothionein-1. In one embodiment, the eukaryotic selectable marker is a neomycin phosphotransferase. In another embodiment, the eukaryotic selectable marker is a histidinol dehydrogenase. In vet another embodiment, the eukaryotic selectable marker is a hygromycin B phosphotransferase. In still another embodiment, the eukaryotic selectable marker is a xanthine-guanine phosphoribosyltransferase. In one embodiment, the eukaryotic selectable marker is a dihydrofolate reductase. In another embodiment, the eukaryotic selectable marker is a tryptophan synthetase. In yet another embodiment, the eukaryotic selectable marker is a puromycin N-acetyl-transferase. In still another embodiment, the eukaryotic selectable marker is a thymidine kinase. In one embodiment, the eukaryotic selectable marker is an adenine phosphoribosyl transferase. In another embodiment, the eukaryotic selectable marker is a glutamine synthetase. In yet another embodiment, the eukaryotic selectable marker is an adenosine deaminase. In still another embodiment, the eukaryotic selectable marker is metallothionein-1.

In certain embodiments of the various expression vectors provided herein, the bacterial selectable marker is an ampicillin resistance gene, a tetracycline resistance gene, a hygromycin resistance gene, a kanamycin resistance gene, a blasticidin resistance gene, or the like. In one embodiment, the bacterial selectable marker is an ampicillin resistance gene. In another embodiment, the bacterial selectable marker is a tetracycline resistance gene. In yet another embodiment, the bacterial selectable marker is a hygromycin resistance gene. In still another embodiment, the bacterial selectable marker is a kanamycin resistance gene. In yet still another embodiment, the bacterial selectable marker is a blasticidin resistance gene.

In one embodiment of various expression vectors provided herein, the first insulator and the second insulator are HS4, the enhancer is a human CMV immediate-early enhancer, the promoter is a human CMV immediate-early promoter, the ITR is piggyBac® ITR, the eukaryotic selectable marker is a glutamine synthetase, and the IRES comprises a polynucleotide sequence of SEQ ID NO:3.

In another embodiment of various expression vectors provided herein, the first insulator and the second insulator are HS4, the enhancer and the promoter are a combo enhancer/promoter, wherein the combo enhancer/promoter is a human CMV immediate-early enhancer/promoter, the ITR is piggyBac® ITR, the eukaryotic selectable marker is a glutamine synthetase, and the IRES comprises a polynucleotide sequence of SEQ ID NO:3.

Thus, in one particular embodiment, the expression vector comprises:

(a) a first expression cassette comprising the following elements in the order of upstream to downstream: a first HS4 insulator, an EASE, a human CMV immediate-early enhancer/promoter, a TPL, an insertion site for a GOI, an IRES comprising a polynucleotide sequence of SEQ ID NO:3, a polynucleotide encoding a glutamine synthetase, a polyA signal, and a second HS4 insulator;

(b) two piggyBac® ITR sequences flanking the first expression cassette;

(c) a second expression cassette comprising a polynucleotide encoding a bacterial selectable marker; and (d) a bacterial plasmid origin of replication.

In another specific embodiment, the expression vector comprises a polynucleotide sequence of SEQ ID NO:4, 5, 6, 7, 8, 26, 27, 28, or 29. In one embodiment, the expression vector comprises a polynucleotide sequence of SEQ ID NO:4. In another embodiment, the expression vector comprises a polynucleotide sequence of SEQ ID NO:5. In yet another embodiment, the expression vector comprises a polynucleotide sequence of SEQ ID NO:6. In still another embodiment, the expression vector comprises a polynucleotide sequence of SEQ ID NO: 7. In yet still another embodiment, the expression vector comprises a polynucleotide sequence of SEQ ID NO:8. In one embodiment, the expression vector comprises a polynucleotide sequence of SEQ ID NO:26. In another embodiment, the expression vector comprises a polynucleotide sequence of SEQ ID NO:27. In yet another embodiment, the expression vector comprises a polynucleotide sequence of SEQ ID NO:28. In still another embodiment, the expression vector comprises a polynucleotide sequence of SEQ ID NO:29.

In yet another specific embodiment, the expression vector consists of a polynucleotide sequence of SEQ ID NO: 4, 5, 6, 7, 8, 26, 27, 28, or 29. In one embodiment, the expression vector consists of a polynucleotide sequence of SEQ ID NO:4. In another embodiment, the expression vector consists of a polynucleotide sequence of SEQ ID NO:5. In yet another embodiment, the expression vector consists of a polynucleotide sequence of SEQ ID NO:6. In still another embodiment, the expression vector consists of a polynucleotide sequence of SEQ ID NO: 7. In yet still another embodiment, the expression vector consists of a polynucleotide sequence of SEQ ID NO:8. In one embodiment, the expression vector consists of a polynucleotide sequence of SEQ ID NO:26. In another embodiment, the expression vector consists of a polynucleotide sequence of SEQ ID NO:27. In yet another embodiment, the expression vector consists of a polynucleotide sequence of SEQ ID NO:28. In still another embodiment, the expression vector consists of a polynucleotide sequence of SEQ ID NO:29.

In yet still another specific embodiment, the expression vector consists essentially of a polynucleotide sequence of SEQ ID NO: 4, 5, 6, 7, 8, 26, 27, 28, or 29. In one embodiment, the expression vector consists essentially of a polynucleotide sequence of SEQ ID NO:4. In another embodiment, the expression vector consists essentially of a polynucleotide sequence of SEQ ID NO: 5. In yet another embodiment, the expression vector consists essentially of a polynucleotide sequence of SEQ ID NO:6. In still another embodiment, the expression vector consists essentially of a polynucleotide sequence of SEQ ID NO:7. In yet still another embodiment, the expression vector consists essentially of a polynucleotide sequence of SEQ ID NO:8. In one embodiment, the expression vector consists essentially of a polynucleotide sequence of SEQ ID NO: 26. In another embodiment, the expression vector consists essentially of a polynucleotide sequence of SEQ ID NO:27. In yet another embodiment, the expression vector consists essentially of a polynucleotide sequence of SEQ ID NO:28. In still another embodiment, the expression vector consists essentially of a polynucleotide sequence of SEQ ID NO:29.

In another specific embodiment, the expression vector comprises a polynucleotide sequence that is at least 60%, 70%, 80%, 90%, or 95% identical to the polynucleotide sequence of SEQ ID NO:4, 5, 6, 7, 8, 26, 27, 28, or 29. In one embodiment, the expression vector comprises a polynucleotide sequence that is at least 60%, 70%, 80%, 90%, or 95% identical to the polynucleotide sequence of SEQ ID NO:4. In another embodiment, the expression vector comprises a polynucleotide sequence that is at least 60%, 70%, 80%, 90%, or 95% identical to the polynucleotide sequence of SEQ ID NO:5. In yet another embodiment, the expression vector comprises a polynucleotide sequence that is at least 60%, 70%, 80%, 90%, or 95% identical to the polynucleotide sequence of SEQ ID NO:6. In still another embodiment, the expression vector comprises a polynucleotide sequence that is at least 60%, 70%, 80%, 90%, or 95% identical to the polynucleotide sequence of SEQ ID NO:7. In yet still another embodiment, the expression vector comprises a polynucleotide sequence that is at least 60%, 70%, 80%, 90%, or 95% identical to the polynucleotide sequence of SEQ ID NO:8. In one embodiment, the expression vector comprises a polynucleotide sequence that is at least 60%, 70%, 80%, 90%, or 95% identical to the polynucleotide sequence of SEQ ID NO:26. In another embodiment, the expression vector comprises a polynucleotide sequence that is at least 60%, 70%, 80%, 90%, or 95% identical to the polynucleotide sequence of SEQ ID NO:27. In yet another embodiment, the expression vector comprises a polynucleotide sequence that is at least 60%, 70%, 80%, 90%, or 95% identical to the polynucleotide sequence of SEQ ID NO:28. In still another embodiment, the expression vector comprises a polynucleotide sequence that is at least 60%, 70%, 80%, 90%, or 95% identical to the polynucleotide sequence of SEQ ID NO:29.

In certain embodiments of the various expression vectors provided herein, the expression vector further comprises the GOI. In some embodiments, the expression vector further comprises the GOI, and the GOI encodes a therapeutic or prophylactic protein. In other embodiments, the expression vector further comprises the GOI, and the GOI encodes a heavy chain or a fragment thereof of a monoclonal antibody. In yet other embodiments, the expression vector further comprises the GOI, and the GOI encodes a light chain or a fragment thereof of a monoclonal antibody.

In yet another aspect, provided herein is a mammalian recombinant host cell comprising a mammalian host cell transfected with the expression vector described herein.

In certain embodiments of various mammalian recombinant host cells provided herein, the mammalian host cell is a CHO cell. In one embodiment, the endogenous glutamine synthetase gene of the CHO cell is knocked out.

In still another aspect, provided herein is a method of producing a polypeptide, comprising culturing the mammalian recombinant host cell described herein, under conditions in which the polypeptide is expressed.

In some embodiments, provided herein is a method of producing a polypeptide, comprising culturing the mammalian recombinant host cell described herein, under conditions in which the polypeptide is expressed, and recovering the polypeptide from the culture.

In another aspect, provided herein is a bacterial recombinant host cell comprising a bacterial host cell transformed with the expression vector described herein.

In yet another aspect, provided herein is a method of propagating an expression vector, comprising culturing the bacterial recombinant host cell described herein, under conditions in which the expression vector is replicated.

In some embodiments, provided herein is a method of propagating an expression vector, comprising culturing the bacterial recombinant host cell described herein, under conditions in which the expression vector is replicated, and recovering the expression vector from the culture.

In still another aspect, provided herein is a mammalian recombinant host cell comprising a mammalian host cell co-transfected with a first expression vector and a second expression vector, wherein the first expression vector and the second expression vector are each expression vectors described herein, wherein the GOI of the first expression vector encodes a light chain of a monoclonal antibody and the GOI of the second expression vector encodes a heavy chain of the monoclonal antibody, and wherein the eukaryotic selectable marker of the first expression vector is different from the eukaryotic selectable marker of the second expression vector.

In yet still another aspect, provided herein is a method of producing a monoclonal antibody, comprising culturing the mammalian recombinant host cell co-transfected with a first expression vector described herein comprising a first GOI encoding the light chain of the monoclonal antibody and a second expression vector described herein comprising a second GOI encoding the heavy chain of the monoclonal antibody, under conditions in which both the light chain and the heavy chain of the monoclonal antibody are expressed.

In some embodiments, provided herein is a method of producing a monoclonal antibody, comprising culturing the mammalian recombinant host cell co-transfected with a first expression vector described herein comprising a first GOI encoding the light chain of the monoclonal antibody and a second expression vector described herein comprising a second GOI encoding the heavy chain of the monoclonal antibody, under conditions in which both the light chain and the heavy chain of the monoclonal antibody are expressed, and recovering the monoclonal antibody from the culture.

In certain embodiments, the method of producing a monoclonal antibody comprises culturing the mammalian recombinant host cell co-transfected with a first expression vector described herein comprising a first GOI encoding the light chain of the monoclonal antibody and a second expression vector described herein comprising a second GOI encoding the heavy chain of the monoclonal antibody, under conditions in which both the light chain and the heavy chain of the monoclonal antibody are expressed, and wherein the eukaryotic selectable marker of the first expression vector is different from the eukaryotic selectable marker of the second expression vector.

In other embodiments, the method of producing a monoclonal antibody comprises culturing the mammalian recombinant host cell co-transfected with a first expression vector described herein comprising a first GOI encoding the light chain of the monoclonal antibody and a second expression vector described herein comprising a second GOI encoding the heavy chain of the monoclonal antibody, under conditions in which both the light chain and the heavy chain of the monoclonal antibody are expressed, and recovering the monoclonal antibody from the culture, and wherein the eukaryotic selectable marker of the first expression vector is different from the eukaryotic selectable marker of the second expression vector.

DETAILED DESCRIPTION OF THE INVENTION

I. General

Figure 1:
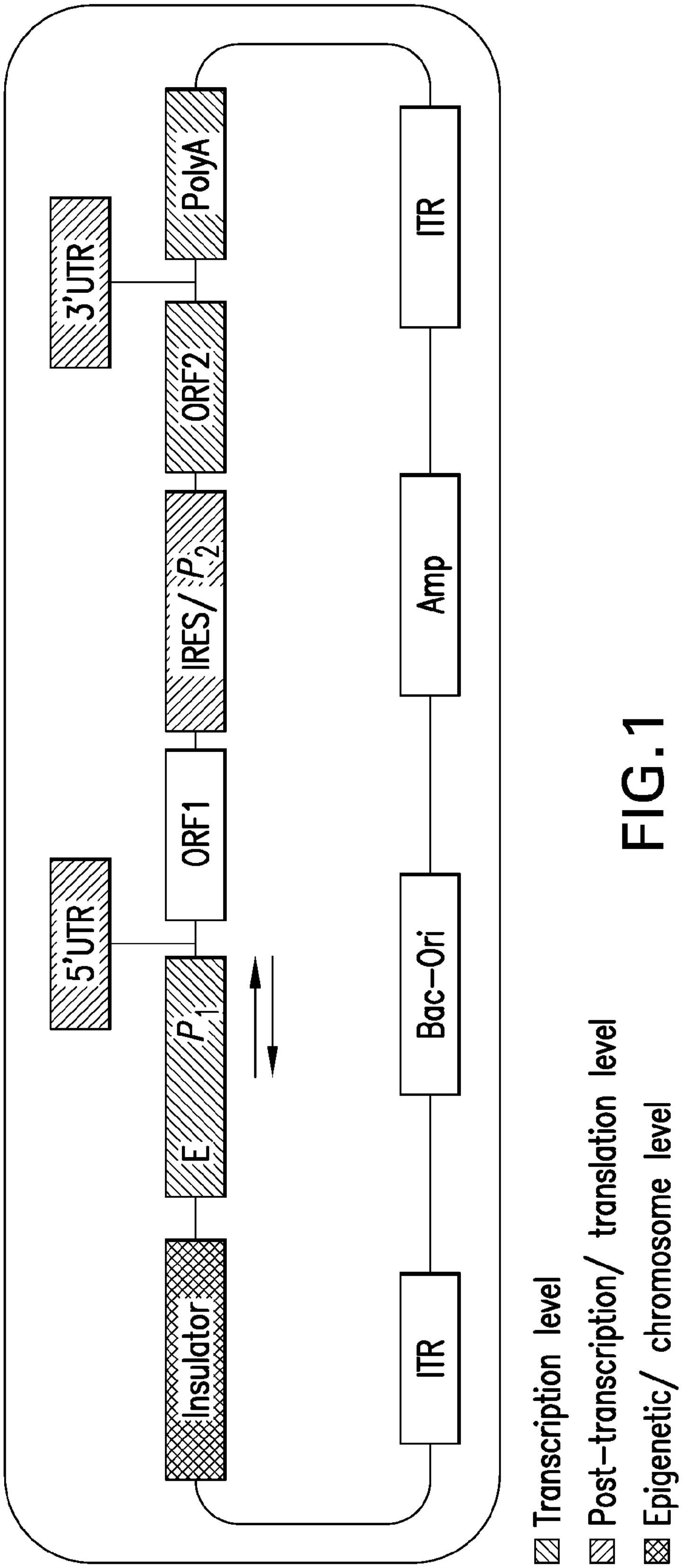
FIG. 1 illustrates an exemplary expression vector with engineered elements. E represents an enhancer: P represents a promoter: ORF represents an open reading frame: UTR represents an untranslated region: IRES represents an internal ribosome entry site: PolyA represents a polyadenylation signal: ITR represents an inverted repeat region, Bac-Ori represents a bacterial origin of replication: Amp represents an ampicillin selectable marker.

The present invention is not to be limited in scope by the specific embodiments described herein. Indeed, various modifications of the invention in addition those described herein will become apparent to those skilled in the art from the foregoing description. Such modifications are intended to fall within the scope of the appended claims.

Patents, patent applications, publications, product descriptions, and protocols are cited throughout this application, the disclosure of such documents are incorporated herein by reference in their entirety for all purposes, and to the same extent as if each individual document was specifically and individually indicated to be incorporated by reference.

II. Molecular Biology and Definitions

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, New York (herein "Sambrook, et al., 1989"): *DNA Cloning: A Practical Approach*, Volumes I and II (D. N. Glover ed. 1985): *Oligonucleotide Synthesis* (M. J. Gait ed. 1984): *Nucleic Acid Hybridization* (B. D. Hames & S. Higgins eds. (1985)): *Transcription And Translation* (B. D. Hames & S. Higgins, eds. (1984)): *Animal Cell Culture* (R. I. Freshney, ed. (1986)); *Immobilized Cells And Enzymes* (IRL Press, (1986)): B. Perbal, *A Practical Guide To Molecular Cloning* (1984): F. M. Ausubel, et al. (eds.), *Current Protocols in Molecular Biology*, John Wiley & Sons, Inc. (1994).

So that the invention may be more readily understood, certain technical and scientific terms are specifically defined below. Unless specifically defined elsewhere in this specification, all other technical and scientific terms use herein have the meaning that would be commonly understood by one of ordinary skill in the art to which this invention belongs when used in similar contexts as used herein.

As used herein, including the appended claims, the singular forms of words such as "a." "an." and "the," include their corresponding plural references unless the context clearly dictates otherwise.

"About" when used to modify a numerically defined parameter, e.g., the length of a polynucleotide discussed herein, means that the parameter may vary by as much as 10% below or above the stated numerical value for that parameter. For example, a polynucleotide of about 100 bases may vary between 90 and 110 bases.

A "coding sequence" is a nucleotide sequence that encodes a biological product of interest (e.g., an RNA, polypeptide, protein, or enzyme) and when expressed, results in production of the product. A coding sequence is "under the control of," "functionally associated with," "operably linked to," or "operably associated with" transcriptional or translational regulatory sequences in a cell when the regulatory sequences direct RNA polymerase-mediated transcription of the coding sequence into RNA, e.g., mRNA, which then may be trans-RNA spliced (if it contains introns) and, optionally, translated into a protein encoded by the coding sequence.

"Consists essentially of" and variations such as "consist essentially of" or "consisting essentially of" as used throughout the specification and claims, indicate the inclusion of any recited elements or group of elements, and the optional inclusion of other elements, of similar or different nature than the recited elements, which do not materially change the basic or novel properties of the specified composition.

"Express" and "expression" mean allowing or causing the information in a gene or coding sequence, e.g., an RNA or DNA, to become manifest: for example, producing a protein by activating the cellular functions involved in transcription and translation of a corresponding gene. A DNA sequence can be expressed in or by a cell to form an "expression product" such as an RNA (e.g., mRNA) or a protein. The expression product itself may also be said to be "expressed" by the cell.

"Expression vector" or "expression construct" means a vehicle (e.g., a plasmid) by which a polynucleotide comprising regulatory sequences operably linked to a coding sequence can be introduced into a host cell where the coding sequence is expressed using the transcription and translation machinery of the host cell.

"Expression cassette" means a polynucleotide that comprises elements sufficient to control expression of a gene, including but not limited to, a promoter operably linked to the gene sequence or operably linked to a multiple cloning site for inserting the gene sequence, and a poly A signal. In some embodiments, the expression cassette further comprises one or more regulatory elements that can regulate the expression of the gene at transcriptional, translational, and/or chromatin levels.

"Promoter" or "promoter sequence" is a segment of DNA that contains a regulatory region capable of recruiting an RNA polymerase (e.g., directly or through other promoter-bound proteins or substances) and initiating transcription of a coding sequence. Within the promoter sequence may be found a transcription initiation site (conveniently defined, for example, by mapping with nuclease S1), as well as protein binding domains (consensus sequences) responsible for the recruiting of RNA polymerase.

"Enhancer" or "enhancer sequence" is a DNA regulatory region that enhances transcription of a promoter independently of its distance, location, or orientation to the promoter. In certain embodiments, the enhancer is immediately adjacent to the promoter. In some embodiments, the enhancer is distant from the promoter. In other embodiments, the promoter and the enhancer are one combined sequence, referred as a "combo enhancer/promoter" herein.

"Internal ribosome entry site" or "IRES" is an RNA element or sequence that allows for translation initiation in a cap-independent manner by recruiting ribosomes directly. As used herein, the term "internal ribosome entry site" or "IRES" also encompasses the DNA sequence that can be transcribed into the RNA sequence that allows for translation initiation in a cap-independent manner by recruiting ribosomes directly. IRES can be a wild type IRES from any species or a variant or mutant thereof, whether naturally occurred or man-made. Examples of IRES that can be used include, but are not limited to, the nucleotide sequence of the 5' nontranslated region of encephalomyocarditis virus (EMCV) (GenBank: M81861.1; Duke et al., Sequence and structural elements that contribute to efficient encephalomyocarditis virus RNA translation. J Virol. 1992 March; 66 (3): 1602-9.). IRES element described by Bochkov & Palmenberg (Translational efficiency of EMCV IRES in bicistronic vectors is dependent upon IRES sequence and gene location. Biotechniques. 2006 September; 41 (3): 283-4). IRES element from expression vector pInSRT-GFP (GenBank LC417349.1). IRES element from expression vector pCeMM-CTAP (SG) (GenBank EF467048.1). IRES element described by Jang & Wimmer (Cap-independent translation of encephalomyocarditis virus RNA: structural elements of the internal ribosomal entry site and involvement of a cellular 57-KD RNA-binding protein. Genes Dev. 1990 September; 4 (9): 1560-72). IRES element from expression vector pIRESneo3 (Clontech/Takara Bio). IRES elements described in WO 2015/016786. WO 2015/021077. WO 2016/003368. WO 2016/074016, or WO 2013/092743, or variants thereof.

"Regulatory element," "regulatory region," or "regulatory sequence," as used herein, refers to a polynucleotide sequence that has the ability to regulate (such as, initiate, activate, enhance, increase, decrease, inhibit, suppress, or silence) expression of a gene. In some embodiments, the regulation is achieved by binding of cellular factors to the polynucleotide sequence. In other embodiments, the regulation is achieved by interaction between cellular factors. The regulation can occur at one or more different levels in the expression process from DNA to protein, including but not limited to transcriptional, translational, or chromatin levels.

"Insulator," as used herein, refers to a class of DNA elements or sequences that possess an ability to isolate the proximal DNA region by preventing the positional effect from the surrounding chromosome area. In certain embodiments, the insulator can block enhancer when the insulator is situated between the enhancer and the promoter. In some embodiments, the insulator can act as barriers that prevent the advance of nearby condensed chromatin that might otherwise silence expression. In other embodiments, the insulator can block enhancer and act as barriers.

"Expression augmenting sequence element" or "EASE" is a DNA element or sequence that can increase expression of a protein when the DNA element or sequence is placed upstream of the promoter that controls the expression of the protein.

"Tripartite leader" or "TPL" is an RNA element or sequence in the 5'-untranslated region of adenovirus late-expressed mRNA that has an ability to initiate translation of the late-expressed mRNA in a cap-independent manner. As used herein, the term "tripartite leader" or "TPL" also encompasses the DNA sequence that can be transcribed into the RNA sequence in the 5'-untranslated region of adenovirus late-expressed mRNA that has an ability to initiate translation of the late-expressed mRNA in a cap-independent manner.

"Inverted terminal repeat" or "ITR." in the context of transposon technology, refers to a DNA element or sequence and its inverted version at either end of a transposon that signals where the breakage and joining should occur.

"Selectable marker" or "selection marker" is a protein which allows the specific selection of cells that express this protein by the addition of a corresponding selecting agent to the culture medium. In certain embodiments, the selectable marker is a eukaryotic selectable marker, which allows selection of eukaryotic cells that express the marker protein. In some embodiments, the selectable marker is a bacterial selectable marker, which allows selection of bacterial cells that express the marker protein.

"Nucleic acid" or "polynucleotide" refers to a single- or double-stranded polymer of bases attached to a sugar phosphate backbone, and includes DNA and RNA molecules.

Each strand of DNA or RNA has a 5' end and a 3' end. "Direction," as used herein, when referring to a DNA, means the 5' to 3' direction of the coding strand for a gene, and, when referring to an RNA, means the 5' to 3' direction of the RNA molecule. When two DNA or RNA fragments are in the "same direction," their 5' to 3' directions align and are in the same direction. When two DNA or RNA fragments are in the "opposite direction," their 5' to 3' directions are opposite.

"Upstream" or "downstream." as used herein, means relative positions of nucleic acid in DNA when referring to a gene or in RNA when referring to a gene transcript. When referring to the 5' to 3' direction in which RNA transcription takes place, upstream is toward the 5' end of the RNA molecule and downstream is toward the 3' end of the RNA. When referring to a double-stranded DNA, upstream is toward the 5' end of the coding strand for the gene and downstream is toward the 3' end of the coding strand. Some genes on the same DNA molecule may be transcribed in opposite directions, so the upstream and downstream areas of the molecule may change depending on which gene is used as the reference.

"Host cell" includes any cell of any organism that is used for the purpose of producing a recombinant protein encoded by an expression vector or propagating the expression vector introduced into the host cell. A "mammalian recombinant host cell" refers to a mammalian host cell that comprises a heterologous expression vector, which may or may not be integrated into the host cell chromosome. A "bacterial recombinant host cell" refers to a bacterial host cell that comprises a heterologous expression vector, which may or may not be integrated into the host cell chromosome.

"Monoclonal antibody" or "mAb." as used herein, refers to a population of substantially homogeneous antibodies, i.e., the antibody molecules constituting the population are identical in amino acid sequence except for possible naturally occurring mutations that may be present in minor amounts. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Kohler et al. (1975) *Nature* 256:495, or may be made by recombinant DNA methods (see, e.g., U.S. Pat. No. 4,816,567). The "monoclonal antibodies" may also be isolated from phage antibody libraries using the techniques described in Clackson et al. (1991) *Nature* 352:624-628 and Marks et al. (1991) *J. Mol. Biol.* 222:581-597, for example. See also Presta (2005) *J. Allergy Clin. Immunol.* 116:731.

In general, the basic antibody structural unit comprises a tetramer. Each tetramer includes two identical pairs of polypeptide chains, each pair having one "light chain" (about 25 kDa) and one "heavy chain" (about 50-70 kDa). The amino-terminal portion of each chain includes a variable region of about 100 to 110 or more amino acids primarily responsible for antigen recognition. The variable regions of each light/heavy chain pair form the antibody binding site. Thus, in general, an intact antibody has two binding sites. The carboxy-terminal portion of the heavy chain may define a constant region primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively.

III. Expression Vectors for Eukaryotic Expression System

In one aspect, provided herein are expression vectors designed for expressing recombinant proteins (e.g., biologics or vaccines) in eukaryotic cells. Recombinant proteins, such as monoclonal antibodies (mAb), are usually produced in mammalian host cells by stably integrating recombinant expression vectors encoding the recombinant protein into the host genome. In biologics development, stable cell line development is a long, complicated, and tedious process. Factors to be considered when designing expression vectors include but are not limited to: 1) efficient integration of the expression vector into the genomic transcriptionally active hot spots; 2) blockage of epigenetic gene silencing activities to ensure long term clone stability; 3) linkage of the GOI and the mammalian selection marker to ensure consistent expression of GOI in selected cells; 4) stable cells to withstand various processes, including continuous perfusion; and 5) fast selection timeline from construction to final clone selection.

In this disclosure, various DNA elements (e.g., regulatory elements, including but not limited to an enhancer, an insulator, a LCR, a MAR, a SAR, an EASE, a TPL, or a UCOE) were selected and engineered into expression vectors. The effects of these engineered expression vectors on stable cell selection and expression level of recombinant proteins were evaluated. In certain embodiments, the innovative combinations of engineered DNA elements (e.g., regulatory elements, including but not limited to an enhancer, an insulator, a LCR, a MAR, a SAR, an EASE, a TPL, or a UCOE) can generate high expression stable cells in a shorter timeline, compared to commercially available expression vectors.

For vector design, first, genome integration is a critical factor that directly impacts the efficiency and robustness in both stable cell line generation and long-term stability. Traditional methods of delivering the whole plasmid into the host cells is using random integration mechanisms through natural intracellular pathways, which lead to extremely low integration efficiency, such as 0.1-40% depending on the cell type and the delivery approach. In addition, the randomly selected integration sites are usually not optimal to support active expression, which reduces the probability of identifying high expressing cell lines. Further, the backbone of the expression vector typically contains elements that support plasmid replication in *E. coli*, which could cause epigenetic-mediated gene silencing after integration into the genome of mammalian cells. To solve these problems, a transposon technology is integrated herein. A transposon is a DNA sequence that can change its position within a genome. The class II transposons, also called DNA transposons, can efficiently transfer DNA via a “cut and paste” mechanism. A specific transposase recognizes transposon-specific ITR sequences located on both ends of the interested DNA fragment and efficiently moves the contents between the ITR sequences to the target chromosomal sites. It has been proposed that the preferred integration sites of these transposon systems are at the euchromatin regions, especially at AT-rich areas, which are potential genomic transcriptionally active hot spots. Another attractive feature of this transposon technology is that the transposase also enables the excision of the transposon in a completely seamless manner, leaving no sequences or mutations behind. Thus, through appropriate vector design, the transposase can remove the unfavorable bacteria-related element completely before integration into the mammalian genome to reduce epigenetic gene silencing. Furthermore, the transposon technology offers a large cargo-carrying capacity (up to 100-200 kb) which enables up to 10 times larger expression cassettes, compared to standard expression plasmid, to be easily integrated into target genome.

Second, the efficiency of delivering an expression vector into host cells is also very important. Depending on the cell type, vector size. DNA delivery approach, and DNA quality, the DNA delivery efficiency can range between 10% and 30%, which results in variations in selection timeline and quality of stably transfected host cells. Any common DNA delivery approach known in the art, such as biological approach (e.g., virus-mediated), chemical approach (e.g., cationic polymer, calcium phosphate, or cationic lipid), or physical approach (e.g., direct injection, biolistic particle delivery, electroporation, laser-irradiation, sonoporation, or magnetic nanoparticle) can be used to achieve optimal efficiency of delivering the expression vectors disclosed herein into host cells.

Third, how to effectively select stable high producers is important. One of the most reliable ways to achieve stable transfection is to select cells by applying a selective pressure, which can be overcome by stably incorporating the plasmid DNA containing an expression cassette encoding a drug-resistance enzyme (eukaryotic selectable marker) into the genome. There are multiple ways to design the expression cassette for the eukaryotic selectable marker. The eukaryotic selectable marker can be driven by a weaker promoter to increase selection stringency, which is one of the popular designs. In that design, the GOI is driven by a different promoter which is independent from the eukaryotic selection marker-containing cassette. Thus, the expression level of GOI in selected stable cells cannot be predicted or controlled, which can lead to low expression in transfection pools and/or clone instability. To resolve this issue, directly linking the GOI and the eukaryotic selection marker in the same expression cassette would be necessary. IRES is a type of regulatory element that can be found in several viruses and cellular RNAs (reviewed in McBratney et, al. Current Opinion in Cell Biology 5:961, 1993). It is an RNA element that allows for translation initiation in a cap-independent manner by recruiting ribosomes directly. Therefore, inserting an IRES sequence between two ORFs allows co-expression of the two genes together in a bicistronic eukaryotic expression cassette (Kaufman R. J., et al., Nucleic Acids Res 19:4485, 1991). The upstream gene translation is initiated at the normal 5' cap, whereas the downstream gene translation is initiated at the IRES element, thereby resulting in co-expression of two independent proteins from a single mRNA transcript. Since IRES-mediated ribosome recruitment ratio is relatively lower, genes encoding drug-resistance enzymes are usually placed downstream of IRES, serving as selection markers. In addition, designing IRES sequence variants to reduce expression level of downstream selection markers can further increase the expression level of the upstream GOI, which is highly desirable in biological applications. However, modulating IRES strength by designing IRES sequence variants has its limitation and is often unpredictable because the effect also depends on other regulatory elements in the expression vector. In addition, manipulating IRES alone can cause cell stress, and sometimes cells cannot be recovered well as high producers. Thus. IRES has not been uniformly utilized in all mammalian stable transfection. In this disclosure, different IRES variants are evaluated and creatively combined with other regulatory elements in vector design to achieve high expression of the GOI and appropriate expression level of the eukaryotic selection marker for stable cell selection.

Fourth, transcription of eukaryotic genes is one of the key steps in protein expression, and it is regulated by a variety of cis- and trans-acting regulatory elements (reviewed by Dillon and Grosveld, Trends Genet. 9:134; 1993). Two of the best characterized cis regulatory elements are promoters and enhancers, which recruit RNA polymerase II and transcriptional activators. However, merely a promoter and an enhancer are not sufficient to consistently maintain a high expression of the GOI due to epigenetic inhibitory effects. Epigenetic effects are stably heritable phenotypes resulting from changes in a chromosome without alterations in the DNA sequence (Berger S L, et al. 2009. Genes & Development. 23:781). Among all epigenetics-mediated gene repression mechanisms, heterochromatinization and position-effect are common pathways that result in gene repression. Cis regulatory elements regulating the chromatin structure and prevent heterochromatinization include but are not limited to LCR (Grosveld F., et al., Cell 51:975, 1987). MAR (Phi-Van et al., Mol Cell Biol 10:2302; 1980). SAR (Gasser and Laemmli. Trends Genet 3:16, 1987), insulator (Kellum and Schedl, Cell 64:941, 1991), and EASE (Aldrich et al., Cytotechnology 28:9, 1998). These elements have been shown to support relatively higher expression of linked genes at distal chromatin sites, although the complete mechanism is not fully understood. One of the common features of these cis elements is their AT-rich sequences, suggesting the lower propensity for chromosome condensation in the local region, which allows for efficient chromosomal transcription activation and prevents position-effect mediated gene silencing. Thus, adding these epigenetic/chromosome level regulatory elements into expression vectors can decrease epigenetic gene silencing and improve long-term stability of selected clones.

Some other cis regulatory elements, such as adenovirus TPL, can enhance protein expression at translation initiation and post-transcriptional levels (Kaufman R. J. PNAS (1985) 82:689). TPL comprises three introns, which are critical to the translation of adenovirus late mRNA in a cap-independent manner. In addition, this element has been suggested in the regulation of mRNA stability and mRNA nuclear export, which also impacts protein expression level. Thus, inserting the TPL sequence downstream of the promoter can increase the efficiency of gene expression significantly at post-transcriptional levels in certain cell types with selected promoters, especially for long mRNA transcripts.

Thus, in this disclosure, different combinations of various DNA elements (e.g., regulatory elements) are evaluated, and some combinations surprisingly decrease the timeline for selecting stable cells and generate high level of protein expression (e.g., up to 5-10 fold increase compared to commercially available expression vectors) in mammalian cells. The results are independent of host cell lines and consistent for various protein modalities, including monoclonal antibodies and Fc-fusion proteins.

In one aspect, provided herein is an expression vector comprising:

(a) a first expression cassette comprising the following elements in the order of upstream to downstream: a promoter operably linked to an insertion site for a GOI, an IRES, a polynucleotide encoding a eukaryotic selectable marker, and a poly A signal;

(b) a second expression cassette comprising a polynucleotide encoding a bacterial selectable marker; and (c) a bacterial plasmid origin of replication.

The two expression cassettes may be arranged in the vector in any direction relative to each other. In some embodiments, transcriptions of the first and the second expression cassettes are in the same direction. In other embodiments, transcriptions of the first and the second expression cassettes are in the opposite directions.

The insertion site typically comprises at least one restriction enzyme (RE) recognition sequence, and may include two or more RE sequences to form a multiple cloning site.

In certain embodiments of the various expression vectors provided herein, the first expression cassette further comprises one or more regulatory elements. In some embodiments, the regulatory element is an enhancer, an insulator, a LCR, a MAR, a SAR, an EASE, a TPL, or a UCOE. In one embodiment, the regulatory element is an enhancer. In another embodiment, the regulatory element is an insulator. In yet another embodiment, the regulatory element is a LCR. In still another embodiment, the regulatory element is a MAR. In one embodiment, the regulatory element is a SAR. In another embodiment, the regulatory element is an EASE. In vet another embodiment, the regulatory element is a TPL. In still another embodiment, the regulatory element is a UCOE. In some embodiments, the first expression cassette further comprises one regulatory element. In other embodiments, the first expression cassette further comprises two regulatory elements. In yet other embodiments, the first expression cassette further comprises three regulatory elements. In still other embodiments, the first expression cassette further comprises four regulatory elements. In some embodiments, the first expression cassette further comprises five regulatory elements. In other embodiments, the first expression cassette further comprises six regulatory elements. In vet other embodiments, the first expression cassette further comprises seven regulatory elements. In still other embodiments, the first expression cassette further comprises eight or more regulatory elements.

In some embodiments, the expression vector further comprises two ITR sequences flanking the first expression cassette. In other embodiments, the expression vector further comprises two ITR sequences flanking the first expression cassette, and the first expression cassette further comprises one or more regulatory elements. In vet other embodiments, the expression vector further comprises two ITR sequences flanking the first expression cassette, and the first expression cassette further comprises one or more regulatory elements selected from the group consisting of an enhancer, an insulator, a LCR, a MAR, a SAR, an EASE, a TPL, and a UCOE. In certain embodiments, the expression vector further comprises two ITR sequences flanking the first expression cassette, and the first expression cassette further comprises one regulatory element selected from the group consisting of an enhancer, an insulator, a LCR, a MAR, a SAR, an EASE, a TPL, and a UCOE. In some embodiments, the expression vector further comprises two ITR sequences flanking the first expression cassette, and the first expression cassette further comprises two regulatory elements selected from the group consisting of an enhancer, an insulator, a LCR, a MAR, a SAR, an EASE, a TPL, and a UCOE. In other embodiments, the expression vector further comprises two ITR sequences flanking the first expression cassette, and the first expression cassette further comprises three regulatory elements selected from the group consisting of an enhancer, an insulator, a LCR, a MAR, a SAR, an EASE, a TPL, and a UCOE. In yet other embodiments, the expression vector further comprises two ITR sequences flanking the first expression cassette, and the first expression cassette further comprises four regulatory elements selected from the group consisting of an enhancer, an insulator, a LCR, a MAR, a SAR, an EASE, a TPL, and a UCOE. In still other embodiments, the expression vector further comprises two ITR sequences flanking the first expression cassette, and the first expression cassette further comprises five regulatory elements selected from the group consisting of an enhancer, an insulator, a LCR, a MAR, a SAR, an EASE, a TPL, and a UCOE. In some embodiments, the expression vector further comprises two ITR sequences flanking the first expression cassette, and the first expression cassette further comprises six regulatory elements selected from the group consisting of an enhancer, an insulator, a LCR, a MAR, a SAR, an EASE, a TPL, and a UCOE. In other embodiments, the expression vector further comprises two ITR sequences flanking the first expression cassette, and the first expression cassette further comprises seven regulatory elements selected from the group consisting of an enhancer, an insulator, a LCR, a MAR, a SAR, an EASE, a TPL, and a UCOE. In yet other embodiments, the expression vector further comprises two ITR sequences flanking the first expression cassette, and the first expression cassette further comprises eight regulatory elements selected from the group consisting of an enhancer, an insulator, a LCR, a MAR, a SAR, an EASE, a TPL, and a UCOE.

IRES that can be used in various embodiments of this disclosure include a wild type IRES from any species or a variant or mutant thereof, whether naturally occurred or man-made. Non-limiting examples of IRES that can be used include the following and variants thereof: the nucleotide sequence of the 5' nontranslated region of encephalomyocarditis virus (EMCV) (GenBank: M81861.1; Duke et al., Sequence and structural elements that contribute to efficient encephalomyocarditis virus RNA translation. J Virol. 1992 March; 66 (3): 1602-9.). IRES element described by Bochkov & Palmenberg (Translational efficiency of EMCV IRES in bicistronic vectors is dependent upon IRES sequence and gene location. Biotechniques. 2006 September; 41 (3): 283-4). IRES element from expression vector pInSRT-GFP (GenBank LC417349.1). IRES element from expression vector pCeMM-CTAP (SG) (GenBank EF467048.1). IRES element described by Jang & Wimmer (Cap-independent translation of encephalomyocarditis virus RNA: structural elements of the internal ribosomal entry site and involvement of a cellular 57-KD RNA-binding protein. Genes Dev. 1990 September; 4 (9): 1560-72). IRES element from expression vector pIRESneo3 (Clontech/Takara Bio), IRES elements described in WO 2015/016786, WO 2015/021077, WO 2016/003368, WO 2016/074016, or WO 2013/092743, or variants thereof.

In other embodiments of the various expression vectors provided herein, the IRES comprises a polynucleotide sequence of SEQ ID NO: 1, 2, 3, 23, 24, or 25. In one embodiment, the IRES comprises a polynucleotide sequence of SEQ ID NO:1. In another embodiment, the IRES comprises a polynucleotide sequence of SEQ ID NO:2. In yet another embodiment, the IRES comprises a polynucleotide sequence of SEQ ID NO:3. In one embodiment, the IRES comprises a polynucleotide sequence of SEQ ID NO:23. In another embodiment, the IRES comprises a polynucleotide sequence of SEQ ID NO:24. In yet another embodiment, the IRES comprises a polynucleotide sequence of SEQ ID NO:25. In one embodiment, the IRES comprises a polynucleotide sequence that is about 90, 95, 96, 97, 98, or 99% identical to the polynucleotide sequence of SEQ ID NO:1. In another embodiment, the IRES comprises a polynucleotide sequence that is about 90, 95, 96, 97, 98, or 99% identical to the polynucleotide sequence of SEQ ID NO:2. In yet another embodiment, the IRES comprises a polynucleotide sequence that is about 90, 95, 96, 97, 98, or 99% identical to the polynucleotide sequence of SEQ ID NO: 3. In one embodiment, the IRES comprises a polynucleotide sequence that is about 90, 95, 96, 97, 98, or 99% identical to the polynucleotide sequence of SEQ ID NO:23. In another embodiment, the IRES comprises a polynucleotide sequence that is about 90, 95, 96, 97, 98, or 99% identical to the polynucleotide sequence of SEQ ID NO:24. In yet another embodiment, the IRES comprises a polynucleotide sequence that is about 90, 95, 96, 97, 98, or 99% identical to the polynucleotide sequence of SEQ ID NO:25.

In some embodiments of the various expression vectors provided herein, the eukaryotic selectable marker is a neomycin phosphotransferase, a histidinol dehydrogenase, a hygromycin B phosphotransferase, a xanthine-guanine phosphoribosyltransferase, a dihydrofolate reductase, a tryptophan synthetase, a puromycin N-acetyl-transferase, a thymidine kinase, an adenine phosphoribosyl transferase, a glutamine synthetase, an adenosine deaminase, or metallothionein-1. In one embodiment, the eukaryotic selectable marker is a neomycin phosphotransferase. In another embodiment, the eukaryotic selectable marker is a histidinol dehydrogenase. In yet another embodiment, the eukaryotic selectable marker is a hygromycin B phosphotransferase. In still another embodiment, the eukaryotic selectable marker is a xanthine-guanine phosphoribosyltransferase. In one embodiment, the eukaryotic selectable marker is a dihydrofolate reductase. In another embodiment, the eukaryotic selectable marker is a tryptophan synthetase. In yet another embodiment, the eukaryotic selectable marker is a puromycin N-acetyl-transferase. In still another embodiment, the eukaryotic selectable marker is a thymidine kinase. In one embodiment, the eukaryotic selectable marker is an adenine phosphoribosyl transferase. In another embodiment, the eukaryotic selectable marker is a glutamine synthetase. In yet another embodiment, the eukaryotic selectable marker is an adenosine deaminase. In still another embodiment, the eukaryotic selectable marker is metallothionein-1.

In certain embodiments of the various expression vectors provided herein, the promoter is a human CMV immediate-early promoter, a human elongation factor 1 alpha (EF1a) promoter, a SV40 promoter, a phosphoglycerate kinase 1 (PGK1) promoter, a human ubiquitin C (Ubc) promoter, a human β-actin promoter, a CAG promoter, a yeast transcription elongation factor 1 (TEF1) promoter, a yeast glyceraldehyde 3-phosphate dehydrogenase (GAPDH) promoter, or a yeast alcohol dehydrogenase 1 (ADH1) promoter. In one embodiment, the promoter is a human CMV immediate-early promoter. In another embodiment, the promoter is a human EF1a promoter. In yet another embodiment, the promoter is a SV40 promoter. In still another embodiment, the promoter is a PGK1 promoter. In one embodiment, the promoter is a human Ubc promoter. In another embodiment, the promoter is a human β-actin promoter. In yet another embodiment, the promoter is a CAG promoter. In still another embodiment, the promoter is a yeast TEF1 promoter. In one embodiment, the promoter is a yeast GAPDH promoter. In another embodiment, the promoter is a yeast ADHI promoter.

In some embodiments of the various expression vectors provided herein, the enhancer is a human CMV immediate-early enhancer, a SV40 enhancer, a BK polyomarvirus (BKPyV) enhancer, an Epstein-Bar virus (EBV) enhancer, a c-Myc enhancer, an immunoglobulin heavy chain (IgH) enhancer, a Sp1-binding enhancer, an AP1-binding enhancer, or a CREB-binding enhancer. In one embodiment, the enhancer is a human CMV immediate-early enhancer. In another embodiment, the enhancer is a SV40 enhancer. In yet another embodiment, the enhancer is a BKPyV enhancer. In still another embodiment, the enhancer is an EBV enhancer. In one embodiment, the enhancer is a c-Myc enhancer. In another embodiment, the enhancer is an IgH enhancer. In yet another embodiment, the enhancer is a Sp1-binding enhancer. In still another embodiment, the enhancer is an API-binding enhancer. In one embodiment, the enhancer is a CREB-binding enhancer.

In certain embodiments, the enhancer is immediately adjacent to the promoter. In some embodiments, the enhancer is distant from the promoter with other DNA fragments between the enhancer and the promoter. In other embodiments, the enhancer is upstream of the promoter. In yet other embodiments, the enhancer is downstream of the promoter. In still other embodiments, the enhancer and the promoter are combined together as a combo enhancer/ promoter. In one specific embodiment, the combo enhancer/promoter is a human CMV immediate-early enhancer/promoter. In another specific embodiment, the combo enhancer/promoter is a synthetic CAG promoter that comprises a CMV immediate-early enhancer and a chicken β-actin promoter.

In other embodiments of the various expression vectors provided herein, the insulator is HMR tRNAThr, Chal UAS, UASrpg, STAR, scs, scs', gypsy, Fab-7, Fab-8, faswb, sns, UR1, RO, Lys 5' A, HS4, 3 HS, BEAD-1, HS2-6, DMD/ICR, 5 HS5, apoB (−57 kb), apoB (+43 kb), or DM1. In one embodiment, the insulator is HMR tRNAThr. In another embodiment, the insulator is Chal UAS. In yet another embodiment, the insulator is UASrpg. In still another embodiment, the insulator is STAR. In one embodiment, the insulator is scs. In another embodiment, the insulator is scs'. In yet another embodiment, the insulator is gypsy. In still another embodiment, the insulator is Fab-7. In one embodiment, the insulator is Fab-8. In another embodiment, the insulator is faswb. In yet another embodiment, the insulator is sns. In still another embodiment, the insulator is URI. In one embodiment, the insulator is RO. In another embodiment, the insulator is Lys 5' A. In yet another embodiment, the insulator is HS4. In still another embodiment, the insulator is 3'HS. In one embodiment, the insulator is BEAD-1. In another embodiment, the insulator is HS2-6. In yet another embodiment, the insulator is DMD/ICR. In still another embodiment, the insulator is 5'HS5. In one embodiment, the insulator is apoB (−57 kb). In another embodiment, the insulator is apoB (+43 kb). In vet another embodiment, the insulator is DM1.

In certain embodiments of various expression vectors provided herein, the first expression cassette further comprises a first insulator and a second insulator. In some embodiments, the first insulator and the second insulators are the same insulator. In some embodiments, the first insulator and the second insulator are different insulators. In other embodiments, the first insulator and the second insulator are in the same direction. In vet other embodiments, the first insulator and the second insulator are in the opposite directions. In still other embodiments, the first insulator and the second insulator are HS4. In yet still other embodiments, the first insulator and the second insulator are HS4 in the opposite directions.

In vet other embodiments of the various expression vectors provided herein, the ITR is Tc1 ITR, Tc3 ITR, Minos ITR, Mos1 ITR, Famar1 ITR, Osmar5 ITR, Fot1 ITR, Impala ITR, ISY100 ITR, Mboumar-9 ITR, Sleeping Beauty ITR, Himar1 ITR, Frog Prince ITR, Hsmar1 ITR, SB100X ITR, piggyBac® ITR, or Tol2 ITR. In one embodiment, the ITR is Tc1 ITR. In another embodiment, the ITR is Tc3 ITR. In yet another embodiment, the ITR is Minos ITR. In still another embodiment, the ITR is Mos1 ITR. In one embodiment, the ITR is Famar1 ITR. In another embodiment, the ITR is Osmar5 ITR. In yet another embodiment, the ITR is Fot1 ITR. In still another embodiment, the ITR is Impala ITR. In one embodiment, the ITR is ISY100 ITR. In another embodiment, the ITR is Mboumar-9 ITR. In yet another embodiment, the ITR is Sleeping Beauty ITR. In still another embodiment, the ITR is Himar1 ITR. In one embodiment, the ITR is Frog Prince ITR. In another embodiment, the ITR is Hsmar1 ITR. In yet another embodiment, the ITR is SB100X ITR. In still another embodiment, the ITR is piggyBac® ITR. In one embodiment, the ITR is Tol2 ITR.

In still other embodiments of the various expression vectors provided herein, the polyA signal is a thymidine kinase gene poly A signal, a SV40 early gene poly A signal, a SV40 late gene poly A signal, a β-globin gene polyA signal, or the like. In some embodiments, the poly A signal is a thymidine kinase gene polyA signal. In certain embodiments, the poly A signal is a SV40 early gene poly A signal. In other embodiments, the poly A signal is a SV40 late gene poly A signal. In yet other embodiments, the poly A signal is a β-globin gene poly A signal.

In certain embodiments of the various expression vectors provided herein, the bacterial selectable marker is an ampicillin resistance gene, a tetracycline resistance gene, a hygromycin resistance gene, a kanamycin resistance gene, a blasticidin resistance gene, or the like. In one embodiment, the bacterial selectable marker is an ampicillin resistance gene. In another embodiment, the bacterial selectable marker is a tetracycline resistance gene. In yet another embodiment, the bacterial selectable marker is a hygromycin resistance gene. In still another embodiment, the bacterial selectable marker is a kanamycin resistance gene. In yet still another embodiment, the bacterial selectable marker is a blasticidin resistance gene.

A bacterial plasmid origin of replication is also present in various expression vectors disclosed herein to facilitate preparation of large quantities of the vector in bacteria cells. Non-limiting examples of plasmid replication origins include pUC origins derived from pBR322.

In another aspect, provided herein is an expression vector comprising:

(a) a first expression cassette comprising the following elements in the order of upstream to downstream: a first insulator, an EASE, a promoter, a TPL, an insertion site for a GOI, an IRES, a polynucleotide encoding a eukaryotic selectable marker, a poly A signal, and a second insulator;
(b) two ITR sequences flanking the first expression cassette;
(c) a second expression cassette comprising a polynucleotide encoding a bacterial selectable marker; and
(d) a bacterial plasmid origin of replication.

The two expression cassettes may be arranged in the vector in any direction relative to each other. In some embodiments, transcriptions of the first and the second expression cassettes are in the same direction. In other embodiments, transcriptions of the first and the second expression cassettes are in the opposite directions.

The insertion site typically comprises at least one RE recognition sequence, and may include two or more RE sequences to form a multiple cloning site.

In some embodiments of various expression vectors provided herein, the first expression cassette further comprises an enhancer. In certain embodiments, the enhancer is located between the EASE and the promoter.

In certain embodiments of the various expression vectors provided herein, the promoter is a human cytomegalovirus (CMV) immediate-early promoter, a human elongation factor 1 alpha (EF1a) promoter, a SV40 promoter, a phosphoglycerate kinase 1 (PGK1) promoter, a human ubiquitin C (Ubc) promoter, a human β-actin promoter, a CAG promoter, a yeast transcription elongation factor 1 (TEF1) promoter, a yeast glyceraldehyde 3-phosphate dehydrogenase (GAPDH) promoter, or a yeast alcohol dehydrogenase 1 (ADHI) promoter. In one embodiment, the promoter is a human CMV immediate-early promoter. In another embodiment, the promoter is a human EF1a promoter. In yet another embodiment, the promoter is a SV40 promoter. In still another embodiment, the promoter is a PGK1 promoter. In one embodiment, the promoter is a human Ubc promoter. In another embodiment, the promoter is a human β-actin promoter. In yet another embodiment, the promoter is a CAG promoter. In still another embodiment, the promoter is a yeast TEF1 promoter. In one embodiment, the promoter is a yeast GAPDH promoter. In another embodiment, the promoter is a yeast ADHI promoter.

In some embodiments of the various expression vectors provided herein, the enhancer is a human CMV immediate-early enhancer, a SV40 enhancer, a BK polyomarvirus (BKPyV) enhancer, an Epstein-Bar virus (EBV) enhancer, a c-Myc enhancer, an immunoglobulin heavy chain (IgH) enhancer, a Sp1-binding enhancer, an API-binding enhancer, or a CREB-binding enhancer. In one embodiment, the enhancer is a human CMV immediate-early enhancer. In another embodiment, the enhancer is a SV40 enhancer. In yet another embodiment, the enhancer is a BKPyV enhancer. In still another embodiment, the enhancer is an EBV enhancer. In one embodiment, the enhancer is a c-Myc enhancer. In another embodiment, the enhancer is an IgH enhancer. In yet another embodiment, the enhancer is a Sp1-binding enhancer. In still another embodiment, the enhancer is an API-binding enhancer. In one embodiment, the enhancer is a CREB-binding enhancer.

In certain embodiments, the enhancer is immediately adjacent to the promoter. In some embodiments, the enhancer is distant from the promoter with other DNA fragments between the enhancer and the promoter. In other embodiments, the enhancer is upstream of the promoter. In yet other embodiments, the enhancer is downstream of the promoter. In still other embodiments, the enhancer and the promoter are combined together as a combo enhancer/promoter. In one specific embodiment, the combo enhancer/promoter is a human CMV immediate-early enhancer/promoter. In another specific embodiment, the combo enhancer/promoter is a synthetic CAG promoter that comprises a CMV immediate-early enhancer and a chicken β-actin promoter.

In other embodiments of the various expression vectors provided herein, the insulator is HMR tRNAThr, Chal UAS, UASrpg, STAR, scs, scs', gypsy, Fab-7, Fab-8, faswb, sns, UR1, RO, Lys 5' A, HS4, 3'HS, BEAD-1, HS2-6, DMD/ICR, 5'HS5, apoB (−57 kb), apoB (+43 kb), or DM1. In one embodiment, the insulator is HMR tRNAThr. In another embodiment, the insulator is Chal UAS. In yet another embodiment, the insulator is UASrpg. In still another embodiment, the insulator is STAR. In one embodiment, the insulator is scs. In another embodiment, the insulator is scs'. In yet another embodiment, the insulator is gypsy. In still another embodiment, the insulator is Fab-7. In one embodiment, the insulator is Fab-8. In another embodiment, the insulator is faswb. In yet another embodiment, the insulator is sns. In still another embodiment, the insulator is URI. In one embodiment, the insulator is RO. In another embodiment, the insulator is Lys 5' A. In yet another embodiment, the insulator is HS4. In still another embodiment, the insulator is 3 HS. In one embodiment, the insulator is BEAD-1. In another embodiment, the insulator is HS2-6. In yet another embodiment, the insulator is DMD/ICR. In still another embodiment, the insulator is 5 HS5. In one embodiment, the insulator is apoB (−57 kb). In another embodiment, the insulator is apoB (+43 kb). In yet another embodiment, the insulator is DM1.

In some embodiments, the first insulator and the second insulators are the same insulator. In some embodiments, the first insulator and the second insulator are different insulators. In other embodiments, the first insulator and the second insulator are in the same direction. In yet other embodiments, the first insulator and the second insulator are in the opposite directions. In still other embodiments, the first insulator and the second insulator are HS4. In yet still other embodiments, the first insulator and the second insulator are HS4 in the opposite directions.

In vet other embodiments of the various expression vectors provided herein, the ITR is Tc1 ITR, Tc3 ITR, Minos ITR, Mos1 ITR, Famar1 ITR, Osmar5 ITR, Fot1 ITR, Impala ITR, ISY100 ITR, Mboumar-9 ITR, Sleeping Beauty ITR, Himar1 ITR, Frog Prince ITR, Hsmar1 ITR, SB100X ITR, piggyBac® ITR, or Tol2 ITR. In one embodiment, the ITR is Tc1 ITR. In another embodiment, the ITR is Tc3 ITR. In yet another embodiment, the ITR is Minos ITR. In still another embodiment, the ITR is Mos1 ITR. In one embodiment, the ITR is Famar1 ITR. In another embodiment, the ITR is Osmar5 ITR. In yet another embodiment, the ITR is Fot1 ITR. In still another embodiment, the ITR is Impala ITR. In one embodiment, the ITR is ISY100 ITR. In another embodiment, the ITR is Mboumar-9) ITR. In yet another embodiment, the ITR is Sleeping Beauty ITR. In still another embodiment, the ITR is Himar1 ITR. In one embodiment, the ITR is Frog Prince ITR. In another embodiment, the ITR is Hsmar1 ITR. In yet another embodiment, the ITR is SB100X ITR. In still another embodiment, the ITR is piggyBac® ITR. In one embodiment, the ITR is Tol2 ITR.

IRES that can be used in various embodiments of this disclosure include a wild type IRES from any species or a variant or mutant thereof, whether naturally occurred or man-made. Non-limiting examples of IRES that can be used include the following and variants thereof: the nucleotide sequence of the 5' nontranslated region of encephalomyocarditis virus (EMCV) (GenBank: M81861.1; Duke et al., Sequence and structural elements that contribute to efficient encephalomyocarditis virus RNA translation. J Virol. 1992 March; 66 (3): 1602-9.). IRES element described by Bochkov & Palmenberg (Translational efficiency of EMCV IRES in bicistronic vectors is dependent upon IRES sequence and gene location. Biotechniques. 2006 September; 41 (3): 283-4). IRES element from expression vector pInSRT-GFP (GenBank LC417349.1). IRES element from expression vector pCeMM-CTAP (SG) (GenBank EF467048.1). IRES element described by Jang & Wimmer (Cap-independent translation of encephalomyocarditis virus RNA: structural elements of the internal ribosomal entry site and involvement of a cellular 57-KD RNA-binding protein. Genes Dev. 1990 September; 4 (9): 1560-72). IRES element from expression vector pIRESneo3 (Clontech/Takara Bio), IRES elements described in WO 2015/016786, WO 2015/021077, WO 2016/003368, WO 2016/074016, or WO 2013/092743, or variants thereof.

In other embodiments of the various expression vectors provided herein, the IRES comprises a polynucleotide sequence of SEQ ID NO: 1, 2, 3, 23, 24, or 25. In one embodiment, the IRES comprises a polynucleotide sequence of SEQ ID NO:1. In another embodiment, the IRES comprises a polynucleotide sequence of SEQ ID NO:2. In yet another embodiment, the IRES comprises a polynucleotide sequence of SEQ ID NO:3. In one embodiment, the IRES comprises a polynucleotide sequence of SEQ ID NO:23. In another embodiment, the IRES comprises a polynucleotide sequence of SEQ ID NO:24. In yet another embodiment, the IRES comprises a polynucleotide sequence of SEQ ID NO:25. In one embodiment, the IRES comprises a polynucleotide sequence that is about 90, 95, 96, 97, 98, or 99% identical to the polynucleotide sequence of SEQ ID NO:1. In another embodiment, the IRES comprises a polynucleotide sequence that is about 90, 95, 96, 97, 98, or 99% identical to the polynucleotide sequence of SEQ ID NO:2. In yet another embodiment, the IRES comprises a polynucleotide sequence that is about 90, 95, 96, 97, 98, or 99% identical to the polynucleotide sequence of SEQ ID NO: 3. In one embodiment, the IRES comprises a polynucleotide sequence that is about 90, 95, 96, 97, 98, or 99% identical to the polynucleotide sequence of SEQ ID NO:23. In another embodiment, the IRES comprises a polynucleotide sequence that is about 90, 95, 96, 97, 98, or 99% identical to the polynucleotide sequence of SEQ ID NO:24. In yet another embodiment, the IRES comprises a polynucleotide sequence that is about 90, 95, 96, 97, 98, or 99% identical to the polynucleotide sequence of SEQ ID NO:25.

In some embodiments of the various expression vectors provided herein, the eukaryotic selectable marker is a neomycin phosphotransferase, a histidinol dehydrogenase, a hygromycin B phosphotransferase, a xanthine-guanine phosphoribosyltransferase, a dihydrofolate reductase, a tryptophan synthetase, a puromycin N-acetyl-transferase, a thymidine kinase, an adenine phosphoribosyl transferase, a glutamine synthetase, an adenosine deaminase, or metallothionein-1. In one embodiment, the eukaryotic selectable marker is a neomycin phosphotransferase. In another embodiment, the eukaryotic selectable marker is a histidinol dehydrogenase. In yet another embodiment, the eukaryotic selectable marker is a hygromycin B phosphotransferase. In still another embodiment, the eukaryotic selectable marker is a xanthine-guanine phosphoribosyltransferase. In one embodiment, the eukaryotic selectable marker is a dihydrofolate reductase. In another embodiment, the eukaryotic selectable marker is a tryptophan synthetase. In yet another embodiment, the eukaryotic selectable marker is a puromycin N-acetyl-transferase. In still another embodiment, the eukaryotic selectable marker is a thymidine kinase. In one embodiment, the eukaryotic selectable marker is an adenine phosphoribosyl transferase. In another embodiment, the eukaryotic selectable marker is a glutamine synthetase. In yet another embodiment, the eukaryotic selectable marker is an adenosine deaminase. In still another embodiment, the eukaryotic selectable marker is metallothionein-1.

In still other embodiments of the various expression vectors provided herein, the polyA signal is a thymidine kinase gene poly A signal, a SV40 early gene polyA signal, a SV40 late gene polyA signal, a β-globin gene polyA signal, or the like. In some embodiments, the polyA signal is a thymidine kinase gene polyA signal. In certain embodiments, the polyA signal is a SV40 early gene poly A signal. In other embodiments, the poly A signal is a SV40 late gene poly A signal. In vet other embodiments, the poly A signal is a β-globin gene polyA signal.

In certain embodiments of the various expression vectors provided herein, the bacterial selectable marker is an ampicillin resistance gene, a tetracycline resistance gene, a hygromycin resistance gene, a kanamycin resistance gene, a blasticidin resistance gene, or the like. In one embodiment, the bacterial selectable marker is an ampicillin resistance gene. In another embodiment, the bacterial selectable marker is a tetracycline resistance gene. In yet another embodiment, the bacterial selectable marker is a hygromycin resistance gene. In still another embodiment, the bacterial selectable marker is a kanamycin resistance gene. In yet still another embodiment, the bacterial selectable marker is a blasticidin resistance gene.

A bacterial plasmid origin of replication is also present in various expression vectors disclosed herein to facilitate preparation of large quantities of the vector in bacteria cells. Non-limiting examples of plasmid replication origins include pUC origins derived from pBR322.

In one embodiment of various expression vectors provided herein, the first insulator and the second insulator are HS4, the enhancer is a human CMV immediate-early enhancer, the promoter is a human CMV immediate-early promoter, the ITR is piggyBac® ITR, the eukaryotic selectable marker is a glutamine synthetase, and the IRES comprises a polynucleotide sequence of SEQ ID NO: 1.

In another embodiment of various expression vectors provided herein, the first insulator and the second insulator are HS4, the enhancer and the promoter are a combo enhancer/promoter, wherein the combo enhancer/promoter is a human CMV immediate-early enhancer/promoter, the ITR is piggyBac® ITR, the eukaryotic selectable marker is a glutamine synthetase, and the IRES comprises a polynucleotide sequence of SEQ ID NO:1.

In one embodiment of various expression vectors provided herein, the first insulator and the second insulator are HS4, the enhancer is a human CMV immediate-early enhancer, the promoter is a human CMV immediate-early promoter, the ITR is piggyBac® ITR, the eukaryotic selectable marker is a glutamine synthetase, and the IRES comprises a polynucleotide sequence of SEQ ID NO:2.

In another embodiment of various expression vectors provided herein, the first insulator and the second insulator are HS4, the enhancer and the promoter are a combo enhancer/promoter, wherein the combo enhancer/promoter is a human CMV immediate-early enhancer/promoter, the ITR is piggyBac® ITR, the eukaryotic selectable marker is a glutamine synthetase, and the IRES comprises a polynucleotide sequence of SEQ ID NO:2.

In one embodiment of various expression vectors provided herein, the first insulator and the second insulator are HS4, the enhancer is a human CMV immediate-early enhancer, the promoter is a human CMV immediate-early promoter, the ITR is piggyBac® ITR, the eukaryotic selectable marker is a glutamine synthetase, and the IRES comprises a polynucleotide sequence of SEQ ID NO:3.

In another embodiment of various expression vectors provided herein, the first insulator and the second insulator are HS4, the enhancer and the promoter are a combo enhancer/promoter, wherein the combo enhancer/promoter is a human CMV immediate-early enhancer/promoter, the ITR is piggyBac® ITR, the eukaryotic selectable marker is a glutamine synthetase, and the IRES comprises a polynucleotide sequence of SEQ ID NO:3.

In one embodiment of various expression vectors provided herein, the first insulator and the second insulator are HS4, the enhancer is a human CMV immediate-early enhancer, the promoter is a human CMV immediate-early promoter, the ITR is piggyBac® ITR, the eukaryotic selectable marker is a glutamine synthetase, and the IRES comprises a polynucleotide sequence of SEQ ID NO:23.

In another embodiment of various expression vectors provided herein, the first insulator and the second insulator are HS4, the enhancer and the promoter are a combo enhancer/promoter, wherein the combo enhancer/promoter is a human CMV immediate-early enhancer/promoter, the ITR is piggyBac® ITR, the eukaryotic selectable marker is a glutamine synthetase, and the IRES comprises a polynucleotide sequence of SEQ ID NO:23.

In one embodiment of various expression vectors provided herein, the first insulator and the second insulator are HS4, the enhancer is a human CMV immediate-early enhancer, the promoter is a human CMV immediate-early promoter, the ITR is piggyBac® ITR, the eukaryotic selectable marker is a glutamine synthetase, and the IRES comprises a polynucleotide sequence of SEQ ID NO:24.

In another embodiment of various expression vectors provided herein, the first insulator and the second insulator are HS4, the enhancer and the promoter are a combo enhancer/promoter, wherein the combo enhancer/promoter is a human CMV immediate-early enhancer/promoter, the ITR is piggyBac® ITR, the eukaryotic selectable marker is a glutamine synthetase, and the IRES comprises a polynucleotide sequence of SEQ ID NO:24.

In one embodiment of various expression vectors provided herein, the first insulator and the second insulator are HS4, the enhancer is a human CMV immediate-early enhancer, the promoter is a human CMV immediate-early promoter, the ITR is piggyBac® ITR, the eukaryotic selectable marker is a glutamine synthetase, and the IRES comprises a polynucleotide sequence of SEQ ID NO:25.

In another embodiment of various expression vectors provided herein, the first insulator and the second insulator are HS4, the enhancer and the promoter are a combo enhancer/promoter, wherein the combo enhancer/promoter is a human CMV immediate-early enhancer/promoter, the ITR is piggyBac® ITR, the eukaryotic selectable marker is a glutamine synthetase, and the IRES comprises a polynucleotide sequence of SEQ ID NO:25.

Thus, in one particular embodiment, the expression vector comprises:

(a) a first expression cassette comprising the following elements in the order of upstream to downstream: a first HS4 insulator, an EASE, a human CMV immediate-early enhancer/promoter, a TPL, an insertion site for a GOI, an IRES comprising a polynucleotide sequence of SEQ ID NO: 1, a polynucleotide encoding a glutamine synthetase, a polyA signal, and a second HS4 insulator;
(b) two piggyBac® ITR sequences flanking the first expression cassette;
(c) a second expression cassette comprising a polynucleotide encoding a bacterial selectable marker; and
(d) a bacterial plasmid origin of replication.

In one particular embodiment, the expression vector comprises:

(a) a first expression cassette comprising the following elements in the order of upstream to downstream: a first HS4 insulator, an EASE, a human CMV immediate-early enhancer/promoter, a TPL, an insertion site for a GOI, an IRES comprising a polynucleotide sequence of SEQ ID NO:2, a polynucleotide encoding a glutamine synthetase, a polyA signal, and a second HS4 insulator;
(b) two piggyBac® ITR sequences flanking the first expression cassette;
(c) a second expression cassette comprising a polynucleotide encoding a bacterial selectable marker; and
(d) a bacterial plasmid origin of replication.

In one particular embodiment, the expression vector comprises:

(a) a first expression cassette comprising the following elements in the order of upstream to downstream: a first HS4 insulator, an EASE, a human CMV immediate-early enhancer/promoter, a TPL, an insertion site for a GOI, an IRES comprising a polynucleotide sequence of SEQ ID NO:3, a polynucleotide encoding a glutamine synthetase, a poly A signal, and a second HS4 insulator;
(b) two piggyBac® ITR sequences flanking the first expression cassette;
(c) a second expression cassette comprising a polynucleotide encoding a bacterial selectable marker; and
(d) a bacterial plasmid origin of replication.

In one particular embodiment, the expression vector comprises:

(a) a first expression cassette comprising the following elements in the order of upstream to downstream: a first HS4 insulator, an EASE, a human CMV immediate-early enhancer/promoter, a TPL, an insertion site for a GOI, an IRES comprising a polynucleotide sequence of SEQ ID NO:23, a polynucleotide encoding a glutamine synthetase, a poly A signal, and a second HS4 insulator;
(b) two piggyBac® ITR sequences flanking the first expression cassette;
(c) a second expression cassette comprising a polynucleotide encoding a bacterial selectable marker; and
(d) a bacterial plasmid origin of replication.

In one particular embodiment, the expression vector comprises:

(a) a first expression cassette comprising the following elements in the order of upstream to downstream: a first HS4 insulator, an EASE, a human CMV immediate-early enhancer/promoter, a TPL, an insertion site for a GOI, an IRES comprising a polynucleotide sequence of SEQ ID NO:24, a polynucleotide encoding a glutamine synthetase, a poly A signal, and a second HS4 insulator;
(b) two piggyBac® ITR sequences flanking the first expression cassette;
(c) a second expression cassette comprising a polynucleotide encoding a bacterial selectable marker; and
(d) a bacterial plasmid origin of replication.

In one particular embodiment, the expression vector comprises:

(a) a first expression cassette comprising the following elements in the order of upstream to downstream: a first HS4 insulator, an EASE, a human CMV immediate-early enhancer/promoter, a TPL, an insertion site for a GOI, an IRES comprising a polynucleotide sequence of SEQ ID NO:25, a polynucleotide encoding a glutamine synthetase, a poly A signal, and a second HS4 insulator;
(b) two piggyBac® ITR sequences flanking the first expression cassette;
(c) a second expression cassette comprising a polynucleotide encoding a bacterial selectable marker; and
(d) a bacterial plasmid origin of replication.

In one specific embodiment, the EASE comprises a polynucleotide sequence that is at least 95%, 96%, 97%, 98%, or 99% identical to the polynucleotide sequence of SEQ ID NO:12. In another embodiment, the EASE comprises the polynucleotide sequence of SEQ ID NO: 12. In yet another embodiment, the EASE consists of the polynucleotide sequence of SEQ ID NO: 12.

In one specific embodiment, the TPL comprises a polynucleotide sequence that is at least 95%, 96%, 97%, 98%, or 99% identical to the polynucleotide sequence of SEQ ID NO:17. In another embodiment, the TPL comprises the polynucleotide sequence of SEQ ID NO: 17. In yet another embodiment, the TPL consists of the polynucleotide sequence of SEQ ID NO: 17.

In one specific embodiment, the gene encoding the glutamine synthetase comprises a polynucleotide sequence that is at least 95%, 96%, 97%, 98%, or 99% identical to the polynucleotide sequence of SEQ ID NO:21. In another embodiment, the gene encoding the glutamine synthetase comprises the polynucleotide sequence of SEQ ID NO:21. In yet another embodiment, the gene encoding the glutamine synthetase consists of the polynucleotide sequence of SEQ ID NO:21.

In one specific embodiment, the human CMV promoter comprises a polynucleotide sequence that is at least 95%, 96%, 97%, 98%, or 99% identical to the polynucleotide sequence of SEQ ID NO:18. In another embodiment, the human CMV promoter comprises the polynucleotide sequence of SEQ ID NO:18. In yet another embodiment, the human CMV promoter consists of the polynucleotide sequence of SEQ ID NO: 18.

In one specific embodiment, the SV40 promoter comprises a polynucleotide sequence that is at least 95%, 96%, 97%, 98%, or 99% identical to the polynucleotide sequence of SEQ ID NO: 15. In another embodiment, the SV40) promoter comprises the polynucleotide sequence of SEQ ID NO:15. In yet another embodiment, the SV40 promoter consists of the polynucleotide sequence of SEQ ID NO: 15.

In one specific embodiment, the SV40 enhancer comprises a polynucleotide sequence that is at least 95%, 96%, 97%, 98%, or 99% identical to the polynucleotide sequence of SEQ ID NO: 22. In another embodiment, the SV40 enhancer promoter comprises the polynucleotide sequence of SEQ ID NO:22. In yet another embodiment, the SV40 enhancer promoter consists of the polynucleotide sequence of SEQ ID NO:22.

In one specific embodiment, the human CMV immediate-early enhancer/promoter comprises a polynucleotide sequence that is at least 95%, 96%, 97%, 98%, or 99% identical to the polynucleotide sequence of SEQ ID NO: 16. In another embodiment, the human CMV immediate-early enhancer/promoter comprises the polynucleotide sequence of SEQ ID NO: 16. In yet another embodiment, the human CMV immediate-early enhancer/promoter consists of the polynucleotide sequence of SEQ ID NO: 16.

In one specific embodiment, the HS4 insulator comprises a polynucleotide sequence that is at least 95%, 96%, 97%, 98%, or 99% identical to the polynucleotide sequence of SEQ ID NO: 11. In another embodiment, the HS4 insulator comprises the polynucleotide sequence of SEQ ID NO:11. In yet another embodiment, the HS4 insulator consists of the polynucleotide sequence of SEQ ID NO: 11.

In one specific embodiment, the 5' piggyBac® ITR comprises a polynucleotide sequence that is at least 95%, 96%, 97%, 98%, or 99% identical to the polynucleotide sequence of SEQ ID NO: 9, and the 3' piggyBac® ITR comprises a polynucleotide sequence that is at least 95%, 96%, 97%, 98%, or 99% identical to the polynucleotide sequence of SEQ ID NO:10. In another embodiment, the 5' piggyBac® ITR comprises the polynucleotide sequence of SEQ ID NO:9, and the 3' piggyBac® ITR comprises the polynucleotide sequence of SEQ ID NO: 10. In yet another embodiment, the 5' piggyBac® ITR consists of the polynucleotide sequence of SEQ ID NO: 9, and the 3' piggyBac® ITR consists of the polynucleotide sequence of SEQ ID NO:10.

In one specific embodiment, the β-globin gene polyA signal comprises a polynucleotide sequence that is at least 95%, 96%, 97%, 98%, or 99% identical to the polynucleotide sequence of SEQ ID NO:13. In another embodiment, the β-globin gene polyA signal comprises the polynucleotide sequence of SEQ ID NO:13. In yet another embodiment, the β-globin gene poly A signal consists of the polynucleotide sequence of SEQ ID NO: 13.

In one specific embodiment, the SV40 late gene polyA signal comprises a polynucleotide sequence that is at least 95%, 96%, 97%, 98%, or 99% identical to the polynucleotide sequence of SEQ ID NO: 14. In another embodiment, the SV40 late gene polyA signal comprises the polynucleotide sequence of SEQ ID NO:14. In yet another embodiment, the SV40 late gene poly A signal consists of the polynucleotide sequence of SEQ ID NO: 14.

In one specific embodiment, the ampicillin resistance gene comprises a polynucleotide sequence that is at least 95%, 96%, 97%, 98%, or 99% identical to the polynucleotide sequence of SEQ ID NO:20. In another embodiment, the ampicillin resistance gene comprises the polynucleotide sequence of SEQ ID NO:20. In yet another embodiment, the ampicillin resistance gene consists of the polynucleotide sequence of SEQ ID NO:20.

In one specific embodiment, the bacterial plasmid origin of replication comprises a polynucleotide sequence that is at least 95%, 96%, 97%, 98%, or 99% identical to the polynucleotide sequence of SEQ ID NO:19. In another embodiment, the bacterial plasmid origin of replication comprises the polynucleotide sequence of SEQ ID NO: 19. In yet another embodiment, the bacterial plasmid origin of replication consists of the polynucleotide sequence of SEQ ID NO: 19.

In one particular embodiment, the expression vector comprises:

(a) a first expression cassette comprising the following elements in the order of upstream to downstream: a first HS4 insulator comprising a polynucleotide sequence of SEQ ID NO: 11, an EASE comprising a polynucleotide sequence of SEQ ID NO: 12, a human CMV immediate-early enhancer/promoter comprising a polynucleotide sequence of SEQ ID NO: 16, a TPL comprising a polynucleotide sequence of SEQ ID NO: 17, an insertion site for a GOI, an IRES comprising a polynucleotide sequence of SEQ ID NO:3, a glutamine synthetase gene comprising a polynucleotide sequence of SEQ ID NO:21, a polyA signal comprising a polynucleotide sequence of SEQ ID NO: 13, and a second HS4 insulator that is identical to the first HS4 insulator but in the opposite direction;
(b) two piggyBac® ITR sequences flanking the first expression cassette, wherein the 5' piggyBac® ITR comprises a polynucleotide sequence of SEQ ID NO:9, and wherein the 3" piggyBac® ITR comprises a polynucleotide sequence of SEQ ID NO: 10;
(c) a second expression cassette comprising a polynucleotide encoding a bacterial selectable marker, wherein the polynucleotide encoding the bacterial selectable marker comprises a polynucleotide sequence of SEQ ID NO:20; and
(d) a bacterial plasmid origin of replication, wherein the bacterial plasmid origin of replication comprises a polynucleotide sequence of SEQ ID NO: 19.

In another particular embodiment, the expression vector comprises:

(a) a first expression cassette comprising the following elements in the order of upstream to downstream: a first HS4 insulator consisting of a polynucleotide sequence of SEQ ID NO: 11, an EASE consisting of a polynucleotide sequence of SEQ ID NO: 12, a human CMV immediate-early enhancer/promoter consisting of a polynucleotide sequence of SEQ ID NO: 16, a TPL consisting of a polynucleotide sequence of SEQ ID NO: 17, an insertion site for a GOI, an IRES consisting of a polynucleotide sequence of SEQ ID NO:3, a glutamine synthetase gene consisting of a polynucleotide sequence of SEQ ID NO:21, a polyA signal consisting of a polynucleotide sequence of SEQ ID NO: 13, and a second HS4 insulator that is identical to the first HS4 insulator but in the opposite direction;
(b) two piggyBac® ITR sequences flanking the first expression cassette, wherein the 5' piggyBac® ITR consists of a polynucleotide sequence of SEQ ID NO:

9, and wherein the 3" piggyBac® ITR consists a polynucleotide sequence of SEQ ID NO: 10;

(c) a second expression cassette comprising a polynucleotide encoding a bacterial selectable marker, wherein the polynucleotide encoding the bacterial selectable marker consists of a polynucleotide sequence of SEQ ID NO:20; and (d) a bacterial plasmid origin of replication, wherein the bacterial plasmid origin of replication consists of a polynucleotide sequence of SEQ ID NO: 19.

In another specific embodiment, the expression vector comprises a polynucleotide sequence of SEQ ID NO:4, 5, 6, 7, 8, 26, 27, 28, or 29. In one embodiment, the expression vector comprises a polynucleotide sequence of SEQ ID NO:4. In another embodiment, the expression vector comprises a polynucleotide sequence of SEQ ID NO:5. In yet another embodiment, the expression vector comprises a polynucleotide sequence of SEQ ID NO:6. In still another embodiment, the expression vector comprises a polynucleotide sequence of SEQ ID NO: 7. In yet still another embodiment, the expression vector comprises a polynucleotide sequence of SEQ ID NO:8. In one embodiment, the expression vector comprises a polynucleotide sequence of SEQ ID NO:26. In another embodiment, the expression vector comprises a polynucleotide sequence of SEQ ID NO:27. In yet another embodiment, the expression vector comprises a polynucleotide sequence of SEQ ID NO:28. In still another embodiment, the expression vector comprises a polynucleotide sequence of SEQ ID NO:29.

In yet another specific embodiment, the expression vector consists of a polynucleotide sequence of SEQ ID NO: 4, 5, 6, 7, 8, 26, 27, 28, or 29. In one embodiment, the expression vector consists of a polynucleotide sequence of SEQ ID NO:4. In another embodiment, the expression vector consists of a polynucleotide sequence of SEQ ID NO:5. In yet another embodiment, the expression vector consists of a polynucleotide sequence of SEQ ID NO:6. In still another embodiment, the expression vector consists of a polynucleotide sequence of SEQ ID NO: 7. In yet still another embodiment, the expression vector consists of a polynucleotide sequence of SEQ ID NO:8. In one embodiment, the expression vector consists of a polynucleotide sequence of SEQ ID NO:26. In another embodiment, the expression vector consists of a polynucleotide sequence of SEQ ID NO:27. In yet another embodiment, the expression vector consists of a polynucleotide sequence of SEQ ID NO:28. In still another embodiment, the expression vector consists of a polynucleotide sequence of SEQ ID NO:29.

In yet still another specific embodiment, the expression vector consists essentially of a polynucleotide sequence of SEQ ID NO: 4, 5, 6, 7, 8, 26, 27, 28, or 29. In one embodiment, the expression vector consists essentially of a polynucleotide sequence of SEQ ID NO:4. In another embodiment, the expression vector consists essentially of a polynucleotide sequence of SEQ ID NO: 5. In yet another embodiment, the expression vector consists essentially of a polynucleotide sequence of SEQ ID NO:6. In still another embodiment, the expression vector consists essentially of a polynucleotide sequence of SEQ ID NO:7. In yet still another embodiment, the expression vector consists essentially of a polynucleotide sequence of SEQ ID NO:8. In one embodiment, the expression vector consists essentially of a polynucleotide sequence of SEQ ID NO: 26. In another embodiment, the expression vector consists essentially of a polynucleotide sequence of SEQ ID NO:27. In yet another embodiment, the expression vector consists essentially of a polynucleotide sequence of SEQ ID NO:28. In still another embodiment, the expression vector consists essentially of a polynucleotide sequence of SEQ ID NO:29.

In another specific embodiment, the expression vector comprises a polynucleotide sequence that is at least 60%, 70%, 80%, 90%, or 95% identical to the polynucleotide sequence of SEQ ID NO:4, 5, 6, 7, 8, 26, 27, 28, or 29. In one embodiment, the expression vector comprises a polynucleotide sequence that is at least 60%, 70%, 80%, 90%, or 95% identical to the polynucleotide sequence of SEQ ID NO:4. In another embodiment, the expression vector comprises a polynucleotide sequence that is at least 60%, 70%, 80%, 90%, or 95% identical to the polynucleotide sequence of SEQ ID NO:5. In yet another embodiment, the expression vector comprises a polynucleotide sequence that is at least 60%, 70%, 80%, 90%, or 95% identical to the polynucleotide sequence of SEQ ID NO:6. In still another embodiment, the expression vector comprises a polynucleotide sequence that is at least 60%, 70%, 80%, 90%, or 95% identical to the polynucleotide sequence of SEQ ID NO:7. In yet still another embodiment, the expression vector comprises a polynucleotide sequence that is at least 60%, 70%, 80%, 90%, or 95% identical to the polynucleotide sequence of SEQ ID NO:8. In one embodiment, the expression vector comprises a polynucleotide sequence that is at least 60%, 70%, 80%, 90%, or 95% identical to the polynucleotide sequence of SEQ ID NO:26. In another embodiment, the expression vector comprises a polynucleotide sequence that is at least 60%, 70%, 80%, 90%, or 95% identical to the polynucleotide sequence of SEQ ID NO:27. In yet another embodiment, the expression vector comprises a polynucleotide sequence that is at least 60%, 70%, 80%, 90%, or 95% identical to the polynucleotide sequence of SEQ ID NO:28. In still another embodiment, the expression vector comprises a polynucleotide sequence that is at least 60%, 70%, 80%, 90%, or 95% identical to the polynucleotide sequence of SEQ ID NO:29.

In another specific embodiment, the expression vector comprises a polynucleotide sequence that is at least 75% identical to the polynucleotide sequence of SEQ ID NO:4, 5, 6, 7, 8, 26, 27, 28, or 29. In one embodiment, the expression vector comprises a polynucleotide sequence that is at least 75% identical to the polynucleotide sequence of SEQ ID NO:4. In another embodiment, the expression vector comprises a polynucleotide sequence that is at least 75% identical to the polynucleotide sequence of SEQ ID NO:5. In yet another embodiment, the expression vector comprises a polynucleotide sequence that is at least 75% identical to the polynucleotide sequence of SEQ ID NO:6. In still another embodiment, the expression vector comprises a polynucleotide sequence that is at least 75% identical to the polynucleotide sequence of SEQ ID NO:7. In yet still another embodiment, the expression vector comprises a polynucleotide sequence that is at least 75% identical to the polynucleotide sequence of SEQ ID NO: 8. In one embodiment, the expression vector comprises a polynucleotide sequence that is at least 75% identical to the polynucleotide sequence of SEQ ID NO:26. In another embodiment, the expression vector comprises a polynucleotide sequence that is at least 75% identical to the polynucleotide sequence of SEQ ID NO:27. In yet another embodiment, the expression vector comprises a polynucleotide sequence that is at least 75% identical to the polynucleotide sequence of SEQ ID NO:28. In still another embodiment, the expression vector comprises a polynucleotide sequence that is at least 75% identical to the polynucleotide sequence of SEQ ID NO: 29.

In another specific embodiment, the expression vector comprises a polynucleotide sequence that is at least 85% identical to the polynucleotide sequence of SEQ ID NO:4, 5, 6, 7, 8, 26, 27, 28, or 29. In one embodiment, the expression vector comprises a polynucleotide sequence that is at least 85% identical to the polynucleotide sequence of SEQ ID NO:4. In another embodiment, the expression vector comprises a polynucleotide sequence that is at least 85% identical to the polynucleotide sequence of SEQ ID NO:5. In yet another embodiment, the expression vector comprises a polynucleotide sequence that is at least 85% identical to the polynucleotide sequence of SEQ ID NO:6. In still another embodiment, the expression vector comprises a polynucleotide sequence that is at least 85% identical to the polynucleotide sequence of SEQ ID NO:7. In yet still another embodiment, the expression vector comprises a polynucleotide sequence that is at least 85% identical to the polynucleotide sequence of SEQ ID NO: 8. In one embodiment, the expression vector comprises a polynucleotide sequence that is at least 85% identical to the polynucleotide sequence of SEQ ID NO:26. In another embodiment, the expression vector comprises a polynucleotide sequence that is at least 85% identical to the polynucleotide sequence of SEQ ID NO:27. In yet another embodiment, the expression vector comprises a polynucleotide sequence that is at least 85% identical to the polynucleotide sequence of SEQ ID NO:28. In still another embodiment, the expression vector comprises a polynucleotide sequence that is at least 85% identical to the polynucleotide sequence of SEQ ID NO: 29.

In another specific embodiment, the expression vector comprises a polynucleotide sequence that is at least 90% identical to the polynucleotide sequence of SEQ ID NO:4, 5, 6, 7, 8, 26, 27, 28, or 29. In one embodiment, the expression vector comprises a polynucleotide sequence that is at least 90% identical to the polynucleotide sequence of SEQ ID NO:4. In another embodiment, the expression vector comprises a polynucleotide sequence that is at least 90% identical to the polynucleotide sequence of SEQ ID NO:5. In yet another embodiment, the expression vector comprises a polynucleotide sequence that is at least 90% identical to the polynucleotide sequence of SEQ ID NO:6. In still another embodiment, the expression vector comprises a polynucleotide sequence that is at least 90% identical to the polynucleotide sequence of SEQ ID NO:7. In yet still another embodiment, the expression vector comprises a polynucleotide sequence that is at least 90% identical to the polynucleotide sequence of SEQ ID NO: 8. In one embodiment, the expression vector comprises a polynucleotide sequence that is at least 90% identical to the polynucleotide sequence of SEQ ID NO:26. In another embodiment, the expression vector comprises a polynucleotide sequence that is at least 90% identical to the polynucleotide sequence of SEQ ID NO:27. In yet another embodiment, the expression vector comprises a polynucleotide sequence that is at least 90% identical to the polynucleotide sequence of SEQ ID NO:28. In still another embodiment, the expression vector comprises a polynucleotide sequence that is at least 90% identical to the polynucleotide sequence of SEQ ID NO: 29.

In another specific embodiment, the expression vector comprises a polynucleotide sequence that is at least 95% identical to the polynucleotide sequence of SEQ ID NO:4, 5, 6, 7, 8, 26, 27, 28, or 29. In one embodiment, the expression vector comprises a polynucleotide sequence that is at least 95% identical to the polynucleotide sequence of SEQ ID NO:4. In another embodiment, the expression vector comprises a polynucleotide sequence that is at least 95% identical to the polynucleotide sequence of SEQ ID NO:5. In yet another embodiment, the expression vector comprises a polynucleotide sequence that is at least 95% identical to the polynucleotide sequence of SEQ ID NO:6. In still another embodiment, the expression vector comprises a polynucleotide sequence that is at least 95% identical to the polynucleotide sequence of SEQ ID NO:7. In yet still another embodiment, the expression vector comprises a polynucleotide sequence that is at least 95% identical to the polynucleotide sequence of SEQ ID NO: 8. In one embodiment, the expression vector comprises a polynucleotide sequence that is at least 95% identical to the polynucleotide sequence of SEQ ID NO:26. In another embodiment, the expression vector comprises a polynucleotide sequence that is at least 95% identical to the polynucleotide sequence of SEQ ID NO:27. In yet another embodiment, the expression vector comprises a polynucleotide sequence that is at least 95% identical to the polynucleotide sequence of SEQ ID NO:28. In still another embodiment, the expression vector comprises a polynucleotide sequence that is at least 95% identical to the polynucleotide sequence of SEQ ID NO: 29.

Polypeptides that can be encoded by the GOI and expressed by various expression vectors described herein include, but are not limited to, therapeutic or prophylactic polypeptides such as adhesion molecules, antibody light and/or heavy chains, cytokines, enzymes, lymphokines, and receptors, etc.

In certain embodiments of the various expression vectors provided herein, the expression vector further comprises the GOI. In some embodiments, the expression vector further comprises the GOI, and the GOI encodes a therapeutic or prophylactic protein. In other embodiments, the expression vector further comprises the GOI, and the GOI encodes a heavy chain or a fragment thereof of a monoclonal antibody. In vet other embodiments, the expression vector further comprises the GOI, and the GOI encodes a light chain or a fragment thereof of a monoclonal antibody.

In yet another aspect, provided herein is a mammalian recombinant host cell comprising a mammalian host cell transfected with the expression vector described herein.

Suitable mammalian host cells include but are not limited to hamster cells, such as CHO, CHO-K1, CHO-DUKX, CHO-DUKX BI, CHO-DG44, CHO-DBX11, CHOK1SV™, HD-BIOP1, CHOZN®, BHK21, BHK TK$^-$, or ExpiCHO, as well as derivatives/descendants of these hamster cell lines. Also suitable are myeloma cells from the mouse, such as NS0 or Sp2/0-AG14 cells, and human cell lines, such as HEK293, Hela, Jerkat, TP1, or PER.C6, as well as derivatives/descendants of these mouse and human cell lines.

In certain embodiments of various mammalian recombinant host cells provided herein, the mammalian host cell is a CHO cell. In one embodiment, the endogenous glutamine synthetase gene of the CHO cell is knocked out. In another embodiment, the mammalian host cell is a CHOK1SV™ cell. In yet another embodiment, the mammalian host cell is a HD-BIOP1 cell. In still another embodiment, the mammalian host cell is a CHOZN® cell.

In still another aspect, provided herein is a method of producing a polypeptide, comprising culturing the mammalian recombinant host cell described herein, under conditions in which the polypeptide is expressed.

In some embodiments, provided herein is a method of producing a polypeptide, comprising culturing the mammalian recombinant host cell described herein, under conditions in which the polypeptide is expressed, and recovering the polypeptide from the culture.

In another aspect, provided herein is a bacterial recombinant host cell comprising a bacterial host cell transformed with the expression vector described herein.

Suitable bacterial host cells include but are not limited to the bacterial host cells that are commonly used for molecular cloning, transformation, and/or propagation of expression vectors by an ordinary person in the art, for example, DH5α™, DH10B™, JM109, TOP10, etc., as well as derivatives and modifications of them.

In yet another aspect, provided herein is a method of propagating an expression vector, comprising culturing the bacterial recombinant host cell described herein, under conditions in which the expression vector is replicated.

In certain embodiments, provided herein is a method of propagating an expression vector, comprising culturing the bacterial recombinant host cell described herein, under conditions in which the expression vector is replicated, and recovering the expression vector from the culture.

In still another aspect, provided herein is a mammalian recombinant host cell comprising a mammalian host cell co-transfected with a first expression vector and a second expression vector, wherein the first expression vector and the second expression vector are the expression vector described herein, wherein the GOI of the first expression vector encodes a light chain of a monoclonal antibody and the GOI of the second expression vector encodes a heavy chain of the monoclonal antibody, and wherein the eukaryotic selectable marker of the first expression vector is different from the eukaryotic selectable marker of the second expression vector.

In one embodiment, provided herein is a CHO recombinant host cell comprising a CHO host cell co-transfected with a first expression vector and a second expression vector, wherein the first expression vector and the second expression vector are the expression vector described herein, wherein the GOI of the first expression vector encodes a light chain of a monoclonal antibody and the GOI of the second expression vector encodes a heavy chain of the monoclonal antibody, and wherein the eukaryotic selectable marker of the first expression vector is different from the eukaryotic selectable marker of the second expression vector.

In another embodiment, provided herein is a CHO recombinant host cell comprising a CHO host cell co-transfected with a first expression vector and a second expression vector, wherein the endogenous glutamine synthetase gene of the CHO cell is knocked out, wherein the first expression vector and the second expression vector are the expression vector described herein, wherein the GOI of the first expression vector encodes a light chain of a monoclonal antibody and the GOI of the second expression vector encodes a heavy chain of the monoclonal antibody, and wherein the eukaryotic selectable marker of the first expression vector is different from the eukaryotic selectable marker of the second expression vector.

In yet still another aspect, provided herein is a method of producing a monoclonal antibody, comprising culturing the mammalian recombinant host cell co-transfected with a first expression vector comprising a first GOI encoding the light chain of the monoclonal antibody and a second expression vector comprising a second GOI encoding the heavy chain of the monoclonal antibody described herein, under conditions in which both the light chain and the heavy chain of the monoclonal antibody are expressed.

In some embodiments, provided herein is a method of producing a monoclonal antibody, comprising culturing the mammalian recombinant host cell co-transfected with a first expression vector comprising a first GOI encoding the light chain of the monoclonal antibody and a second expression vector comprising a second GOI encoding the heavy chain of the monoclonal antibody described herein, under conditions in which both the light chain and the heavy chain of the monoclonal antibody are expressed, and recovering the monoclonal antibody from the culture.

In certain embodiments, the method of producing a monoclonal antibody comprises culturing the mammalian recombinant host cell co-transfected with a first expression vector comprising a first GOI encoding the light chain of the monoclonal antibody and a second expression vector comprising a second GOI encoding the heavy chain of the monoclonal antibody described herein, under conditions in which both the light chain and the heavy chain of the monoclonal antibody are expressed, and wherein the eukaryotic selectable marker of the first expression vector is different from the eukaryotic selectable marker of the second expression vector.

In other embodiments, the method of producing a monoclonal antibody comprises culturing the mammalian recombinant host cell co-transfected with a first expression vector comprising a first GOI encoding the light chain of the monoclonal antibody and a second expression vector comprising a second GOI encoding the heavy chain of the monoclonal antibody described herein, under conditions in which both the light chain and the heavy chain of the monoclonal antibody are expressed, and recovering the monoclonal antibody from the culture, and wherein the eukaryotic selectable marker of the first expression vector is different from the eukaryotic selectable marker of the second expression vector.

In one embodiment, provided herein is a method of producing a monoclonal antibody, comprising culturing the CHO recombinant host cell co-transfected with a first expression vector comprising a first GOI encoding the light chain of the monoclonal antibody and a second expression vector comprising a second GOI encoding the heavy chain of the monoclonal antibody described herein, under conditions in which both the light chain and the heavy chain of the monoclonal antibody are expressed.

In another embodiment, provided herein is a method of producing a monoclonal antibody, comprising culturing the CHO recombinant host cell co-transfected with a first expression vector comprising a first GOI encoding the light chain of the monoclonal antibody and a second expression vector comprising a second GOI encoding the heavy chain of the monoclonal antibody described herein, under conditions in which both the light chain and the heavy chain of the monoclonal antibody are expressed, and recovering the monoclonal antibody from the culture.

In certain embodiments, the method of producing a monoclonal antibody comprises culturing the CHO recombinant host cell co-transfected with a first expression vector comprising a first GOI encoding the light chain of the monoclonal antibody and a second expression vector comprising a second GOI encoding the heavy chain of the monoclonal antibody described herein, under conditions in which both the light chain and the heavy chain of the monoclonal antibody are expressed, and wherein the eukaryotic selectable marker of the first expression vector is different from the eukaryotic selectable marker of the second expression vector.

In other embodiments, the method of producing a monoclonal antibody comprises culturing the CHO recombinant host cell co-transfected with a first expression vector comprising a first GOI encoding the light chain of the monoclonal antibody and a second expression vector comprising a second GOI encoding the heavy chain of the monoclonal antibody described herein, under conditions in which both the light chain and the heavy chain of the monoclonal antibody are expressed, and recovering the monoclonal antibody from the culture, and wherein the eukaryotic selectable marker of the first expression vector is different from the eukaryotic selectable marker of the second expression vector.

In another embodiment, provided herein is a method of producing a monoclonal antibody, comprising culturing the CHO recombinant host cell co-transfected with a first expression vector comprising a first GOI encoding the light chain of the monoclonal antibody and a second expression vector comprising a second GOI encoding the heavy chain of the monoclonal antibody described herein, under conditions in which both the light chain and the heavy chain of the monoclonal antibody are expressed, wherein the endogenous glutamine synthetase gene of the CHO cell is knocked out.

In another embodiment, provided herein is a method of producing a monoclonal antibody, comprising culturing the CHO recombinant host cell co-transfected with a first expression vector comprising a first GOI encoding the light chain of the monoclonal antibody and a second expression vector comprising a second GOI encoding the heavy chain of the monoclonal antibody described herein, under conditions in which both the light chain and the heavy chain of the monoclonal antibody are expressed, and recovering the monoclonal antibody from the culture, wherein the endogenous glutamine synthetase gene of the CHO cell is knocked out.

In certain embodiments, the method of producing a monoclonal antibody comprises culturing the CHO recombinant host cell co-transfected with a first expression vector comprising a first GOI encoding the light chain of the monoclonal antibody and a second expression vector comprising a second GOI encoding the heavy chain of the monoclonal antibody described herein, under conditions in which both the light chain and the heavy chain of the monoclonal antibody are expressed, wherein the endogenous glutamine synthetase gene of the CHO cell is knocked out, and wherein the eukaryotic selectable marker of the first expression vector is different from the eukaryotic selectable marker of the second expression vector.

In certain embodiments, the method of producing a monoclonal antibody comprises culturing the CHO recombinant host cell co-transfected with a first expression vector comprising a first GOI encoding the light chain of the monoclonal antibody and a second expression vector comprising a second GOI encoding the heavy chain of the monoclonal antibody described herein, under conditions in which both the light chain and the heavy chain of the monoclonal antibody are expressed, and recovering the monoclonal antibody from the culture, wherein the endogenous glutamine synthetase gene of the CHO cell is knocked out, and wherein the eukaryotic selectable marker of the first expression vector is different from the eukaryotic selectable marker of the second expression vector.

In any embodiments of various expression vectors, host cells, methods of propagating expression vectors, methods of producing polypeptides encoded by the GOI, or methods of producing monoclonal antibodies, the polynucleotide sequence for an individual vector element or component (e.g., regulatory elements, including but not limited to an enhancer, an insulator, a LCR, a MAR, a SAR, an EASE, or a TPL) can be obtained from a different species than the species from which the sequences disclosed herein are obtained. For example, a species variant of a human β-globin poly A signal, such as a mouse or hamster β-globin poly A signal, can be used in the expression vectors. Similarly, a species variant of an adenovirus TPL, such as a human adenovirus B TPL, a human adenovirus C TPL, a human adenovirus E TPL, or an ovine adenovirus TPL, can be used in the expression vectors.

EXAMPLES

These examples are intended to further clarify the present invention and not to limit the invention. Any composition or method, in whole or in part, set forth in the examples form a part of the present invention.

Example 1: Construction of Expression Vectors

FIG. 1 illustrates an exemplary innovative expression vector comprising a combination of engineered elements, which were selected to maximize protein expression in mammalian cells. In FIG. 1, E represents an enhancer: P represents a promoter: ORF represents an open reading frame: UTR represents an untranslated region: IRES represents an internal ribosome entry site: PolyA represents a polyadenylation signal: ITR represents an inverted repeat region, Bac-Ori represents a bacterial origin of replication: Amp represents an ampicillin selectable marker.

The DNA sequence information of plasmid pUC19 and various fragments, such as EASE, CMV Enhancer/Promoter, TPL, IRES, mammalian selection marker, and PolyA, were obtained from the public domain. The polynucleotides of pUC19 and these fragments were synthesized by Blue Heron Biotech, LLC, WA. A variety of expression vectors with GOI were constructed as shown in FIGS. 2A-2E, using NEBuilder HiFi DNA Assembly Cloning Kit (New England Biolabs, Beverly, MA).

The DNA sequences of selected elements or expression vectors are shown as follows:

IRES-1 (Genes Dev. 4(9):1560-72 (1990), SEQ ID NO: 1):
cccctaacgttactggccgaagccgcttggaataaggccggtgtgcgtttgtctatatgttattttccaccatattgccgtcttttggcaatgtgaggg cccggaaacctggccctgtcttcttgacgagcattcctaggggtctttcccctctcgccaaaggaatgcaaggtctgttgaatgtcgtgaaggaag cagttectctggaagatcttgaagacaaacaacgtctgtagcgaccctttgcaggcagcggaaccccccacctggcgacaggtgcctctgcgg ccaaaagccacgtgtataagatacacctgcaaaggcggcacaaccccagtgccacgttgtgagttggatagttgtggaaagagtcaaatggctc tcctcaagcgtattcaacaaggggctgaaggatgcccagaaggtaccccattgtatgggatctgatctggggcctcggtgcacatgctttacatgt gtttagtcgaggttaaaaaacgtctaggccccccgaaccacggggacgtggttttcctttgaaaaacacgatgataatatggccacaacc IRES-2 (SEQ ID NO: 2):
cccctaacgttactggccgaagccgcttggaataaggccggtgtgcgtttgtctatatgttattttccaccatattgccgtcttttggcaatgtgaggg cccggaaacctggccctgtatcttgacgagcattcctaggggtctttcccctctcgccaaaggaatgcaaggtctgttgaatgtcgtgaaggaag cagttectctggaagatcttgaagacaaacaacgtctgtagcgaccctttgcaggcagcggaaccccccacctggcgacaggtgcctctgcgg ccaaaagccacgtgtataagatacacctgcaaaggcggcacaaccccagtgccacgttgtgagttggatagttgtggaaagagtcaaatggctc tcctcaagcgtattcaacaaggggctgaaggatgcccagaaggtaccccattgtatgggatctgatctggggcctcggtgcacatgctttacatgt gtttagtcgaggttaaaaaacgtctaggccccccgaaccacggggacgtggttttcctttgaaaaacacgatgataa IRES-3 (SEQ ID NO: 3):
cccctaacgttactggccgaagccgcttggaataaggccggtgtgcgtttgtctatatgttattttccaccatattgccgtcttttggcaatgtgaggg cccggaaacctggccctgtcttcttgacgagcattcctaggggtctttcccctctcgccaaaggaatgcaaggtctgttgaatgtcgtgaaggaag cagttectctggaagatcttgaagacaaacaacgtctgtagcgaccctttgcaggcagcggaaccccccacctggcgacaggtgcctctgcgg ccaaaagccacgtgtataagatacacctgcaaaggcggcacaaccccagtgccacgttgtgagttggatagttgtggaaagagtcaaatggctc tcctcaagcgtattcaacaaggggctgaaggatgcccagaaggtaccccattgtatgggatctgatctggggcctcggtgcacatgctttacatgt gtttagtcgaggttaaaaaacgtctaggccccccgaaccacggggacgtggttttcctttgaaaaacacg IRES-4 (SEQ ID NO: 23):
cccctaacgttactggccgaagccgcttggaataaggccggtgtgcgtttgtctatatgttattttccaccatattgccgtcttttggcaatgtgaggg cccggaaacctggccctgtcttcttgacgagcattcctaggggtctttcccctctcgccaaaggaatgcaaggtctgttgaatgtcgtgaaggaag cagttectctggaagatcttgaagacaaacaacgtctgtagcgaccctttgcaggcagcggaaccccccacctggcgacaggtgcctctgcgg ccaaaagccacgtgtataagatacacctgcaaaggcggcacaaccccagtgccacgttgtgagttggatagttgtggaaagagtcaaatggctc tcctcaagcgtattcaacaaggggctgaaggatgcccagaaggtaccccattgtatgggatctgatctggggcctcggtgcacatgctttacatgt gtttagtcgaggttaaaaaaacgtctaggccccccgaaccacggggacgtggttttcctttgaaaaacacgatgataatatggccacaacc -continued IRES-5 (SEQ ID NO: 24):
cccctaacgttactggccgaagccgcttggaataaggccggtgtgcgtttgtctatatgttattttccaccatattgccgtcttttggcaatgtgaggg cccggaaacctggccctgtcttcttgacgagcattcctaggggtctttcccctctcgccaaaggaatgcaaggtctgttgaatgtcgtgaaggaag cagttcctctggaagatcttgaagacaaacaacgtctgtagcgaccctttgcaggcagcggaacccccacctggcgacaggtgcctctgcgg ccaaaagccacgtgtataagatacacctgcaaaggcggcacaaccccagtgccacgttgtgagttggatagttgtggaaagagtcaaatggctc tcctcaagcgtattcaacaaggggctgaaggatgcccagaaggtaccccattgtatgggatctgatctggggcctcggtgcacatgctttacatgt gtttagtcgaggttaaaaaaacgtctaggccccccgaaccacggggacgtggttttcctttgaaaaacacgatgataa IRES-6 (SEQ ID NO: 25):
cccctaacgttactggccgaagccgcttggaataaggccggtgtgcgtttgtctatatgttattttccaccatattgccgtcttttggcaatgtgaggg cccggaaacctggccctgtcttcttgacgagcattcctaggggtctttcccctctcgccaaaggaatgcaaggtctgttgaatgtcgtgaaggaag cagttcctctggaagatcttgaagacaaacaacgtctgtagcgaccctttgcaggcagcggaacccccacctggcgacaggtgcctctgcgg ccaaaagccacgtgtataagatacacctgcaaaggcggcacaaccccagtgccacgttgtgagttggatagttgtggaaagagtcaaatggctc tcctcaagcgtattcaacaaggggctgaaggatgcccagaaggtaccccattgtatgggatctgatctggggcctcggtgcacatgctttacatgt gtttagtcgaggttaaaaaaacgtctaggccccccgaaccacggggacgtggttttcctttgaaaaacacg pCLD116 (SEQ ID NO: 4):
1 CCAATGATCT TAAGTTAACC CTAGAAAGAT AATCATATTG TGACGTACGT TAAAGATAAT CATGCGTAAA ATTGACGCAT 81 GTGTTTTATC GGTCTGTATA TCGAGGTTTA TTTATTAATT TGAATAGATA TTAAGTTTTA TTATATTTAC ACTTACATAC 161 TAATAATAAA TTCAACAAAC AATTTATTTA TGTTTATTTA TTTATTAAAA AAAAACAAAA ACTCAAAATT TCTTCTATAA 241 AGTAACAAAA CTTTTATCGA ATTTGCAGCC CGGGACTAGC TAGAGGGACA GCCCCCCCCC AAAGCCCCCA GGGATGTAAT 321 TACGTCCCTC CCCCGCTAGG GGGCAGCAGC GAGCCGCCCG GGGCTCCGCT CCGGTCCGGC GCTCCCCCCG CATCCCCGAG 401 CCGGCAGCGT GCGGGGACAG CCCGGGCACG GGGAAGGTGG CACGGGATCG CTTTCCTCTG AACGCTTCTC GCTGCTCTTT 481 GAGCCTGCAG ACACCTGGGG GGATACGGGG AAAACTTAAG ATCCGACCGG TGCTGTGGAA TGTGTGTCAG TTAGGGTGTG 561 GAAAGTCCCC AGGCTCCCCA GCAGGCAGAA GTATGCAAAG CATGCATCTC AATTAGTCAG CAACCAGGTG TGGAAAGTCC 641 CCAGGCTCCC CAGCAGGCAG AAGTATGCAA AGCATGCATC TCAATTAGTC AGCAACCATA GTCCCGCCCC TAACTCCGCC 721 CATCCCGCCC CTAACTCCGC CCAGTTCCGC CCATTCTCCG CTCCATCGTT CAGATTTTAC CACATTTGTA GAGGTTTTAC 801 TTGCTTTAAA AAACCTCCCA CACCTCCCCC TGAACCTGAA ACATAAAATG AATGCAATTG TTGTTGTTAA CTTGTTTATT 881 GCAGCTTATA ATGGTTACAA ATAAAGCAAT AGCATCACAA ATTTCACAAA TAAAGCATTT TTTTCACTGC ATTCTAGTTG 961 TGGTTTGTCC AAACTCATCA ATGTATCTTA TCATGTCTGC TCGAAGCGGC CGGCCGCCCC GACTCTAGAT TAGTTTTTGT 1041 ATTGGAAGGG CTCGTCGCCA GTCTCATTGA GAAGGCATGT GCGGACGATG GCTTCTGTCA CTGCAAAGGG GTCACAATTG -continued

```
1121  GCAGAGGGGC GGCGGTCTTC AAAGTAACCT TTCTTCTCCT GGCCGACAGT CCGGGGAATG CGGATGCTGG CACTGCGATT
1201  GGCGACACCA GCAGAAAAGT CGTTGATGTT GGACGTTTCG TGGAACCCAG TCAGACGACG GGCATTGTCC AGGCCCCCCT
1281  TGGGATCGTA GGCTCGAATG TGGTACCGGT GCCGCTTGCT TAGTTTCTCG ATGGCCTCCT CGATGTGCTT CAGACCATTC
1361  TCCTCCCGCA TGGCCTTGGT GCTAAAGTTG GTATGGCAGC CTGCACCATT CCAGTTCCCA GGAATGGGCT TGGGGTCAAA
1441  GGTTGCTATT ACCCCAAAGT CTTCACATAC TCGATGCAAG ATGAAACGGG CCACCCAGAG ATGATCTCCC ATGCGGATTC
1521  CTTCACAGGG TCCTATTTGG AACTCCCACT GGGCAGGCAT GACCTCAGCA TTTGTTCCTG TAATCTTGAC CCCAGCATAC
1601  AAGCAGGCGC GGTAGTGAGC CTCCACGATA TCCCTGCCAT AGGCTTTGTC TGCGCCCACA CCACAGTAAT ACGGACCTTG
1681  GGGCCCAGGA AAGCCATTGG AAGGCCAACC AAAAGGGTGC CCATCTGTTC CCATCAGAGT ATACTCCTGT TCCATTCCAA
1761  ACCAGGGGTG CTGGTTGCTC ACCATGTCCA TTATCCGTTT ACACGAGTGC CTTAAATTGG TCTCTGCAGG CTTCCGGTTG
1841  TACTTGAAAA CTTCACAGAA CACCAGCTTG TTGGGATCTC TGCGGAAGGG GTCCCGAAAC ATGGCAACAG GGCTGAGATA
1921  CATGTCACTG TTGGAGCCCT CAGACTGAAA GGTACTAGAG CCATCAAAAT TCCACTCAGG TAACTCTTCT ACACACTTGG
2001  GCTCACAGTC CAGGGTGCGG GTTTTGCAGC GCAGTCCTTC TCCAGTACCA TCAACCCAGA TATACATGGC TTGGACTTTC
2081  TCACCCTGGG GCAGGCACAA GTACATTTGC TTGATGTTTT TGTTCAAGTG GGAACTTGCT GAGGTGGCCA TGGTGGCGGC
2161  TTTGCAAAAG CCTAGGCCTC CAAAAAAGCC TCCTCACTAC TTCTGGAATA GCTCAGAGGC CGAGGCGGCC TCGGCCTCTG
2241  CATAAATAAA AAAAATTAGT CAGCGATGGG GCGGAGAATG GGCGGAACTG GGCGGAGTTA GGGGCGGGAT GGGCGGAGTT
2321  AGGGGCGGGA CTATGGTTGC TGACTAATTG AGATGCAATC ACTGACACAC ATTCCACAGC TGCCTCGCGC GTTTCGGTGA
2401  TGACGGTGAA AACCTCTGAC ACATGCAGCT CCCGGAGACG GTCACAGCTT GTCTGTAAGC GGATGCCGGG AGCAGACAAG
2481  CCCGTCAGGG CGCGTCAGCG GGTGTTGGCG GGTGTCGGGG CGCAGCCATG ACCCAGTCAC GTAGCGATAG CGGAGTGTAT
2561  ACTGGCTTAA CTATGCGGCA TCAGAGCAGA TTGTACTGAG CCTCGAGCGA TGTACGGGCC AGATATACGC GTTGACATTG
2641  ATTATTGACT AGTTATTAAT AGTAATCAAT TACGGGGTCA TTAGTTCATA GCCCATATAT GGAGTTCCGC GTTACATAAC
2721  TTACGGTAAA TGGCCCGCCT GGCTGACCGC CCAACGACCC CCGCCCATTG ACGTCAATAA TGACGTATGT TCCCATAGTA
2801  ACGCCAATAG GGACTTTCCA TTGACGTCAA TGGGTGGACT ATTTACGGTA AACTGCCCAC TTGGCAGTAC ATCAAGTGTA
2881  TCATATGCCA AGTACGCCCC CTATTGACGT CAATGACGGT AAATGGCCCG CCTGGCATTA TGCCCAGTAC ATGACCTTAT
2961  GGGACTTTCC TACTTGGCAG TACATCTACG TATTAGTCAT CGCTATTACC ATGGTGATGC GGTTTTGGCA GTACATCAAT
3041  GGGCGTGGAT AGCGGTTTGA CTCACGGGGA TTTCCAAGTC TCCACCCCAT TGACGTCAAT GGGAGTTTGT TTTGGCACCA
3121  AAATCAACGG GACTTTCCAA AATGTCGTAA CAACTCCGCC CCATTGACGC AAATGGGCGG TAGGCGTGTA CGGTGGGAGG
3201  TCTATATAAG CAGAGCTCTC TGGCTAACTA GAGAACCCAC TGCTTACTGG CTTATCGAAA TTAATACGAC TCACTATAGC
```

-continued

```
3281  AATTGCACGT GTGGCCACAG GTAAGTTTAA AGCTCAGGTC GAGACCGGGC CTTTGTCCGG CGCTCCCTTG GAGCCTACCT
3361  AGACTCAGCC GGCTCTCCAC GCTTTGCCTG ACCCTGCTTG CTCAACTCTA CGTCTTTGTT TCGTTTTCTG TTCCTTTCTC
3441  TCCACAGGCG GATCCGAATT CTGAAGATCT AGATCCCCCT CGCTTTCTTG CTGTCCAATT TCTATTAAAG GTTCCTTTGT
3521  TCCCTAAGTC CAACTACTAA ACTGGGGGAT ATTATGAAGG GCCTTGAGCA TCTGGATTCT GCCTAATAAA AAACATTTAT
3601  TTTCATTGCA ATGATGTATT TAAATTATTT CTGAATATTT TACTAAAAAG GGAATGTGGG AGGTCAGTGC ATTTAAAACA
3681  TAAAGAAATG AAGAGGGGGA TCTTCGCGAA TCCATCGATG AGGGACAGCC CCCCCCCAAA GCCCCCAGGG ATGTAATTAC
3761  GTCCCTCCCC CGCTAGGGGG CAGCAGCGAG CCGCCCGGGG CTCCGCTCCG GTCCGGCGCT CCCCCCGCAT CCCCGAGCCG
3841  GCAGCGTGCG GGGACAGCCC GGGCACGGGG AAGGTGGCAC GGGATCGCTT TCCTCTGAAC GCTTCTCGCT GCTCTTTGAG
3921  CCTGCAGACA CCTGGGGGGA TACGGGGAAA ATAGACACCG CGGTGGAGCT CCAGCTTTTG TTCCCTTTAG TGAGGGTTAA
4001  TTAGTTCTTA ATACGACTCA CTATAGGGCG AATTGGCTAC CGGGCCGCCC ATCGAGGGTA TCATAAGCTT ATATCTATAA
4081  CAAGAAAATA TATATATAAT AAGTTATCAC GTAAGTAGAA CATGAAATAA CAATATAATT ATCGTATGAG TTAAATCTTA
4161  AAAGTCACGT AAAAGATAAT CATGCGTCAT TTTGACTCAC GCGGTCGTTA TAGTTCAAAA TCAGTGACAC TTACCGCATT
4241  GACAAGCACG CCTCACGGGA GCTCCAAGCG GCGACTGAGA TGTCCTAAAT GCACAGCGAC GGATTCGCGC TATTTAGAAA
4321  GAGAGAGCAA TATTTCAAGA ATGCATGCGT CAATTTTACG CAGACTATCT TTCTAGGGTT AAATCGATAT CGGAAAGAAC
4401  ATGTGAGCAA AAGGCCAGCA AAAGGCCAGG AACCGTAAAA AGGCCGCGTT GCTGGCGTTT TTCCATAGGC TCCGCCCCCC
4481  TGACGAGCAT CACAAAAATC GACGCTCAAG TCAGAGGTGG CGAAACCCGA CAGGACTATA AAGATACCAG GCGTTTCCCC
4561  CTGGAAGCTC CCTCGTGCGC TCTCCTGTTC CGACCCTGCC GCTTACCGGA TACCTGTCCG CCTTTCTCCC TTCGGGAAGC
4641  GTGGCGCTTT CTCATAGCTC ACGCTGTAGG TATCTCAGTT CGGTGTAGGT CGTTCGCTCC AAGCTGGGCT GTGTGCACGA
4721  ACCCCCCGTT CAGCCCGACC GCTGCGCCTT ATCCGGTAAC TATCGTCTTG AGTCCAACCC GGTAAGACAC GACTTATCGC
4801  CACTGGCAGC AGCCACTGGT AACAGGATTA GCAGAGCGAG GTATGTAGGC GGTGCTACAG AGTTCTTGAA GTGGTGGCCT
4881  AACTACGGCT ACACTAGAAG AACAGTATTT GGTATCTGCG CTCTGCTGAA GCCAGTTACC TTCGGAAAAA GAGTTGGTAG
4961  CTCTTGATCC GGCAAACAAA CCACCGCTGG TAGCGGTGGT TTTTTTGTTT GCAAGCAGCA GATTACGCGC AGAAAAAAAG
5041  GATCTCAAGA AGATCCTTTG ATCTTTTCTA CGGGGTCTGA CGCTCAGTGG AACGAAAACT CACGTTAAGG GATTTTGGTC
5121  ATGAGATTAT CAAAAAGGAT CTTCACCTAG ATCCTTTTAA ATTAAAAATG AAGTTTTAAA TCAATCTAAA GTATATATGA
5201  GTAAACTTGG TCTGACAGTT ACCAATGCTT AATCAGTGAG GCACCTATCT CAGCGATCTG TCTATTTCGT TCATCCATAG
5281  TTGCCTGACT CCCCGTCGTG TAGATAACTA CGATACGGGA GGGCTTACCA TCTGGCCCCA GTGCTGCAAT GATACCGCGA
5361  GACCCACGCT CACCGGCTCC AGATTTATCA GCAATAAACC AGCCAGCCGG AAGGGCCGAG CGCAGAAGTG GTCCTGCAAC
```

-continued

```
5441  TTTATCCGCC TCCATCCAGT CTATTAATTG TTGCCGGGAA GCTAGAGTAA GTAGTTCGCC AGTTAATAGT TTGCGCAACG

5521  TTGTTGCCAT TGCTACAGGC ATCGTGGTGT CACGCTCGTC GTTTGGTATG GCTTCATTCA GCTCCGGTTC CCAACGATCA

5601  AGGCGAGTTA CATGATCCCC CATGTTGTGC AAAAAAGCGG TTAGCTCCTT CGGTCCTCCG ATCGTTGTCA GAAGTAAGTT

5681  GGCCGCAGTG TTATCACTCA TGGTTATGGC AGCACTGCAT AATTCTCTTA CTGTCATGCC ATCCGTAAGA TGCTTTTCTG

5761  TGACTGGTGA GTACTCAACC AAGTCATTCT GAGAATAGTG TATGCGGCGA CCGAGTTGCT CTTGCCCGGC GTCAATACGG

5841  GATAATACCG CGCCACATAG CAGAACTTTA AAAGTGCTCA TCATTGGAAA ACGTTCTTCG GGGCGAAAAC TCTCAAGGAT

5921  CTTACCGCTG TTGAGATCCA GTTCGATGTA ACCCACTCGT GCACCCAACT GATCTTCAGC ATCTTTTACT TTCACCAGCG

6001  TTTCTGGGTG AGCAAAAACA GGAAGGCAAA ATGCCGCAAA AAAGGGAATA AGGGCGACAC GGAAATGTTG AATACTCATA

6081  CTCTTCCTTT TTCAATATTA TTGAAGCATT TATCAGGGTT ATTGTCTCAT GAGCGGATAC ATATTTGAAT GTATTTAGAA

6161  AAATAAACAA ATAGGGGTTC CGCGCACATT TCCCCGAAAA GTGCCACCTG ACGTC

pCLD21 (SEQ ID NO: 5):
   1  CCTTCCCTTC TACCACACCC TAATTGTAAT CCATTTTAAT TTCCTGGTCA CAGTCCTGTC TCTCCTTCCA TTGTACCTTG

  81  CCCTTTTCTA AAGAGCGACT GCAAAGTATG TTTGCGTAGG TGAGGATCTA AAACTTTATG AGGTACGAAC ATCACAGAAT

 161  TACTTTGTAA TTTCAGTTTA TTGTAGGCTT GGCTTTTTGG GGAGGGTTTA CGTCTTAGAC CTCTTAGTGC TTCTTTGTTT

 241  CATGGTGTTC TAACTTCGAA GCATCTCTGT AGCTTTAATG GATTCCTTTT CTGAAAGCTT TGCTCTCTTT CTTCCCCCTC

 321  GGCTTTCTCT TAGGCAAGAG GGCTAACTGT AAAGTAAGGC TTACTGCCTT GTGTTTCCAA ATGTGTCCGA AGAGGAAGTG

 401  TCTTCTGTGA ATCCTGTTAT GCATGAATAA CAGGAAATAG AAAGAAATTC ACTTTCATTA TTATAAAAGT AATATGTTCG

 481  TTTAAAAAAT TCTAATGAAG AGCTGGAGAT GCAACCCAGG GGTAGAGCAC ACACTCAGCA TGCAGGAGGC CCTGGGTCCA

 561  ATCTTGGAAT CTCCTCTCAG TTAACCTGAT CTCTAGCTGA TTAGTAGTGA GTGCAAGCCC ACTTTCCTCT TCTGCCTCAT

 641  TGCTCAGTGA TAACAGCTGT TAAACTTTGT CTTATTCTAA AACTACCTCT GTGCAAATGC TAGCACAATA ATATATATCA

 721  TATGCACATG ATTTTTTTTT TATCTTGAAA AGTAAGTCAG TATAGCTACA AAGTTCACTT GGCATTGTCA ACATTTCACA

 801  GGCGTAATAT TCCTCCTCTA GTACTGTCCT CTTCATTCTT TGTGACCAAG TTTGGAGAGA GTGCACAAAT GCCAGGGAGG

 881  TTTGTGGGAA GGTTTCTCAT GTTCTGGTAA GGCGAGTAAG AAAATAGTCT CATGCAGGTG AAATGAGTGC TATGCAGTAT

 961  ATATTATACC AGAGAACAGC AAATGACCAA ATTCACACTG AACTAGTTCA GTAAAATTGG CTTTGTCAAA GCTTTCCTTG

1041  CTTAAAATGT AATTCCCTGT CATCCTAGTT CTGGTCTGGA TTCTTTTCCT GGAGTCTTGA CTTCCAGATT CCCTGTGGAC

1121  TTTTGTTTGA GTTTCAAGCT TTTGAAATAT AGAAACCTAT CTAACTTAAC AAACTTGGGA GAGAAAAGAC TCCAGAACAA

1201  CTGAAAACAG ACCAGGCTAA ATGAATAGAC TTTATTCCTC TCTTCTTACC TGCAGTTTTC AGATATGCAG AGTTGGAGCG
```

-continued

```
1281 GATCTTAGAG GTTGATTCAT TCATGCCTGA AGAAAACACA TTTTATAGAC CCTGTGCCCA AGTTCGTGGT GGACATCACC
1361 CTTTATTTAC TAATTGCACT ACATAACAGG CATTTTAGAA GACTGCTCCA GTCAGAGACC CCGCCTTAGA GGAATCTGTA
1441 AACCCTGAAC TCCTATCACT CATGAGCACT AGTTATGTTT GGAATGCCGT ATTAAAACAA AAGTTACATT TCTAAACTTA
1521 AAATTTTCTA GCACAGAGAC AGTGGGAGTA GCTAACTTTG ATAGACATTT TTCTACTAAA AGTCTTTCTA AGTACATAAT
1601 CTTCTGTAAG TTGGAAAACA GCAAAATAGA ACGTCTCCTA CGTAGTTAAT CTTTTTGCAT AATTTGCACA TGTAGGAGTT
1681 ATTAGTATAC GGGTAAGTTT TCACTTTTTC CCCCAACTGG AGTGTCTTGT GGCTGGGTTT GAAAAAGGGA ACGGGAGGCC
1761 GCTGGAGGGG ATTGGTAAAT GAGATAAAAC ACCACTCATT CAACTCAGTG ACTCAGCATT TAAATTTTCC ATAAAAGGAT
1841 TAAAGGAAAA TTAAACAAAT TCTTAAAGCC AAGACTCTGG AGAAACTTGT TGGTGTGCTT TAGTTTTCAC TGTTATGACT
1921 CATGAATTTA TGCATAAATT AGTACATTTA TAAAAACATA GCCTTTTTAG AGTTTTCTGT TTGGCTAAAG TGCCATTGTT
2001 AGCATTTGGA ATTACCTTTT TATGTCTTAT ATTTTTTCCA AATAAAAATA AATGTTTCTG CTGTCTTACT ACTGAAACTA
2081 CGTTGTGAGC ACTTTAAATT TCTCAAAGCA GTTTCGCCTG TTATACTTGG CGCTTAGTCA TCGTCGTACA CAACAGGACC
2161 TGATTAAGAA GGCTGTGCTG CCTCTAAGCC GGGCTAGATT GTAGCCACTA GCAACCAGGC TGCAATAATT TCCCTTTGAT
2241 GACATCATCC ACTGTGGAAG AACCCAGTTG CTTCAGCCAG TCGAACTATA CAGTTCCAAC CTCATCAAAT ATGGCATCTC
2321 CCTTGCCTGC TATAGCAGGG GGAGGAAAAA ATGCCACCAT CTTTTTAATC TAGCAAGCTT CTCTTTTCTT CATCTTTTTT
2401 TTTTTCTTTT AAAAAAATTC TGATCATGGA TGCTTCTTCC GATCCCTATT TGCCTTATGA CGGGGGAGGA GACAATATCC
2481 CCTTGAGGGA ATTACATAAA AGAGGTAAGA GCATCCCCTT GCTCTGAATC CTCTGTTGGT TGTTGTGCAT GCGGCTGGGC
2561 GGTTCTGGGG ACAGGCTGTC TGTTGTCCTC TTGCTGCAAT GTGCTGCTTA GTTGCCCTGC CTTGTTGCTG TGGGAGAATG
2641 CGACCTTCCC AGCAGGGCTG GCCCTCCCTG ATTGTTTGCT CTGTGCAGAT TAGCCCTGCT TCAGATCACA TAGGGCTGCA
2721 GACTCCATCT TCTGTGTGAA AATGCTTTCG GTTTGATTGC AGAAATAAGC TGCCTTTACA GCCAGCTAAA GTCCTGGTGG
2801 TTGGTTGGCA CCTGCAAAGT AGTATTTTTG TACCTCTGGA AACTTATATT TTCTTTACAC AGCAATATCA AGTGCCGGTA
2881 TGCCATTCTG TTTTGGCTGC TGCCAATTAC CATGTAGACT TTGCACCACA GAGTAATAGT AAAAGCTCCT AGCTGCATTT
2961 TATAACATTT AAAAATAGCA GGAAAGAAGA ATTATTTTTG ATTTAACATG TTTTTGTCAT TTAACGTCTT AACTGATTGA
3041 CATACTATAT TGTCTGTCTC GTGGGTATCT TGTACAACTT GATAGGATAA AGCAATTTAG TTTTTTTTTT TTTTTTTAAA
3121 TACATCCAGA ATGTAAGTCG TCAGTAGTTT TCGAACAGAT AAGTAATGGT GTTAATCTTT TGGCAGGCTT TGCCTTGGTC
3201 TCCTTAAAGC TAATTAGGTG TTACTTAATT AAACTGCTCT TTTGCTCATT TTCTTAAATT ATTTTTTTAA AAGATAGTTG
3281 GCATTTGCTG TTCTAGAAAT AAACTTCAAG AAACATTCTT TAGCCAGATG ACTTCATGTA TGAGCCATGT TAGTTTGAAT
3361 TATTTGCTTG GTGTTATAAA CTTTATGGTT TAATACCAAC TTTTATTATG TTTACAAGGT AAATAAGGAA AATTTCAAGT
```

-continued

```
3441 ACATTTTGTA TCCTGAGAAC AAATTTAAGT TCCATAGAAT TTAGGAATTA CAATGTATTC AACAGATACT TACTTGTCAT
3521 ACTGTGCCTG CAAAACAATA ATTAGACTCT GAACAGGTGC AACAATTTTC TGTAGAATTA GACAAGTCTT CTTTTGGCAG
3601 GTGTTACTAA GTAGGCCATT TCCCAAGGAA CAGGGAATTT GCCAGGCTTT TGTGGTGGAG AGAATAGAAT GAATAAATGC
3681 TGTGGGGAGT AAAGAGCTTG TCAGAAGATG ATTAGTTCTG TGGCACCAAA ACCAAGAGAT CAGTTTTCCT GTGAGAAGTA
3761 AAGGAAGCAT TGTAGAAAAA TAGATGTGTT GAAGTCTACC GGTGGAGTTC CGCGTTACAT AACTTACGGT AAATGGCCCG
3841 CCTGGCTGAC CGCCCAACGA CCCCCGCCCA TTGACGTCAA TAATGACGTA TGTTCCCATA GTAACGCCAA TAGGGACTTT
3921 CCATTGACGT CAATGGGTGG AGTATTTACG GTAAACTGCC CACTTGGCAG TACATCAAGT GTATCATATG CCAAGTACGC
4001 CCCCTATTGA CGTCAATGAC GGTAAATGGC CCGCCTGGCA TTATGCCCAG TACATGACCT TATGGGACTT TCCTACTTGG
4081 CAGTACATCT ACGTATTAGT CATCGCTATT ACCATTGTGA TGCGGTTTTG GCAGTACATC AATGGGCGTG GATAGCGGTT
4161 TGACTCACGG GGATTTCCAA GTCTCCACCC CATTGACGTC AATGGGAGTT TGTTTTGGCA CCAAAATCAA CGGGACTTTC
4241 CAAAATGTCG TAACAACTCC GCCCCATTGA CGCAAATGGG CGGTAGGCGT GTACGGTGGG AGGTCTATAT AAGCAGAGCT
4321 CGTTTAGTGA ACCGTCAGAT CTACCTCTTC CGCATCGCTG TCTGCGAGGG CCAGCTGTTG GGGTGAGTAC TCCCTCTCAA
4401 AAGCGGGCAT GACTTCTGCG CTAAGATTGT CAGTTTCCAA AAACGAGGAG GATTTGATAT TCACCTGGCC CGCGGTGATG
4481 CCTTTGAGGG TGGCCGCGTC CATCTGGTCA GAAAAGACAA TCTTTTTGTT GTCAAGCTTC CTTGATGATG TCATACTTAT
4561 CCTGTCCCTT TTTTTTCCAC AGCTCGCGGT TGAGGACAAA CTCTTCGCGG TCTTTCCAGT ACTCTTGGAT CGGAAACCCG
4641 TCGGCCTCCG AACGGTACTC CGCCACCGAG GGACCTGAGC GAGTCCGCAT CGACCGGATC GGAAAACCTC GGATCCGAAT
4721 TCATAGATAA CTGATCCAGT GCCCCTAACG TTACTGGCCG AAGCCGCTTG GAATAAGGCC GGTGTGCGTT TGTCTATATG
4801 TTATTTTCCA CCATATTGCC GTCTTTTGGC AATGTGAGGG CCCGGAAACC TGGCCCTGTC TTCTTGACGA GCATTCCTAG
4881 GGGTCTTTCC CCTCTCGCCA AAGGAATGCA AGGTCTGTTG AATGTCGTGA AGGAAGCAGT TCCTCTGGAA GCTTCTTGAA
4961 GACAAACAAC GTCTGTAGCG ACCCTTTGCA GGCAGCGGAA CCCCCCACCT GGCGACAGGT GCCTCTGCGG CCAAAAGCCA
5041 CGTGTATAAG ATACACCTGC AAAGGCGGCA CAACCCCAGT GCCACGTTGT GAGTTGGATA GTTGTGGAAA GAGTCAAATG
5121 GCTCTCCTCA AGCGTATTCA ACAAGGGGCT GAAGGATGCC CAGAAGGTAC CCCATTGTAT GGGATCTGAT CTGGGGCCTC
5201 GGTGCACATG CTTTACATGT GTTTAGTCGA GGTTAAAAAA CGTCTAGGCC CCCCGAACCA CGGGGACGTG GTTTTCCTTT
5281 GAAAAACACG ATGATAATAT GGCCACAACC ATGGCCACCT CAGCAAGTTC CCACTTGAAC AAAAACATCA AGCAAATGTA
5361 CTTGTGCCTG CCCCAGGGTG AGAAAGTCCA AGCCATGTAT ATCTGGGTTG ATGGTACTGG AGAAGGACTG CGCTGCAAAA
5441 CCCGCACCCT GGACTGTGAG CCCAAGTGTG TAGAAGAGTT ACCTGAGTGG AATTTTGATG GCTCTAGTAC CTTTCAGTCT
5521 GAGGGCTCCA ACAGTGACAT GTATCTCAGC CCTGTTGCCA TGTTTCGGGA CCCCTTCCGC AGAGATCCCA ACAAGCTGGT
```

-continued

```
5601  GTTCTGTGAA GTTTTCAAGT ACAACCGGAA GCCTGCAGAG ACCAATTTAA GGCACTCGTG TAAACGGATA ATGGACATGG
5681  TGAGCAACCA GCACCCCTGG TTTGGAATGG AACAGGAGTA TACTCTGATG GGAACAGATG GGCACCCTTT TGGTTGGCCT
5761  TCCAATGGCT TTCCTGGGCC CCAAGGTCCG TATTACTGTG GTGTGGGCGC AGACAAAGCC TATGGCAGGG ATATCGTGGA
5841  GGCTCACTAC CGCGCCTGCT TGTATGCTGG GGTCAAGATT ACAGGAACAA ATGCTGAGGT CATGCCTGCC CAGTGGGAGT
5921  TCCAAATAGG ACCCTGTGAA GGAATCCGCA TGGGAGATCA TCTCTGGGTG GCCCGTTTCA TCTTGCATCG AGTATGTGAA
6001  GACTTTGGGG TAATAGCAAC CTTTGACCCC AAGCCCATTC CTGGGAACTG GAATGGTGCA GGCTGCCATA CCAACTTTAG
6081  CACCAAGGCC ATGCGGGAGG AGAATGGTCT GAAGCACATC GAGGAGGCCA TCGAGAAACT AAGCAAGCGG CACCGGTACC
6161  ACATTCGAGC CTACGATCCC AAGGGGGGCC TGGACAATGC CCGTCGTCTG ACTGGGTTCC ACGAAACGTC CAACATCAAC
6241  GACTTTTCTG CTGGTGTCGC CAATCGCAGT GCCAGCATCC GCATTCCCCG GACTGTCGGC CAGGAGAAGA AAGGTTACTT
6321  TGAAGACCGC CGCCCCTCTG CCAATTGTGA CCCCTTTGCA GTGACAGAAG CCATCGTCCG CACATGCCTT CTCAATGAGA
6401  CTGGCGACGA GCCCTTCCAA TACAAAAACT AATCTAGATC CCCCTCGCTT TCTTGCTGTC CAATTTCTAT TAAAGGTTCC
6481  TTTGTTCCCT AAGTCCAACT ACTAAACTGG GGGATATTAT GAAGGGCCTT GAGCATCTGG ATTCTGCCTA ATAAAAAACA
6561  TTTATTTTCA TTGCAATGAT GTATTTAAAT TATTTCTGAA TATTTTACTA AAAAGGGAAT GTGGGAGGTC AGTGCATTTA
6641  AAACATAAAG AAATGAAGAG GGGGATCTTC GCGACCTGCA GGTCTCCCTA TAGTGAGTCG TATTAATTTC GATAAGCCAG
6721  CTGCATTAAT GAATCGGCCA ACGCGCGGGG AGAGGCGGTT TGCGTATTGG GCGCTCTTCC GCTTCCTCGC TCACTGACTC
6801  GCTGCGCTCG GTCGTTCGGC TGCGGCGAGC GGTATCAGCT CACTCAAAGG CGGTAATACG GTTATCCACA GAATCAGGGG
6881  ATAACGCAGG AAAGAACATG TGAGCAAAAG GCCAGCAAAA GGCCAGGAAC CGTAAAAAGG CCGCGTTGCT GGCGTTTTTC
6961  CATAGGCTCC GCCCCCCTGA CGAGCATCAC AAAAATCGAC GCTCAAGTCA GAGGTGGCGA AACCCGACAG GACTATAAAG
7041  ATACCAGGCG TTTCCCCCTG GAAGCTCCCT CGTGCGCTCT CCTGTTCCGA CCCTGCCGCT TACCGGATAC CTGTCCGCCT
7121  TTCTCCCTTC GGGAAGCGTG GCGCTTTCTC ATAGCTCACG CTGTAGGTAT CTCAGTTCGG TGTAGGTCGT TCGCTCCAAG
7201  CTGGGCTGTG TGCACGAACC CCCCGTTCAG CCCGACCGCT GCGCCTTATC CGGTAACTAT CGTCTTGAGT CCAACCCGGT
7281  AAGACACGAC TTATCGCCAC TGGCAGCAGC CACTGGTAAC AGGATTAGCA GAGCGAGGTA TGTAGGCGGT GCTACAGAGT
7361  TCTTGAAGTG GTGGCCTAAC TACGGCTACA CTAGAAGGAC AGTATTTGGT ATCTGCGCTC TGCTGAAGCC AGTTACCTTC
7441  GGAAAAAGAG TTGGTAGCTC TTGATCCGGC AAACAAACCA CCGCTGGTAG CGGTGGTTTT TTTGTTTGCA AGCAGCAGAT
7521  TACGCGCAGA AAAAAAGGAT CTCAAGAAGA TCCTTTGATC TTTTCTACGG GGTCTGACGC TCAGTGGAAC GAAAACTCAC
7601  GTTAAGGGAT TTTGGTCATG AGATTATCAA AAAGGATCTT CACCTAGATC CTTTTAAATT AAAAATGAAG TTTTAAATCA
7681  ATCTAAAGTA TATATGAGTA AACTTGGTCT GACAGTTACC AATGCTTAAT CAGTGAGGCA CCTATCTCAG CGATCTGTCT
```

-continued

```
7761  ATTTCGTTCA TCCATAGTTG CCTGACTCCC CGTCGTGTAG ATAACTACGA TACGGGAGGG CTTACCATCT GGCCCCAGTG
7841  CTGCAATGAT ACCGCGAGAC CCACGCTCAC CGGCTCCAGA TTTATCAGCA ATAAACCAGC CAGCCGGAAG GGCCGAGCGC
7921  AGAAGTGGTC CTGCAACTTT ATCCGCCTCC ATCCAGTCTA TTAATTGTTG CCGGGAAGCT AGAGTAAGTA GTTCGCCAGT
8001  TAATAGTTTG CGCAACGTTG TTGCCATTGC TACAGGCATC GTGGTGTCAC GCTCGTCGTT TGGTATGGCT TCATTCAGCT
8081  CCGGTTCCCA ACGATCAAGG CGAGTTACAT GATCCCCCAT GTTGTGCAAA AAAGCGGTTA GCTCCTTCGG TCCTCCGATC
8161  GTTGTCAGAA GTAAGTTGGC CGCAGTGTTA TCACTCATGG TTATGGCAGC ACTGCATAAT TCTCTTACTG TCATGCCATC
8241  CGTAAGATGC TTTTCTGTGA CTGGTGAGTA CTCAACCAAG TCATTCTGAG AATAGTGTAT GCGGCGACCG AGTTGCTCTT
8321  GCCCGGCGTC AATACGGGAT AATACCGCGC CACATAGCAG AACTTTAAAA GTGCTCATCA TTGGAAAACG TTCTTCGGGG
8401  CGAAAACTCT CAAGGATCTT ACCGCTGTTG AGATCCAGTT CGATGTAACC CACTCGTGCA CCCAACTGAT CTTCAGCATC
8481  TTTTACTTTC ACCAGCGTTT CTGGGTGAGC AAAAACAGGA AGGCAAAATG CCGCAAAAAA GGGAATAAGG GCGACACGGA
8561  AATGTTGAAT ACTCATACTC TTCCTTTTTC AATATTATTG AAGCATTTAT CAGGGTTATT GTCTCATGAG CGGATACATA
8641  TTTGAATGTA TTTAGAAAAA TAAACAAATA GGGGTTCCGC GCACATTTCC CCGAAAAGTG CCACCTGACG TCTAAGAAAC
8721  CATTATTATC ATGACATTAA CCTATAAAAA TAGGCGTATC ACGAGGCCCT TTCGTCTCGC GCGTTTCGGT GATGACGGTG
8801  AAAACCTCTG ACACATGCAG CTCCCGGAGA CGGTCACAGC TTGTCTGTAA GCGGATGCCG GGAGCAGACA AGCCCGTCAG
8881  GGCGCGTCAG CGGGTGTTGG CGGGTGTCGG GGCTGGCTTA ACTATGCGGC ATCAGAGCAG ATTGTACTGA GAGTGCACCA
8961  TATCGACGCT CTCCCTTATG CGACTCCTGC ATTAGGAAGC AGCCCAGTAG TAGGTTGAGG CCGTTGAGCA CCGCCGCCGC
9041  AAGGAATGGT GCATGCAAGG AGATGGCGCC CAACAGTCCC CCGGCCACGG GGCCTGCCAC CATACCCACG CCGAAACAAG
9121  CGCTCATGAG CCCGAAGTGG CGAGCCCGAT CTTCCCCATC GGTGATGTCG GCGATATAGG CGCCAGCAAC CGCACCTGTG
9201  GCGCCGGTGA TGCCGGCCAC GATGCGTCCG GCGTAGAGGA TCTGGCTAGC GATGACCCTG CTGATTGGTT CGCTGACCAT
9281  TTCCGGGGTG CGGAACGGCG TTACCAGAAA CTCAGAAGGT TCGTCCAACC AAACCGACTC TGACGGCAGT TTACGAGAGA
9361  GATGATAGGG TCTGCTTCAG TAAGCCAGAT GCTACACAAT TAGGCTTGTA CATATTGTCG TTAGAACGCG GCTACAATTA
9441  ATACATAACC TTATGTATCA TACACATACG ATTTAGGTGA CACTATAGAA TACACCTGCA GGACGCGTAC TGAGAGCGCT
9521  ATTCTGAACT TTTCTTTTGT TC
```

pCLD22 (SEQ ID NO: 6):

```
  1  CCTTCCCTTC TACCACACCC TAATTGTAAT CCATTTTAAT TTCCTGGTCA CAGTCCTGTC TCTCCTTCCA TTGTACCTTG
 81  CCCTTTTCTA AAGAGCGACT GCAAAGTATG TTTGCGTAGG TGAGGATCTA AAACTTTATG AGGTACGAAC ATCACAGAAT
161  TACTTTGTAA TTTCAGTTTA TTGTAGGCTT GGCTTTTTGG GGAGGGTTTA CGTCTTAGAC CTCTTAGTGC TTCTTTGTTT
241  CATGGTGTTC TAACTTCGAA GCATCTCTGT AGCTTTAATG GATTCCTTTT CTGAAAGCTT TGCTCTCTTT CTTCCCCCTC
```

-continued

```
 321  GGCTTTCTCT TAGGCAAGAG GGCTAACTGT AAAGTAAGGC TTACTGCCTT GTGTTTCCAA ATGTGTCCGA AGAGGAAGTG
 401  TCTTCTGTGA ATCCTGTTAT GCATGAATAA CAGGAAATAG AAAGAAATTC ACTTTCATTA TTATAAAAGT AATATGTTCG
 481  TTTAAAAAAT TCTAATGAAG AGCTGGAGAT GCAACCCAGG GGTAGAGCAC ACACTCAGCA TGCAGGAGGC CCTGGGTCCA
 561  ATCTTGGAAT CTCCTCTCAG TTAACCTGAT CTCTAGCTGA TTAGTAGTGA GTGCAAGCCC ACTTTCCTCT TCTGCCTCAT
 641  TGCTCAGTGA TAACAGCTGT TAAACTTTGT CTTATTCTAA AACTACCTCT GTGCAAATGC TAGCACAATA ATATATATCA
 721  TATGCACATG ATTTTTTTTT TATCTTGAAA AGTAAGTCAG TATAGCTACA AAGTTCACTT GGCATTGTCA ACATTTCACA
 801  GGCGTAATAT TCCTCCTCTA GTACTGTCCT CTTCATTCTT TGTGACCAAG TTTGGAGAGA GTGCACAAAT GCCAGGGAGG
 881  TTTGTGGGAA GGTTTCTCAT GTTCTGGTAA GGCGAGTAAG AAAATAGTCT CATGCAGGTG AAATGAGTGC TATGCAGTAT
 961  ATATTATACC AGAGAACAGC AAATGACCAA ATTCACACTG AACTAGTTCA GTAAAATTGG CTTTGTCAAA GCTTTCCTTG
1041  CTTAAAATGT AATTCCCTGT CATCCTAGTT CTGGTCTGGA TTCTTTTCCT GGAGTCTTGA CTTCCAGATT CCCTGTGGAC
1121  TTTTGTTTGA GTTTCAAGCT TTTGAAATAT AGAAACCTAT CTAACTTAAC AAACTTGGGA GAGAAAAGAC TCCAGAACAA
1201  CTGAAAACAG ACCAGGCTAA ATGAATAGAC TTTATTCCTC TCTTCTTACC TGCAGTTTTC AGATATGCAG AGTTGGAGCG
1281  GATCTTAGAG GTTGATTCAT TCATGCCTGA AGAAAACACA TTTTATAGAC CCTGTGCCCA AGTTCGTGGT GGACATCACC
1361  CTTTATTTAC TAATTGCACT ACATAACAGG CATTTTAGAA GACTGCTCCA GTCAGAGACC CCGCCTTAGA GGAATCTGTA
1441  AACCCTGAAC TCCTATCACT CATGAGCACT AGTTATGTTT GGAATGCCGT ATTAAAACAA AAGTTACATT TCTAAACTTA
1521  AAATTTTCTA GCACAGAGAC AGTGGGAGTA GCTAACTTTG ATAGACATTT TTCTACTAAA AGTCTTTCTA AGTACATAAT
1601  CTTCTGTAAG TTGGAAAACA GCAAAATAGA ACGTCTCCTA CGTAGTTAAT CTTTTTGCAT AATTTGCACA TGTAGGAGTT
1681  ATTAGTATAC GGGTAAGTTT TCACTTTTTC CCCCAACTGG AGTGTCTTGT GGCTGGGTTT GAAAAAGGGA ACGGGAGGCC
1761  GCTGGAGGGG ATTGGTAAAT GAGATAAAAC ACCACTCATT CAACTCAGTG ACTCAGCATT TAAATTTTCC ATAAAAGGAT
1841  TAAAGGAAAA TTAAACAAAT TCTTAAAGCC AAGACTCTGG AGAAACTTGT TGGTGTGCTT TAGTTTTCAC TGTTATGACT
1921  CATGAATTTA TGCATAAATT AGTACATTTA TAAAAACATA GCCTTTTTAG AGTTTTCTGT TTGGCTAAAG TGCCATTGTT
2001  AGCATTTGGA ATTACCTTTT TATGTCTTAT ATTTTTTCCA AATAAAAATA AATGTTTCTG CTGTCTTACT ACTGAAACTA
2081  CGTTGTGAGC ACTTTAAATT TCTCAAAGCA GTTTCGCCTG TTATACTTGG CGCTTAGTCA TCGTCGTACA CAACAGGACC
2161  TGATTAAGAA GGCTGTGCTG CCTCTAAGCC GGGCTAGATT GTAGCCACTA GCAACCAGGC TGCAATAATT TCCCTTTGAT
2241  GACATCATCC ACTGTGGAAG AACCCAGTTG CTTCAGCCAG TCGAACTATA CAGTTCCAAC CTCATCAAAT ATGGCATCTC
2321  CCTTGCCTGC TATAGCAGGG GGAGGAAAAA ATGCCACCAT CTTTTTAATC TAGCAAGCTT CTCTTTTCTT CATCTTTTTT
2401  TTTTTCTTTT AAAAAAATTC TGATCATGGA TGCTTCTTCC GATCCCTATT TGCCTTATGA CGGGGGAGGA GACAATATCC
```

-continued

```
2481  CCTTGAGGGA ATTACATAAA AGAGGTAAGA GCATCCCCTT GCTCTGAATC CTCTGTTGGT TGTTGTGCAT GCGGCTGGGC
2561  GGTTCTGGGG ACAGGCTGTC TGTTGTCCTC TTGCTGCAAT GTGCTGCTTA GTTGCCCTGC CTTGTTGCTG TGGGAGAATG
2641  CGACCTTCCC AGCAGGGCTG GCCCTCCCTG ATTGTTTGCT CTGTGCAGAT TAGCCCTGCT TCAGATCACA TAGGGCTGCA
2721  GACTCCATCT TCTGTGTGAA AATGCTTTCG GTTTGATTGC AGAAATAAGC TGCCTTTACA GCCAGCTAAA GTCCTGGTGG
2801  TTGGTTGGCA CCTGCAAAGT AGTATTTTTG TACCTCTGGA AACTTATATT TTCTTTACAC AGCAATATCA AGTGCCGGTA
2881  TGCCATTCTG TTTTGGCTGC TGCCAATTAC CATGTAGACT TTGCACCACA GAGTAATAGT AAAAGCTCCT AGCTGCATTT
2961  TATAACATTT AAAAATAGCA GGAAAGAAGA ATTATTTTTG ATTTAACATG TTTTTGTCAT TTAACGTCTT AACTGATTGA
3041  CATACTATAT TGTCTGTCTC GTGGGTATCT TGTACAACTT GATAGGATAA AGCAATTTAG TTTTTTTTTT TTTTTTTAAA
3121  TACATCCAGA ATGTAAGTCG TCAGTAGTTT TCGAACAGAT AAGTAATGGT GTTAATCTTT TGGCAGGCTT TGCCTTGGTC
3201  TCCTTAAAGC TAATTAGGTG TTACTTAATT AAACTGCTCT TTTGCTCATT TTCTTAAATT ATTTTTTTAA AAGATAGTTG
3281  GCATTTGCTG TTCTAGAAAT AAACTTCAAG AAACATTCTT TAGCCAGATG ACTTCATGTA TGAGCCATGT TAGTTTGAAT
3361  TATTTGCTTG GTGTTATAAA CTTTATGGTT TAATACCAAC TTTTATTATG TTTACAAGGT AAATAAGGAA AATTTCAAGT
3441  ACATTTTGTA TCCTGAGAAC AAATTTAAGT TCCATAGAAT TTAGGAATTA CAATGTATTC AACAGATACT TACTTGTCAT
3521  ACTGTGCCTG CAAAACAATA ATTAGACTCT GAACAGGTGC AACAATTTTC TGTAGAATTA GACAAGTCTT CTTTTGGCAG
3601  GTGTTACTAA GTAGGCCATT TCCCAAGGAA CAGGGAATTT GCCAGGCTTT TGTGGTGGAG AGAATAGAAT GAATAAATGC
3681  TGTGGGGAGT AAAGAGCTTG TCAGAAGATG ATTAGTTCTG TGGCACCAAA ACCAAGAGAT CAGTTTTCCT GTGAGAAGTA
3761  AAGGAAGCAT TGTAGAAAAA TAGATGTGTT GAAGTCTACC GGTGGAGTTC CGCGTTACAT AACTTACGGT AAATGGCCCG
3841  CCTGGCTGAC CGCCCAACGA CCCCCGCCCA TTGACGTCAA TAATGACGTA TGTTCCCATA GTAACGCCAA TAGGGACTTT
3921  CCATTGACGT CAATGGGTGG AGTATTTACG GTAAACTGCC CACTTGGCAG TACATCAAGT GTATCATATG CCAAGTACGC
4001  CCCCTATTGA CGTCAATGAC GGTAAATGGC CCGCCTGGCA TTATGCCCAG TACATGACCT TATGGGACTT TCCTACTTGG
4081  CAGTACATCT ACGTATTAGT CATCGCTATT ACCATTGTGA TGCGGTTTTG GCAGTACATC AATGGGCGTG GATAGCGGTT
4161  TGACTCACGG GGATTTCCAA GTCTCCACCC CATTGACGTC AATGGGAGTT TGTTTTGGCA CCAAAATCAA CGGGACTTTC
4241  CAAAATGTCG TAACAACTCC GCCCCATTGA CGCAAATGGG CGGTAGGCGT GTACGGTGGG AGGTCTATAT AAGCAGAGCT
4321  CGTTTAGTGA ACCGTCAGAT CTACCTCTTC CGCATCGCTG TCTGCGAGGG CCAGCTGTTG GGGTGAGTAC TCCCTCTCAA
4401  AAGCGGGCAT GACTTCTGCG CTAAGATTGT CAGTTTCCAA AAACGAGGAG GATTTGATAT TCACCTGGCC CGCGGTGATG
4481  CCTTTGAGGG TGGCCGCGTC CATCTGGTCA GAAAAGACAA TCTTTTTGTT GTCAAGCTTC CTTGATGATG TCATACTTAT
4561  CCTGTCCCTT TTTTTTCCAC AGCTCGCGGT TGAGGACAAA CTCTTCGCGG TCTTTCCAGT ACTCTTGGAT CGGAAACCCG
```

-continued

```
4641  TCGGCCTCCG AACGGTACTC CGCCACCGAG GGACCTGAGC GAGTCCGCAT CGACCGGATC GGAAAACCTC GGATCCGAAT
4721  TCATAGATAA CTGATCCAGT GCCCCTAACG TTACTGGCCG AAGCCGCTTG GAATAAGGCC GGTGTGCGTT TGTCTATATG
4801  TTATTTTCCA CCATATTGCC GTCTTTTGGC AATGTGAGGG CCCGGAAACC TGGCCCTGTC TTCTTGACGA GCATTCCTAG
4881  GGGTCTTTCC CCTCTCGCCA AAGGAATGCA AGGTCTGTTG AATGTCGTGA AGGAAGCAGT TCCTCTGGAA GCTTCTTGAA
4961  GACAAACAAC GTCTGTAGCG ACCCTTTGCA GGCAGCGGAA CCCCCCACCT GGCGACAGGT GCCTCTGCGG CCAAAAGCCA
5041  CGTGTATAAG ATACACCTGC AAAGGCGGCA CAACCCCAGT GCCACGTTGT GAGTTGGATA GTTGTGGAAA GAGTCAAATG
5121  GCTCTCCTCA AGCGTATTCA ACAAGGGGCT GAAGGATGCC CAGAAGGTAC CCCATTGTAT GGGATCTGAT CTGGGGCCTC
5201  GGTGCACATG CTTTACATGT GTTTAGTCGA GGTTAAAAAA CGTCTAGGCC CCCCGAACCA CGGGGACGTG GTTTTCCTTT
5281  GAAAAACACG ATGGCCACCT CAGCAAGTTC CCACTTGAAC AAAAACATCA AGCAAATGTA CTTGTGCCTG CCCCAGGGTG
5361  AGAAAGTCCA AGCCATGTAT ATCTGGGTTG ATGGTACTGG AGAAGGACTG CGCTGCAAAA CCCGCACCCT GGACTGTGAG
5441  CCCAAGTGTG TAGAAGAGTT ACCTGAGTGG AATTTTGATG GCTCTAGTAC CTTTCAGTCT GAGGGCTCCA ACAGTGACAT
5521  GTATCTCAGC CCTGTTGCCA TGTTTCGGGA CCCCTTCCGC AGAGATCCCA ACAAGCTGGT GTTCTGTGAA GTTTTCAAGT
5601  ACAACCGGAA GCCTGCAGAG ACCAATTTAA GGCACTCGTG TAAACGGATA ATGGACATGG TGAGCAACCA GCACCCCTGG
5681  TTTGGAATGG AACAGGAGTA TACTCTGATG GGAACAGATG GGCACCCTTT TGGTTGGCCT TCCAATGGCT TTCCTGGGCC
5761  CCAAGGTCCG TATTACTGTG GTGTGGGCGC AGACAAAGCC TATGGCAGGG ATATCGTGGA GGCTCACTAC CGCGCCTGCT
5841  TGTATGCTGG GGTCAAGATT ACAGGAACAA ATGCTGAGGT CATGCCTGCC CAGTGGGAGT TCCAAATAGG ACCCTGTGAA
5921  GGAATCCGCA TGGGAGATCA TCTCTGGGTG GCCCGTTTCA TCTTGCATCG AGTATGTGAA GACTTTGGGG TAATAGCAAC
6001  CTTTGACCCC AAGCCCATTC CTGGGAACTG GAATGGTGCA GGCTGCCATA CCAACTTTAG CACCAAGGCC ATGCGGGAGG
6081  AGAATGGTCT GAAGCACATC GAGGAGGCCA TCGAGAAACT AAGCAAGCGG CACCGGTACC ACATTCGAGC CTACGATCCC
6161  AAGGGGGGCC TGGACAATGC CCGTCGTCTG ACTGGGTTCC ACGAAACGTC CAACATCAAC GACTTTTCTG CTGGTGTCGC
6241  CAATCGCAGT GCCAGCATCC GCATTCCCCG GACTGTCGGC CAGGAGAAGA AAGGTTACTT TGAAGACCGC CGCCCCTCTG
6321  CCAATTGTGA CCCCTTTGCA GTGACAGAAG CCATCGTCCG CACATGCCTT CTCAATGAGA CTGGCGACGA GCCCTTCCAA
6401  TACAAAAACT AATCTAGATC CCCCTCGCTT TCTTGCTGTC CAATTTCTAT TAAAGGTTCC TTTGTTCCCT AAGTCCAACT
6481  ACTAAACTGG GGGATATTAT GAAGGGCCTT GAGCATCTGG ATTCTGCCTA ATAAAAAACA TTTATTTTCA TTGCAATGAT
6561  GTATTTAAAT TATTTCTGAA TATTTTACTA AAAAGGGAAT GTGGGAGGTC AGTGCATTTA AAACATAAAG AAATGAAGAG
6641  GGGGATCTTC GCGACCTGCA GGTCTCCCTA TAGTGAGTCG TATTAATTTC GATAAGCCAG CTGCATTAAT GAATCGGCCA
6721  ACGCGCGGGG AGAGGCGGTT TGCGTATTGG GCGCTCTTCC GCTTCCTCGC TCACTGACTC GCTGCGCTCG GTCGTTCGGC
```

-continued

```
6801  TGCGGCGAGC GGTATCAGCT CACTCAAAGG CGGTAATACG GTTATCCACA GAATCAGGGG ATAACGCAGG AAAGAACATG
6881  TGAGCAAAAG GCCAGCAAAA GGCCAGGAAC CGTAAAAAGG CCGCGTTGCT GGCGTTTTTC CATAGGCTCC GCCCCCCTGA
6961  CGAGCATCAC AAAAATCGAC GCTCAAGTCA GAGGTGGCGA AACCCGACAG GACTATAAAG ATACCAGGCG TTTCCCCCTG
7041  GAAGCTCCCT CGTGCGCTCT CCTGTTCCGA CCCTGCCGCT TACCGGATAC CTGTCCGCCT TTCTCCCTTC GGGAAGCGTG
7121  GCGCTTTCTC ATAGCTCACG CTGTAGGTAT CTCAGTTCGG TGTAGGTCGT TCGCTCCAAG CTGGGCTGTG TGCACGAACC
7201  CCCCGTTCAG CCCGACCGCT GCGCCTTATC CGGTAACTAT CGTCTTGAGT CCAACCCGGT AAGACACGAC TTATCGCCAC
7281  TGGCAGCAGC CACTGGTAAC AGGATTAGCA GAGCGAGGTA TGTAGGCGGT GCTACAGAGT TCTTGAAGTG GTGGCCTAAC
7361  TACGGCTACA CTAGAAGGAC AGTATTTGGT ATCTGCGCTC TGCTGAAGCC AGTTACCTTC GGAAAAAGAG TTGGTAGCTC
7441  TTGATCCGGC AAACAAACCA CCGCTGGTAG CGGTGGTTTT TTTGTTTGCA AGCAGCAGAT TACGCGCAGA AAAAAAGGAT
7521  CTCAAGAAGA TCCTTTGATC TTTTCTACGG GGTCTGACGC TCAGTGGAAC GAAAACTCAC GTTAAGGGAT TTTGGTCATG
7601  AGATTATCAA AAAGGATCTT CACCTAGATC CTTTTAAATT AAAAATGAAG TTTTAAATCA ATCTAAAGTA TATATGAGTA
7681  AACTTGGTCT GACAGTTACC AATGCTTAAT CAGTGAGGCA CCTATCTCAG CGATCTGTCT ATTTCGTTCA TCCATAGTTG
7761  CCTGACTCCC CGTCGTGTAG ATAACTACGA TACGGGAGGG CTTACCATCT GGCCCCAGTG CTGCAATGAT ACCGCGAGAC
7841  CCACGCTCAC CGGCTCCAGA TTTATCAGCA ATAAACCAGC CAGCCGGAAG GGCCGAGCGC AGAAGTGGTC CTGCAACTTT
7921  ATCCGCCTCC ATCCAGTCTA TTAATTGTTG CCGGGAAGCT AGAGTAAGTA GTTCGCCAGT TAATAGTTTG CGCAACGTTG
8001  TTGCCATTGC TACAGGCATC GTGGTGTCAC GCTCGTCGTT TGGTATGGCT TCATTCAGCT CCGGTTCCCA ACGATCAAGG
8081  CGAGTTACAT GATCCCCCAT GTTGTGCAAA AAAGCGGTTA GCTCCTTCGG TCCTCCGATC GTTGTCAGAA GTAAGTTGGC
8161  CGCAGTGTTA TCACTCATGG TTATGGCAGC ACTGCATAAT TCTCTTACTG TCATGCCATC CGTAAGATGC TTTTCTGTGA
8241  CTGGTGAGTA CTCAACCAAG TCATTCTGAG AATAGTGTAT GCGGCGACCG AGTTGCTCTT GCCCGGCGTC AATACGGGAT
8321  AATACCGCGC CACATAGCAG AACTTTAAAA GTGCTCATCA TTGGAAAACG TTCTTCGGGG CGAAAACTCT CAAGGATCTT
8401  ACCGCTGTTG AGATCCAGTT CGATGTAACC CACTCGTGCA CCCAACTGAT CTTCAGCATC TTTTACTTTC ACCAGCGTTT
8481  CTGGGTGAGC AAAAACAGGA AGGCAAAATG CCGCAAAAAA GGGAATAAGG GCGACACGGA AATGTTGAAT ACTCATACTC
8561  TTCCTTTTTC AATATTATTG AAGCATTTAT CAGGGTTATT GTCTCATGAG CGGATACATA TTTGAATGTA TTTAGAAAAA
8641  TAAACAAATA GGGGTTCCGC GCACATTTCC CCGAAAAGTG CCACCTGACG TCTAAGAAAC CATTATTATC ATGACATTAA
8721  CCTATAAAAA TAGGCGTATC ACGAGGCCCT TTCGTCTCGC GCGTTTCGGT GATGACGGTG AAAACCTCTG ACACATGCAG
8801  CTCCCGGAGA CGGTCACAGC TTGTCTGTAA GCGGATGCCG GGAGCAGACA AGCCCGTCAG GGCGCGTCAG CGGGTGTTGG
8881  CGGGTGTCGG GGCTGGCTTA ACTATGCGGC ATCAGAGCAG ATTGTACTGA GAGTGCACCA TATCGACGCT CTCCCTTATG
```

-continued

```
8961  CGACTCCTGC ATTAGGAAGC AGCCCAGTAG TAGGTTGAGG CCGTTGAGCA CCGCCGCCGC AAGGAATGGT GCATGCAAGG

9041  AGATGGCGCC CAACAGTCCC CCGGCCACGG GGCCTGCCAC CATACCCACG CCGAAACAAG CGCTCATGAG CCCGAAGTGG

9121  CGAGCCCGAT CTTCCCCATC GGTGATGTCG GCGATATAGG CGCCAGCAAC CGCACCTGTG GCGCCGGTGA TGCCGGCCAC

9201  GATGCGTCCG GCGTAGAGGA TCTGGCTAGC GATGACCCTG CTGATTGGTT CGCTGACCAT TTCCGGGGTG CGGAACGGCG

9281  TTACCAGAAA CTCAGAAGGT TCGTCCAACC AAACCGACTC TGACGGCAGT TTACGAGAGA GATGATAGGG TCTGCTTCAG

9361  TAAGCCAGAT GCTACACAAT TAGGCTTGTA CATATTGTCG TTAGAACGCG GCTACAATTA ATACATAACC TTATGTATCA

9441  TACACATACG ATTTAGGTGA CACTATAGAA TACACCTGCA GGACGCGTAC TGAGAGCGCT ATTCTGAACT TTTCTTTTGT

9521  TC
```

pCLD12 (SEQ ID NO: 7):

```
   1  CCCTAGAAAG ATAATCATAT TGTGACGTAC GTTAAAGATA ATCATGCGTA AAATTGACGC ATGTGTTTTA TCGGTCTGTA

  81  TATCGAGGTT TATTTATTAA TTTGAATAGA TATTAAGTTT TATTATATTT ACACTTACAT ACTAATAATA AATTCAACAA

 161  ACAATTTATT TATGTTTATT TATTTATTAA AAAAAAACAA AAACTCAAAA TTTCTTCTAT AAAGTAACAA AACTTTTATC

 241  GAATTTGCAG CCCGGGACTA GCTAGAGGGA CAGCCCCCCC CCAAAGCCCC CAGGGATGTA ATTACGTCCC TCCCCCGCTA

 321  GGGGGCAGCA GCGAGCCGCC CGGGGCTCCG CTCCGGTCCG GCGCTCCCCC CGCATCCCCG AGCCGGCAGC GTGCGGGGAC

 401  AGCCCGGGCA CGGGGAAGGT GGCACGGGAT CGCTTTCCTC TGAACGCTTC TCGCTGCTCT TTGAGCCTGC AGACACCTGG

 481  GGGGATACGG GGAAAACTTA AGATCCGACC GGACGCGTAC TGAGAGCGCT ATTCTGAACT TTTCTTTTGT TCCCTTCCCT

 561  TCTACCACAC CCTAATTGTA ATCCATTTTA ATTTCCTGGT CACAGTCCTG TCTCTCCTTC CATTGTACCT TGCCCTTTTC

 641  TAAAGAGCGA CTGCAAAGTA TGTTTGCGTA GGTGAGGATC TAAAACTTTA TGAGGTACGA ACATCACAGA ATTACTTTGT

 721  AATTTCAGTT TATTGTAGGC TTGGCTTTTT GGGGAGGGTT TACGTCTTAG ACCTCTTAGT GCTTCTTTGT TTCATGGTGT

 801  TCTAACTTCG AAGCATCTCT GTAGCTTTAA TGGATTCCTT TTCTGAAAGC TTTGCTCTCT TTCTTCCCCC TCGGCTTTCT

 881  CTTAGGCAAG AGGGCTAACT GTAAAGTAAG GCTTACTGCC TTGTGTTTCC AAATGTGTCC GAAGAGGAAG TGTCTTCTGT

 961  GAATCCTGTT ATGCATGAAT AACAGGAAAT AGAAAGAAAT TCACTTTCAT TATTATAAAA GTAATATGTT CGTTTAAAAA

1041  ATTCTAATGA AGAGCTGGAG ATGCAACCCA GGGGTAGAGC ACACACTCAG CATGCAGGAG GCCCTGGGTC CAATCTTGGA

1121  ATCTCCTCTC AGTTAACCTG ATCTCTAGCT GATTAGTAGT GAGTGCAAGC CCACTTTCCT CTTCTGCCTC ATTGCTCAGT

1201  GATAACAGCT GTTAAACTTT GTCTTATTCT AAAACTACCT CTGTGCAAAT GCTAGCACAA TAATATATAT CATATGCACA

1281  TGATTTTTTT TTTATCTTGA AAAGTAAGTC AGTATAGCTA CAAAGTTCAC TTGGCATTGT CAACATTTCA CAGGCGTAAT

1361  ATTCCTCCTC TAGTACTGTC CTCTTCATTC TTTGTGACCA AGTTTGGAGA GAGTGCACAA ATGCCAGGGA GGTTTGTGGG
```

-continued

```
1441  AAGGTTTCTC ATGTTCTGGT AAGGCGAGTA AGAAAATAGT CTCATGCAGG TGAAATGAGT GCTATGCAGT ATATATTATA
1521  CCAGAGAACA GCAAATGACC AAATTCACAC TGAACTAGTT CAGTAAAATT GGCTTTGTCA AAGCTTTCCT TGCTTAAAAT
1601  GTAATTCCCT GTCATCCTAG TTCTGGTCTG GATTCTTTTC CTGGAGTCTT GACTTCCAGA TTCCCTGTGG ACTTTTGTTT
1681  GAGTTTCAAG CTTTTGAAAT ATAGAAACCT ATCTAACTTA ACAAACTTGG GAGAGAAAAG ACTCCAGAAC AACTGAAAAC
1761  AGACCAGGCT AAATGAATAG ACTTTATTCC TCTCTTCTTA CCTGCAGTTT TCAGATATGC AGAGTTGGAG CGGATCTTAG
1841  AGGTTGATTC ATTCATGCCT GAAGAAAACA CATTTTATAG ACCCTGTGCC CAAGTTCGTG GTGGACATCA CCCTTTATTT
1921  ACTAATTGCA CTACATAACA GGCATTTTAG AAGACTGCTC CAGTCAGAGA CCCCGCCTTA GAGGAATCTG TAAACCCTGA
2001  ACTCCTATCA CTCATGAGCA CTAGTTATGT TTGGAATGCC GTATTAAAAC AAAAGTTACA TTTCTAAACT TAAAATTTTC
2081  TAGCACAGAG ACAGTGGGAG TAGCTAACTT TGATAGACAT TTTTCTACTA AAAGTCTTTC TAAGTACATA ATCTTCTGTA
2161  AGTTGGAAAA CAGCAAAATA GAACGTCTCC TACGTAGTTA ATCTTTTTGC ATAATTTGCA CATGTAGGAG TTATTAGTAT
2241  ACGGGTAAGT TTTCACTTTT TCCCCCAACT GGAGTGTCTT GTGGCTGGGT TTGAAAAAGG GAACGGGAGG CCGCTGGAGG
2321  GGATTGGTAA ATGAGATAAA ACACCACTCA TTCAACTCAG TGACTCAGCA TTTAAATTTT CCATAAAAGG ATTAAAGGAA
2401  AATTAAACAA ATTCTTAAAG CCAAGACTCT GGAGAAACTT GTTGGTGTGC TTTAGTTTTC ACTGTTATGA CTCATGAATT
2481  TATGCATAAA TTAGTACATT TATAAAAACA TAGCCTTTTT AGAGTTTTCT GTTTGGCTAA AGTGCCATTG TTAGCATTTG
2561  GAATTACCTT TTTATGTCTT ATATTTTTTC CAAATAAAAA TAAATGTTTC TGCTGTCTTA CTACTGAAAC TACGTTGTGA
2641  GCACTTTAAA TTTCTCAAAG CAGTTTCGCC TGTTATACTT GGCGCTTAGT CATCGTCGTA CACAACAGGA CCTGATTAAG
2721  AAGGCTGTGC TGCCTCTAAG CCGGGCTAGA TTGTAGCCAC TAGCAACCAG GCTGCAATAA TTTCCCTTTG ATGACATCAT
2801  CCACTGTGGA AGAACCCAGT TGCTTCAGCC AGTCGAACTA TACAGTTCCA ACCTCATCAA ATATGGCATC TCCCTTGCCT
2881  GCTATAGCAG GGGGAGGAAA AAATGCCACC ATCTTTTTAA TCTAGCAAGC TTCTCTTTTC TTCATCTTTT TTTTTTTCTT
2961  TTAAAAAAAT TCTGATCATG GATGCTTCTT CCGATCCCTA TTTGCCTTAT GACGGGGGAG GAGACAATAT CCCCTTGAGG
3041  GAATTACATA AAAGAGGTAA GAGCATCCCC TTGCTCTGAA TCCTCTGTTG GTTGTTGTGC ATGCGGCTGG GCGGTTCTGG
3121  GGACAGGCTG TCTGTTGTCC TCTTGCTGCA ATGTGCTGCT TAGTTGCCCT GCCTTGTTGC TGTGGGAGAA TGCGACCTTC
3201  CCAGCAGGGC TGGCCCTCCC TGATTGTTTG CTCTGTGCAG ATTAGCCCTG CTTCAGATCA CATAGGGCTG CAGACTCCAT
3281  CTTCTGTGTG AAAATGCTTT CGGTTTGATT GCAGAAATAA GCTGCCTTTA CAGCCAGCTA AAGTCCTGGT GGTTGGTTGG
3361  CACCTGCAAA GTAGTATTTT TGTACCTCTG GAAACTTATA TTTTCTTTAC ACAGCAATAT CAAGTGCCGG TATGCCATTC
3441  TGTTTTGGCT GCTGCCAATT ACCATGTAGA CTTTGCACCA CAGAGTAATA GTAAAAGCTC CTAGCTGCAT TTTATAACAT
3521  TTAAAAATAG CAGGAAAGAA GAATTATTTT TGATTTAACA TGTTTTTGTC ATTTAACGTC TTAACTGATT GACATACTAT
```

-continued

```
3601 ATTGTCTGTC TCGTGGGTAT CTTGTACAAC TTGATAGGAT AAAGCAATTT AGTTTTTTTT TTTTTTTTTA AATACATCCA
3681 GAATGTAAGT CGTCAGTAGT TTTCGAACAG ATAAGTAATG GTGTTAATCT TTTGGCAGGC TTTGCCTTGG TCTCCTTAAA
3761 GCTAATTAGG TGTTACTTAA TTAAACTGCT CTTTTGCTCA TTTTCTTAAA TTATTTTTTT AAAAGATAGT TGGCATTTGC
3841 TGTTCTAGAA ATAAACTTCA AGAAACATTC TTTAGCCAGA TGACTTCATG TATGAGCCAT GTTAGTTTGA ATTATTTGCT
3921 TGGTGTTATA AACTTTATGG TTTAATACCA ACTTTTATTA TGTTTACAAG GTAAATAAGG AAAATTTCAA GTACATTTTG
4001 TATCCTGAGA ACAAATTTAA GTTCCATAGA ATTTAGGAAT TACAATGTAT TCAACAGATA CTTACTTGTC ATACTGTGCC
4081 TGCAAAACAA TAATTAGACT CTGAACAGGT GCAACAATTT TCTGTAGAAT TAGACAAGTC TTCTTTTGGC AGGTGTTACT
4161 AAGTAGGCCA TTTCCCAAGG AACAGGGAAT TTGCCAGGCT TTTGTGGTGG AGAGAATAGA ATGAATAAAT GCTGTGGGGA
4241 GTAAAGAGCT TGTCAGAAGA TGATTAGTTC TGTGGCACCA AAACCAAGAG ATCAGTTTTC CTGTGAGAAG TAAAGGAAGC
4321 ATTGTAGAAA AATAGATGTG TTGAAGTCTA CCGGTGGAGT TCCGCGTTAC ATAACTTACG GTAAATGGCC CGCCTGGCTG
4401 ACCGCCCAAC GACCCCCGCC CATTGACGTC AATAATGACG TATGTTCCCA TAGTAACGCC AATAGGGACT TTCCATTGAC
4481 GTCAATGGGT GGAGTATTTA CGGTAAACTG CCCACTTGGC AGTACATCAA GTGTATCATA TGCCAAGTAC GCCCCCTATT
4561 GACGTCAATG ACGGTAAATG GCCCGCCTGG CATTATGCCC AGTACATGAC CTTATGGGAC TTTCCTACTT GGCAGTACAT
4641 CTACGTATTA GTCATCGCTA TTACCATTGT GATGCGGTTT TGGCAGTACA TCAATGGGCG TGGATAGCGG TTTGACTCAC
4721 GGGGATTTCC AAGTCTCCAC CCCATTGACG TCAATGGGAG TTTGTTTTGG CACCAAAATC AACGGGACTT TCCAAAATGT
4801 CGTAACAACT CCGCCCCATT GACGCAAATG GGCGGTAGGC GTGTACGGTG GGAGGTCTAT ATAAGCAGAG CTCGTTTAGT
4881 GAACCGTCAG ATCTACCTCT TCCGCATCGC TGTCTGCGAG GGCCAGCTGT TGGGGTGAGT ACTCCCTCTC AAAAGCGGGC
4961 ATGACTTCTG CGCTAAGATT GTCAGTTTCC AAAAACGAGG AGGATTTGAT ATTCACCTGG CCCGCGGTGA TGCCTTTGAG
5041 GGTGGCCGCG TCCATCTGGT CAGAAAAGAC AATCTTTTTG TTGTCAAGCT TCCTTGATGA TGTCATACTT ATCCTGTCCC
5121 TTTTTTTTCC ACAGCTCGCG GTTGAGGACA AACTCTTCGC GGTCTTTCCA GTACTCTTGG ATCGGAAACC CGTCGGCCTC
5201 CGAACGGTAC TCCGCCACCG AGGGACCTGA GCGAGTCCGC ATCGACCGGA TCGGAAAACC TCGGATCCGA ATTCATAGAT
5281 AACTGATCCA GTGCCCCTAA CGTTACTGGC CGAAGCCGCT TGGAATAAGG CCGGTGTGCG TTTGTCTATA TGTTATTTTC
5361 CACCATATTG CCGTCTTTTG GCAATGTGAG GGCCCGGAAA CCTGGCCCTG TCTTCTTGAC GAGCATTCCT AGGGGTCTTT
5441 CCCCTCTCGC CAAAGGAATG CAAGGTCTGT TGAATGTCGT GAAGGAAGCA GTTCCTCTGG AAGCTTCTTG AAGACAAACA
5521 ACGTCTGTAG CGACCCTTTG CAGGCAGCGG AACCCCCCAC CTGGCGACAG GTGCCTCTGC GGCCAAAAGC CACGTGTATA
5601 AGATACACCT GCAAAGGCGG CACAACCCCA GTGCCACGTT GTGAGTTGGA TAGTTGTGGA AAGAGTCAAA TGGCTCTCCT
5681 CAAGCGTATT CAACAAGGGG CTGAAGGATG CCCAGAAGGT ACCCCATTGT ATGGGATCTG ATCTGGGGCC TCGGTGCACA
```

-continued

```
5761  TGCTTTACAT GTGTTTAGTC GAGGTTAAAA AACGTCTAGG CCCCCCGAAC CACGGGGACG TGGTTTTCCT TTGAAAAACA
5841  CGATGATAAT ATGGCCACAA CCATGGCCAC CTCAGCAAGT TCCCACTTGA ACAAAAACAT CAAGCAAATG TACTTGTGCC
5921  TGCCCCAGGG TGAGAAAGTC CAAGCCATGT ATATCTGGGT TGATGGTACT GGAGAAGGAC TGCGCTGCAA AACCCGCACC
6001  CTGGACTGTG AGCCCAAGTG TGTAGAAGAG TTACCTGAGT GGAATTTTGA TGGCTCTAGT ACCTTTCAGT CTGAGGGCTC
6081  CAACAGTGAC ATGTATCTCA GCCCTGTTGC CATGTTTCGG GACCCCTTCC GCAGAGATCC CAACAAGCTG GTGTTCTGTG
6161  AAGTTTTCAA GTACAACCGG AAGCCTGCAG AGACCAATTT AAGGCACTCG TGTAAACGGA TAATGGACAT GGTGAGCAAC
6241  CAGCACCCCT GGTTTGGAAT GGAACAGGAG TATACTCTGA TGGGAACAGA TGGGCACCCT TTTGGTTGGC CTTCCAATGG
6321  CTTTCCTGGG CCCCAAGGTC CGTATTACTG TGGTGTGGGC GCAGACAAAG CCTATGGCAG GGATATCGTG GAGGCTCACT
6401  ACCGCGCCTG CTTGTATGCT GGGGTCAAGA TTACAGGAAC AAATGCTGAG GTCATGCCTG CCCAGTGGGA GTTCCAAATA
6481  GGACCCTGTG AAGGAATCCG CATGGGAGAT CATCTCTGGG TGGCCCGTTT CATCTTGCAT CGAGTATGTG AAGACTTTGG
6561  GGTAATAGCA ACCTTTGACC CCAAGCCCAT TCCTGGGAAC TGGAATGGTG CAGGCTGCCA TACCAACTTT AGCACCAAGG
6641  CCATGCGGGA GGAGAATGGT CTGAAGCACA TCGAGGAGGC CATCGAGAAA CTAAGCAAGC GGCACCGGTA CCACATTCGA
6721  GCCTACGATC CCAAGGGGGG CCTGGACAAT GCCCGTCGTC TGACTGGGTT CCACGAAACG TCCAACATCA ACGACTTTTC
6801  TGCTGGTGTC GCCAATCGCA GTGCCAGCAT CCGCATTCCC CGGACTGTCG GCCAGGAGAA GAAAGGTTAC TTTGAAGACC
6881  GCCGCCCCTC TGCCAATTGT GACCCCTTTG CAGTGACAGA AGCCATCGTC CGCACATGCC TTCTCAATGA GACTGGCGAC
6961  GAGCCCTTCC AATACAAAAA CTAATCTAGA TCCCCCTCGC TTTCTTGCTG TCCAATTTCT ATTAAAGGTT CCTTTGTTCC
7041  CTAAGTCCAA CTACTAAACT GGGGGATATT ATGAAGGGCC TTGAGCATCT GGATTCTGCC TAATAAAAAA CATTTATTTT
7121  CATTGCAATG ATGTATTTAA ATTATTTCTG AATATTTTAC TAAAAAGGGA ATGTGGGAGG TCAGTGCATT TAAAACATAA
7201  AGAAATGAAG AGGGGGATCT TCGCGATACT GCATCGATGA GGGACAGCCC CCCCCCAAAG CCCCCAGGGA TGTAATTACG
7281  TCCCTCCCCC GCTAGGGGGC AGCAGCGAGC CGCCCGGGGC TCCGCTCCGG TCCGGCGCTC CCCCCGCATC CCCGAGCCGG
7361  CAGCGTGCGG GGACAGCCCG GGCACGGGGA AGGTGGCACG GGATCGCTTT CCTCTGAACG CTTCTCGCTG CTCTTTGAGC
7441  CTGCAGACAC CTGGGGGGAT ACGGGGAAAA TAGACACCGC GGTGGAGCTC CAGCTTTTGT TCCCTTTAGT GAGGGTTAAT
7521  TAGTTCTTAA TACGACTCAC TATAGGGCGA ATTGGCTACC GGGCCGCCCA TCGAGGGTAT CATAAGCTTA TATCTATAAC
7601  AAGAAAATAT ATATATAATA AGTTATCACG TAAGTAGAAC ATGAAATAAC AATATAATTA TCGTATGAGT TAAATCTTAA
7681  AAGTCACGTA AAAGATAATC ATGCGTCATT TTGACTCACG CGGTCGTTAT AGTTCAAAAT CAGTGACACT TACCGCATTG
7761  ACAAGCACGC CTCACGGGAG CTCCAAGCGG CGACTGAGAT GTCCTAAATG CACAGCGACG GATTCGCGCT ATTTAGAAAG
7841  AGAGAGCAAT ATTTCAAGAA TGCATGCGTC AATTTTACGC AGACTATCTT TCTAGGGTTA AATCGATAGA TGCGATCCTG
```

-continued

```
7921  CAGGTCTCCC TATAGTGAGT CGTATTAATT TCGATAAGCC AGCTGCATTA ATGAATCGGC CAACGCGCGG GGAGAGGCGG
8001  TTTGCGTATT GGGCGCTCTT CCGCTTCCTC GCTCACTGAC TCGCTGCGCT CGGTCGTTCG GCTGCGGCGA GCGGTATCAG
8081  CTCACTCAAA GGCGGTAATA CGGTTATCCA CAGAATCAGG GGATAACGCA GGAAAGAACA TGTGAGCAAA AGGCCAGCAA
8161  AAGGCCAGGA ACCGTAAAAA GGCCGCGTTG CTGGCGTTTT TCCATAGGCT CCGCCCCCCT GACGAGCATC ACAAAAATCG
8241  ACGCTCAAGT CAGAGGTGGC GAAACCCGAC AGGACTATAA AGATACCAGG CGTTTCCCCC TGGAAGCTCC CTCGTGCGCT
8321  CTCCTGTTCC GACCCTGCCG CTTACCGGAT ACCTGTCCGC CTTTCTCCCT TCGGGAAGCG TGGCGCTTTC TCATAGCTCA
8401  CGCTGTAGGT ATCTCAGTTC GGTGTAGGTC GTTCGCTCCA AGCTGGGCTG TGTGCACGAA CCCCCCGTTC AGCCCGACCG
8481  CTGCGCCTTA TCCGGTAACT ATCGTCTTGA GTCCAACCCG GTAAGACACG ACTTATCGCC ACTGGCAGCA GCCACTGGTA
8561  ACAGGATTAG CAGAGCGAGG TATGTAGGCG GTGCTACAGA GTTCTTGAAG TGGTGGCCTA ACTACGGCTA CACTAGAAGG
8641  ACAGTATTTG GTATCTGCGC TCTGCTGAAG CCAGTTACCT TCGGAAAAAG AGTTGGTAGC TCTTGATCCG GCAAACAAAC
8721  CACCGCTGGT AGCGGTGGTT TTTTTGTTTG CAAGCAGCAG ATTACGCGCA GAAAAAAAGG ATCTCAAGAA GATCCTTTGA
8801  TCTTTTCTAC GGGGTCTGAC GCTCAGTGGA ACGAAAACTC ACGTTAAGGG ATTTTGGTCA TGAGATTATC AAAAAGGATC
8881  TTCACCTAGA TCCTTTTAAA TTAAAAATGA AGTTTTAAAT CAATCTAAAG TATATATGAG TAAACTTGGT CTGACAGTTA
8961  CCAATGCTTA ATCAGTGAGG CACCTATCTC AGCGATCTGT CTATTTCGTT CATCCATAGT TGCCTGACTC CCCGTCGTGT
9041  AGATAACTAC GATACGGGAG GGCTTACCAT CTGGCCCCAG TGCTGCAATG ATACCGCGAG ACCCACGCTC ACCGGCTCCA
9121  GATTTATCAG CAATAAACCA GCCAGCCGGA AGGGCCGAGC GCAGAAGTGG TCCTGCAACT TTATCCGCCT CCATCCAGTC
9201  TATTAATTGT TGCCGGGAAG CTAGAGTAAG TAGTTCGCCA GTTAATAGTT TGCGCAACGT TGTTGCCATT GCTACAGGCA
9281  TCGTGGTGTC ACGCTCGTCG TTTGGTATGG CTTCATTCAG CTCCGGTTCC CAACGATCAA GGCGAGTTAC ATGATCCCCC
9361  ATGTTGTGCA AAAAAGCGGT TAGCTCCTTC GGTCCTCCGA TCGTTGTCAG AAGTAAGTTG GCCGCAGTGT TATCACTCAT
9441  GGTTATGGCA GCACTGCATA ATTCTCTTAC TGTCATGCCA TCCGTAAGAT GCTTTTCTGT GACTGGTGAG TACTCAACCA
9521  AGTCATTCTG AGAATAGTGT ATGCGGCGAC CGAGTTGCTC TTGCCCGGCG TCAATACGGG ATAATACCGC GCCACATAGC
9601  AGAACTTTAA AAGTGCTCAT CATTGGAAAA CGTTCTTCGG GGCGAAAACT CTCAAGGATC TTACCGCTGT TGAGATCCAG
9681  TTCGATGTAA CCCACTCGTG CACCCAACTG ATCTTCAGCA TCTTTTACTT TCACCAGCGT TTCTGGGTGA GCAAAAACAG
9761  GAAGGCAAAA TGCCGCAAAA AAGGGAATAA GGGCGACACG GAAATGTTGA ATACTCATAC TCTTCCTTTT TCAATATTAT
9841  TGAAGCATTT ATCAGGGTTA TTGTCTCATG AGCGGATACA TATTTGAATG TATTTAGAAA AATAAACAAA TAGGGGTTCC
9921  GCGCACATTT CCCCGAAAAG TGCCACCTGA CGTCTAAGAA ACCATTATTA TCATGACATT AACCTATAAA AATAGGCGTA
10001 TCACGAGGCC CTTTCGTCTC GCGCGTTTCG GTGATGACGG TGAAAACCTC TGACACATGC AGCTCCCGGA GACGGTCACA
```

-continued

```
10081 GCTTGTCTGT AAGCGGATGC CGGGAGCAGA CAAGCCCGTC AGGGCGCGTC AGCGGGTGTT GGCGGGTGTC GGGGCTGGCT

10161 TAACTATGCG GCATCAGAGC AGATTGTACT GAGAGTGCAC CATATCGACG CTCTCCCTTA TGCGACTCCT GCATTAGGAA

10241 GCAGCCCAGT AGTAGGTTGA GGCCGTTGAG CACCGCCGCC GCAAGGAATG GTGCATGCAA GGAGATGGCG CCCAACAGTC

10321 CCCCGGCCAC GGGGCCTGCC ACCATACCCA CGCCGAAACA AGCGCTCATG AGCCCGAAGT GGCGAGCCCG ATCTTCCCCA

10401 TCGGTGATGT CGGCGATATA GGCGCCAGCA ACCGCACCTG TGGCGCCGGT GATGCCGGCC ACGATGCGTC CGGCGTAGAG

10481 GATCTGGCTA GCGATGACCC TGCTGATTGG TTCGCTGACC ATTTCCGGGG TGCGGAACGG CGTTACCAGA AACTCAGAAG

10561 GTTCGTCCAA CCAAACCGAC TCTGACGGCA GTTTACGAGA GAGATGATAG GGTCTGCTTC AGTAAGCCAG ATGCTACACA

10641 ATTAGGCTTG TACATATTGT CGTTAGAACG CGGCTACAAT TAATACATAA CCTTATGTAT CATACACATA CGATTTAGGT

10721 GACACTATAG AATACACCTG CAGGACGTCC CAATGATCTT AAGTTAA
```

pCLD14 (SEQ ID NO: 8):

```
   1 CCCTAGAAAG ATAATCATAT TGTGACGTAC GTTAAAGATA ATCATGCGTA AAATTGACGC ATGTGTTTTA TCGGTCTGTA

  81 TATCGAGGTT TATTTATTAA TTTGAATAGA TATTAAGTTT TATTATATTT ACACTTACAT ACTAATAATA AATTCAACAA

 161 ACAATTTATT TATGTTTATT TATTTATTAA AAAAAAACAA AAACTCAAAA TTTCTTCTAT AAAGTAACAA AACTTTTATC

 241 GAATTTGCAG CCCGGGACTA GCTAGAGGGA CAGCCCCCCC CCAAAGCCCC CAGGGATGTA ATTACGTCCC TCCCCCGCTA

 321 GGGGGCAGCA GCGAGCCGCC CGGGGCTCCG CTCCGGTCCG GCGCTCCCCC CGCATCCCCG AGCCGGCAGC GTGCGGGGAC

 401 AGCCCGGGCA CGGGGAAGGT GGCACGGGAT CGCTTTCCTC TGAACGCTTC TCGCTGCTCT TTGAGCCTGC AGACACCTGG

 481 GGGGATACGG GGAAAACTTA AGATCCGACC GGACGCGTAC TGAGAGCGCT ATTCTGAACT TTTCTTTTGT TCCCTTCCCT

 561 TCTACCACAC CCTAATTGTA ATCCATTTTA ATTTCCTGGT CACAGTCCTG TCTCTCCTTC CATTGTACCT TGCCCTTTTC

 641 TAAAGAGCGA CTGCAAAGTA TGTTTGCGTA GGTGAGGATC TAAAACTTTA TGAGGTACGA ACATCACAGA ATTACTTTGT

 721 AATTTCAGTT TATTGTAGGC TTGGCTTTTT GGGGAGGGTT TACGTCTTAG ACCTCTTAGT GCTTCTTTGT TTCATGGTGT

 801 TCTAACTTCG AAGCATCTCT GTAGCTTTAA TGGATTCCTT TTCTGAAAGC TTTGCTCTCT TTCTTCCCCC TCGGCTTTCT

 881 CTTAGGCAAG AGGGCTAACT GTAAAGTAAG GCTTACTGCC TTGTGTTTCC AAATGTGTCC GAAGAGGAAG TGTCTTCTGT

 961 GAATCCTGTT ATGCATGAAT AACAGGAAAT AGAAAGAAAT TCACTTTCAT TATTATAAAA GTAATATGTT CGTTTAAAAA

1041 ATTCTAATGA AGAGCTGGAG ATGCAACCCA GGGGTAGAGC ACACACTCAG CATGCAGGAG GCCCTGGGTC CAATCTTGGA

1121 ATCTCCTCTC AGTTAACCTG ATCTCTAGCT GATTAGTAGT GAGTGCAAGC CCACTTTCCT CTTCTGCCTC ATTGCTCAGT

1201 GATAACAGCT GTTAAACTTT GTCTTATTCT AAAACTACCT CTGTGCAAAT GCTAGCACAA TAATATATAT CATATGCACA

1281 TGATTTTTTT TTTATCTTGA AAAGTAAGTC AGTATAGCTA CAAAGTTCAC TTGGCATTGT CAACATTTCA CAGGCGTAAT

1361 ATTCCTCCTC TAGTACTGTC CTCTTCATTC TTTGTGACCA AGTTTGGAGA GAGTGCACAA ATGCCAGGGA GGTTTGTGGG
```

-continued

```
1441  AAGGTTTCTC ATGTTCTGGT AAGGCGAGTA AGAAAATAGT CTCATGCAGG TGAAATGAGT GCTATGCAGT ATATATTATA
1521  CCAGAGAACA GCAAATGACC AAATTCACAC TGAACTAGTT CAGTAAAATT GGCTTTGTCA AAGCTTTCCT TGCTTAAAAT
1601  GTAATTCCCT GTCATCCTAG TTCTGGTCTG GATTCTTTTC CTGGAGTCTT GACTTCCAGA TTCCCTGTGG ACTTTTGTTT
1681  GAGTTTCAAG CTTTTGAAAT ATAGAAACCT ATCTAACTTA ACAAACTTGG GAGAGAAAAG ACTCCAGAAC AACTGAAAAC
1761  AGACCAGGCT AAATGAATAG ACTTTATTCC TCTCTTCTTA CCTGCAGTTT TCAGATATGC AGAGTTGGAG CGGATCTTAG
1841  AGGTTGATTC ATTCATGCCT GAAGAAAACA CATTTTATAG ACCCTGTGCC CAAGTTCGTG GTGGACATCA CCCTTTATTT
1921  ACTAATTGCA CTACATAACA GGCATTTTAG AAGACTGCTC CAGTCAGAGA CCCCGCCTTA GAGGAATCTG TAAACCCTGA
2001  ACTCCTATCA CTCATGAGCA CTAGTTATGT TTGGAATGCC GTATTAAAAC AAAAGTTACA TTTCTAAACT TAAAATTTTC
2081  TAGCACAGAG ACAGTGGGAG TAGCTAACTT TGATAGACAT TTTTCTACTA AAAGTCTTTC TAAGTACATA ATCTTCTGTA
2161  AGTTGGAAAA CAGCAAAATA GAACGTCTCC TACGTAGTTA ATCTTTTTGC ATAATTTGCA CATGTAGGAG TTATTAGTAT
2241  ACGGGTAAGT TTTCACTTTT TCCCCCAACT GGAGTGTCTT GTGGCTGGGT TTGAAAAAGG GAACGGGAGG CCGCTGGAGG
2321  GGATTGGTAA ATGAGATAAA ACACCACTCA TTCAACTCAG TGACTCAGCA TTTAAATTTT CCATAAAAGG ATTAAAGGAA
2401  AATTAAACAA ATTCTTAAAG CCAAGACTCT GGAGAAACTT GTTGGTGTGC TTTAGTTTTC ACTGTTATGA CTCATGAATT
2481  TATGCATAAA TTAGTACATT TATAAAAACA TAGCCTTTTT AGAGTTTTCT GTTTGGCTAA AGTGCCATTG TTAGCATTTG
2561  GAATTACCTT TTTATGTCTT ATATTTTTTC CAAATAAAAA TAAATGTTTC TGCTGTCTTA CTACTGAAAC TACGTTGTGA
2641  GCACTTTAAA TTTCTCAAAG CAGTTTCGCC TGTTATACTT GGCGCTTAGT CATCGTCGTA CACAACAGGA CCTGATTAAG
2721  AAGGCTGTGC TGCCTCTAAG CCGGGCTAGA TTGTAGCCAC TAGCAACCAG GCTGCAATAA TTTCCCTTTG ATGACATCAT
2801  CCACTGTGGA AGAACCCAGT TGCTTCAGCC AGTCGAACTA TACAGTTCCA ACCTCATCAA ATATGGCATC TCCCTTGCCT
2881  GCTATAGCAG GGGGAGGAAA AAATGCCACC ATCTTTTTAA TCTAGCAAGC TTCTCTTTTC TTCATCTTTT TTTTTTTCTT
2961  TTAAAAAAAT TCTGATCATG GATGCTTCTT CCGATCCCTA TTTGCCTTAT GACGGGGGAG GAGACAATAT CCCCTTGAGG
3041  GAATTACATA AAAGAGGTAA GAGCATCCCC TTGCTCTGAA TCCTCTGTTG GTTGTTGTGC ATGCGGCTGG GCGGTTCTGG
3121  GGACAGGCTG TCTGTTGTCC TCTTGCTGCA ATGTGCTGCT TAGTTGCCCT GCCTTGTTGC TGTGGGAGAA TGCGACCTTC
3201  CCAGCAGGGC TGGCCCTCCC TGATTGTTTG CTCTGTGCAG ATTAGCCCTG CTTCAGATCA CATAGGGCTG CAGACTCCAT
3281  CTTCTGTGTG AAAATGCTTT CGGTTTGATT GCAGAAATAA GCTGCCTTTA CAGCCAGCTA AAGTCCTGGT GGTTGGTTGG
3361  CACCTGCAAA GTAGTATTTT TGTACCTCTG GAAACTTATA TTTTCTTTAC ACAGCAATAT CAAGTGCCGG TATGCCATTC
3441  TGTTTTGGCT GCTGCCAATT ACCATGTAGA CTTTGCACCA CAGAGTAATA GTAAAAGCTC CTAGCTGCAT TTTATAACAT
3521  TTAAAAATAG CAGGAAAGAA GAATTATTTT TGATTTAACA TGTTTTTGTC ATTTAACGTC TTAACTGATT GACATACTAT
```

-continued

```
3601  ATTGTCTGTC TCGTGGGTAT CTTGTACAAC TTGATAGGAT AAAGCAATTT AGTTTTTTTT TTTTTTTTTA AATACATCCA
3681  GAATGTAAGT CGTCAGTAGT TTTCGAACAG ATAAGTAATG GTGTTAATCT TTTGGCAGGC TTTGCCTTGG TCTCCTTAAA
3761  GCTAATTAGG TGTTACTTAA TTAAACTGCT CTTTTGCTCA TTTTCTTAAA TTATTTTTTT AAAAGATAGT TGGCATTTGC
3841  TGTTCTAGAA ATAAACTTCA AGAAACATTC TTTAGCCAGA TGACTTCATG TATGAGCCAT GTTAGTTTGA ATTATTTGCT
3921  TGGTGTTATA AACTTTATGG TTTAATACCA ACTTTTATTA TGTTTACAAG GTAAATAAGG AAAATTTCAA GTACATTTTG
4001  TATCCTGAGA ACAAATTTAA GTTCCATAGA ATTTAGGAAT TACAATGTAT TCAACAGATA CTTACTTGTC ATACTGTGCC
4081  TGCAAAACAA TAATTAGACT CTGAACAGGT GCAACAATTT TCTGTAGAAT TAGACAAGTC TTCTTTTGGC AGGTGTTACT
4161  AAGTAGGCCA TTTCCCAAGG AACAGGGAAT TTGCCAGGCT TTTGTGGTGG AGAGAATAGA ATGAATAAAT GCTGTGGGGA
4241  GTAAAGAGCT TGTCAGAAGA TGATTAGTTC TGTGGCACCA AAACCAAGAG ATCAGTTTTC CTGTGAGAAG TAAAGGAAGC
4321  ATTGTAGAAA AATAGATGTG TTGAAGTCTA CCGGTGGAGT TCCGCGTTAC ATAACTTACG GTAAATGGCC CGCCTGGCTG
4401  ACCGCCCAAC GACCCCCGCC CATTGACGTC AATAATGACG TATGTTCCCA TAGTAACGCC AATAGGGACT TTCCATTGAC
4481  GTCAATGGGT GGAGTATTTA CGGTAAACTG CCCACTTGGC AGTACATCAA GTGTATCATA TGCCAAGTAC GCCCCCTATT
4561  GACGTCAATG ACGGTAAATG GCCCGCCTGG CATTATGCCC AGTACATGAC CTTATGGGAC TTTCCTACTT GGCAGTACAT
4641  CTACGTATTA GTCATCGCTA TTACCATTGT GATGCGGTTT TGGCAGTACA TCAATGGGCG TGGATAGCGG TTTGACTCAC
4721  GGGGATTTCC AAGTCTCCAC CCCATTGACG TCAATGGGAG TTTGTTTTGG CACCAAAATC AACGGGACTT TCCAAAATGT
4801  CGTAACAACT CCGCCCCATT GACGCAAATG GGCGGTAGGC GTGTACGGTG GGAGGTCTAT ATAAGCAGAG CTCGTTTAGT
4881  GAACCGTCAG ATCTACCTCT TCCGCATCGC TGTCTGCGAG GGCCAGCTGT TGGGGTGAGT ACTCCCTCTC AAAAGCGGGC
4961  ATGACTTCTG CGCTAAGATT GTCAGTTTCC AAAAACGAGG AGGATTTGAT ATTCACCTGG CCCGCGGTGA TGCCTTTGAG
5041  GGTGGCCGCG TCCATCTGGT CAGAAAAGAC AATCTTTTTG TTGTCAAGCT TCCTTGATGA TGTCATACTT ATCCTGTCCC
5121  TTTTTTTTCC ACAGCTCGCG GTTGAGGACA AACTCTTCGC GGTCTTTCCA GTACTCTTGG ATCGGAAACC CGTCGGCCTC
5201  CGAACGGTAC TCCGCCACCG AGGGACCTGA GCGAGTCCGC ATCGACCGGA TCGGAAAACC TCGGATCCGA ATTCATAGAT
5281  AACTGATCCA GTGCCCCTAA CGTTACTGGC CGAAGCCGCT TGGAATAAGG CCGGTGTGCG TTTGTCTATA TGTTATTTTC
5361  CACCATATTG CCGTCTTTTG GCAATGTGAG GGCCCGGAAA CCTGGCCCTG TCTTCTTGAC GAGCATTCCT AGGGGTCTTT
5441  CCCCTCTCGC CAAAGGAATG CAAGGTCTGT TGAATGTCGT GAAGGAAGCA GTTCCTCTGG AAGCTTCTTG AAGACAAACA
5521  ACGTCTGTAG CGACCCTTTG CAGGCAGCGG AACCCCCCAC CTGGCGACAG GTGCCTCTGC GGCCAAAAGC CACGTGTATA
5601  AGATACACCT GCAAAGGCGG CACAACCCCA GTGCCACGTT GTGAGTTGGA TAGTTGTGGA AAGAGTCAAA TGGCTCTCCT
5681  CAAGCGTATT CAACAAGGGG CTGAAGGATG CCCAGAAGGT ACCCCATTGT ATGGGATCTG ATCTGGGGCC TCGGTGCACA
```

-continued

```
5761  TGCTTTACAT GTGTTTAGTC GAGGTTAAAA AACGTCTAGG CCCCCCGAAC CACGGGGACG TGGTTTTCCT TTGAAAAACA
5841  CGATGGCCAC CTCAGCAAGT TCCCACTTGA ACAAAAACAT CAAGCAAATG TACTTGTGCC TGCCCCAGGG TGAGAAAGTC
5921  CAAGCCATGT ATATCTGGGT TGATGGTACT GGAGAAGGAC TGCGCTGCAA AACCCGCACC CTGGACTGTG AGCCCAAGTG
6001  TGTAGAAGAG TTACCTGAGT GGAATTTTGA TGGCTCTAGT ACCTTTCAGT CTGAGGGCTC CAACAGTGAC ATGTATCTCA
6081  GCCCTGTTGC CATGTTTCGG GACCCCTTCC GCAGAGATCC CAACAAGCTG GTGTTCTGTG AAGTTTTCAA GTACAACCGG
6161  AAGCCTGCAG AGACCAATTT AAGGCACTCG TGTAAACGGA TAATGGACAT GGTGAGCAAC CAGCACCCCT GGTTTGGAAT
6241  GGAACAGGAG TATACTCTGA TGGGAACAGA TGGGCACCCT TTTGGTTGGC CTTCCAATGG CTTTCCTGGG CCCCAAGGTC
6321  CGTATTACTG TGGTGTGGGC GCAGACAAAG CCTATGGCAG GGATATCGTG GAGGCTCACT ACCGCGCCTG CTTGTATGCT
6401  GGGGTCAAGA TTACAGGAAC AAATGCTGAG GTCATGCCTG CCCAGTGGGA GTTCCAAATA GGACCCTGTG AAGGAATCCG
6481  CATGGGAGAT CATCTCTGGG TGGCCCGTTT CATCTTGCAT CGAGTATGTG AAGACTTTGG GGTAATAGCA ACCTTTGACC
6561  CCAAGCCCAT TCCTGGGAAC TGGAATGGTG CAGGCTGCCA TACCAACTTT AGCACCAAGG CCATGCGGGA GGAGAATGGT
6641  CTGAAGCACA TCGAGGAGGC CATCGAGAAA CTAAGCAAGC GGCACCGGTA CCACATTCGA GCCTACGATC CCAAGGGGGG
6721  CCTGGACAAT GCCCGTCGTC TGACTGGGTT CCACGAAACG TCCAACATCA ACGACTTTTC TGCTGGTGTC GCCAATCGCA
6801  GTGCCAGCAT CCGCATTCCC CGGACTGTCG GCCAGGAGAA GAAAGGTTAC TTTGAAGACC GCCGCCCCTC TGCCAATTGT
6881  GACCCCTTTG CAGTGACAGA AGCCATCGTC CGCACATGCC TTCTCAATGA GACTGGCGAC GAGCCCTTCC AATACAAAAA
6961  CTAATCTAGA TCCCCCTCGC TTTCTTGCTG TCCAATTTCT ATTAAAGGTT CCTTTGTTCC CTAAGTCCAA CTACTAAACT
7041  GGGGGATATT ATGAAGGGCC TTGAGCATCT GGATTCTGCC TAATAAAAAA CATTTATTTT CATTGCAATG ATGTATTTAA
7121  ATTATTTCTG AATATTTTAC TAAAAAGGGA ATGTGGGAGG TCAGTGCATT TAAAACATAA AGAAATGAAG AGGGGGATCT
7201  TCGCGATACT GCATCGATGA GGGACAGCCC CCCCCCAAAG CCCCCAGGGA TGTAATTACG TCCCTCCCCC GCTAGGGGGC
7281  AGCAGCGAGC CGCCCGGGGC TCCGCTCCGG TCCGGCGCTC CCCCCGCATC CCCGAGCCGG CAGCGTGCGG GGACAGCCCG
7361  GGCACGGGGA AGGTGGCACG GGATCGCTTT CCTCTGAACG CTTCTCGCTG CTCTTTGAGC CTGCAGACAC CTGGGGGGAT
7441  ACGGGGAAAA TAGACACCGC GGTGGAGCTC CAGCTTTTGT TCCCTTTAGT GAGGGTTAAT TAGTTCTTAA TACGACTCAC
7521  TATAGGGCGA ATTGGCTACC GGGCCGCCCA TCGAGGGTAT CATAAGCTTA TATCTATAAC AAGAAAATAT ATATATAATA
7601  AGTTATCACG TAAGTAGAAC ATGAAATAAC AATATAATTA TCGTATGAGT TAAATCTTAA AAGTCACGTA AAAGATAATC
7681  ATGCGTCATT TTGACTCACG CGGTCGTTAT AGTTCAAAAT CAGTGACACT TACCGCATTG ACAAGCACGC CTCACGGGAG
7761  CTCCAAGCGG CGACTGAGAT GTCCTAAATG CACAGCGACG GATTCGCGCT ATTTAGAAAG AGAGAGCAAT ATTTCAAGAA
7841  TGCATGCGTC AATTTTACGC AGACTATCTT TCTAGGGTTA AATCGATAGA TGCGATCCTG CAGGTCTCCC TATAGTGAGT
```

-continued

```
7921  CGTATTAATT TCGATAAGCC AGCTGCATTA ATGAATCGGC CAACGCGCGG GGAGAGGCGG TTTGCGTATT GGGCGCTCTT
8001  CCGCTTCCTC GCTCACTGAC TCGCTGCGCT CGGTCGTTCG GCTGCGGCGA GCGGTATCAG CTCACTCAAA GGCGGTAATA
8081  CGGTTATCCA CAGAATCAGG GGATAACGCA GGAAAGAACA TGTGAGCAAA AGGCCAGCAA AAGGCCAGGA ACCGTAAAAA
8161  GGCCGCGTTG CTGGCGTTTT TCCATAGGCT CCGCCCCCCT GACGAGCATC ACAAAAATCG ACGCTCAAGT CAGAGGTGGC
8241  GAAACCCGAC AGGACTATAA AGATACCAGG CGTTTCCCCC TGGAAGCTCC CTCGTGCGCT CTCCTGTTCC GACCCTGCCG
8321  CTTACCGGAT ACCTGTCCGC CTTTCTCCCT TCGGGAAGCG TGGCGCTTTC TCATAGCTCA CGCTGTAGGT ATCTCAGTTC
8401  GGTGTAGGTC GTTCGCTCCA AGCTGGGCTG TGTGCACGAA CCCCCCGTTC AGCCCGACCG CTGCGCCTTA TCCGGTAACT
8481  ATCGTCTTGA GTCCAACCCG GTAAGACACG ACTTATCGCC ACTGGCAGCA GCCACTGGTA ACAGGATTAG CAGAGCGAGG
8561  TATGTAGGCG GTGCTACAGA GTTCTTGAAG TGGTGGCCTA ACTACGGCTA CACTAGAAGG ACAGTATTTG GTATCTGCGC
8641  TCTGCTGAAG CCAGTTACCT TCGGAAAAAG AGTTGGTAGC TCTTGATCCG GCAAACAAAC CACCGCTGGT AGCGGTGGTT
8721  TTTTTGTTTG CAAGCAGCAG ATTACGCGCA GAAAAAAAGG ATCTCAAGAA GATCCTTTGA TCTTTTCTAC GGGGTCTGAC
8801  GCTCAGTGGA ACGAAAACTC ACGTTAAGGG ATTTTGGTCA TGAGATTATC AAAAAGGATC TTCACCTAGA TCCTTTTAAA
8881  TTAAAAATGA AGTTTTAAAT CAATCTAAAG TATATATGAG TAAACTTGGT CTGACAGTTA CCAATGCTTA ATCAGTGAGG
8961  CACCTATCTC AGCGATCTGT CTATTTCGTT CATCCATAGT TGCCTGACTC CCCGTCGTGT AGATAACTAC GATACGGGAG
9041  GGCTTACCAT CTGGCCCCAG TGCTGCAATG ATACCGCGAG ACCCACGCTC ACCGGCTCCA GATTTATCAG CAATAAACCA
9121  GCCAGCCGGA AGGGCCGAGC GCAGAAGTGG TCCTGCAACT TTATCCGCCT CCATCCAGTC TATTAATTGT TGCCGGGAAG
9201  CTAGAGTAAG TAGTTCGCCA GTTAATAGTT TGCGCAACGT TGTTGCCATT GCTACAGGCA TCGTGGTGTC ACGCTCGTCG
9281  TTTGGTATGG CTTCATTCAG CTCCGGTTCC CAACGATCAA GGCGAGTTAC ATGATCCCCC ATGTTGTGCA AAAAAGCGGT
9361  TAGCTCCTTC GGTCCTCCGA TCGTTGTCAG AAGTAAGTTG GCCGCAGTGT TATCACTCAT GGTTATGGCA GCACTGCATA
9441  ATTCTCTTAC TGTCATGCCA TCCGTAAGAT GCTTTTCTGT GACTGGTGAG TACTCAACCA AGTCATTCTG AGAATAGTGT
9521  ATGCGGCGAC CGAGTTGCTC TTGCCCGGCG TCAATACGGG ATAATACCGC GCCACATAGC AGAACTTTAA AAGTGCTCAT
9601  CATTGGAAAA CGTTCTTCGG GGCGAAAACT CTCAAGGATC TTACCGCTGT TGAGATCCAG TTCGATGTAA CCCACTCGTG
9681  CACCCAACTG ATCTTCAGCA TCTTTTACTT TCACCAGCGT TTCTGGGTGA GCAAAAACAG GAAGGCAAAA TGCCGCAAAA
9761  AAGGGAATAA GGGCGACACG GAAATGTTGA ATACTCATAC TCTTCCTTTT TCAATATTAT TGAAGCATTT ATCAGGGTTA
9841  TTGTCTCATG AGCGGATACA TATTTGAATG TATTTAGAAA AATAAACAAA TAGGGGTTCC GCGCACATTT CCCCGAAAAG
9921  TGCCACCTGA CGTCTAAGAA ACCATTATTA TCATGACATT AACCTATAAA AATAGGCGTA TCACGAGGCC CTTTCGTCTC
10001 GCGCGTTTCG GTGATGACGG TGAAAACCTC TGACACATGC AGCTCCCGGA GACGGTCACA GCTTGTCTGT AAGCGGATGC
```

-continued

```
10081  CGGGAGCAGA CAAGCCCGTC AGGGCGCGTC AGCGGGTGTT GGCGGGTGTC GGGGCTGGCT TAACTATGCG GCATCAGAGC
10161  AGATTGTACT GAGAGTGCAC CATATCGACG CTCTCCCTTA TGCGACTCCT GCATTAGGAA GCAGCCCAGT AGTAGGTTGA
10241  GGCCGTTGAG CACCGCCGCC GCAAGGAATG GTGCATGCAA GGAGATGGCG CCCAACAGTC CCCCGGCCAC GGGGCCTGCC
10321  ACCATACCCA CGCCGAAACA AGCGCTCATG AGCCCGAAGT GGCGAGCCCG ATCTTCCCCA TCGGTGATGT CGGCGATATA
10401  GGCGCCAGCA ACCGCACCTG TGGCGCCGGT GATGCCGGCC ACGATGCGTC CGGCGTAGAG GATCTGGCTA GCGATGACCC
10481  TGCTGATTGG TTCGCTGACC ATTTCCGGGG TGCGGAACGG CGTTACCAGA AACTCAGAAG GTTCGTCCAA CCAAACCGAC
10561  TCTGACGGCA GTTTACGAGA GAGATGATAG GGTCTGCTTC AGTAAGCCAG ATGCTACACA ATTAGGCTTG TACATATTGT
10641  CGTTAGAACG CGGCTACAAT TAATACATAA CCTTATGTAT CATACACATA CGATTTAGGT GACACTATAG AATACACCTG
10721  CAGGACGTCC CAATGATCTT AAGTTAA

pCLD13 (SEQ ID NO: 26):
    1  CCCTAGAAAG ATAATCATAT TGTGACGTAC GTTAAAGATA ATCATGCGTA AAATTGACGC ATGTGTTTTA TCGGTCTGTA
   81  TATCGAGGTT TATTTATTAA TTTGAATAGA TATTAAGTTT TATTATATTT ACACTTACAT ACTAATAATA AATTCAACAA
  161  ACAATTTATT TATGTTTATT TATTTATTAA AAAAAAACAA AAACTCAAAA TTTCTTCTAT AAAGTAACAA AACTTTTATC
  241  GAATTTGCAG CCCGGGACTA GCTAGAGGGA CAGCCCCCCC CCAAAGCCCC CAGGGATGTA ATTACGTCCC TCCCCCGCTA
  321  GGGGGCAGCA GCGAGCCGCC CGGGGCTCCG CTCCGGTCCG GCGCTCCCCC CGCATCCCCG AGCCGGCAGC GTGCGGGGAC
  401  AGCCCGGGCA CGGGGAAGGT GGCACGGGAT CGCTTTCCTC TGAACGCTTC TCGCTGCTCT TTGAGCCTGC AGACACCTGG
  481  GGGGATACGG GGAAAACTTA AGATCCGACC GGACGCGTAC TGAGAGCGCT ATTCTGAACT TTTCTTTTGT TCCCTTCCCT
  561  TCTACCACAC CCTAATTGTA ATCCATTTTA ATTTCCTGGT CACAGTCCTG TCTCTCCTTC CATTGTACCT TGCCCTTTTC
  641  TAAAGAGCGA CTGCAAAGTA TGTTTGCGTA GGTGAGGATC TAAAACTTTA TGAGGTACGA ACATCACAGA ATTACTTTGT
  721  AATTTCAGTT TATTGTAGGC TTGGCTTTTT GGGGAGGGTT TACGTCTTAG ACCTCTTAGT GCTTCTTTGT TTCATGGTGT
  801  TCTAACTTCG AAGCATCTCT GTAGCTTTAA TGGATTCCTT TTCTGAAAGC TTTGCTCTCT TTCTTCCCCC TCGGCTTTCT
  881  CTTAGGCAAG AGGGCTAACT GTAAAGTAAG GCTTACTGCC TTGTGTTTCC AAATGTGTCC GAAGAGGAAG TGTCTTCTGT
  961  GAATCCTGTT ATGCATGAAT AACAGGAAAT AGAAAGAAAT TCACTTTCAT TATTATAAAA GTAATATGTT CGTTTAAAAA
 1041  ATTCTAATGA AGAGCTGGAG ATGCAACCCA GGGGTAGAGC ACACACTCAG CATGCAGGAG GCCCTGGGTC CAATCTTGGA
 1121  ATCTCCTCTC AGTTAACCTG ATCTCTAGCT GATTAGTAGT GAGTGCAAGC CCACTTTCCT CTTCTGCCTC ATTGCTCAGT
 1201  GATAACAGCT GTTAAACTTT GTCTTATTCT AAAACTACCT CTGTGCAAAT GCTAGCACAA TAATATATAT CATATGCACA
 1281  TGATTTTTTT TTTATCTTGA AAAGTAAGTC AGTATAGCTA CAAAGTTCAC TTGGCATTGT CAACATTTCA CAGGCGTAAT
```

-continued

```
1361  ATTCCTCCTC TAGTACTGTC CTCTTCATTC TTTGTGACCA AGTTTGGAGA GAGTGCACAA ATGCCAGGGA GGTTTGTGGG
1441  AAGGTTTCTC ATGTTCTGGT AAGGCGAGTA AGAAAATAGT CTCATGCAGG TGAAATGAGT GCTATGCAGT ATATATTATA
1521  CCAGAGAACA GCAAATGACC AAATTCACAC TGAACTAGTT CAGTAAAATT GGCTTTGTCA AAGCTTTCCT TGCTTAAAAT
1601  GTAATTCCCT GTCATCCTAG TTCTGGTCTG GATTCTTTTC CTGGAGTCTT GACTTCCAGA TTCCCTGTGG ACTTTTGTTT
1681  GAGTTTCAAG CTTTTGAAAT ATAGAAACCT ATCTAACTTA ACAAACTTGG GAGAGAAAAG ACTCCAGAAC AACTGAAAAC
1761  AGACCAGGCT AAATGAATAG ACTTTATTCC TCTCTTCTTA CCTGCAGTTT TCAGATATGC AGAGTTGGAG CGGATCTTAG
1841  AGGTTGATTC ATTCATGCCT GAAGAAAACA CATTTTATAG ACCCTGTGCC CAAGTTCGTG GTGGACATCA CCCTTTATTT
1921  ACTAATTGCA CTACATAACA GGCATTTTAG AAGACTGCTC CAGTCAGAGA CCCCGCCTTA GAGGAATCTG TAAACCCTGA
2001  ACTCCTATCA CTCATGAGCA CTAGTTATGT TTGGAATGCC GTATTAAAAC AAAAGTTACA TTTCTAAACT TAAAATTTTC
2081  TAGCACAGAG ACAGTGGGAG TAGCTAACTT TGATAGACAT TTTTCTACTA AAAGTCTTTC TAAGTACATA ATCTTCTGTA
2161  AGTTGGAAAA CAGCAAAATA GAACGTCTCC TACGTAGTTA ATCTTTTTGC ATAATTTGCA CATGTAGGAG TTATTAGTAT
2241  ACGGGTAAGT TTTCACTTTT TCCCCCAACT GGAGTGTCTT GTGGCTGGGT TTGAAAAAGG GAACGGGAGG CCGCTGGAGG
2321  GGATTGGTAA ATGAGATAAA ACACCACTCA TTCAACTCAG TGACTCAGCA TTTAAATTTT CCATAAAAGG ATTAAAGGAA
2401  AATTAAACAA ATTCTTAAAG CCAAGACTCT GGAGAAACTT GTTGGTGTGC TTTAGTTTTC ACTGTTATGA CTCATGAATT
2481  TATGCATAAA TTAGTACATT TATAAAAACA TAGCCTTTTT AGAGTTTTCT GTTTGGCTAA AGTGCCATTG TTAGCATTTG
2561  GAATTACCTT TTTATGTCTT ATATTTTTTC CAAATAAAAA TAAATGTTTC TGCTGTCTTA CTACTGAAAC TACGTTGTGA
2641  GCACTTTAAA TTTCTCAAAG CAGTTTCGCC TGTTATACTT GGCGCTTAGT CATCGTCGTA CACAACAGGA CCTGATTAAG
2721  AAGGCTGTGC TGCCTCTAAG CCGGGCTAGA TTGTAGCCAC TAGCAACCAG GCTGCAATAA TTTCCCTTTG ATGACATCAT
2801  CCACTGTGGA AGAACCCAGT TGCTTCAGCC AGTCGAACTA TACAGTTCCA ACCTCATCAA ATATGGCATC TCCCTTGCCT
2881  GCTATAGCAG GGGGAGGAAA AAATGCCACC ATCTTTTTAA TCTAGCAAGC TTCTCTTTTC TTCATCTTTT TTTTTTTCTT
2961  TTAAAAAAAT TCTGATCATG GATGCTTCTT CCGATCCCTA TTTGCCTTAT GACGGGGGAG GAGACAATAT CCCCTTGAGG
3041  GAATTACATA AAAGAGGTAA GAGCATCCCC TTGCTCTGAA TCCTCTGTTG GTTGTTGTGC ATGCGGCTGG GCGGTTCTGG
3121  GGACAGGCTG TCTGTTGTCC TCTTGCTGCA ATGTGCTGCT TAGTTGCCCT GCCTTGTTGC TGTGGGAGAA TGCGACCTTC
3201  CCAGCAGGGC TGGCCCTCCC TGATTGTTTG CTCTGTGCAG ATTAGCCCTG CTTCAGATCA CATAGGGCTG CAGACTCCAT
3281  CTTCTGTGTG AAAATGCTTT CGGTTTGATT GCAGAAATAA GCTGCCTTTA CAGCCAGCTA AAGTCCTGGT GGTTGGTTGG
3361  CACCTGCAAA GTAGTATTTT TGTACCTCTG GAAACTTATA TTTTCTTTAC ACAGCAATAT CAAGTGCCGG TATGCCATTC
3441  TGTTTTGGCT GCTGCCAATT ACCATGTAGA CTTTGCACCA CAGAGTAATA GTAAAAGCTC CTAGCTGCAT TTTATAACAT
```

-continued

```
3521  TTAAAAATAG CAGGAAAGAA GAATTATTTT TGATTTAACA TGTTTTTGTC ATTTAACGTC TTAACTGATT GACATACTAT
3601  ATTGTCTGTC TCGTGGGTAT CTTGTACAAC TTGATAGGAT AAAGCAATTT AGTTTTTTTT TTTTTTTTTA AATACATCCA
3681  GAATGTAAGT CGTCAGTAGT TTTCGAACAG ATAAGTAATG GTGTTAATCT TTTGGCAGGC TTTGCCTTGG TCTCCTTAAA
3761  GCTAATTAGG TGTTACTTAA TTAAACTGCT CTTTTGCTCA TTTTCTTAAA TTATTTTTTT AAAAGATAGT TGGCATTTGC
3841  TGTTCTAGAA ATAAACTTCA AGAAACATTC TTTAGCCAGA TGACTTCATG TATGAGCCAT GTTAGTTTGA ATTATTTGCT
3921  TGGTGTTATA AACTTTATGG TTTAATACCA ACTTTTATTA TGTTTACAAG GTAAATAAGG AAAATTTCAA GTACATTTTG
4001  TATCCTGAGA ACAAATTTAA GTTCCATAGA ATTTAGGAAT TACAATGTAT TCAACAGATA CTTACTTGTC ATACTGTGCC
4081  TGCAAAACAA TAATTAGACT CTGAACAGGT GCAACAATTT TCTGTAGAAT TAGACAAGTC TTCTTTTGGC AGGTGTTACT
4161  AAGTAGGCCA TTTCCCAAGG AACAGGGAAT TTGCCAGGCT TTTGTGGTGG AGAGAATAGA ATGAATAAAT GCTGTGGGGA
4241  GTAAAGAGCT TGTCAGAAGA TGATTAGTTC TGTGGCACCA AAACCAAGAG ATCAGTTTTC CTGTGAGAAG TAAAGGAAGC
4321  ATTGTAGAAA AATAGATGTG TTGAAGTCTA CCGGTGGAGT TCCGCGTTAC ATAACTTACG GTAAATGGCC CGCCTGGCTG
4401  ACCGCCCAAC GACCCCCGCC CATTGACGTC AATAATGACG TATGTTCCCA TAGTAACGCC AATAGGGACT TTCCATTGAC
4481  GTCAATGGGT GGAGTATTTA CGGTAAACTG CCCACTTGGC AGTACATCAA GTGTATCATA TGCCAAGTAC GCCCCCTATT
4561  GACGTCAATG ACGGTAAATG GCCCGCCTGG CATTATGCCC AGTACATGAC CTTATGGGAC TTTCCTACTT GGCAGTACAT
4641  CTACGTATTA GTCATCGCTA TTACCATTGT GATGCGGTTT TGGCAGTACA TCAATGGGCG TGGATAGCGG TTTGACTCAC
4721  GGGGATTTCC AAGTCTCCAC CCCATTGACG TCAATGGGAG TTTGTTTTGG CACCAAAATC AACGGGACTT TCCAAAATGT
4801  CGTAACAACT CCGCCCCATT GACGCAAATG GGCGGTAGGC GTGTACGGTG GGAGGTCTAT ATAAGCAGAG CTCGTTTAGT
4881  GAACCGTCAG ATCTACCTCT TCCGCATCGC TGTCTGCGAG GGCCAGCTGT TGGGGTGAGT ACTCCCTCTC AAAAGCGGGC
4961  ATGACTTCTG CGCTAAGATT GTCAGTTTCC AAAAACGAGG AGGATTTGAT ATTCACCTGG CCCGCGGTGA TGCCTTTGAG
5041  GGTGGCCGCG TCCATCTGGT CAGAAAAGAC AATCTTTTTG TTGTCAAGCT TCCTTGATGA TGTCATACTT ATCCTGTCCC
5121  TTTTTTTTCC ACAGCTCGCG GTTGAGGACA AACTCTTCGC GGTCTTTCCA GTACTCTTGG ATCGGAAACC CGTCGGCCTC
5201  CGAACGGTAC TCCGCCACCG AGGGACCTGA GCGAGTCCGC ATCGACCGGA TCGGAAAACC TCGGATCCGA ATTCATAGAT
5281  AACTGATCCA GTGCCCCTAA CGTTACTGGC CGAAGCCGCT TGGAATAAGG CCGGTGTGCG TTTGTCTATA TGTTATTTTC
5361  CACCATATTG CCGTCTTTTG GCAATGTGAG GGCCCGGAAA CCTGGCCCTG TCTTCTTGAC GAGCATTCCT AGGGGTCTTT
5441  CCCCTCTCGC CAAAGGAATG CAAGGTCTGT TGAATGTCGT GAAGGAAGCA GTTCCTCTGG AAGCTTCTTG AAGACAAACA
5521  ACGTCTGTAG CGACCCTTTG CAGGCAGCGG AACCCCCCAC CTGGCGACAG GTGCCTCTGC GGCCAAAAGC CACGTGTATA
5601  AGATACACCT GCAAAGGCGG CACAACCCCA GTGCCACGTT GTGAGTTGGA TAGTTGTGGA AAGAGTCAAA TGGCTCTCCT
```

-continued

```
5681  CAAGCGTATT CAACAAGGGG CTGAAGGATG CCCAGAAGGT ACCCCATTGT ATGGGATCTG ATCTGGGGCC TCGGTGCACA
5761  TGCTTTACAT GTGTTTAGTC GAGGTTAAAA AACGTCTAGG CCCCCCGAAC CACGGGGACG TGGTTTTCCT TTGAAAAACA
5841  CGATGATAAA TGGCCACCTC AGCAAGTTCC CACTTGAACA AAAACATCAA GCAAATGTAC TTGTGCCTGC CCCAGGGTGA
5921  GAAAGTCCAA GCCATGTATA TCTGGGTTGA TGGTACTGGA GAAGGACTGC GCTGCAAAAC CCGCACCCTG GACTGTGAGC
6001  CCAAGTGTGT AGAAGAGTTA CCTGAGTGGA ATTTTGATGG CTCTAGTACC TTTCAGTCTG AGGGCTCCAA CAGTGACATG
6081  TATCTCAGCC CTGTTGCCAT GTTTCGGGAC CCCTTCCGCA GAGATCCCAA CAAGCTGGTG TTCTGTGAAG TTTTCAAGTA
6161  CAACCGGAAG CCTGCAGAGA CCAATTTAAG GCACTCGTGT AAACGGATAA TGGACATGGT GAGCAACCAG CACCCCTGGT
6241  TTGGAATGGA ACAGGAGTAT ACTCTGATGG GAACAGATGG GCACCCTTTT GGTTGGCCTT CCAATGGCTT TCCTGGGCCC
6321  CAAGGTCCGT ATTACTGTGG TGTGGGCGCA GACAAAGCCT ATGGCAGGGA TATCGTGGAG GCTCACTACC GCGCCTGCTT
6401  GTATGCTGGG GTCAAGATTA CAGGAACAAA TGCTGAGGTC ATGCCTGCCC AGTGGGAGTT CCAAATAGGA CCCTGTGAAG
6481  GAATCCGCAT GGGAGATCAT CTCTGGGTGG CCCGTTTCAT CTTGCATCGA GTATGTGAAG ACTTTGGGGT AATAGCAACC
6561  TTTGACCCCA AGCCCATTCC TGGGAACTGG AATGGTGCAG GCTGCCATAC CAACTTTAGC ACCAAGGCCA TGCGGGAGGA
6641  GAATGGTCTG AAGCACATCG AGGAGGCCAT CGAGAAACTA AGCAAGCGGC ACCGGTACCA CATTCGAGCC TACGATCCCA
6721  AGGGGGGCCT GGACAATGCC CGTCGTCTGA CTGGGTTCCA CGAAACGTCC AACATCAACG ACTTTTCTGC TGGTGTCGCC
6801  AATCGCAGTG CCAGCATCCG CATTCCCCGG ACTGTCGGCC AGGAGAAGAA AGGTTACTTT GAAGACCGCC GCCCCTCTGC
6881  CAATTGTGAC CCCTTTGCAG TGACAGAAGC CATCGTCCGC ACATGCCTTC TCAATGAGAC TGGCGACGAG CCCTTCCAAT
6961  ACAAAAACTA ATCTAGATCC CCCTCGCTTT CTTGCTGTCC AATTTCTATT AAAGGTTCCT TTGTTCCCTA AGTCCAACTA
7041  CTAAACTGGG GGATATTATG AAGGGCCTTG AGCATCTGGA TTCTGCCTAA TAAAAAACAT TTATTTTCAT TGCAATGATG
7121  TATTTAAATT ATTTCTGAAT ATTTTACTAA AAAGGGAATG TGGGAGGTCA GTGCATTTAA AACATAAAGA AATGAAGAGG
7201  GGGATCTTCG CGATACTGCA TCGATGAGGG ACAGCCCCCC CCCAAAGCCC CCAGGGATGT AATTACGTCC CTCCCCCGCT
7281  AGGGGGCAGC AGCGAGCCGC CCGGGGCTCC GCTCCGGTCC GGCGCTCCCC CCGCATCCCC GAGCCGGCAG CGTGCGGGGA
7361  CAGCCCGGGC ACGGGGAAGG TGGCACGGGA TCGCTTTCCT CTGAACGCTT CTCGCTGCTC TTTGAGCCTG CAGACACCTG
7441  GGGGGATACG GGGAAAATAG ACACCGCGGT GGAGCTCCAG CTTTTGTTCC CTTTAGTGAG GGTTAATTAG TTCTTAATAC
7521  GACTCACTAT AGGGCGAATT GGCTACCGGG CCGCCCATCG AGGGTATCAT AAGCTTATAT CTATAACAAG AAAATATATA
7601  TATAATAAGT TATCACGTAA GTAGAACATG AAATAACAAT ATAATTATCG TATGAGTTAA ATCTTAAAAG TCACGTAAAA
7681  GATAATCATG CGTCATTTTG ACTCACGCGG TCGTTATAGT TCAAAATCAG TGACACTTAC CGCATTGACA AGCACGCCTC
7761  ACGGGAGCTC CAAGCGGCGA CTGAGATGTC CTAAATGCAC AGCGACGGAT TCGCGCTATT TAGAAAGAGA GAGCAATATT
```

-continued

```
7841  TCAAGAATGC ATGCGTCAAT TTTACGCAGA CTATCTTTCT AGGGTTAAAT CGATAGATGC GATCCTGCAG GTCTCCCTAT
7921  AGTGAGTCGT ATTAATTTCG ATAAGCCAGC TGCATTAATG AATCGGCCAA CGCGCGGGGA GAGGCGGTTT GCGTATTGGG
8001  CGCTCTTCCG CTTCCTCGCT CACTGACTCG CTGCGCTCGG TCGTTCGGCT GCGGCGAGCG GTATCAGCTC ACTCAAAGGC
8081  GGTAATACGG TTATCCACAG AATCAGGGGA TAACGCAGGA AAGAACATGT GAGCAAAAGG CCAGCAAAAG GCCAGGAACC
8161  GTAAAAAGGC CGCGTTGCTG GCGTTTTTCC ATAGGCTCCG CCCCCCTGAC GAGCATCACA AAAATCGACG CTCAAGTCAG
8241  AGGTGGCGAA ACCCGACAGG ACTATAAAGA TACCAGGCGT TTCCCCCTGG AAGCTCCCTC GTGCGCTCTC CTGTTCCGAC
8321  CCTGCCGCTT ACCGGATACC TGTCCGCCTT TCTCCCTTCG GGAAGCGTGG CGCTTTCTCA TAGCTCACGC TGTAGGTATC
8401  TCAGTTCGGT GTAGGTCGTT CGCTCCAAGC TGGGCTGTGT GCACGAACCC CCCGTTCAGC CCGACCGCTG CGCCTTATCC
8481  GGTAACTATC GTCTTGAGTC CAACCCGGTA AGACACGACT TATCGCCACT GGCAGCAGCC ACTGGTAACA GGATTAGCAG
8561  AGCGAGGTAT GTAGGCGGTG CTACAGAGTT CTTGAAGTGG TGGCCTAACT ACGGCTACAC TAGAAGGACA GTATTTGGTA
8641  TCTGCGCTCT GCTGAAGCCA GTTACCTTCG GAAAAAGAGT TGGTAGCTCT TGATCCGGCA AACAAACCAC CGCTGGTAGC
8721  GGTGGTTTTT TTGTTTGCAA GCAGCAGATT ACGCGCAGAA AAAAAGGATC TCAAGAAGAT CCTTTGATCT TTTCTACGGG
8801  GTCTGACGCT CAGTGGAACG AAAACTCACG TTAAGGGATT TTGGTCATGA GATTATCAAA AAGGATCTTC ACCTAGATCC
8881  TTTTAAATTA AAAATGAAGT TTTAAATCAA TCTAAAGTAT ATATGAGTAA ACTTGGTCTG ACAGTTACCA ATGCTTAATC
8961  AGTGAGGCAC CTATCTCAGC GATCTGTCTA TTTCGTTCAT CCATAGTTGC CTGACTCCCC GTCGTGTAGA TAACTACGAT
9041  ACGGGAGGGC TTACCATCTG GCCCCAGTGC TGCAATGATA CCGCGAGACC CACGCTCACC GGCTCCAGAT TTATCAGCAA
9121  TAAACCAGCC AGCCGGAAGG GCCGAGCGCA GAAGTGGTCC TGCAACTTTA TCCGCCTCCA TCCAGTCTAT TAATTGTTGC
9201  CGGGAAGCTA GAGTAAGTAG TTCGCCAGTT AATAGTTTGC GCAACGTTGT TGCCATTGCT ACAGGCATCG TGGTGTCACG
9281  CTCGTCGTTT GGTATGGCTT CATTCAGCTC CGGTTCCCAA CGATCAAGGC GAGTTACATG ATCCCCCATG TTGTGCAAAA
9361  AAGCGGTTAG CTCCTTCGGT CCTCCGATCG TTGTCAGAAG TAAGTTGGCC GCAGTGTTAT CACTCATGGT TATGGCAGCA
9441  CTGCATAATT CTCTTACTGT CATGCCATCC GTAAGATGCT TTTCTGTGAC TGGTGAGTAC TCAACCAAGT CATTCTGAGA
9521  ATAGTGTATG CGGCGACCGA GTTGCTCTTG CCCGGCGTCA ATACGGGATA ATACCGCGCC ACATAGCAGA ACTTTAAAAG
9601  TGCTCATCAT TGGAAAACGT TCTTCGGGGC GAAAACTCTC AAGGATCTTA CCGCTGTTGA GATCCAGTTC GATGTAACCC
9681  ACTCGTGCAC CCAACTGATC TTCAGCATCT TTTACTTTCA CCAGCGTTTC TGGGTGAGCA AAAACAGGAA GGCAAAATGC
9761  CGCAAAAAAG GGAATAAGGG CGACACGGAA ATGTTGAATA CTCATACTCT TCCTTTTTCA ATATTATTGA AGCATTTATC
9841  AGGGTTATTG TCTCATGAGC GGATACATAT TTGAATGTAT TTAGAAAAAT AAACAAATAG GGGTTCCGCG CACATTTCCC
9921  CGAAAAGTGC CACCTGACGT CTAAGAAACC ATTATTATCA TGACATTAAC CTATAAAAAT AGGCGTATCA CGAGGCCCTT
```

-continued

```
10001 TCGTCTCGCG CGTTTCGGTG ATGACGGTGA AAACCTCTGA CACATGCAGC TCCCGGAGAC GGTCACAGCT TGTCTGTAAG
10081 CGGATGCCGG GAGCAGACAA GCCCGTCAGG GCGCGTCAGC GGGTGTTGGC GGGTGTCGGG GCTGGCTTAA CTATGCGGCA
10161 TCAGAGCAGA TTGTACTGAG AGTGCACCAT ATCGACGCTC TCCCTTATGC GACTCCTGCA TTAGGAAGCA GCCCAGTAGT
10241 AGGTTGAGGC CGTTGAGCAC CGCCGCCGCA AGGAATGGTG CATGCAAGGA GATGGCGCCC AACAGTCCCC CGGCCACGGG
10321 GCCTGCCACC ATACCCACGC CGAAACAAGC GCTCATGAGC CCGAAGTGGC GAGCCCGATC TTCCCCATCG GTGATGTCGG
10401 CGATATAGGC GCCAGCAACC GCACCTGTGG CGCCGGTGAT GCCGGCCACG ATGCGTCCGG CGTAGAGGAT CTGGCTAGCG
10481 ATGACCCTGC TGATTGGTTC GCTGACCATT TCCGGGGTGC GGAACGGCGT TACCAGAAAC TCAGAAGGTT CGTCCAACCA
10561 AACCGACTCT GACGGCAGTT TACGAGAGAG ATGATAGGGT CTGCTTCAGT AAGCCAGATG CTACACAATT AGGCTTGTAC
10641 ATATTGTCGT TAGAACGCGG CTACAATTAA TACATAACCT TATGTATCAT ACACATACGA TTTAGGTGAC ACTATAGAAT
10721 ACACCTGCAG GACGTCCCAA TGATCTTAAG TTAA
```

pCLD15 (SEQ ID NO: 27):

```
   1 CCCTAGAAAG ATAATCATAT TGTGACGTAC GTTAAAGATA ATCATGCGTA AAATTGACGC ATGTGTTTTA TCGGTCTGTA
  81 TATCGAGGTT TATTTATTAA TTTGAATAGA TATTAAGTTT TATTATATTT ACACTTACAT ACTAATAATA AATTCAACAA
 161 ACAATTTATT TATGTTTATT TATTTATTAA AAAAAAACAA AAACTCAAAA TTTCTTCTAT AAAGTAACAA AACTTTTATC
 241 GAATTTGCAG CCCGGGACTA GCTAGAGGGA CAGCCCCCCC CCAAAGCCCC CAGGGATGTA ATTACGTCCC TCCCCCGCTA
 321 GGGGGCAGCA GCGAGCCGCC CGGGGCTCCG CTCCGGTCCG GCGCTCCCCC CGCATCCCCG AGCCGGCAGC GTGCGGGGAC
 401 AGCCCGGGCA CGGGGAAGGT GGCACGGGAT CGCTTTCCTC TGAACGCTTC TCGCTGCTCT TTGAGCCTGC AGACACCTGG
 481 GGGGATACGG GGAAAACTTA AGATCCGACC GGACGCGTAC TGAGAGCGCT ATTCTGAACT TTTCTTTTGT TCCCTTCCCT
 561 TCTACCACAC CCTAATTGTA ATCCATTTTA ATTTCCTGGT CACAGTCCTG TCTCTCCTTC CATTGTACCT TGCCCTTTTC
 641 TAAAGAGCGA CTGCAAAGTA TGTTTGCGTA GGTGAGGATC TAAAACTTTA TGAGGTACGA ACATCACAGA ATTACTTTGT
 721 AATTTCAGTT TATTGTAGGC TTGGCTTTTT GGGGAGGGTT TACGTCTTAG ACCTCTTAGT GCTTCTTTGT TTCATGGTGT
 801 TCTAACTTCG AAGCATCTCT GTAGCTTTAA TGGATTCCTT TTCTGAAAGC TTTGCTCTCT TTCTTCCCCC TCGGCTTTCT
 881 CTTAGGCAAG AGGGCTAACT GTAAAGTAAG GCTTACTGCC TTGTGTTTCC AAATGTGTCC GAAGAGGAAG TGTCTTCTGT
 961 GAATCCTGTT ATGCATGAAT AACAGGAAAT AGAAAGAAAT TCACTTTCAT TATTATAAAA GTAATATGTT CGTTTAAAAA
1041 ATTCTAATGA AGAGCTGGAG ATGCAACCCA GGGGTAGAGC ACACACTCAG CATGCAGGAG GCCCTGGGTC CAATCTTGGA
1121 ATCTCCTCTC AGTTAACCTG ATCTCTAGCT GATTAGTAGT GAGTGCAAGC CCACTTTCCT CTTCTGCCTC ATTGCTCAGT
1201 GATAACAGCT GTTAAACTTT GTCTTATTCT AAAACTACCT CTGTGCAAAT GCTAGCACAA TAATATATAT CATATGCACA
1281 TGATTTTTTT TTTATCTTGA AAAGTAAGTC AGTATAGCTA CAAAGTTCAC TTGGCATTGT CAACATTTCA CAGGCGTAAT
```

-continued

```
1361  ATTCCTCCTC TAGTACTGTC CTCTTCATTC TTTGTGACCA AGTTTGGAGA GAGTGCACAA ATGCCAGGGA GGTTTGTGGG
1441  AAGGTTTCTC ATGTTCTGGT AAGGCGAGTA AGAAAATAGT CTCATGCAGG TGAAATGAGT GCTATGCAGT ATATATTATA
1521  CCAGAGAACA GCAAATGACC AAATTCACAC TGAACTAGTT CAGTAAAATT GGCTTTGTCA AAGCTTTCCT TGCTTAAAAT
1601  GTAATTCCCT GTCATCCTAG TTCTGGTCTG GATTCTTTTC CTGGAGTCTT GACTTCCAGA TTCCCTGTGG ACTTTTGTTT
1681  GAGTTTCAAG CTTTTGAAAT ATAGAAACCT ATCTAACTTA ACAAACTTGG GAGAGAAAAG ACTCCAGAAC AACTGAAAAC
1761  AGACCAGGCT AAATGAATAG ACTTTATTCC TCTCTTCTTA CCTGCAGTTT TCAGATATGC AGAGTTGGAG CGGATCTTAG
1841  AGGTTGATTC ATTCATGCCT GAAGAAAACA CATTTTATAG ACCCTGTGCC CAAGTTCGTG GTGGACATCA CCCTTTATTT
1921  ACTAATTGCA CTACATAACA GGCATTTTAG AAGACTGCTC CAGTCAGAGA CCCCGCCTTA GAGGAATCTG TAAACCCTGA
2001  ACTCCTATCA CTCATGAGCA CTAGTTATGT TTGGAATGCC GTATTAAAAC AAAAGTTACA TTTCTAAACT TAAAATTTTC
2081  TAGCACAGAG ACAGTGGGAG TAGCTAACTT TGATAGACAT TTTTCTACTA AAAGTCTTTC TAAGTACATA ATCTTCTGTA
2161  AGTTGGAAAA CAGCAAAATA GAACGTCTCC TACGTAGTTA ATCTTTTTGC ATAATTTGCA CATGTAGGAG TTATTAGTAT
2241  ACGGGTAAGT TTTCACTTTT TCCCCCAACT GGAGTGTCTT GTGGCTGGGT TTGAAAAAGG GAACGGGAGG CCGCTGGAGG
2321  GGATTGGTAA ATGAGATAAA ACACCACTCA TTCAACTCAG TGACTCAGCA TTTAAATTTT CCATAAAAGG ATTAAAGGAA
2401  AATTAAACAA ATTCTTAAAG CCAAGACTCT GGAGAAACTT GTTGGTGTGC TTTAGTTTTC ACTGTTATGA CTCATGAATT
2481  TATGCATAAA TTAGTACATT TATAAAAACA TAGCCTTTTT AGAGTTTTCT GTTTGGCTAA AGTGCCATTG TTAGCATTTG
2561  GAATTACCTT TTTATGTCTT ATATTTTTTC CAAATAAAAA TAAATGTTTC TGCTGTCTTA CTACTGAAAC TACGTTGTGA
2641  GCACTTTAAA TTTCTCAAAG CAGTTTCGCC TGTTATACTT GGCGCTTAGT CATCGTCGTA CACAACAGGA CCTGATTAAG
2721  AAGGCTGTGC TGCCTCTAAG CCGGGCTAGA TTGTAGCCAC TAGCAACCAG GCTGCAATAA TTTCCCTTTG ATGACATCAT
2801  CCACTGTGGA AGAACCCAGT TGCTTCAGCC AGTCGAACTA TACAGTTCCA ACCTCATCAA ATATGGCATC TCCCTTGCCT
2881  GCTATAGCAG GGGGAGGAAA AAATGCCACC ATCTTTTTAA TCTAGCAAGC TTCTCTTTTC TTCATCTTTT TTTTTTTCTT
2961  TTAAAAAAAT TCTGATCATG GATGCTTCTT CCGATCCCTA TTTGCCTTAT GACGGGGGAG GAGACAATAT CCCCTTGAGG
3041  GAATTACATA AAAGAGGTAA GAGCATCCCC TTGCTCTGAA TCCTCTGTTG GTTGTTGTGC ATGCGGCTGG GCGGTTCTGG
3121  GGACAGGCTG TCTGTTGTCC TCTTGCTGCA ATGTGCTGCT TAGTTGCCCT GCCTTGTTGC TGTGGGAGAA TGCGACCTTC
3201  CCAGCAGGGC TGGCCCTCCC TGATTGTTTG CTCTGTGCAG ATTAGCCCTG CTTCAGATCA CATAGGGCTG CAGACTCCAT
3281  CTTCTGTGTG AAAATGCTTT CGGTTTGATT GCAGAAATAA GCTGCCTTTA CAGCCAGCTA AAGTCCTGGT GGTTGGTTGG
3361  CACCTGCAAA GTAGTATTTT TGTACCTCTG GAAACTTATA TTTTCTTTAC ACAGCAATAT CAAGTGCCGG TATGCCATTC
3441  TGTTTTGGCT GCTGCCAATT ACCATGTAGA CTTTGCACCA CAGAGTAATA GTAAAAGCTC CTAGCTGCAT TTTATAACAT
```

-continued

```
3521  TTAAAAATAG CAGGAAAGAA GAATTATTTT TGATTTAACA TGTTTTTGTC ATTTAACGTC TTAACTGATT GACATACTAT
3601  ATTGTCTGTC TCGTGGGTAT CTTGTACAAC TTGATAGGAT AAAGCAATTT AGTTTTTTTT TTTTTTTTTA AATACATCCA
3681  GAATGTAAGT CGTCAGTAGT TTTCGAACAG ATAAGTAATG GTGTTAATCT TTTGGCAGGC TTTGCCTTGG TCTCCTTAAA
3761  GCTAATTAGG TGTTACTTAA TTAAACTGCT CTTTTGCTCA TTTTCTTAAA TTATTTTTTT AAAAGATAGT TGGCATTTGC
3841  TGTTCTAGAA ATAAACTTCA AGAAACATTC TTTAGCCAGA TGACTTCATG TATGAGCCAT GTTAGTTTGA ATTATTTGCT
3921  TGGTGTTATA AACTTTATGG TTTAATACCA ACTTTTATTA TGTTTACAAG GTAAATAAGG AAAATTTCAA GTACATTTTG
4001  TATCCTGAGA ACAAATTTAA GTTCCATAGA ATTTAGGAAT TACAATGTAT TCAACAGATA CTTACTTGTC ATACTGTGCC
4081  TGCAAAACAA TAATTAGACT CTGAACAGGT GCAACAATTT TCTGTAGAAT TAGACAAGTC TTCTTTTGGC AGGTGTTACT
4161  AAGTAGGCCA TTTCCCAAGG AACAGGGAAT TTGCCAGGCT TTTGTGGTGG AGAGAATAGA ATGAATAAAT GCTGTGGGGA
4241  GTAAAGAGCT TGTCAGAAGA TGATTAGTTC TGTGGCACCA AAACCAAGAG ATCAGTTTTC CTGTGAGAAG TAAAGGAAGC
4321  ATTGTAGAAA AATAGATGTG TTGAAGTCTA CCGGTGGAGT TCCGCGTTAC ATAACTTACG GTAAATGGCC CGCCTGGCTG
4401  ACCGCCCAAC GACCCCCGCC CATTGACGTC AATAATGACG TATGTTCCCA TAGTAACGCC AATAGGGACT TTCCATTGAC
4481  GTCAATGGGT GGAGTATTTA CGGTAAACTG CCCACTTGGC AGTACATCAA GTGTATCATA TGCCAAGTAC GCCCCCTATT
4561  GACGTCAATG ACGGTAAATG GCCCGCCTGG CATTATGCCC AGTACATGAC CTTATGGGAC TTTCCTACTT GGCAGTACAT
4641  CTACGTATTA GTCATCGCTA TTACCATTGT GATGCGGTTT TGGCAGTACA TCAATGGGCG TGGATAGCGG TTTGACTCAC
4721  GGGGATTTCC AAGTCTCCAC CCCATTGACG TCAATGGGAG TTTGTTTTGG CACCAAAATC AACGGGACTT TCCAAAATGT
4801  CGTAACAACT CCGCCCCATT GACGCAAATG GGCGGTAGGC GTGTACGGTG GGAGGTCTAT ATAAGCAGAG CTCGTTTAGT
4881  GAACCGTCAG ATCTACCTCT TCCGCATCGC TGTCTGCGAG GGCCAGCTGT TGGGGTGAGT ACTCCCTCTC AAAAGCGGGC
4961  ATGACTTCTG CGCTAAGATT GTCAGTTTCC AAAAACGAGG AGGATTTGAT ATTCACCTGG CCCGCGGTGA TGCCTTTGAG
5041  GGTGGCCGCG TCCATCTGGT CAGAAAAGAC AATCTTTTTG TTGTCAAGCT TCCTTGATGA TGTCATACTT ATCCTGTCCC
5121  TTTTTTTTCC ACAGCTCGCG GTTGAGGACA AACTCTTCGC GGTCTTTCCA GTACTCTTGG ATCGGAAACC CGTCGGCCTC
5201  CGAACGGTAC TCCGCCACCG AGGGACCTGA GCGAGTCCGC ATCGACCGGA TCGGAAAACC TCGGATCCGA ATTCATAGAT
5281  AACTGATCCA GTGCCCCTAA CGTTACTGGC CGAAGCCGCT TGGAATAAGG CCGGTGTGCG TTTGTCTATA TGTTATTTTC
5361  CACCATATTG CCGTCTTTTG GCAATGTGAG GGCCCGGAAA CCTGGCCCTG TCTTCTTGAC GAGCATTCCT AGGGGTCTTT
5441  CCCCTCTCGC CAAAGGAATG CAAGGTCTGT TGAATGTCGT GAAGGAAGCA GTTCCTCTGG AAGCTTCTTG AAGACAAACA
5521  ACGTCTGTAG CGACCCTTTG CAGGCAGCGG AACCCCCCAC CTGGCGACAG GTGCCTCTGC GGCCAAAAGC CACGTGTATA
5601  AGATACACCT GCAAAGGCGG CACAACCCCA GTGCCACGTT GTGAGTTGGA TAGTTGTGGA AAGAGTCAAA TGGCTCTCCT
```

-continued

```
5681  CAAGCGTATT CAACAAGGGG CTGAAGGATG CCCAGAAGGT ACCCCATTGT ATGGGATCTG ATCTGGGGCC TCGGTGCACA
5761  TGCTTTACAT GTGTTTAGTC GAGGTTAAAA AAACGTCTAG GCCCCCCGAA CCACGGGGAC GTGGTTTTCC TTTGAAAAAC
5841  ACGATGATAA TATGGCCACA ACCATGGCCA CCTCAGCAAG TTCCCACTTG AACAAAAACA TCAAGCAAAT GTACTTGTGC
5921  CTGCCCCAGG GTGAGAAAGT CCAAGCCATG TATATCTGGG TTGATGGTAC TGGAGAAGGA CTGCGCTGCA AAACCCGCAC
6001  CCTGGACTGT GAGCCCAAGT GTGTAGAAGA GTTACCTGAG TGGAATTTTG ATGGCTCTAG TACCTTTCAG TCTGAGGGCT
6081  CCAACAGTGA CATGTATCTC AGCCCTGTTG CCATGTTTCG GGACCCCTTC CGCAGAGATC CCAACAAGCT GGTGTTCTGT
6161  GAAGTTTTCA AGTACAACCG GAAGCCTGCA GAGACCAATT TAAGGCACTC GTGTAAACGG ATAATGGACA TGGTGAGCAA
6241  CCAGCACCCC TGGTTTGGAA TGGAACAGGA GTATACTCTG ATGGGAACAG ATGGGCACCC TTTTGGTTGG CCTTCCAATG
6321  GCTTTCCTGG GCCCCAAGGT CCGTATTACT GTGGTGTGGG CGCAGACAAA GCCTATGGCA GGGATATCGT GGAGGCTCAC
6401  TACCGCGCCT GCTTGTATGC TGGGGTCAAG ATTACAGGAA CAAATGCTGA GGTCATGCCT GCCCAGTGGG AGTTCCAAAT
6481  AGGACCCTGT GAAGGAATCC GCATGGGAGA TCATCTCTGG GTGGCCCGTT TCATCTTGCA TCGAGTATGT GAAGACTTTG
6561  GGGTAATAGC AACCTTTGAC CCCAAGCCCA TTCCTGGGAA CTGGAATGGT GCAGGCTGCC ATACCAACTT TAGCACCAAG
6641  GCCATGCGGG AGGAGAATGG TCTGAAGCAC ATCGAGGAGG CCATCGAGAA ACTAAGCAAG CGGCACCGGT ACCACATTCG
6721  AGCCTACGAT CCCAAGGGGG GCCTGGACAA TGCCCGTCGT CTGACTGGGT TCCACGAAAC GTCCAACATC AACGACTTTT
6801  CTGCTGGTGT CGCCAATCGC AGTGCCAGCA TCCGCATTCC CCGGACTGTC GGCCAGGAGA AGAAAGGTTA CTTTGAAGAC
6881  CGCCGCCCCT CTGCCAATTG TGACCCCTTT GCAGTGACAG AAGCCATCGT CCGCACATGC CTTCTCAATG AGACTGGCGA
6961  CGAGCCCTTC CAATACAAAA ACTAATCTAG ATCCCCCTCG CTTTCTTGCT GTCCAATTTC TATTAAAGGT TCCTTTGTTC
7041  CCTAAGTCCA ACTACTAAAC TGGGGGATAT TATGAAGGGC CTTGAGCATC TGGATTCTGC CTAATAAAAA ACATTTATTT
7121  TCATTGCAAT GATGTATTTA AATTATTTCT GAATATTTTA CTAAAAAGGG AATGTGGGAG GTCAGTGCAT TTAAAACATA
7201  AAGAAATGAA GAGGGGGATC TTCGCGATAC TGCATCGATG AGGGACAGCC CCCCCCCAAA GCCCCCAGGG ATGTAATTAC
7281  GTCCCTCCCC CGCTAGGGGG CAGCAGCGAG CCGCCCGGGG CTCCGCTCCG GTCCGGCGCT CCCCCCGCAT CCCCGAGCCG
7361  GCAGCGTGCG GGGACAGCCC GGGCACGGGG AAGGTGGCAC GGGATCGCTT TCCTCTGAAC GCTTCTCGCT GCTCTTTGAG
7441  CCTGCAGACA CCTGGGGGGA TACGGGGAAA ATAGACACCG CGGTGGAGCT CCAGCTTTTG TTCCCTTTAG TGAGGGTTAA
7521  TTAGTTCTTA ATACGACTCA CTATAGGGCG AATTGGCTAC CGGGCCGCCC ATCGAGGGTA TCATAAGCTT ATATCTATAA
7601  CAAGAAAATA TATATATAAT AAGTTATCAC GTAAGTAGAA CATGAAATAA CAATATAATT ATCGTATGAG TTAAATCTTA
7681  AAAGTCACGT AAAAGATAAT CATGCGTCAT TTTGACTCAC GCGGTCGTTA TAGTTCAAAA TCAGTGACAC TTACCGCATT
7761  GACAAGCACG CCTCACGGGA GCTCCAAGCG GCGACTGAGA TGTCCTAAAT GCACAGCGAC GGATTCGCGC TATTTAGAAA
```

-continued

```
7841  GAGAGAGCAA TATTTCAAGA ATGCATGCGT CAATTTTACG CAGACTATCT TTCTAGGGTT AAATCGATAG ATGCGATCCT
7921  GCAGGTCTCC CTATAGTGAG TCGTATTAAT TTCGATAAGC CAGCTGCATT AATGAATCGG CCAACGCGCG GGGAGAGGCG
8001  GTTTGCGTAT TGGGCGCTCT TCCGCTTCCT CGCTCACTGA CTCGCTGCGC TCGGTCGTTC GGCTGCGGCG AGCGGTATCA
8081  GCTCACTCAA AGGCGGTAAT ACGGTTATCC ACAGAATCAG GGGATAACGC AGGAAAGAAC ATGTGAGCAA AAGGCCAGCA
8161  AAAGGCCAGG AACCGTAAAA AGGCCGCGTT GCTGGCGTTT TTCCATAGGC TCCGCCCCCC TGACGAGCAT CACAAAAATC
8241  GACGCTCAAG TCAGAGGTGG CGAAACCCGA CAGGACTATA AAGATACCAG GCGTTTCCCC CTGGAAGCTC CCTCGTGCGC
8321  TCTCCTGTTC CGACCCTGCC GCTTACCGGA TACCTGTCCG CCTTTCTCCC TTCGGGAAGC GTGGCGCTTT CTCATAGCTC
8401  ACGCTGTAGG TATCTCAGTT CGGTGTAGGT CGTTCGCTCC AAGCTGGGCT GTGTGCACGA ACCCCCCGTT CAGCCCGACC
8481  GCTGCGCCTT ATCCGGTAAC TATCGTCTTG AGTCCAACCC GGTAAGACAC GACTTATCGC CACTGGCAGC AGCCACTGGT
8561  AACAGGATTA GCAGAGCGAG GTATGTAGGC GGTGCTACAG AGTTCTTGAA GTGGTGGCCT AACTACGGCT ACACTAGAAG
8641  GACAGTATTT GGTATCTGCG CTCTGCTGAA GCCAGTTACC TTCGGAAAAA GAGTTGGTAG CTCTTGATCC GGCAAACAAA
8721  CCACCGCTGG TAGCGGTGGT TTTTTTGTTT GCAAGCAGCA GATTACGCGC AGAAAAAAAG GATCTCAAGA AGATCCTTTG
8801  ATCTTTTCTA CGGGGTCTGA CGCTCAGTGG AACGAAAACT CACGTTAAGG GATTTTGGTC ATGAGATTAT CAAAAAGGAT
8881  CTTCACCTAG ATCCTTTTAA ATTAAAAATG AAGTTTTAAA TCAATCTAAA GTATATATGA GTAAACTTGG TCTGACAGTT
8961  ACCAATGCTT AATCAGTGAG GCACCTATCT CAGCGATCTG TCTATTTCGT TCATCCATAG TTGCCTGACT CCCCGTCGTG
9041  TAGATAACTA CGATACGGGA GGGCTTACCA TCTGGCCCCA GTGCTGCAAT GATACCGCGA GACCCACGCT CACCGGCTCC
9121  AGATTTATCA GCAATAAACC AGCCAGCCGG AAGGGCCGAG CGCAGAAGTG GTCCTGCAAC TTTATCCGCC TCCATCCAGT
9201  CTATTAATTG TTGCCGGGAA GCTAGAGTAA GTAGTTCGCC AGTTAATAGT TTGCGCAACG TTGTTGCCAT TGCTACAGGC
9281  ATCGTGGTGT CACGCTCGTC GTTTGGTATG GCTTCATTCA GCTCCGGTTC CCAACGATCA AGGCGAGTTA CATGATCCCC
9361  CATGTTGTGC AAAAAAGCGG TTAGCTCCTT CGGTCCTCCG ATCGTTGTCA GAAGTAAGTT GGCCGCAGTG TTATCACTCA
9441  TGGTTATGGC AGCACTGCAT AATTCTCTTA CTGTCATGCC ATCCGTAAGA TGCTTTTCTG TGACTGGTGA GTACTCAACC
9521  AAGTCATTCT GAGAATAGTG TATGCGGCGA CCGAGTTGCT CTTGCCCGGC GTCAATACGG GATAATACCG CGCCACATAG
9601  CAGAACTTTA AAAGTGCTCA TCATTGGAAA ACGTTCTTCG GGGCGAAAAC TCTCAAGGAT CTTACCGCTG TTGAGATCCA
9681  GTTCGATGTA ACCCACTCGT GCACCCAACT GATCTTCAGC ATCTTTTACT TTCACCAGCG TTTCTGGGTG AGCAAAAACA
9761  GGAAGGCAAA ATGCCGCAAA AAAGGGAATA AGGGCGACAC GGAAATGTTG AATACTCATA CTCTTCCTTT TTCAATATTA
9841  TTGAAGCATT TATCAGGGTT ATTGTCTCAT GAGCGGATAC ATATTTGAAT GTATTTAGAA AAATAAACAA ATAGGGGTTC
9921  CGCGCACATT TCCCCGAAAA GTGCCACCTG ACGTCTAAGA AACCATTATT ATCATGACAT TAACCTATAA AAATAGGCGT
```

-continued

```
10001  ATCACGAGGC CCTTTCGTCT CGCGCGTTTC GGTGATGACG GTGAAAACCT CTGACACATG CAGCTCCCGG AGACGGTCAC
10081  AGCTTGTCTG TAAGCGGATG CCGGGAGCAG ACAAGCCCGT CAGGGCGCGT CAGCGGGTGT TGGCGGGTGT CGGGGCTGGC
10161  TTAACTATGC GGCATCAGAG CAGATTGTAC TGAGAGTGCA CCATATCGAC GCTCTCCCTT ATGCGACTCC TGCATTAGGA
10241  AGCAGCCCAG TAGTAGGTTG AGGCCGTTGA GCACCGCCGC CGCAAGGAAT GGTGCATGCA AGGAGATGGC GCCCAACAGT
10321  CCCCCGGCCA CGGGGCCTGC CACCATACCC ACGCCGAAAC AAGCGCTCAT GAGCCCGAAG TGGCGAGCCC GATCTTCCCC
10401  ATCGGTGATG TCGGCGATAT AGGCGCCAGC AACCGCACCT GTGGCGCCGG TGATGCCGGC CACGATGCGT CCGGCGTAGA
10481  GGATCTGGCT AGCGATGACC CTGCTGATTG GTTCGCTGAC CATTTCCGGG GTGCGGAACG GCGTTACCAG AAACTCAGAA
10561  GGTTCGTCCA ACCAAACCGA CTCTGACGGC AGTTTACGAG AGAGATGATA GGGTCTGCTT CAGTAAGCCA GATGCTACAC
10641  AATTAGGCTT GTACATATTG TCGTTAGAAC GCGGCTACAA TTAATACATA ACCTTATGTA TCATACACAT ACGATTTAGG
10721  TGACACTATA GAATACACCT GCAGGACGTC CCAATGATCT TAAGTTAA
```

pCLD16 (SEQ ID NO: 28):

```
   1  CCCTAGAAAG ATAATCATAT TGTGACGTAC GTTAAAGATA ATCATGCGTA AAATTGACGC ATGTGTTTTA TCGGTCTGTA
  81  TATCGAGGTT TATTTATTAA TTTGAATAGA TATTAAGTTT TATTATATTT ACACTTACAT ACTAATAATA AATTCAACAA
 161  ACAATTTATT TATGTTTATT TATTTATTAA AAAAAAACAA AAACTCAAAA TTTCTTCTAT AAAGTAACAA AACTTTTATC
 241  GAATTTGCAG CCCGGGACTA GCTAGAGGGA CAGCCCCCCC CCAAAGCCCC CAGGGATGTA ATTACGTCCC TCCCCCGCTA
 321  GGGGGCAGCA GCGAGCCGCC CGGGGCTCCG CTCCGGTCCG GCGCTCCCCC CGCATCCCCG AGCCGGCAGC GTGCGGGGAC
 401  AGCCCGGGCA CGGGGAAGGT GGCACGGGAT CGCTTTCCTC TGAACGCTTC TCGCTGCTCT TTGAGCCTGC AGACACCTGG
 481  GGGGATACGG GGAAAACTTA AGATCCGACC GGACGCGTAC TGAGAGCGCT ATTCTGAACT TTTCTTTTGT TCCCTTCCCT
 561  TCTACCACAC CCTAATTGTA ATCCATTTTA ATTTCCTGGT CACAGTCCTG TCTCTCCTTC CATTGTACCT TGCCCTTTTC
 641  TAAAGAGCGA CTGCAAAGTA TGTTTGCGTA GGTGAGGATC TAAAACTTTA TGAGGTACGA ACATCACAGA ATTACTTTGT
 721  AATTTCAGTT TATTGTAGGC TTGGCTTTTT GGGGAGGGTT TACGTCTTAG ACCTCTTAGT GCTTCTTTGT TTCATGGTGT
 801  TCTAACTTCG AAGCATCTCT GTAGCTTTAA TGGATTCCTT TTCTGAAAGC TTTGCTCTCT TTCTTCCCCC TCGGCTTTCT
 881  CTTAGGCAAG AGGGCTAACT GTAAAGTAAG GCTTACTGCC TTGTGTTTCC AAATGTGTCC GAAGAGGAAG TGTCTTCTGT
 961  GAATCCTGTT ATGCATGAAT AACAGGAAAT AGAAAGAAAT TCACTTTCAT TATTATAAAA GTAATATGTT CGTTTAAAAA
1041  ATTCTAATGA AGAGCTGGAG ATGCAACCCA GGGGTAGAGC ACACACTCAG CATGCAGGAG GCCCTGGGTC CAATCTTGGA
1121  ATCTCCTCTC AGTTAACCTG ATCTCTAGCT GATTAGTAGT GAGTGCAAGC CCACTTTCCT CTTCTGCCTC ATTGCTCAGT
1201  GATAACAGCT GTTAAACTTT GTCTTATTCT AAAACTACCT CTGTGCAAAT GCTAGCACAA TAATATATAT CATATGCACA
```

-continued

```
1281  TGATTTTTTT TTTATCTTGA AAAGTAAGTC AGTATAGCTA CAAAGTTCAC TTGGCATTGT CAACATTTCA CAGGCGTAAT
1361  ATTCCTCCTC TAGTACTGTC CTCTTCATTC TTTGTGACCA AGTTTGGAGA GAGTGCACAA ATGCCAGGGA GGTTTGTGGG
1441  AAGGTTTCTC ATGTTCTGGT AAGGCGAGTA AGAAAATAGT CTCATGCAGG TGAAATGAGT GCTATGCAGT ATATATTATA
1521  CCAGAGAACA GCAAATGACC AAATTCACAC TGAACTAGTT CAGTAAAATT GGCTTTGTCA AAGCTTTCCT TGCTTAAAAT
1601  GTAATTCCCT GTCATCCTAG TTCTGGTCTG GATTCTTTTC CTGGAGTCTT GACTTCCAGA TTCCCTGTGG ACTTTTGTTT
1681  GAGTTTCAAG CTTTTGAAAT ATAGAAACCT ATCTAACTTA ACAAACTTGG GAGAGAAAAG ACTCCAGAAC AACTGAAAAC
1761  AGACCAGGCT AAATGAATAG ACTTTATTCC TCTCTTCTTA CCTGCAGTTT TCAGATATGC AGAGTTGGAG CGGATCTTAG
1841  AGGTTGATTC ATTCATGCCT GAAGAAAACA CATTTTATAG ACCCTGTGCC CAAGTTCGTG GTGGACATCA CCCTTTATTT
1921  ACTAATTGCA CTACATAACA GGCATTTTAG AAGACTGCTC CAGTCAGAGA CCCCGCCTTA GAGGAATCTG TAAACCCTGA
2001  ACTCCTATCA CTCATGAGCA CTAGTTATGT TTGGAATGCC GTATTAAAAC AAAAGTTACA TTTCTAAACT TAAAATTTTC
2081  TAGCACAGAG ACAGTGGGAG TAGCTAACTT TGATAGACAT TTTTCTACTA AAAGTCTTTC TAAGTACATA ATCTTCTGTA
2161  AGTTGGAAAA CAGCAAAATA GAACGTCTCC TACGTAGTTA ATCTTTTTGC ATAATTTGCA CATGTAGGAG TTATTAGTAT
2241  ACGGGTAAGT TTTCACTTTT TCCCCCAACT GGAGTGTCTT GTGGCTGGGT TTGAAAAAGG GAACGGGAGG CCGCTGGAGG
2321  GGATTGGTAA ATGAGATAAA ACACCACTCA TTCAACTCAG TGACTCAGCA TTTAAATTTT CCATAAAAGG ATTAAAGGAA
2401  AATTAAACAA ATTCTTAAAG CCAAGACTCT GGAGAAACTT GTTGGTGTGC TTTAGTTTTC ACTGTTATGA CTCATGAATT
2481  TATGCATAAA TTAGTACATT TATAAAAACA TAGCCTTTTT AGAGTTTTCT GTTTGGCTAA AGTGCCATTG TTAGCATTTG
2561  GAATTACCTT TTTATGTCTT ATATTTTTTC CAAATAAAAA TAAATGTTTC TGCTGTCTTA CTACTGAAAC TACGTTGTGA
2641  GCACTTTAAA TTTCTCAAAG CAGTTTCGCC TGTTATACTT GGCGCTTAGT CATCGTCGTA CACAACAGGA CCTGATTAAG
2721  AAGGCTGTGC TGCCTCTAAG CCGGGCTAGA TTGTAGCCAC TAGCAACCAG GCTGCAATAA TTTCCCTTTG ATGACATCAT
2801  CCACTGTGGA AGAACCCAGT TGCTTCAGCC AGTCGAACTA TACAGTTCCA ACCTCATCAA ATATGGCATC TCCCTTGCCT
2881  GCTATAGCAG GGGGAGGAAA AAATGCCACC ATCTTTTTAA TCTAGCAAGC TTCTCTTTTC TTCATCTTTT TTTTTTTCTT
2961  TTAAAAAAAT TCTGATCATG GATGCTTCTT CCGATCCCTA TTTGCCTTAT GACGGGGGAG GAGACAATAT CCCCTTGAGG
3041  GAATTACATA AAAGAGGTAA GAGCATCCCC TTGCTCTGAA TCCTCTGTTG GTTGTTGTGC ATGCGGCTGG GCGGTTCTGG
3121  GGACAGGCTG TCTGTTGTCC TCTTGCTGCA ATGTGCTGCT TAGTTGCCCT GCCTTGTTGC TGTGGGAGAA TGCGACCTTC
3201  CCAGCAGGGC TGGCCCTCCC TGATTGTTTG CTCTGTGCAG ATTAGCCCTG CTTCAGATCA CATAGGGCTG CAGACTCCAT
3281  CTTCTGTGTG AAAATGCTTT CGGTTTGATT GCAGAAATAA GCTGCCTTTA CAGCCAGCTA AAGTCCTGGT GGTTGGTTGG
3361  CACCTGCAAA GTAGTATTTT TGTACCTCTG GAAACTTATA TTTTCTTTAC ACAGCAATAT CAAGTGCCGG TATGCCATTC
```

-continued

```
3441  TGTTTTGGCT GCTGCCAATT ACCATGTAGA CTTTGCACCA CAGAGTAATA GTAAAAGCTC CTAGCTGCAT TTTATAACAT
3521  TTAAAAATAG CAGGAAAGAA GAATTATTTT TGATTTAACA TGTTTTTGTC ATTTAACGTC TTAACTGATT GACATACTAT
3601  ATTGTCTGTC TCGTGGGTAT CTTGTACAAC TTGATAGGAT AAAGCAATTT AGTTTTTTTT TTTTTTTTTA AATACATCCA
3681  GAATGTAAGT CGTCAGTAGT TTTCGAACAG ATAAGTAATG GTGTTAATCT TTTGGCAGGC TTTGCCTTGG TCTCCTTAAA
3761  GCTAATTAGG TGTTACTTAA TTAAACTGCT CTTTTGCTCA TTTTCTTAAA TTATTTTTTT AAAAGATAGT TGGCATTTGC
3841  TGTTCTAGAA ATAAACTTCA AGAAACATTC TTTAGCCAGA TGACTTCATG TATGAGCCAT GTTAGTTTGA ATTATTTGCT
3921  TGGTGTTATA AACTTTATGG TTTAATACCA ACTTTTATTA TGTTTACAAG GTAAATAAGG AAAATTTCAA GTACATTTTG
4001  TATCCTGAGA ACAAATTTAA GTTCCATAGA ATTTAGGAAT TACAATGTAT TCAACAGATA CTTACTTGTC ATACTGTGCC
4081  TGCAAAACAA TAATTAGACT CTGAACAGGT GCAACAATTT TCTGTAGAAT TAGACAAGTC TTCTTTTGGC AGGTGTTACT
4161  AAGTAGGCCA TTTCCCAAGG AACAGGGAAT TTGCCAGGCT TTTGTGGTGG AGAGAATAGA ATGAATAAAT GCTGTGGGGA
4241  GTAAAGAGCT TGTCAGAAGA TGATTAGTTC TGTGGCACCA AAACCAAGAG ATCAGTTTTC CTGTGAGAAG TAAAGGAAGC
4321  ATTGTAGAAA AATAGATGTG TTGAAGTCTA CCGGTGGAGT TCCGCGTTAC ATAACTTACG GTAAATGGCC CGCCTGGCTG
4401  ACCGCCCAAC GACCCCCGCC CATTGACGTC AATAATGACG TATGTTCCCA TAGTAACGCC AATAGGGACT TTCCATTGAC
4481  GTCAATGGGT GGAGTATTTA CGGTAAACTG CCCACTTGGC AGTACATCAA GTGTATCATA TGCCAAGTAC GCCCCCTATT
4561  GACGTCAATG ACGGTAAATG GCCCGCCTGG CATTATGCCC AGTACATGAC CTTATGGGAC TTTCCTACTT GGCAGTACAT
4641  CTACGTATTA GTCATCGCTA TTACCATTGT GATGCGGTTT TGGCAGTACA TCAATGGGCG TGGATAGCGG TTTGACTCAC
4721  GGGGATTTCC AAGTCTCCAC CCCATTGACG TCAATGGGAG TTTGTTTTGG CACCAAAATC AACGGGACTT TCCAAAATGT
4801  CGTAACAACT CCGCCCCATT GACGCAAATG GGCGGTAGGC GTGTACGGTG GGAGGTCTAT ATAAGCAGAG CTCGTTTAGT
4881  GAACCGTCAG ATCTACCTCT TCCGCATCGC TGTCTGCGAG GGCCAGCTGT TGGGGTGAGT ACTCCCTCTC AAAAGCGGGC
4961  ATGACTTCTG CGCTAAGATT GTCAGTTTCC AAAAACGAGG AGGATTTGAT ATTCACCTGG CCCGCGGTGA TGCCTTTGAG
5041  GGTGGCCGCG TCCATCTGGT CAGAAAAGAC AATCTTTTTG TTGTCAAGCT TCCTTGATGA TGTCATACTT ATCCTGTCCC
5121  TTTTTTTTCC ACAGCTCGCG GTTGAGGACA AACTCTTCGC GGTCTTTCCA GTACTCTTGG ATCGGAAACC CGTCGGCCTC
5201  CGAACGGTAC TCCGCCACCG AGGGACCTGA GCGAGTCCGC ATCGACCGGA TCGGAAAACC TCGGATCCGA ATTCATAGAT
5281  AACTGATCCA GTGCCCCTAA CGTTACTGGC CGAAGCCGCT TGGAATAAGG CCGGTGTGCG TTTGTCTATA TGTTATTTTC
5361  CACCATATTG CCGTCTTTTG GCAATGTGAG GGCCCGGAAA CCTGGCCCTG TCTTCTTGAC GAGCATTCCT AGGGGTCTTT
5441  CCCCTCTCGC CAAAGGAATG CAAGGTCTGT TGAATGTCGT GAAGGAAGCA GTTCCTCTGG AAGCTTCTTG AAGACAAACA
5521  ACGTCTGTAG CGACCCTTTG CAGGCAGCGG AACCCCCCAC CTGGCGACAG GTGCCTCTGC GGCCAAAAGC CACGTGTATA
```

-continued

```
5601  AGATACACCT GCAAAGGCGG CACAACCCCA GTGCCACGTT GTGAGTTGGA TAGTTGTGGA AAGAGTCAAA TGGCTCTCCT
5681  CAAGCGTATT CAACAAGGGG CTGAAGGATG CCCAGAAGGT ACCCCATTGT ATGGGATCTG ATCTGGGGCC TCGGTGCACA
5761  TGCTTTACAT GTGTTTAGTC GAGGTTAAAA AAACGTCTAG GCCCCCCGAA CCACGGGGAC GTGGTTTTCC TTTGAAAAAC
5841  ACGATGATAA ATGGCCACCT CAGCAAGTTC CCACTTGAAC AAAAACATCA AGCAAATGTA CTTGTGCCTG CCCCAGGGTG
5921  AGAAAGTCCA AGCCATGTAT ATCTGGGTTG ATGGTACTGG AGAAGGACTG CGCTGCAAAA CCCGCACCCT GGACTGTGAG
6001  CCCAAGTGTG TAGAAGAGTT ACCTGAGTGG AATTTTGATG GCTCTAGTAC CTTTCAGTCT GAGGGCTCCA ACAGTGACAT
6081  GTATCTCAGC CCTGTTGCCA TGTTTCGGGA CCCCTTCCGC AGAGATCCCA ACAAGCTGGT GTTCTGTGAA GTTTTCAAGT
6161  ACAACCGGAA GCCTGCAGAG ACCAATTTAA GGCACTCGTG TAAACGGATA ATGGACATGG TGAGCAACCA GCACCCCTGG
6241  TTTGGAATGG AACAGGAGTA TACTCTGATG GGAACAGATG GGCACCCTTT TGGTTGGCCT TCCAATGGCT TTCCTGGGCC
6321  CCAAGGTCCG TATTACTGTG GTGTGGGCGC AGACAAAGCC TATGGCAGGG ATATCGTGGA GGCTCACTAC CGCGCCTGCT
6401  TGTATGCTGG GGTCAAGATT ACAGGAACAA ATGCTGAGGT CATGCCTGCC CAGTGGGAGT TCCAAATAGG ACCCTGTGAA
6481  GGAATCCGCA TGGGAGATCA TCTCTGGGTG GCCCGTTTCA TCTTGCATCG AGTATGTGAA GACTTTGGGG TAATAGCAAC
6561  CTTTGACCCC AAGCCCATTC CTGGGAACTG GAATGGTGCA GGCTGCCATA CCAACTTTAG CACCAAGGCC ATGCGGGAGG
6641  AGAATGGTCT GAAGCACATC GAGGAGGCCA TCGAGAAACT AAGCAAGCGG CACCGGTACC ACATTCGAGC CTACGATCCC
6721  AAGGGGGGCC TGGACAATGC CCGTCGTCTG ACTGGGTTCC ACGAAACGTC CAACATCAAC GACTTTTCTG CTGGTGTCGC
6801  CAATCGCAGT GCCAGCATCC GCATTCCCCG GACTGTCGGC CAGGAGAAGA AAGGTTACTT TGAAGACCGC CGCCCCTCTG
6881  CCAATTGTGA CCCCTTTGCA GTGACAGAAG CCATCGTCCG CACATGCCTT CTCAATGAGA CTGGCGACGA GCCCTTCCAA
6961  TACAAAAACT AATCTAGATC CCCCTCGCTT TCTTGCTGTC CAATTTCTAT TAAAGGTTCC TTTGTTCCCT AAGTCCAACT
7041  ACTAAACTGG GGGATATTAT GAAGGGCCTT GAGCATCTGG ATTCTGCCTA ATAAAAAACA TTTATTTTCA TTGCAATGAT
7121  GTATTTAAAT TATTTCTGAA TATTTTACTA AAAAGGGAAT GTGGGAGGTC AGTGCATTTA AAACATAAAG AAATGAAGAG
7201  GGGGATCTTC GCGATACTGC ATCGATGAGG GACAGCCCCC CCCCAAAGCC CCCAGGGATG TAATTACGTC CCTCCCCCGC
7281  TAGGGGGCAG CAGCGAGCCG CCCGGGGCTC CGCTCCGGTC CGGCGCTCCC CCCGCATCCC CGAGCCGGCA GCGTGCGGGG
7361  ACAGCCCGGG CACGGGGAAG GTGGCACGGG ATCGCTTTCC TCTGAACGCT TCTCGCTGCT CTTTGAGCCT GCAGACACCT
7441  GGGGGGATAC GGGGAAAATA GACACCGCGG TGGAGCTCCA GCTTTTGTTC CCTTTAGTGA GGGTTAATTA GTTCTTAATA
7521  CGACTCACTA TAGGGCGAAT TGGCTACCGG GCCGCCCATC GAGGGTATCA TAAGCTTATA TCTATAACAA GAAAATATAT
7601  ATATAATAAG TTATCACGTA AGTAGAACAT GAAATAACAA TATAATTATC GTATGAGTTA AATCTTAAAA GTCACGTAAA
7681  AGATAATCAT GCGTCATTTT GACTCACGCG GTCGTTATAG TTCAAAATCA GTGACACTTA CCGCATTGAC AAGCACGCCT
```

-continued

```
7761  CACGGGAGCT CCAAGCGGCG ACTGAGATGT CCTAAATGCA CAGCGACGGA TTCGCGCTAT TTAGAAAGAG AGAGCAATAT
7841  TTCAAGAATG CATGCGTCAA TTTTACGCAG ACTATCTTTC TAGGGTTAAA TCGATAGATG CGATCCTGCA GGTCTCCCTA
7921  TAGTGAGTCG TATTAATTTC GATAAGCCAG CTGCATTAAT GAATCGGCCA ACGCGCGGGG AGAGGCGGTT TGCGTATTGG
8001  GCGCTCTTCC GCTTCCTCGC TCACTGACTC GCTGCGCTCG GTCGTTCGGC TGCGGCGAGC GGTATCAGCT CACTCAAAGG
8081  CGGTAATACG GTTATCCACA GAATCAGGGG ATAACGCAGG AAAGAACATG TGAGCAAAAG GCCAGCAAAA GGCCAGGAAC
8161  CGTAAAAAGG CCGCGTTGCT GGCGTTTTTC CATAGGCTCC GCCCCCCTGA CGAGCATCAC AAAAATCGAC GCTCAAGTCA
8241  GAGGTGGCGA AACCCGACAG GACTATAAAG ATACCAGGCG TTTCCCCCTG GAAGCTCCCT CGTGCGCTCT CCTGTTCCGA
8321  CCCTGCCGCT TACCGGATAC CTGTCCGCCT TTCTCCCTTC GGGAAGCGTG GCGCTTTCTC ATAGCTCACG CTGTAGGTAT
8401  CTCAGTTCGG TGTAGGTCGT TCGCTCCAAG CTGGGCTGTG TGCACGAACC CCCCGTTCAG CCCGACCGCT GCGCCTTATC
8481  CGGTAACTAT CGTCTTGAGT CCAACCCGGT AAGACACGAC TTATCGCCAC TGGCAGCAGC CACTGGTAAC AGGATTAGCA
8561  GAGCGAGGTA TGTAGGCGGT GCTACAGAGT TCTTGAAGTG GTGGCCTAAC TACGGCTACA CTAGAAGGAC AGTATTTGGT
8641  ATCTGCGCTC TGCTGAAGCC AGTTACCTTC GGAAAAAGAG TTGGTAGCTC TTGATCCGGC AAACAAACCA CCGCTGGTAG
8721  CGGTGGTTTT TTTGTTTGCA AGCAGCAGAT TACGCGCAGA AAAAAAGGAT CTCAAGAAGA TCCTTTGATC TTTTCTACGG
8801  GGTCTGACGC TCAGTGGAAC GAAAACTCAC GTTAAGGGAT TTTGGTCATG AGATTATCAA AAAGGATCTT CACCTAGATC
8881  CTTTTAAATT AAAAATGAAG TTTTAAATCA ATCTAAAGTA TATATGAGTA AACTTGGTCT GACAGTTACC AATGCTTAAT
8961  CAGTGAGGCA CCTATCTCAG CGATCTGTCT ATTTCGTTCA TCCATAGTTG CCTGACTCCC CGTCGTGTAG ATAACTACGA
9041  TACGGGAGGG CTTACCATCT GGCCCCAGTG CTGCAATGAT ACCGCGAGAC CCACGCTCAC CGGCTCCAGA TTTATCAGCA
9121  ATAAACCAGC CAGCCGGAAG GGCCGAGCGC AGAAGTGGTC CTGCAACTTT ATCCGCCTCC ATCCAGTCTA TTAATTGTTG
9201  CCGGGAAGCT AGAGTAAGTA GTTCGCCAGT TAATAGTTTG CGCAACGTTG TTGCCATTGC TACAGGCATC GTGGTGTCAC
9281  GCTCGTCGTT TGGTATGGCT TCATTCAGCT CCGGTTCCCA ACGATCAAGG CGAGTTACAT GATCCCCCAT GTTGTGCAAA
9361  AAAGCGGTTA GCTCCTTCGG TCCTCCGATC GTTGTCAGAA GTAAGTTGGC CGCAGTGTTA TCACTCATGG TTATGGCAGC
9441  ACTGCATAAT TCTCTTACTG TCATGCCATC CGTAAGATGC TTTTCTGTGA CTGGTGAGTA CTCAACCAAG TCATTCTGAG
9521  AATAGTGTAT GCGGCGACCG AGTTGCTCTT GCCCGGCGTC AATACGGGAT AATACCGCGC CACATAGCAG AACTTTAAAA
9601  GTGCTCATCA TTGGAAAACG TTCTTCGGGG CGAAAACTCT CAAGGATCTT ACCGCTGTTG AGATCCAGTT CGATGTAACC
9681  CACTCGTGCA CCCAACTGAT CTTCAGCATC TTTTACTTTC ACCAGCGTTT CTGGGTGAGC AAAAACAGGA AGGCAAAATG
9761  CCGCAAAAAA GGGAATAAGG GCGACACGGA AATGTTGAAT ACTCATACTC TTCCTTTTTC AATATTATTG AAGCATTTAT
9841  CAGGGTTATT GTCTCATGAG CGGATACATA TTTGAATGTA TTTAGAAAAA TAAACAAATA GGGGTTCCGC GCACATTTCC
```

-continued

```
 9921  CCGAAAAGTG CCACCTGACG TCTAAGAAAC CATTATTATC ATGACATTAA CCTATAAAAA TAGGCGTATC ACGAGGCCCT

10001  TTCGTCTCGC GCGTTTCGGT GATGACGGTG AAAACCTCTG ACACATGCAG CTCCCGGAGA CGGTCACAGC TTGTCTGTAA

10081  GCGGATGCCG GGAGCAGACA AGCCCGTCAG GGCGCGTCAG CGGGTGTTGG CGGGTGTCGG GGCTGGCTTA ACTATGCGGC

10161  ATCAGAGCAG ATTGTACTGA GAGTGCACCA TATCGACGCT CTCCCTTATG CGACTCCTGC ATTAGGAAGC AGCCCAGTAG

10241  TAGGTTGAGG CCGTTGAGCA CCGCCGCCGC AAGGAATGGT GCATGCAAGG AGATGGCGCC CAACAGTCCC CCGGCCACGG

10321  GGCCTGCCAC CATACCCACG CCGAAACAAG CGCTCATGAG CCCGAAGTGG CGAGCCCGAT CTTCCCCATC GGTGATGTCG

10401  GCGATATAGG CGCCAGCAAC CGCACCTGTG GCGCCGGTGA TGCCGGCCAC GATGCGTCCG GCGTAGAGGA TCTGGCTAGC

10481  GATGACCCTG CTGATTGGTT CGCTGACCAT TTCCGGGGTG CGGAACGGCG TTACCAGAAA CTCAGAAGGT TCGTCCAACC

10561  AAACCGACTC TGACGGCAGT TTACGAGAGA GATGATAGGG TCTGCTTCAG TAAGCCAGAT GCTACACAAT TAGGCTTGTA

10641  CATATTGTCG TTAGAACGCG GCTACAATTA ATACATAACC TTATGTATCA TACACATACG ATTTAGGTGA CACTATAGAA

10721  TACACCTGCA GGACGTCCCA ATGATCTTAA GTTAA
```

pCLD17 (SEQ ID NO: 29):

```
    1  CCCTAGAAAG ATAATCATAT TGTGACGTAC GTTAAAGATA ATCATGCGTA AAATTGACGC ATGTGTTTTA TCGGTCTGTA

   81  TATCGAGGTT TATTTATTAA TTTGAATAGA TATTAAGTTT TATTATATTT ACACTTACAT ACTAATAATA AATTCAACAA

  161  ACAATTTATT TATGTTTATT TATTTATTAA AAAAAAACAA AAACTCAAAA TTTCTTCTAT AAAGTAACAA AACTTTTATC

  241  GAATTTGCAG CCCGGGACTA GCTAGAGGGA CAGCCCCCCC CCAAAGCCCC CAGGGATGTA ATTACGTCCC TCCCCCGCTA

  321  GGGGGCAGCA GCGAGCCGCC CGGGGCTCCG CTCCGGTCCG GCGCTCCCCC CGCATCCCCG AGCCGGCAGC GTGCGGGGAC

  401  AGCCCGGGCA CGGGGAAGGT GGCACGGGAT CGCTTTCCTC TGAACGCTTC TCGCTGCTCT TTGAGCCTGC AGACACCTGG

  481  GGGGATACGG GGAAAACTTA AGATCCGACC GGACGCGTAC TGAGAGCGCT ATTCTGAACT TTTCTTTTGT TCCCTTCCCT

  561  TCTACCACAC CCTAATTGTA ATCCATTTTA ATTTCCTGGT CACAGTCCTG TCTCTCCTTC CATTGTACCT TGCCCTTTTC

  641  TAAAGAGCGA CTGCAAAGTA TGTTTGCGTA GGTGAGGATC TAAAACTTTA TGAGGTACGA ACATCACAGA ATTACTTTGT

  721  AATTTCAGTT TATTGTAGGC TTGGCTTTTT GGGGAGGGTT TACGTCTTAG ACCTCTTAGT GCTTCTTTGT TTCATGGTGT

  801  TCTAACTTCG AAGCATCTCT GTAGCTTTAA TGGATTCCTT TTCTGAAAGC TTTGCTCTCT TTCTTCCCCC TCGGCTTTCT

  881  CTTAGGCAAG AGGGCTAACT GTAAAGTAAG GCTTACTGCC TTGTGTTTCC AAATGTGTCC GAAGAGGAAG TGTCTTCTGT

  961  GAATCCTGTT ATGCATGAAT AACAGGAAAT AGAAAGAAAT TCACTTTCAT TATTATAAAA GTAATATGTT CGTTTAAAAA

 1041  ATTCTAATGA AGAGCTGGAG ATGCAACCCA GGGGTAGAGC ACACACTCAG CATGCAGGAG GCCCTGGGTC CAATCTTGGA

 1121  ATCTCCTCTC AGTTAACCTG ATCTCTAGCT GATTAGTAGT GAGTGCAAGC CCACTTTCCT CTTCTGCCTC ATTGCTCAGT

 1201  GATAACAGCT GTTAAACTTT GTCTTATTCT AAAACTACCT CTGTGCAAAT GCTAGCACAA TAATATATAT CATATGCACA
```

-continued

```
1281  TGATTTTTTT TTTATCTTGA AAAGTAAGTC AGTATAGCTA CAAAGTTCAC TTGGCATTGT CAACATTTCA CAGGCGTAAT
1361  ATTCCTCCTC TAGTACTGTC CTCTTCATTC TTTGTGACCA AGTTTGGAGA GAGTGCACAA ATGCCAGGGA GGTTTGTGGG
1441  AAGGTTTCTC ATGTTCTGGT AAGGCGAGTA AGAAAATAGT CTCATGCAGG TGAAATGAGT GCTATGCAGT ATATATTATA
1521  CCAGAGAACA GCAAATGACC AAATTCACAC TGAACTAGTT CAGTAAAATT GGCTTTGTCA AAGCTTTCCT TGCTTAAAAT
1601  GTAATTCCCT GTCATCCTAG TTCTGGTCTG GATTCTTTTC CTGGAGTCTT GACTTCCAGA TTCCCTGTGG ACTTTTGTTT
1681  GAGTTTCAAG CTTTTGAAAT ATAGAAACCT ATCTAACTTA ACAAACTTGG GAGAGAAAAG ACTCCAGAAC AACTGAAAAC
1761  AGACCAGGCT AAATGAATAG ACTTTATTCC TCTCTTCTTA CCTGCAGTTT TCAGATATGC AGAGTTGGAG CGGATCTTAG
1841  AGGTTGATTC ATTCATGCCT GAAGAAAACA CATTTTATAG ACCCTGTGCC CAAGTTCGTG GTGGACATCA CCCTTTATTT
1921  ACTAATTGCA CTACATAACA GGCATTTTAG AAGACTGCTC CAGTCAGAGA CCCCGCCTTA GAGGAATCTG TAAACCCTGA
2001  ACTCCTATCA CTCATGAGCA CTAGTTATGT TTGGAATGCC GTATTAAAAC AAAAGTTACA TTTCTAAACT TAAAATTTTC
2081  TAGCACAGAG ACAGTGGGAG TAGCTAACTT TGATAGACAT TTTTCTACTA AAAGTCTTTC TAAGTACATA ATCTTCTGTA
2161  AGTTGGAAAA CAGCAAAATA GAACGTCTCC TACGTAGTTA ATCTTTTTGC ATAATTTGCA CATGTAGGAG TTATTAGTAT
2241  ACGGGTAAGT TTTCACTTTT TCCCCCAACT GGAGTGTCTT GTGGCTGGGT TTGAAAAAGG GAACGGGAGG CCGCTGGAGG
2321  GGATTGGTAA ATGAGATAAA ACACCACTCA TTCAACTCAG TGACTCAGCA TTTAAATTTT CCATAAAAGG ATTAAAGGAA
2401  AATTAAACAA ATTCTTAAAG CCAAGACTCT GGAGAAACTT GTTGGTGTGC TTTAGTTTTC ACTGTTATGA CTCATGAATT
2481  TATGCATAAA TTAGTACATT TATAAAAACA TAGCCTTTTT AGAGTTTTCT GTTTGGCTAA AGTGCCATTG TTAGCATTTG
2561  GAATTACCTT TTTATGTCTT ATATTTTTTC CAAATAAAAA TAAATGTTTC TGCTGTCTTA CTACTGAAAC TACGTTGTGA
2641  GCACTTTAAA TTTCTCAAAG CAGTTTCGCC TGTTATACTT GGCGCTTAGT CATCGTCGTA CACAACAGGA CCTGATTAAG
2721  AAGGCTGTGC TGCCTCTAAG CCGGGCTAGA TTGTAGCCAC TAGCAACCAG GCTGCAATAA TTTCCCTTTG ATGACATCAT
2801  CCACTGTGGA AGAACCCAGT TGCTTCAGCC AGTCGAACTA TACAGTTCCA ACCTCATCAA ATATGGCATC TCCCTTGCCT
2881  GCTATAGCAG GGGGAGGAAA AAATGCCACC ATCTTTTTAA TCTAGCAAGC TTCTCTTTTC TTCATCTTTT TTTTTTTCTT
2961  TTAAAAAAAT TCTGATCATG GATGCTTCTT CCGATCCCTA TTTGCCTTAT GACGGGGGAG GAGACAATAT CCCCTTGAGG
3041  GAATTACATA AAAGAGGTAA GAGCATCCCC TTGCTCTGAA TCCTCTGTTG GTTGTTGTGC ATGCGGCTGG GCGGTTCTGG
3121  GGACAGGCTG TCTGTTGTCC TCTTGCTGCA ATGTGCTGCT TAGTTGCCCT GCCTTGTTGC TGTGGGAGAA TGCGACCTTC
3201  CCAGCAGGGC TGGCCCTCCC TGATTGTTTG CTCTGTGCAG ATTAGCCCTG CTTCAGATCA CATAGGGCTG CAGACTCCAT
3281  CTTCTGTGTG AAAATGCTTT CGGTTTGATT GCAGAAATAA GCTGCCTTTA CAGCCAGCTA AAGTCCTGGT GGTTGGTTGG
3361  CACCTGCAAA GTAGTATTTT TGTACCTCTG GAAACTTATA TTTTCTTTAC ACAGCAATAT CAAGTGCCGG TATGCCATTC
```

-continued

```
3441  TGTTTTGGCT GCTGCCAATT ACCATGTAGA CTTTGCACCA CAGAGTAATA GTAAAAGCTC CTAGCTGCAT TTTATAACAT
3521  TTAAAAATAG CAGGAAAGAA GAATTATTTT TGATTTAACA TGTTTTTGTC ATTTAACGTC TTAACTGATT GACATACTAT
3601  ATTGTCTGTC TCGTGGGTAT CTTGTACAAC TTGATAGGAT AAAGCAATTT AGTTTTTTTT TTTTTTTTTA AATACATCCA
3681  GAATGTAAGT CGTCAGTAGT TTTCGAACAG ATAAGTAATG GTGTTAATCT TTTGGCAGGC TTTGCCTTGG TCTCCTTAAA
3761  GCTAATTAGG TGTTACTTAA TTAAACTGCT CTTTTGCTCA TTTTCTTAAA TTATTTTTTT AAAAGATAGT TGGCATTTGC
3841  TGTTCTAGAA ATAAACTTCA AGAAACATTC TTTAGCCAGA TGACTTCATG TATGAGCCAT GTTAGTTTGA ATTATTTGCT
3921  TGGTGTTATA AACTTTATGG TTTAATACCA ACTTTTATTA TGTTTACAAG GTAAATAAGG AAAATTTCAA GTACATTTTG
4001  TATCCTGAGA ACAAATTTAA GTTCCATAGA ATTTAGGAAT TACAATGTAT TCAACAGATA CTTACTTGTC ATACTGTGCC
4081  TGCAAAACAA TAATTAGACT CTGAACAGGT GCAACAATTT TCTGTAGAAT TAGACAAGTC TTCTTTTGGC AGGTGTTACT
4161  AAGTAGGCCA TTTCCCAAGG AACAGGGAAT TTGCCAGGCT TTTGTGGTGG AGAGAATAGA ATGAATAAAT GCTGTGGGGA
4241  GTAAAGAGCT TGTCAGAAGA TGATTAGTTC TGTGGCACCA AAACCAAGAG ATCAGTTTTC CTGTGAGAAG TAAAGGAAGC
4321  ATTGTAGAAA AATAGATGTG TTGAAGTCTA CCGGTGGAGT TCCGCGTTAC ATAACTTACG GTAAATGGCC CGCCTGGCTG
4401  ACCGCCCAAC GACCCCCGCC CATTGACGTC AATAATGACG TATGTTCCCA TAGTAACGCC AATAGGGACT TTCCATTGAC
4481  GTCAATGGGT GGAGTATTTA CGGTAAACTG CCCACTTGGC AGTACATCAA GTGTATCATA TGCCAAGTAC GCCCCCTATT
4561  GACGTCAATG ACGGTAAATG GCCCGCCTGG CATTATGCCC AGTACATGAC CTTATGGGAC TTTCCTACTT GGCAGTACAT
4641  CTACGTATTA GTCATCGCTA TTACCATTGT GATGCGGTTT TGGCAGTACA TCAATGGGCG TGGATAGCGG TTTGACTCAC
4721  GGGGATTTCC AAGTCTCCAC CCCATTGACG TCAATGGGAG TTTGTTTTGG CACCAAAATC AACGGGACTT TCCAAAATGT
4801  CGTAACAACT CCGCCCCATT GACGCAAATG GGCGGTAGGC GTGTACGGTG GGAGGTCTAT ATAAGCAGAG CTCGTTTAGT
4881  GAACCGTCAG ATCTACCTCT TCCGCATCGC TGTCTGCGAG GGCCAGCTGT TGGGGTGAGT ACTCCCTCTC AAAAGCGGGC
4961  ATGACTTCTG CGCTAAGATT GTCAGTTTCC AAAAACGAGG AGGATTTGAT ATTCACCTGG CCCGCGGTGA TGCCTTTGAG
5041  GGTGGCCGCG TCCATCTGGT CAGAAAAGAC AATCTTTTTG TTGTCAAGCT TCCTTGATGA TGTCATACTT ATCCTGTCCC
5121  TTTTTTTTCC ACAGCTCGCG GTTGAGGACA AACTCTTCGC GGTCTTTCCA GTACTCTTGG ATCGGAAACC CGTCGGCCTC
5201  CGAACGGTAC TCCGCCACCG AGGGACCTGA GCGAGTCCGC ATCGACCGGA TCGGAAAACC TCGGATCCGA ATTCATAGAT
5281  AACTGATCCA GTGCCCCTAA CGTTACTGGC CGAAGCCGCT TGGAATAAGG CCGGTGTGCG TTTGTCTATA TGTTATTTTC
5361  CACCATATTG CCGTCTTTTG GCAATGTGAG GGCCCGGAAA CCTGGCCCTG TCTTCTTGAC GAGCATTCCT AGGGGTCTTT
5441  CCCCTCTCGC CAAAGGAATG CAAGGTCTGT TGAATGTCGT GAAGGAAGCA GTTCCTCTGG AAGCTTCTTG AAGACAAACA
5521  ACGTCTGTAG CGACCCTTTG CAGGCAGCGG AACCCCCCAC CTGGCGACAG GTGCCTCTGC GGCCAAAAGC CACGTGTATA
```

-continued

```
5601  AGATACACCT GCAAAGGCGG CACAACCCCA GTGCCACGTT GTGAGTTGGA TAGTTGTGGA AAGAGTCAAA TGGCTCTCCT
5681  CAAGCGTATT CAACAAGGGG CTGAAGGATG CCCAGAAGGT ACCCCATTGT ATGGGATCTG ATCTGGGGCC TCGGTGCACA
5761  TGCTTTACAT GTGTTTAGTC GAGGTTAAAA AAACGTCTAG GCCCCCCGAA CCACGGGGAC GTGGTTTTCC TTTGAAAAAC
5841  ACGATGGCCA CCTCAGCAAG TTCCCACTTG AACAAAAACA TCAAGCAAAT GTACTTGTGC CTGCCCCAGG GTGAGAAAGT
5921  CCAAGCCATG TATATCTGGG TTGATGGTAC TGGAGAAGGA CTGCGCTGCA AAACCCGCAC CCTGGACTGT GAGCCCAAGT
6001  GTGTAGAAGA GTTACCTGAG TGGAATTTTG ATGGCTCTAG TACCTTTCAG TCTGAGGGCT CCAACAGTGA CATGTATCTC
6081  AGCCCTGTTG CCATGTTTCG GGACCCCTTC CGCAGAGATC CCAACAAGCT GGTGTTCTGT GAAGTTTTCA AGTACAACCG
6161  GAAGCCTGCA GAGACCAATT TAAGGCACTC GTGTAAACGG ATAATGGACA TGGTGAGCAA CCAGCACCCC TGGTTTGGAA
6241  TGGAACAGGA GTATACTCTG ATGGGAACAG ATGGGCACCC TTTTGGTTGG CCTTCCAATG GCTTTCCTGG GCCCCAAGGT
6321  CCGTATTACT GTGGTGTGGG CGCAGACAAA GCCTATGGCA GGGATATCGT GGAGGCTCAC TACCGCGCCT GCTTGTATGC
6401  TGGGGTCAAG ATTACAGGAA CAAATGCTGA GGTCATGCCT GCCCAGTGGG AGTTCCAAAT AGGACCCTGT GAAGGAATCC
6481  GCATGGGAGA TCATCTCTGG GTGGCCCGTT TCATCTTGCA TCGAGTATGT GAAGACTTTG GGTAATAGC AACCTTTGAC
6561  CCCAAGCCCA TTCCTGGGAA CTGGAATGGT GCAGGCTGCC ATACCAACTT TAGCACCAAG GCCATGCGGG AGGAGAATGG
6641  TCTGAAGCAC ATCGAGGAGG CCATCGAGAA ACTAAGCAAG CGGCACCGGT ACCACATTCG AGCCTACGAT CCCAAGGGGG
6721  GCCTGGACAA TGCCCGTCGT CTGACTGGGT TCCACGAAAC GTCCAACATC AACGACTTTT CTGCTGGTGT CGCCAATCGC
6801  AGTGCCAGCA TCCGCATTCC CCGGACTGTC GGCCAGGAGA AGAAAGGTTA CTTTGAAGAC CGCCGCCCCT CTGCCAATTG
6881  TGACCCCTTT GCAGTGACAG AAGCCATCGT CCGCACATGC CTTCTCAATG AGACTGGCGA CGAGCCCTTC CAATACAAAA
6961  ACTAATCTAG ATCCCCCTCG CTTTCTTGCT GTCCAATTTC TATTAAAGGT TCCTTTGTTC CCTAAGTCCA ACTACTAAAC
7041  TGGGGGATAT TATGAAGGGC CTTGAGCATC TGGATTCTGC CTAATAAAAA ACATTTATTT TCATTGCAAT GATGTATTTA
7121  AATTATTTCT GAATATTTTA CTAAAAAGGG AATGTGGGAG GTCAGTGCAT TTAAAACATA AAGAAATGAA GAGGGGGATC
7201  TTCGCGATAC TGCATCGATG AGGGACAGCC CCCCCCCAAA GCCCCCAGGG ATGTAATTAC GTCCCTCCCC CGCTAGGGGG
7281  CAGCAGCGAG CCGCCCGGGG CTCCGCTCCG GTCCGGCGCT CCCCCCGCAT CCCCGAGCCG GCAGCGTGCG GGGACAGCCC
7361  GGGCACGGGG AAGGTGGCAC GGGATCGCTT TCCTCTGAAC GCTTCTCGCT GCTCTTTGAG CCTGCAGACA CCTGGGGGGA
7441  TACGGGGAAA ATAGACACCG CGGTGGAGCT CCAGCTTTTG TTCCCTTTAG TGAGGGTTAA TTAGTTCTTA ATACGACTCA
7521  CTATAGGGCG AATTGGCTAC CGGGCCGCCC ATCGAGGGTA TCATAAGCTT ATATCTATAA CAAGAAAATA TATATATAAT
7601  AAGTTATCAC GTAAGTAGAA CATGAAATAA CAATATAATT ATCGTATGAG TTAAATCTTA AAAGTCACGT AAAAGATAAT
7681  CATGCGTCAT TTTGACTCAC GCGGTCGTTA TAGTTCAAAA TCAGTGACAC TTACCGCATT GACAAGCACG CCTCACGGGA
```

-continued

```
7761  GCTCCAAGCG GCGACTGAGA TGTCCTAAAT GCACAGCGAC GGATTCGCGC TATTTAGAAA GAGAGAGCAA TATTTCAAGA
7841  ATGCATGCGT CAATTTTACG CAGACTATCT TTCTAGGGTT AAATCGATAG ATGCGATCCT GCAGGTCTCC CTATAGTGAG
7921  TCGTATTAAT TTCGATAAGC CAGCTGCATT AATGAATCGG CCAACGCGCG GGGAGAGGCG GTTTGCGTAT TGGGCGCTCT
8001  TCCGCTTCCT CGCTCACTGA CTCGCTGCGC TCGGTCGTTC GGCTGCGGCG AGCGGTATCA GCTCACTCAA AGGCGGTAAT
8081  ACGGTTATCC ACAGAATCAG GGGATAACGC AGGAAAGAAC ATGTGAGCAA AAGGCCAGCA AAAGGCCAGG AACCGTAAAA
8161  AGGCCGCGTT GCTGGCGTTT TTCCATAGGC TCCGCCCCCC TGACGAGCAT CACAAAAATC GACGCTCAAG TCAGAGGTGG
8241  CGAAACCCGA CAGGACTATA AAGATACCAG GCGTTTCCCC CTGGAAGCTC CCTCGTGCGC TCTCCTGTTC CGACCCTGCC
8321  GCTTACCGGA TACCTGTCCG CCTTTCTCCC TTCGGGAAGC GTGGCGCTTT CTCATAGCTC ACGCTGTAGG TATCTCAGTT
8401  CGGTGTAGGT CGTTCGCTCC AAGCTGGGCT GTGTGCACGA ACCCCCCGTT CAGCCCGACC GCTGCGCCTT ATCCGGTAAC
8481  TATCGTCTTG AGTCCAACCC GGTAAGACAC GACTTATCGC CACTGGCAGC AGCCACTGGT AACAGGATTA GCAGAGCGAG
8561  GTATGTAGGC GGTGCTACAG AGTTCTTGAA GTGGTGGCCT AACTACGGCT ACACTAGAAG GACAGTATTT GGTATCTGCG
8641  CTCTGCTGAA GCCAGTTACC TTCGGAAAAA GAGTTGGTAG CTCTTGATCC GGCAAACAAA CCACCGCTGG TAGCGGTGGT
8721  TTTTTGTTT GCAAGCAGCA GATTACGCGC AGAAAAAAAG GATCTCAAGA AGATCCTTTG ATCTTTTCTA CGGGGTCTGA
8801  CGCTCAGTGG AACGAAAACT CACGTTAAGG GATTTTGGTC ATGAGATTAT CAAAAAGGAT CTTCACCTAG ATCCTTTTAA
8881  ATTAAAAATG AAGTTTTAAA TCAATCTAAA GTATATATGA GTAAACTTGG TCTGACAGTT ACCAATGCTT AATCAGTGAG
8961  GCACCTATCT CAGCGATCTG TCTATTTCGT TCATCCATAG TTGCCTGACT CCCCGTCGTG TAGATAACTA CGATACGGGA
9041  GGGCTTACCA TCTGGCCCCA GTGCTGCAAT GATACCGCGA GACCCACGCT CACCGGCTCC AGATTTATCA GCAATAAACC
9121  AGCCAGCCGG AAGGGCCGAG CGCAGAAGTG GTCCTGCAAC TTTATCCGCC TCCATCCAGT CTATTAATTG TTGCCGGGAA
9201  GCTAGAGTAA GTAGTTCGCC AGTTAATAGT TTGCGCAACG TTGTTGCCAT TGCTACAGGC ATCGTGGTGT CACGCTCGTC
9281  GTTTGGTATG GCTTCATTCA GCTCCGGTTC CCAACGATCA AGGCGAGTTA CATGATCCCC CATGTTGTGC AAAAAAGCGG
9361  TTAGCTCCTT CGGTCCTCCG ATCGTTGTCA GAAGTAAGTT GGCCGCAGTG TTATCACTCA TGGTTATGGC AGCACTGCAT
9441  AATTCTCTTA CTGTCATGCC ATCCGTAAGA TGCTTTTCTG TGACTGGTGA GTACTCAACC AAGTCATTCT GAGAATAGTG
9521  TATGCGGCGA CCGAGTTGCT CTTGCCCGGC GTCAATACGG GATAATACCG CGCCACATAG CAGAACTTTA AAAGTGCTCA
9601  TCATTGGAAA ACGTTCTTCG GGGCGAAAAC TCTCAAGGAT CTTACCGCTG TTGAGATCCA GTTCGATGTA ACCCACTCGT
9681  GCACCCAACT GATCTTCAGC ATCTTTTACT TTCACCAGCG TTTCTGGGTG AGCAAAAACA GGAAGGCAAA ATGCCGCAAA
9761  AAAGGGAATA AGGGCGACAC GGAAATGTTG AATACTCATA CTCTTCCTTT TTCAATATTA TTGAAGCATT TATCAGGGTT
9841  ATTGTCTCAT GAGCGGATAC ATATTTGAAT GTATTTAGAA AAATAAACAA ATAGGGGTTC CGCGCACATT TCCCCGAAAA
```

-continued

```
 9921  GTGCCACCTG ACGTCTAAGA AACCATTATT ATCATGACAT TAACCTATAA AAATAGGCGT ATCACGAGGC CCTTTCGTCT

10001  CGCGCGTTTC GGTGATGACG GTGAAAACCT CTGACACATG CAGCTCCCGG AGACGGTCAC AGCTTGTCTG TAAGCGGATG

10081  CCGGGAGCAG ACAAGCCCGT CAGGGCGCGT CAGCGGGTGT TGGCGGGTGT CGGGGCTGGC TTAACTATGC GGCATCAGAG

10161  CAGATTGTAC TGAGAGTGCA CCATATCGAC GCTCTCCCTT ATGCGACTCC TGCATTAGGA AGCAGCCCAG TAGTAGGTTG

10241  AGGCCGTTGA GCACCGCCGC CGCAAGGAAT GGTGCATGCA AGGAGATGGC GCCCAACAGT CCCCCGGCCA CGGGGCCTGC

10321  CACCATACCC ACGCCGAAAC AAGCGCTCAT GAGCCCGAAG TGGCGAGCCC GATCTTCCCC ATCGGTGATG TCGGCGATAT

10401  AGGCGCCAGC AACCGCACCT GTGGCGCCGG TGATGCCGGC CACGATGCGT CCGGCGTAGA GGATCTGGCT AGCGATGACC

10481  CTGCTGATTG GTTCGCTGAC CATTTCCGGG GTGCGGAACG GCGTTACCAG AAACTCAGAA GGTTCGTCCA ACCAAACCGA

10561  CTCTGACGGC AGTTTACGAG AGAGATGATA GGGTCTGCTT CAGTAAGCCA GATGCTACAC AATTAGGCTT GTACATATTG

10641  TCGTTAGAAC GCGGCTACAA TTAATACATA ACCTTATGTA TCATACACAT ACGATTTAGG TGACACTATA GAATACACCT

10721  GCAGGACGTC CCAATGATCT TAAGTTAA
```

5' ITR (Virology 172(1), 156-169 (1989), GenBank: J04364.2, SEQ ID NO: 9):
ccctagaaagataatcatattgtgacgtacgttaaagataatcatgcgtaaaattgacgcatg 3' ITR (Virology 172(1), 156-169 (1989), GenBank: J04364.2, SEQ ID NO: 10):
catgcgtcaattttacgcagactatctttctaggg HS4 Insulator (Cell 74(3):505-14 (1993), Proc Natl Acad Sci USA. 94(2):575-80 (1997),
GenBank: U78775.2, SEQ ID NO: 11):
gagctcacggggacagcccccccccaaagcccccagggatgtaattacgtccctcccccgctagggggcagcagcgagccgcccggggct ccgctccggtccggcgctccccccgcatccccgagccggcagcgtgcggggacagcccgggcacggggaaggtggcacgggatcgctttc ctctgaacgcttctcgctgctctttgagcctgcagacacctgggggggatacggggaaaaagctttaggctgaaagagagatttagaatgacagaa tcatagaacggcctgggttgcaaaggagcacagtgctcatccagatccaacccccctgctatgtgcagggtcatcaaccagcagcccaggctgc ccagagccacatccagcctggccttgaatgcctgcagggatggggcatccacagcctccttgggcaacctgttcagtgcgtcaccaccctctgg gggaaaaactgcctcctcatatccaacccaaacctcccctgtctcagtgtaaagccattcccccttgtcctatcaaggggggagtttgctgtgacatt gttggtctggggtgacacatgtttgccaattcagtgcatcacggagaggcagatcttggggataaggaagtgcaggacagcatggacgtgggac atgcaggtgttgagggctctgggacactctccaagtcacagcgttcagaacagccttaaggataagaagataggatagaaggacaaagagcaa gttaaaacccagcatggagaggagcacaaaaaggccacagacactgctggtccctgtgtctgagcctgcatgtttgatggtgtctggatgcaag cagaaggggtggaagagcttgcctggagagatacagctgggtcagtaggactgggacaggcagctggagaattgccatgtagatgttcataca atcgtcaaatcatgaaggctggaaaagccctccaagatccccaagaccaaccccaacccacccaccgtgcccactggccatgtccctcagtgc cacatccccacagttcttcatcacctccagggacggtgacccccccacctccgtgggcagctgtgccactgcagcaccgctctttggagaaggt -continued aaatcttgctaaatccagcccgaccctcccctggcacaacgtaaggccattatctctcatccaactccaggacggagtcagtgagaatatt EASE (Cytotechnology 28(1-3):9-17 (1998), GenBank: AF193761.1, SEQ ID NO: 12):
gaattctgaacttttcttttgttcccttcccttctaccacaccctaattgtaatccattttaatttcctggtcacagtcctgtctctccttccattgtaccttgcc cttttctaaagagcgactgcaaagtatgtttgcgtaggtgaggatctaaaactttatgaggtacgaacatcacagaattactttgtaatttcagtttattg taggcttggcttttttggggagggtttacgtcttagacctcttagtgcttctttgtttcatggtgttctaacttcgaagcatctctgtagctttaatggattcct tttctgaaagctttgctctctttcttccccctcggctttctcttaggcaagagggctaactgtaaagtaaggcttactgccttgtgtttccaaatgtgtccg aagaggaagtgtcttctgtgaatcctgttatgcatgaataacaggaaatagaaagaaattcactttcattattataaaagtaatatgttcgtttaaaaaat tctaatgaagagctggagatgcaacccaggggtagagcacacactcagcatgcaggaggccctgggtccaatcttggaatctcctctcagttaa cctgatctctagctgattagtagtgagtgcaagcccactttcctcttctgcctcattgctcagtgataacagctgttaaactttgtcttattctaaaactac ctctgtgcaaatgctagcacaataatatatatcatatgcacatgattttttttttatcttgaaaagtaagtcagtatagctacaaagttcacttggcattgtc aacatttcacaggcgtaatattcctcctctagtactgtcctcttcattctttgtgaccaagtttggagagagtgcacaaatgccagggaggtttgtggg aaggtttctcatgttctggtaaggcgagtaagaaaatagtctcatgcaggtgaaatgagtgctatgcagtatatattataccagagaacagcaaatg accaaattcacactgaactagttcagtaaaattggctttgtcaaagctttccttgcttaaaatgtaattccctgtcatcctagttctggtctggattcttttc ctggagtcttgacttccagattccctgtggacttttgtttgagtttcaagcttttgaaatatagaaacctatctaacttaacaaacttgggagagaaaag actccagaacaactgaaaacagaccaggctaaatgaatagactttattcctctcttcttacctgcagttttcagatatgcagagttggagcggatctta gaggttgattcattcatgcctgaagaaaacacattttatagaccctgtgcccaagttcgtggtggacatcaccctttatttactaattgcactacataac aggcattttagaagactgctccagtcagagaccccgccttagaggaatctgtaaaccctgaactcctatcactcatgagcactagttatgtttggaat gccgtattaaaacaaaagttacatttctaaacttaaaattttctagcacagagacagtgggagtagctaactttgatagacatttttctactaaaagtctt tctaagtacataatcttctgtaagttggaaaacagcaaaatagaacgtctcctacgtagttaatctttttgcataatttgcacatgtaggagttattagtat acgggtaagttttcactttttcccccaactggagtgtcttgtggctgggtttgaaaaagggaacgggaggccgctggaggggattggtaaatgaga taaaacaccactcattcaactcagtgactcagcatttaaattttccataaaaggattaaaggaaaattaaacaaattcttaaagccaagactctggag aaacttgttggtgtgctttagttttcactgttatgactcatgaatttatgcataaattagtacatttataaaaacatagcctttttagagttttctgtttggctaa agtgccattgttagcatttggaattacctttttatgtcttatattttttccaaataaaaataaatgtttctgctgtcttactactgaaactacgttgtgagcact ttaaatttctcaaagcagtttcgcctgttatacttggcgcttagtcatcgtcgtacacaacaggacctgattaagaaggctgtgctgcctctaagccgg gctagattgtagccactagcaaccaggctgcaataatttccctttgatgacatcatccactgtggaagaacccagttgcttcagccagtcgaactat acagttccaacctcatcaaatatggcatctcccttgcctgctatagcaggggggaggaaaaaatgccaccatctttttaatctagcaagcttctcttttct tcatctttttttttttcttttaaaaaaattctgatcatggatgcttcttccgatccctatttgccttatgacgggggaggagacaatatccccttgagggaat -continued

```
tacataaaagaggtaagagcatccccttgctctgaatcctctgttggttgttgtgcatgcggctgggcggttctggggacaggctgtctgttgtcctc

ttgctgcaatgtgctgcttagttgccctgccttgttgctgtgggagaatgcgaccttcccagcagggctggccctccctgattgtttgctctgtgcag

attagccctgcttcagatcacatagggctgcagactccatcttctgtgtgaaaatgctttcggtttgattgcagaaataagctgcctttacagccagct

aaagtcctggtggttggttggcacctgcaaagtagtatttttgtacctctggaaacttatattttctttacacagcaatatcaagtgccggtatgccattc

tgttttggctgctgccaattaccatgtagactttgcaccacagagtaatagtaaaagctcctagctgcattttataacatttaaaaatagcaggaaaga

agaattattttgatttaacatgtttttgtcatttaacgtcttaactgattgacatactatattgtctgtctcgtgggtatcttgtacaacttgataggataaag

caatttagtttttttttttttttaaatacatccagaatgtaagtcgtcagtagttttcgaacagataagtaatggtgttaatcttttggcaggctttgccttgg

tctccttaaagctaattaggtgttacttaattaaactgctcttttgctcattttcttaaattatttttttaaaagatagttggcatttgctgttctagaaataaact

tcaagaaacattctttagccagatgacttcatgtatgagccatgttagtttgaattatttgcttggtgttataaactttatggtttaataccaacttttattatg

tttacaaggtaaataaggaaaatttcaagtacattttgtatcctgagaacaaatttaagttccatagaatttaggaattacaatgtattcaacagatactt

acttgtcatactgtgcctgcaaaacaataattagactctgaacaggtgcaacaattttctgtagaattctgtgcttagtaaaaggttgctttttatatttg

agagaaatctatttaaagatcatggcccatattttgtgcatatttttttctgtataccatttccatatatgtgtgtgtgtgtacatatatgtatatatataaaat

gttagaacatttgaggaaatagctaaaagtacaaaagtaatgttttctaatttttactccccgaggttatttctttttttccttgttttcctttctctttgttccta

tcatcagtttctagtaatactcttattgaacagtgattattcaaatgtcacattatttattaatcagcatttaaatggtaaaaccagacagaccatactttct

ctgagtgatgacaacatccatttttagtaatgataaactagaagggtcaggcttgatagtctttgtcaggactaatttatagactgtaaaggccaaaag

aaataagaaatgtcaaaactcttgtgaaactagacatacagatattaccaagagagaaactagaaaaaaaaattctgtgacatggccttaatttgcc

aggcaccatcgtgaaggcctaaacccctcttagaagctcactcagatgccatcctgcttctctgatgagacttcctgtcaatacaaacatggtttag

gaagaatgagtgtttgcagtataaaccagttatttactagccttactttaagaatatactgtagtgtccttgagagagaaggtgtttgttttctgtaatttat

gacccttttgaaaccatagatcagcacaaaggaactggggatatggaaatgggaacataacttaaatccagaaaagtgaatcagattccctgtga

ggacaaaatgcaatatttagaaataggatctttaggctgggagggagaaaagaggaaaaaaatgaaagtataacatttttcataagtataagatttc

ataaaaaaatgaaatctataacatagagggtgttgataaagtaagcatggatatgtttagtaaagccgacagagctaagaattagctttgtgagtaat

tggacttaatcaaacttttcaaggtgggatacaaatgaataattgtagaataaatggataaaagaatatgaataaaatgaatagtgagtaaaaattaa

aaatgaagctttttacttaagtgcatattgtagtggctagaacaaatagattcaaaatagaaatcatttatatattcttgattagaagataaaatgttatttt

agaaatagccatctttggaagtaaatttgctatgttgaacaaccaggttttcataatttgtctcttatttttttttcaggaagaaaaaaaaacttgacttattt

gtactgctaagttttattcaatgtgcttgcttgcttaaatttttaatgaagttttagtcatttggtggtcaaattcctttttatctactaatcgcttttcgtggcttt

ggcttttaaaattgtatttactgcatttatttgtgtgtattaggagtcaggtggccatatgtgccatggcatgtgtatggaagcacttgtggacatgaatc

ttctctttccacatgtgtgggccactggaatcaaactagtgtcaggcttggcagcaatttttaatgcactgagccttctcaccacccccctggacttttgt
```

Figure 2B:
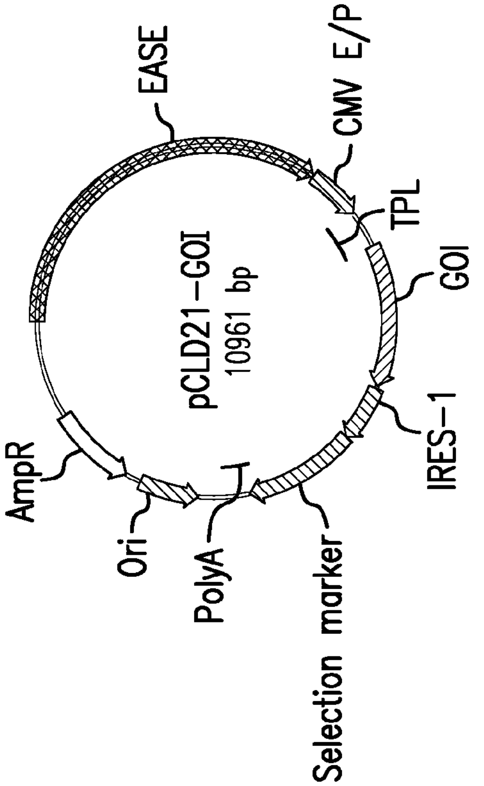
FIGS. 2A-2E illustrate the structure of exemplary expression vectors with GOI: pCLD116-GOI (FIG. 2A), pCLD21-GOI (FIG. 2B), pCLD22-GOI (FIG. 2C), pCLD12-HOI (FIG. 2D), and pCLD14-GOI (FIG. 2E).
Figure 2C:
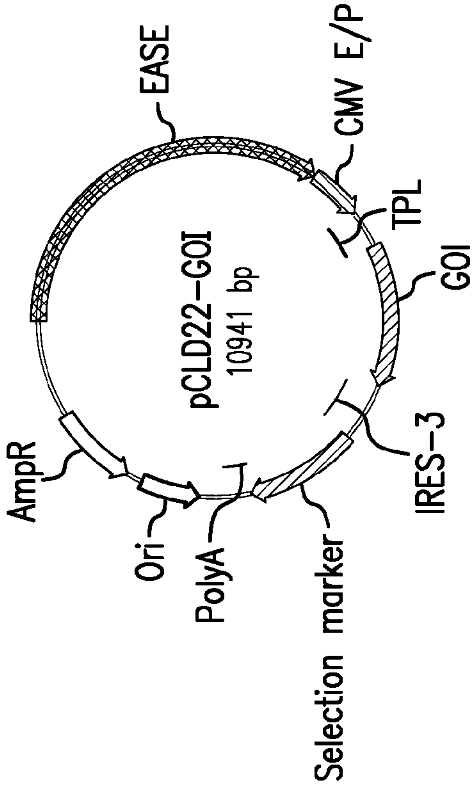
Figure 2A:
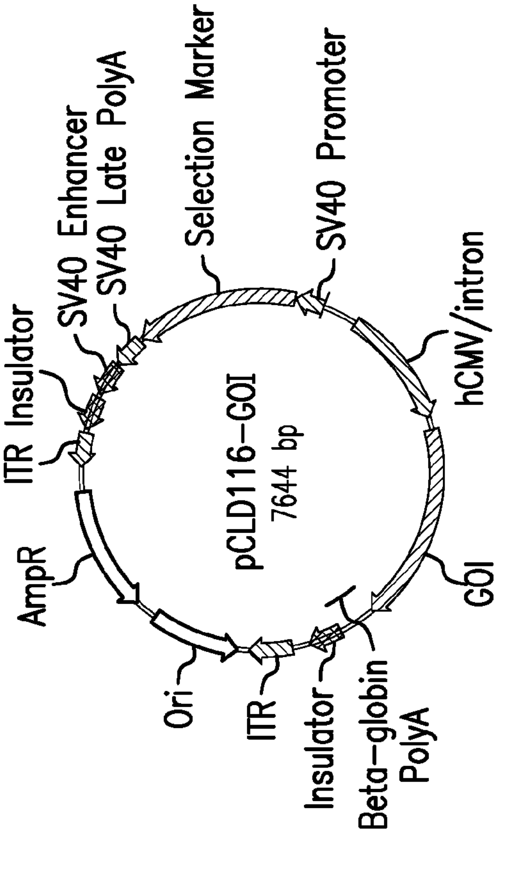
Figure 2D:
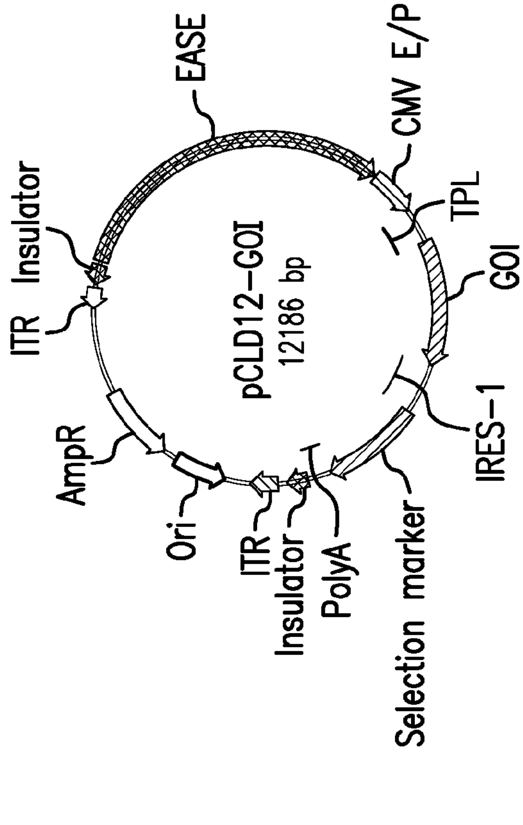
Figure 2E:
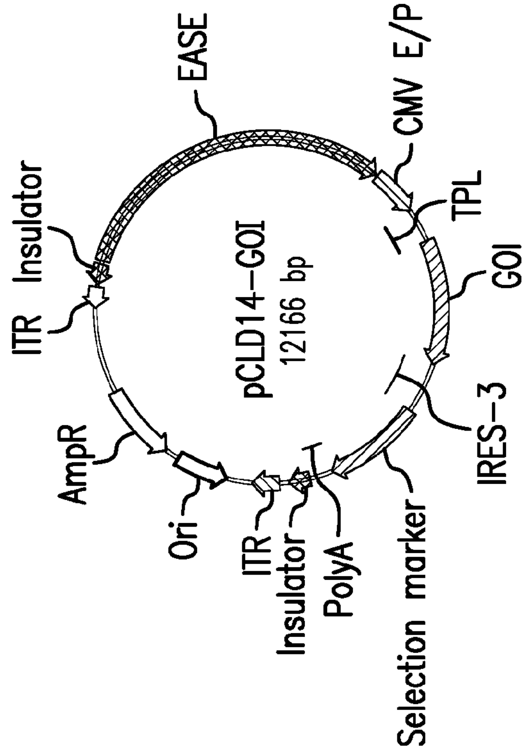

-continued ggggcagaaggggacaagtttaatattttatttactccatgtagaaagcctttaaaaaatgtagaaagcctttaaactacctattgttttatttgaattatg aagctcttgtgtttatataaattacagttaggtactgtggagactaatggtagctacaatagtaatattaatagctaaaacttagtagaatctgattgagt taatttggccctttccatcataaggtactcttcccaagcatcacatgacctgtgcttaagtctggtgggggcttatggctttgatattgaaaacaaatcg tcaaggatgttaatttcttgttactgctattacactgaattttctatggctctttaggagaggaagagacaagtcttcttttggcaggtgttactaagtagg ccatttcccaaggaacagggaatttgccaggcttttgtggtggagagaatagaatgaataaatgctgtggggagtaaagagcttgtcagaagatg attagttctgtggcaccaaaaccaagagatcagttttcctgtgagaagtaaaggaagcattgtagaaaaatagatgtgttgaagtct Beta-globin polyA (Proc Natl Acad Sci USA 87(10):3924-8 (1990), GenBank: AH001475, SEQ ID NO: 13):
tgccctggcccacaagtatcactaagctcgctttcttgctgtccaatttctattaaaggttcctttgttccctaagtccaactactaaactgggggatatt atgaagggccttgagcatctggattctgcctaataaaaaacatttattttcattgcaatgatgtatttaaattatttctgaatattttactaaaaagggaatg tgggaggtcagtgcatttaaaacataaagaaatgaagagctagttcaaaccttgggaaaatacactatatcttaaa SV40 late polyA (Mol Cell Biol. 9(10):4248-58 (1989), GenBank: J02400.1, SEQ ID NO: 14):
cagacatgataagatacattgatgagtttggacaaaccacaactagaatgcagtgaaaaaaatgctttatttgtgaaatttgtgatgctattgctttattt gtaaccattataagctgcaataaacaagttaacaacaacaattgcattcattttatgtttcaggttcagggggaggtgtgggaggttttttaaagcaag taaaacctctacaaatgtggta SV40 promoter (Nature 273(5658):113-20 (1978), Proc. Natl. Acad. Sci. USA 81 (1):23-27 (1984), GenBank: J02400.1, SEQ ID NO: 15):
tgcatctcaattagtcagcaaccatagtcccgcccctaactccgcccatcccgcccctaactccgcccagttccgcccattctccgccccatcgct gactaattttttttatttatgcagaggccgaggccgcctcggcctctgagctattccagaagtagtgaggaggcttttttggaggcctaggcttttgca aa hCMV immediate-early enhancer/promoter (derived from GenBank X17403.1, SEQ ID NO: 16):
ggagttccgcgttacataacttacggtaaatggcccgcctggctgaccgcccaacgacccccgcccattgacgtcaataatgacgtatgttcccat agtaacgccaatagggactttccattgacgtcaatgggtggagtatttacggtaaactgcccacttggcagtacatcaagtgtatcatatgccaagt acgcccccctattgacgtcaatgacggtaaatggcccgcctggcattatgcccagtacatgaccttatgggactttcctacttggcagtacatctacgt attagtcatcgctattaccatggtgatgcggttttggcagtacatcaatgggcgtggatagcggtttgactcacggggatttccaagtctccacccca ttgacgtcaatgggagtttgttttggcaccaaaatcaacgggactttccaaaatgtcgtaacaactccgccccattgacgcaaatgggcggtaggc gtgtacggtgggaggtctatataagcagagctcgtttagtgaaccgtcagatc -continued TPL (SEQ ID NO: 17):
ctcttccgcatcgctgtctgcgagggccagctgttggggtgagtactccctctcaaaagcgggcatgacttctgcgctaagattgtcagtttccaaa aacgaggaggatttgatattcacctggcccgcggtgatgcctttgagggtggccgcgtccatctggtcagaaaagacaatctttttgttgtcaagct tccttgatgatgtcatacttatcctgtcccttttttttccacagctcgcggttgaggacaaactcttcgcggtctttccagtactcttggatcggaaaccc gtcggcctccgaacggtactccgccaccgagggacctgagcgagtccgcatcgaccggatcggaaaacctc hCMV promoter/intron in pCLD116 (derived from GenBank X17403.1, SEQ ID NO: 18):
gttacataacttacggtaaatggcccgcctggctgaccgcccaacgacccccgcccattgacgtcaataatgacgtatgttcccatagtaacgcca atagggactttccattgacgtcaatgggtggagtatttacggtaaactgcccacttggcagtacatcaagtgtatcatatgccaagtacgccccctat tgacgtcaatgacggtaaatggcccgcctggcattatgcccagtacatgaccttatgggactttcctacttggcagtacatctacgtattagtcatcg ctattaccatggtgatgcggttttggcagtacatcaatgggcgtggatagcggtttgactcacggggatttccaagtctccaccccattgacgtcaat gggagtttgttttggcaccaaaatcaacgggactttccaaaatgtcgtaacaactccgccccattgacgcaaatgggcggtaggcgtgtacggtg ggaggtctatataagcagagctcgtttagtgaaccgtcagatc pUC replication origin On (SEQ ID NO: 19):
tttccataggctccgcccccctgacgagcatcacaaaaatcgacgctcaagtcagaggtggcgaaacccgacaggactataaagataccaggc gtttccccctggaagctccctcgtgcgctctcctgttccgaccctgccgcttaccggatacctgtccgcctttctcccttcgggaagcgtggcgcttt ctcatagctcacgctgtaggtatctcagttcggtgtaggtcgttcgctccaagctgggctgtgtgcacgaaccccccgttcagcccgaccgctgcg ccttatccggtaactatcgtcttgagtccaacccggtaagacacgacttatcgccactggcagcagccactggtaacaggattagcagagcgagg tatgtaggcggtgctacagagttcttgaagtggtggcctaactacggctacactagaaggacagtatttggtatctgcgctctgctgaagccagtta ccttcggaaaaagagttggtagctcttgatccggcaaacaaaccaccgctggtagcggtggtttttttgtttgcaagcagcagattacgcgcagaa aaaaaggatctcaa Ampicillin resistance gene (SEQ ID NO: 20):
ttaccaatgcttaatcagtgaggcacctatctcagcgatctgtctatttcgttcatccatagttgcctgactccccgtcgtgtagataactacgatacgg gagggcttaccatctggccccagtgctgcaatgataccgcgagacccacgctcaccggctccagatttatcagcaataaaccagccagccgga agggccgagcgcagaagtggtcctgcaactttatccgcctccatccagtctattaattgttgccgggaagctagagtaagtagttcgccagttaata gtttgcgcaacgttgttgccattgctacaggcatcgtggtgtcacgctcgtcgtttggtatggcttcattcagctccggttcccaacgatcaaggcga gttacatgatcccccatgttgtgcaaaaaagcggttagctccttcggtcctccgatcgttgtcagaagtaagttggccgcagtgttatcactcatggtt atggcagcactgcataattctcttactgtcatgccatccgtaagatgcttttctgtgactggtgagtactcaaccaagtcattctgagaatagtgtatgc -continued ggcgaccgagttgctcttgcccggcgtcaatacgggataataccgcgccacatagcagaactttaaaagtgctcatcattggaaaacgttcttcgg ggcgaaaactctcaaggatcttaccgctgttgagatccagttcgatgtaacccactcgtgcacccaactgatcttcagcatcttttactttcaccagc gtttctgggtgagcaaaaacaggaaggcaaaatgccgcaaaaaagggaataagggcgacacggaaatgttgaatactcat GS gene (SEQ ID NO: 21):
atggccacctcagcaagttcccacttgaacaaaaacatcaagcaaatgtacttgtgcctgccccagggtgagaaagtccaagccatgtatatctg ggttgatggtactggagaaggactgcgctgcaaaacccgcaccctggactgtgagcccaagtgtgtagaagagttacctgagtggaattttgatg gctctagtacctttcagtctgagggctccaacagtgacatgtatctcagccctgttgccatgtttcgggaccccttccgcagagatcccaacaagct ggtgttctgtgaagttttcaagtacaaccggaagcctgcagagaccaatttaaggcactcgtgtaaacggataatggacatggtgagcaaccagc acccctggtttggaatggaacaggagtatactctgatgggaacagatgggcaccatttggttggccttccaatggattcctgggccccaaggtc cgtattactgtggtgtgggcgcagacaaagcctatggcagggatatcgtggaggctcactaccgcgcctgcttgtatgctggggtcaagattaca ggaacaaatgctgaggtcatgcctgcccagtgggagttccaaataggaccctgtgaaggaatccgcatgggagatcatctctgggtggcccgttt catcttgcatcgagtatgtgaagactttggggtaatagcaacctttgaccccaagcccattcctgggaactggaatggtgcaggctgccataccaa ctttagcaccaaggccatgcgggaggagaatggtctgaagcacatcgaggaggccatcgagaaactaagcaagcggcaccggtaccacattc gagcctacgatcccaagggggcctggacaatgcccgtcgtctgactgggttccacgaaacgtccaacatcaacgacttttctgctggtgtcgcc aatcgcagtgccagcatccgcattccccggactgtcggccaggagaagaaaggttactttgaagaccgccgcccctctgccaattgtgacccctt tgcagtgacagaagccatcgtccgcacatgccttctcaatgagactggcgacgagcccttccaatacaaaaactaa SV40 enhancer (SEQ ID NO: 22):
gctgtggaatgtgtgtcagttagggtgtggaaagtccccaggctccccagcaggcagaagtatgcaaagcatgcatctcaattagtcagcaacca ggtgtggaaagtccccaggctccccagcaggcagaagtatgcaaagcatgcatctcaattagtcagcaaccatagtcccgcccctaactccgcc catcccgcccctaactccgcccagttccgcccattctccgctccatcg The coding sequence for the GOI was synthesized by Blue Heron Biotech, LLC, WA and inserted into pCLD116 (FIG. 2A), pCLD21 (FIG. 2B), pCLD22 (FIG. 2C), pCLD12 (FIG. 2D), or pCLD14 (FIG. 2E). In pCLD21-GOI, pCLD22-GOI, pCLD12-GOI, or pCLD14-GOI, the GOI coding sequence was driven by a hCMV immediate-early enhancer/promoter with adenovirus TPL. The eukaryotic selectable marker was connected with GOI through IRES and followed by a Poly A signal. Chicken β-globin HS4 insulator and piggyBac® ITR were placed at the interface of bacteria backbone and mammalian expression cassettes. EASE was placed at 5' of the hCMV immediate-early enhancer/promoter. Standard ampicillin resistant (AmpR) gene and pUC replication origin (Ori) were used for plasmid replication in *E, coli.*

For expression of multiple-chain recombinant proteins, such as monoclonal antibodies, a first expression vector encoding a first GOI (e.g., light chain) and a second expression vector encoding a second GOI (e.g., heavy chain) were co-transfected into mammalian host cells. The eukaryotic selection markers for the first expression vector and the second expression vector are different to ensure sufficient selection pressure for both of the polypeptides.

To compare with a commercially available expression vector, the coding sequence for the GOI was inserted into pEE14.4 (Lonza. U.K.), after digested with restriction enzymes. HindIII and EcoRI (New England Biolabs, MA).

Example 2: Host CHO Cell Lines

Various host CHO cell lines, including CHOK1SV™ (Lonza: Slough. U.K.). HD-BIOP1 (Horizon Discovery. U.K.). CHOZN® (Sigma-Aldrich. St. Louis, MO) and Merck proprietary GS knock-out CHO host cell lines CHO-1. CHO-2, and CHO-3, were used.

Example 3: Selection of Stably Transfected Cell Lines

Transposase mRNA was synthesized by using MEGA-script® T7 Kit (Thermo Fisher Scientific. MA). Plasmids were prepared by using QIAGEN kit (QIAGEN. Germany). Plasmid and Transposase mRNA were co-transfected into CHO host cells through electroporation. After the recovery period, transfected cells were selected in appropriate selection media. CD-CHO (Thermo Fisher Scientific, Waltham, MA). The stable cells were then evaluated using a shake flask fed-batch process when viability reached ~90%. Cells were seeded at $0.5 \times 10^6$ viable cells/mL in chemically defined Dynamis™ medium (Thermo Fisher Scientific, Waltham, MA). Chemically defined feeding media, Cell-Boost 7a and Cell Boost 7b (GE Healthcare Life Sciences, Logan, UT), were supplemented daily into culture together with D-glucose (Sigma-Aldrich, St. Louis, MO). Glucose and lactate levels were measured everyday using the RAN-DOX RX imola chemistry analyzer (Crumlin, UK). Cell density and viability were measured using a Beckman Coulter ViCELL cell counter (Beckman Coulter, Indianapolis, IN).

Figure 3:
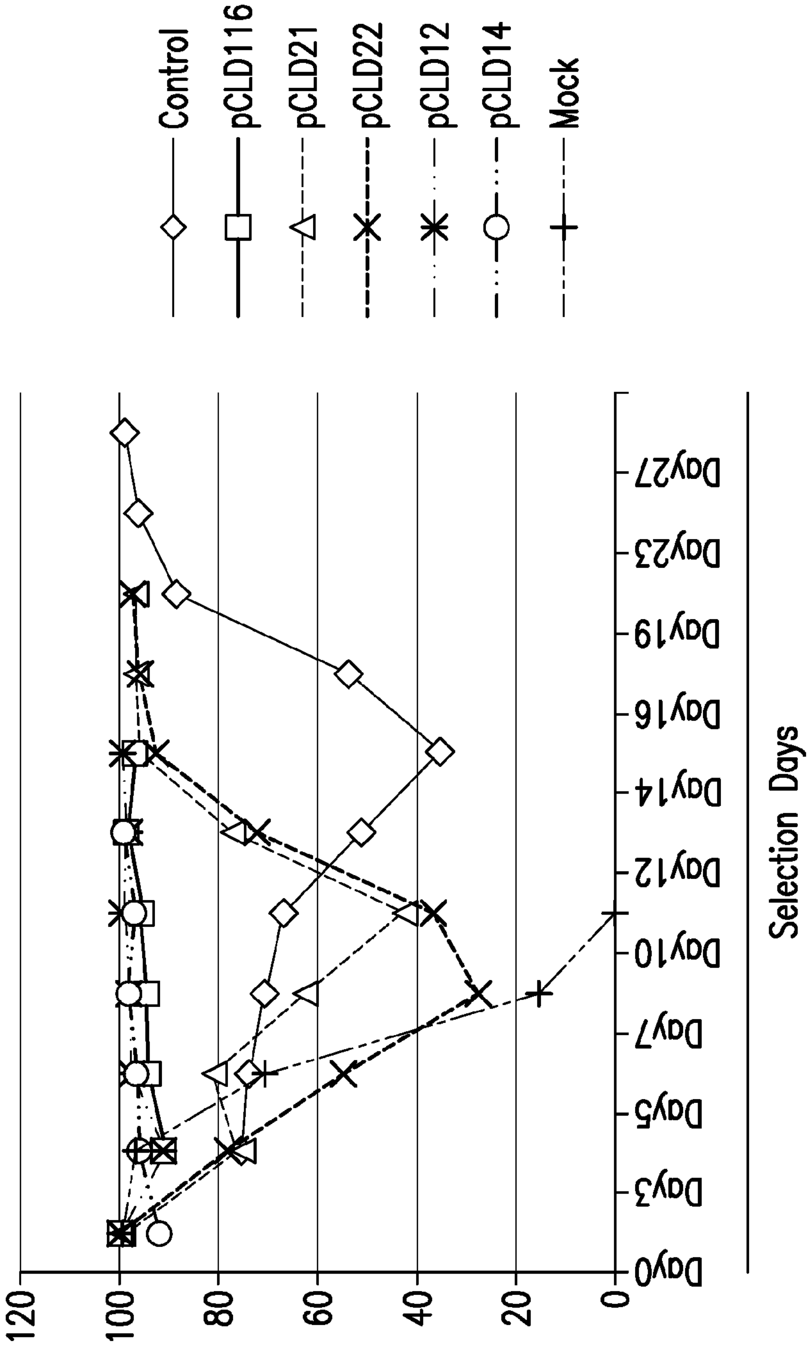
FIG. 3 shows that the expression vectors using transposon technology significantly reduced selection time for stable expressing cells.
Figure 4:
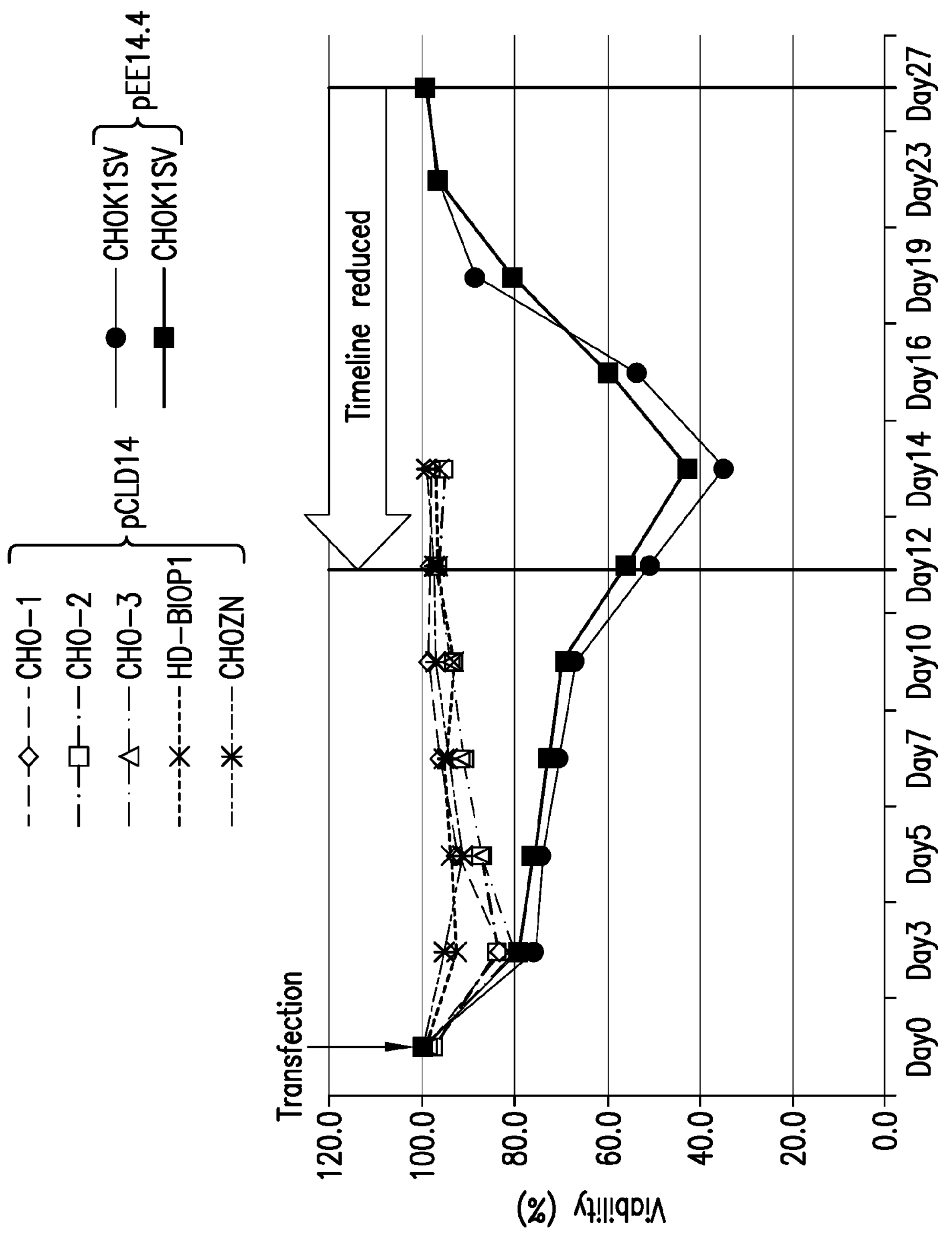
FIG. 4 shows that the shortened selection time for stable expressing cells is independent of host cell lines.

FIG. 3 demonstrates that all expression vectors illustrated in FIGS. 2A-2E reduced the selection time for stably transfected cells, compared to the control vector pEE14.4. The results showed that the selection stringency varies depending on the vector design. Without transposon technology, pCLD22 exhibited higher stringency than pCLD21 and the control vector (FIG. 3). However, with transposon technology, the stable recovery rates for pCLD116, pCLD12, and pCLD14 were significantly improved for up to two weeks, compared to the control vector, which suggests a higher genomic integration efficiency (FIG. 3). The reduction of selection time for stably transfected cells is independent of host cell lines (FIG. 4).

Example 4: Expression of a Monoclonal Antibody Using the Designed Expression Vectors The light chain and the heavy chain of an exemplary monoclonal antibody were separately cloned into two expression vectors with the same design except the mammalian selection marker. Monoclonal antibody production levels, i.e., titers, were determined using Protein-A HPLC (Waters. MA).

Figure 5:
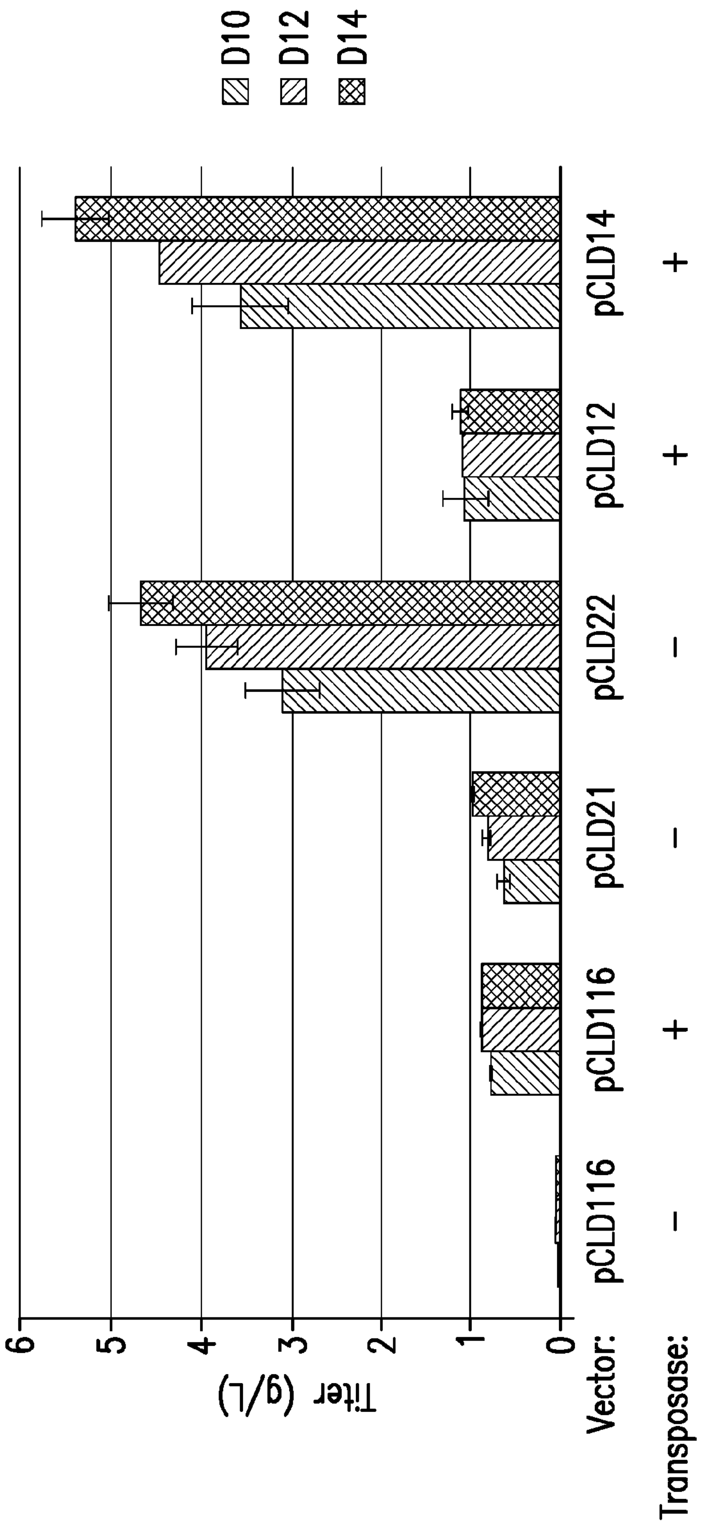
FIG. 5 demonstrates that high expression of a monoclonal antibody was achieved by engineering expression vectors with appropriate configurations.

FIG. 5 demonstrates that the expression of the monoclonal antibody highly depends on the vector design combining various regulatory elements. For the low expressing vector design, pCLD116, transposon technology increased the expression level by up to 10-fold (FIG. 5). But, with selected regulatory elements, including TPL. IRES, and EASE, pCLD21 was able to achieve similar expression level, compared to pCLD116 co-transfected with transposase mRNA (FIG. 5). In addition, by reducing the strength of IRES through deletion of nucleotides from its 3' end, pCLD22 further increased the expression level by up to 5-fold (FIG. 5). On the other hand, transposon technology on top of regulatory elements, including TPL. IRES, and EASE, has marginal effect on further increasing the expression level, demonstrated by comparison between pCLD12 and pCLD21 and comparison between pCLD14 and pCLD22 (FIG. 5).

Example 5: Comparison Between the Effects of IRES-1 and IRES-3

Vectors pCLD12 and pCLD14 were selected to evaluate the effects of the nucleotide length of IRES on the level of antibody expression, quality of the antibody product. DNA and RNA copy numbers of the heavy chain (HC) and light chain (LC) in a stable clone.

HC and LC of an antibody were constructed into pCLD12 or pCLD14 with different length of IRES and IRES-linked selection marker glutamine synthetase (GS) or neomycin phosphotransferase (Neo). In FIG. 6. HC-GS represents the expression construct comprising HC, followed by IRES then GS selection marker: LC-Neo represents the expression construct comprising LC, followed by IRES then Neo selection marker: LC-GS represents the expression construct comprising LC, followed by IRES then GS selection marker: HC-Neo represents the expression construct comprising HC, followed by IRES then Neo selection marker.

Figure 6A:
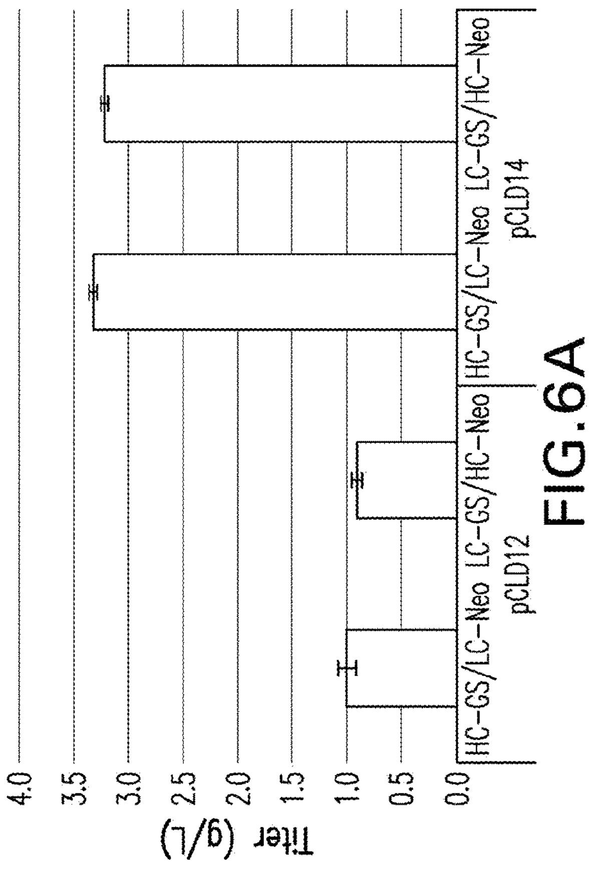
FIGS. 6A-6D demonstrate the effect of the nucleotide length of IRES on titer (FIG. 6A), specific productivity (FIG. 6B), aggregate level (FIG. 6C), and mannose level (FIG. 6D) of a monoclonal antibody production.
Figure 6B:
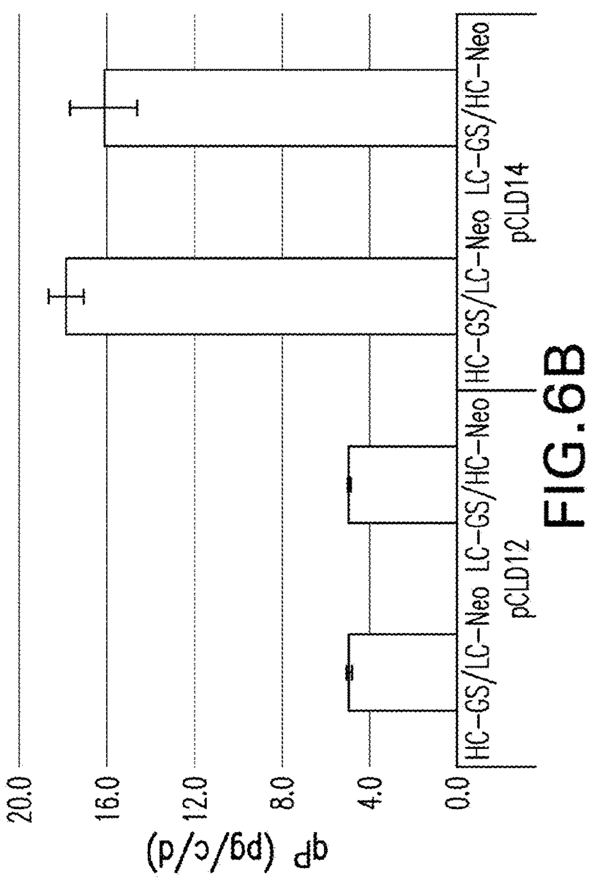
Figure 6C:
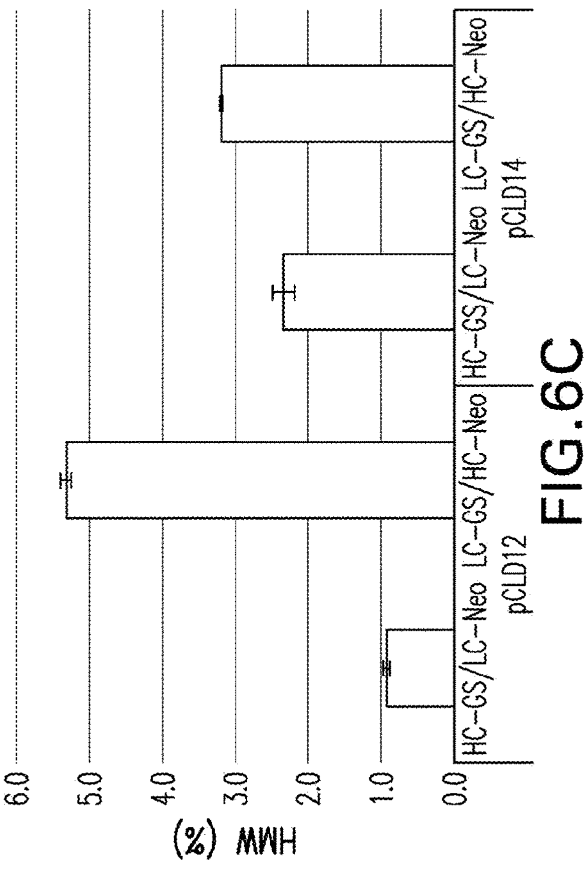
Figure 6D:
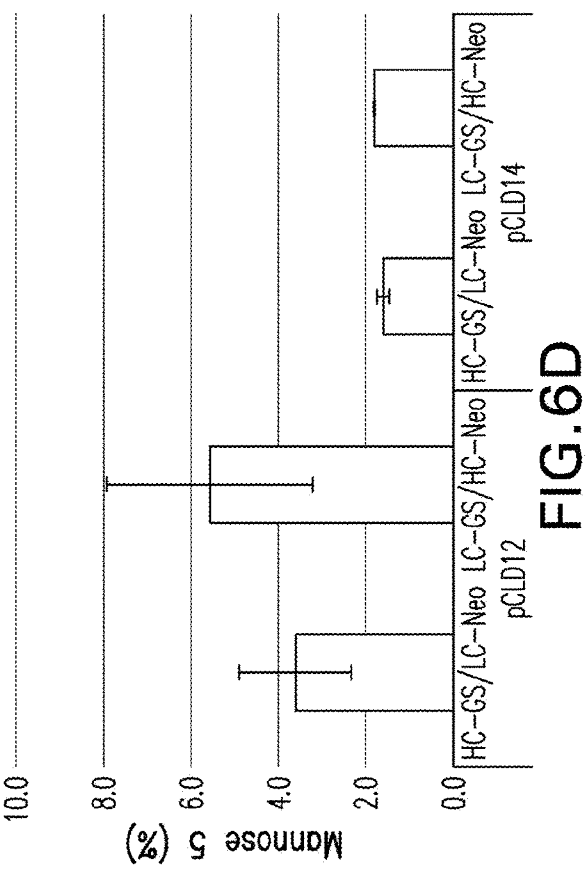

A pair of HC expression construct and LC expression construct were co-transfected into CHO host cells, and the host cells were selected with a medium containing G418 and without glutamine until the cell viability reached 90%. The stably selected pools were evaluated for mAb production through fed-batch production, pCLD14 with IRES-3 demonstrated higher mAb titer (FIG. 6A) and higher specific productivity (protein produced per cell per day. FIG. 6B) than pCLD12 with IRES-1. Product quality was assessed by high molecular weight (HMW) aggregation level (FIG. 6C) and mannose 5 level (FIG. 6D), pCLD14 with IRES-3 demonstrated better or equivalent product qualities compared to pCLD12 with IRES-1.

Figure 7A:
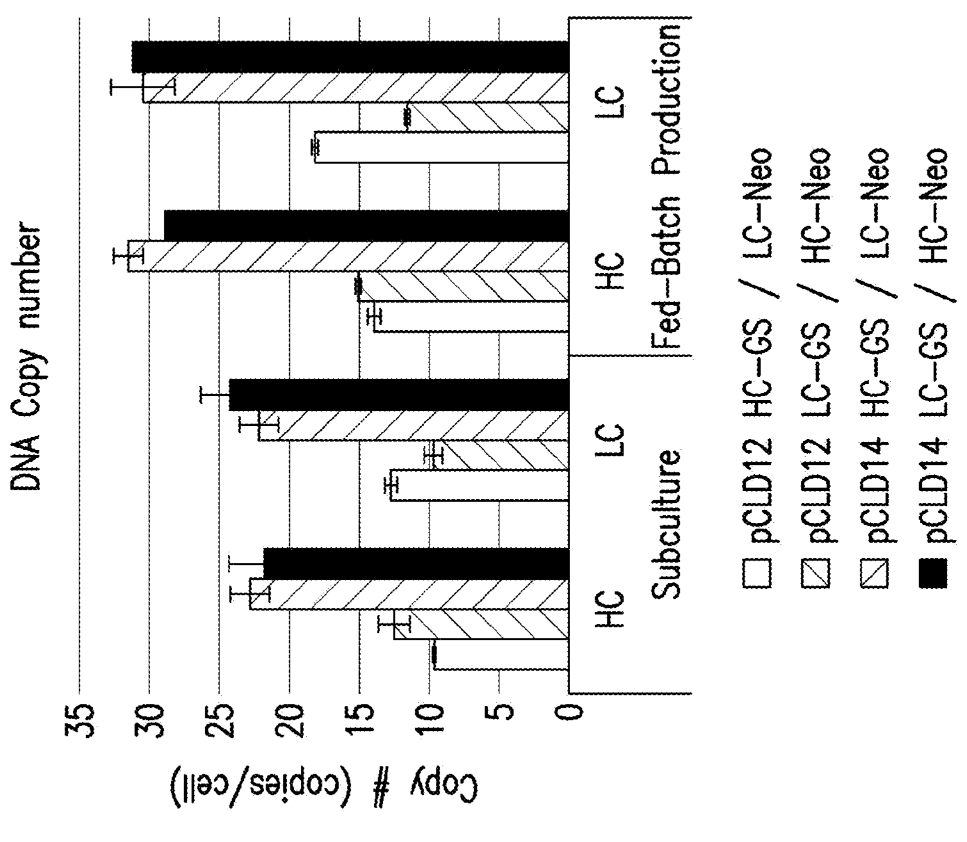
FIGS. 7A and 7B demonstrate the effect of the nucleotide length of IRES on DNA copy number (FIG. 7A) and mRNA level (FIG. 7B) of GOI encoding a monoclonal antibody heavy chain or light chain.
Figure 7B:
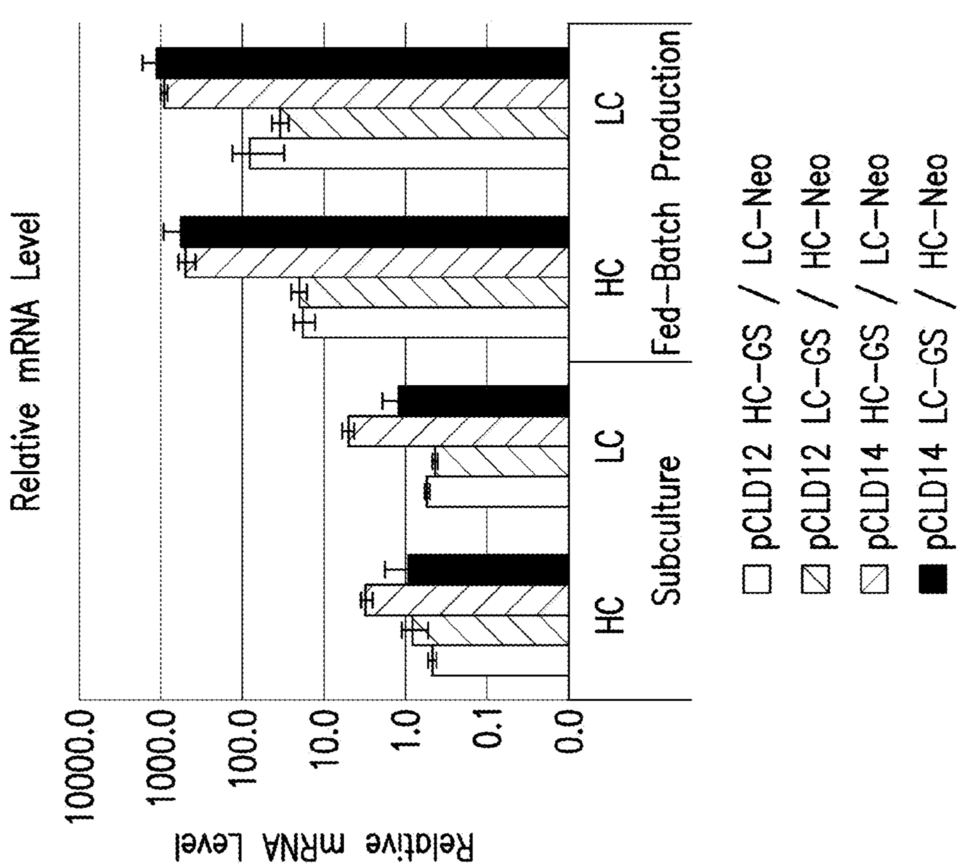

Genomic DNA was extracted from the CHO cells using DNeasy Blood and Tissue Kit (QIAGEN, Germany). Total RNA from the CHO cells was extracted using RNeasy Plus Mini Kit (QIAGEN, Germany), cDNAs was prepared from the RNA samples by reverse transcription using SuperScript IV VILO Master Mix (Thermo Fisher Scientific, MA). Manufacturer-recommended protocols were followed for the extraction of DNA or RNA, and for RNA reverse transcription. QX200 Droplet Digital PCR (ddPCR) System (Bio-Rad, Hercules, CA) was performed to determine the copy number of the HC gene and the LC gene, and to quantify the transcript level of the HC mRNA and the LC mRNA. Fluorescently-labeled oligo nucleotide probes for the ddPCR reactions were designed using the Primer Express Software (Applied Biosystems, Thermo Fisher Scientific, MA) and synthesized by Invitrogen (Thermo Fisher Scientific, MA). FIGS. 7A and 7B show higher DNA copy numbers and higher transcript levels associated with pCLD14 than with pCLD12, which further demonstrates that vector pCLD14 with IRES-3 is a better choice than vector pCLD12 with IRES-1.

In summary, the above examples demonstrated that the vector configurations with innovative combination of regulatory elements result in shortened selection time for stable clones, increased DNA copy number and RNA transcript levels, increased protein expression, and improved product quality.

SEQUENCE LISTING

The present application is being filed with a computer readable form (CRF) copy of the Sequence Listing. The CRF entitled 24617WOPCT_SEQLIST.txt, which was created on Sep. 23, 2019 and is 141,567 bytes in size, is incorporated herein by reference in its entirety.

What is claimed is:

1. An expression vector comprising:

(a) a first expression cassette comprising the following elements in the order of upstream to downstream: a promoter operably linked to an insertion site for a gene of interest (GOI), an internal ribosome entry site (IRES), wherein the IRES consists of a polynucleotide sequence of SEQ ID NO: 3, a polynucleotide encoding a eukaryotic selectable marker, and a polyadenylation (polyA) signal;

(b) a second expression cassette comprising a polynucleotide encoding a bacterial selectable marker; and (c) a bacterial plasmid origin of replication;

wherein optionally the first expression cassette further comprises one or more regulatory element; and wherein optionally the regulatory element is an enhancer, an insulator, a locus control region (LCR), a matrix attachment region (MAR), a scaffold attachment region (SAR), an expression augmenting sequence element (EASE), an adenovirus tripartite leader (TPL), or a ubiquitous chromatin opening element (UCOE).

2. The expression vector of claim 1, further comprising two inverted terminal repeat (ITR) sequences flanking the first expression cassette.

3. The expression vector of claim 2, wherein (a) the eukaryotic selectable marker is a neomycin phosphotransferase, a histidinol dehydrogenase, a hygromycin B phosphotransferase, a xanthine-guanine phosphoribosyltransferase, a dihydrofolate reductase, a tryptophan synthetase, a puromycin N-acetyl-transferase, a thymidine kinase, an adenine phosphoribosyl transferase, a glutamine synthetase, an adenosine deaminase, or metallothionein-1; wherein optionally the eukaryotic selectable marker is a glutamine synthetase or a neomycin phosphotransferase;

(b) the promoter is a human cytomegalovirus (CMV) immediate-early promoter, a human elongation factor 1 alpha (EF1a) promoter, a SV40 promoter, a phosphoglycerate kinase 1 (PGK1) promoter, a human ubiquitin C (Ubc) promoter, a human β-actin promoter, a CAG promoter, a yeast transcription elongation factor 1 (TEF1) promoter, a yeast glyceraldehyde 3-phosphate dehydrogenase (GAPDH) promoter, or a yeast alcohol dehydrogenase 1 (ADH1) promoter; wherein optionally the promoter is a human CMV immediate-early promoter;

(c) the enhancer is a CMV immediate-early enhancer; and/or (d) the insulator is HS4.

4. An expression vector comprising:

(a) a first expression cassette comprising the following elements in the order of upstream to downstream: a first insulator, an EASE, a promoter, a TPL, an insertion site for a GOI, an IRES, a polynucleotide encoding a eukaryotic selectable marker, a polyA signal, and a second insulator;

(b) two ITR sequences flanking the first expression cassette;

(c) a second expression cassette comprising a polynucleotide encoding a bacterial selectable marker; and (d) a bacterial plasmid origin of replication;

wherein optionally the first expression cassette further comprises an enhancer;

wherein optionally the enhancer is located between the EASE and the promoter;

wherein optionally the enhancer is a human CMV immediate-early enhancer;

wherein optionally the promoter is a human CMV immediate-early promoter;

wherein optionally the first and the second insulators are HS4;

wherein optionally the eukaryotic selectable marker is a glutamine synthetase or a neomycin phosphotransferase; and wherein the IRES consists of a polynucleotide sequence of SEQ ID NO: 3.

5. An expression vector, (a) comprising a polynucleotide sequence of SEQ ID NO: 6 or 8;

(b) consisting of a polynucleotide sequence of SEQ ID NO: 6 or 8; or (c) consisting essentially of a polynucleotide sequence of SEQ ID NO: 6 or 8.

6. The expression vector of claim 5, wherein the polynucleotide sequence is SEQ ID NO:8.

7. The expression vector of claim 4, wherein the first expression cassette further comprises the GOI encoding (a) a therapeutic or prophylactic protein;

(b) a light chain of a monoclonal antibody; or (c) a heavy chain of a monoclonal antibody.

8. An isolated host cell comprising the expression vector of claim 7, wherein optionally the host cell is a mammalian host cell or a bacterial host cell; wherein optionally the mammalian host cell is a CHO cell; and wherein optionally the endogenous glutamine synthetase gene of the CHO cell is knocked out.

9. A method of producing a polypeptide encoded by a GOI, comprising culturing the host cell of claim 8 in vitro under conditions in which the polypeptide is expressed, wherein the expression vector comprises the GOI encoding the polypeptide; and wherein the method further comprises recovering the polypeptide from the culture.

10. A method of propagating an expression vector, comprising culturing the host cell of claim 8 in vitro under conditions in which the expression vector is replicated; and wherein optionally the method further comprises recovering the expression vector from the culture.

11. An isolated host cell comprising a first expression vector of claim 4 and a second expression vector of claim 4, wherein the first expression vector further comprises a first GOI encoding a light chain of a monoclonal antibody or fragments thereof; wherein the second expression vector further comprises a second GOI encoding a heavy chain of the monoclonal antibody or fragments thereof; and wherein the eukaryotic selectable marker of the first expression vector is different from the eukaryotic selectable marker of the second expression vector.

12. A method of producing a monoclonal antibody, comprising culturing the host cell of claim 11 in vitro under conditions in which the light chain of the monoclonal antibody and the heavy chain of the monoclonal antibody are expressed; and wherein optionally the method further comprises recovering the monoclonal antibody from the culture.

* * * * *